(12) United States Patent
Logtenberg et al.

(10) Patent No.: US 10,844,127 B2
(45) Date of Patent: Nov. 24, 2020

(54) ANTIBODIES THAT BIND EGFR AND ERBB3

(71) Applicant: Merus N.V., Utrecht (NL)

(72) Inventors: Ton Logtenberg, Utrecht (NL); Mark Throsby, Utrecht (NL); Robertus Cornelis Roovers, Utrecht (NL)

(73) Assignee: Merus N.V., Utrecht (NL)

( * ) Notice: Subject to any disclaimer, the term of this patent is extended or adjusted under 35 U.S.C. 154(b) by 108 days.

(21) Appl. No.: 15/121,619

(22) PCT Filed: Feb. 27, 2015

(86) PCT No.: PCT/NL2015/050124
§ 371 (c)(1),
(2) Date: Aug. 25, 2016

(87) PCT Pub. No.: WO2015/130172
PCT Pub. Date: Sep. 3, 2015

(65) Prior Publication Data
US 2017/0058035 A1 Mar. 2, 2017

(30) Foreign Application Priority Data
Feb. 28, 2014 (EP) .................................... 14157351

(51) Int. Cl.
C07K 16/00 (2006.01)
C07K 16/28 (2006.01)
C07K 16/32 (2006.01)

(52) U.S. Cl.
CPC .......... *C07K 16/2863* (2013.01); *C07K 16/32* (2013.01); *C07K 2317/31* (2013.01); *C07K 2317/565* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,801,687 A | 1/1989 | Ngo | |
| 4,816,567 A | 3/1989 | Cabilly et al. | |
| 5,151,504 A | 9/1992 | Croze | |
| 5,731,168 A | 3/1998 | Carter et al. | |
| 7,642,228 B2 | 1/2010 | Carter et al. | |
| 7,705,103 B2 | 4/2010 | Sherman et al. | |
| 8,349,574 B2 | 1/2013 | Bates et al. | |
| 8,592,562 B2 | 11/2013 | Kannan et al. | |
| 8,628,774 B2 | 1/2014 | Gurney et al. | |
| 9,248,181 B2 | 2/2016 | De Kruif et al. | |
| 9,248,182 B2 | 2/2016 | De Kruif et al. | |
| 9,358,286 B2 | 6/2016 | De Kruif et al. | |
| 9,551,208 B2 | 1/2017 | Ma et al. | |
| 2003/0078385 A1 | 4/2003 | Arathoon et al. | |
| 2004/0071696 A1 | 4/2004 | Adams et al. | |
| 2006/0212956 A1 | 9/2006 | Crocker et al. | |
| 2009/0182127 A1 | 7/2009 | Kjaergaard et al. | |
| 2009/0191559 A1 | 7/2009 | Huang et al. | |
| 2010/0015133 A1 | 1/2010 | Igawa et al. | |
| 2010/0183615 A1 | 7/2010 | Kufer et al. | |
| 2010/0286374 A1 | 11/2010 | Kannan et al. | |
| 2011/0077163 A1 | 3/2011 | Doranz | |
| 2011/0195454 A1 | 8/2011 | Mcwhirter et al. | |
| 2012/0107306 A1 | 5/2012 | Elis et al. | |
| 2013/0071859 A1 | 3/2013 | Bates et al. | |
| 2013/0084297 A1* | 4/2013 | Daly ..................... | C07K 16/32 424/139.1 |
| 2013/0115208 A1 | 5/2013 | Ho et al. | |
| 2013/0259867 A1 | 10/2013 | Amler et al. | |
| 2013/0336981 A1 | 12/2013 | de Kruif et al. | |
| 2014/0072579 A1 | 3/2014 | De Kruif et al. | |
| 2014/0120096 A1 | 5/2014 | Bakker et al. | |
| 2014/0140999 A1 | 5/2014 | De Kruif et al. | |
| 2015/0013996 A1 | 1/2015 | Davies et al. | |
| 2015/0139996 A1 | 5/2015 | De Kruif et al. | |
| 2015/0196637 A1 | 7/2015 | De Kruif et al. | |

FOREIGN PATENT DOCUMENTS

| | | |
|---|---|---|
| EP | 0120694 A2 | 10/1984 |
| EP | 0314161 A1 | 5/1989 |
| EP | 0481790 A2 | 4/1992 |
| EP | 0523949 A1 | 1/1993 |
| EP | 1870459 A1 | 12/2007 |
| EP | 2604625 A1 | 6/2013 |
| JP | H 11-500915 A | 1/1999 |

(Continued)

OTHER PUBLICATIONS

Berglund et al, Protein Science, 2008, 17:606-613.*
Corada (Blood, 2001; 97:1679-84).*
Kulkarni-Kale et al. Nucleic Acid Research, 2005, 33:W168-W171.*
De Genst et al., Developmental and Comparative Immunology, 2006, 30:187-98.*
Ward et al. (Nature, 1989, 341:544-546).*
Barthelemy et al. (Journal of Biological Chemistry, 2008, 283:3639-3654).*

(Continued)

*Primary Examiner* — Mark Halvorson

(74) *Attorney, Agent, or Firm* — Sterne, Kessler, Goldstein & Fox P.L.L.C.

(57) ABSTRACT

The invention relates in one aspect to bispecific antibodies comprising a first antigen-binding site that binds EGFR and a second antigen-binding site that binds Erb B-3, wherein the antibody has a half maximal growth inhibitory concentration (IC50) of less than 200 pM for inhibiting EGFR and/or Erb B-3 ligand induced growth of Bx PC3 cells or Bx PC3-luc2 cells. Further described are method for producing the bispecific antibodies and means and methods for the treatment of subjects with the antibodies.

18 Claims, 46 Drawing Sheets

Specification includes a Sequence Listing.

(56) References Cited

FOREIGN PATENT DOCUMENTS

| | | |
|---|---|---|
| JP | 2011/508604 A | 3/2011 |
| WO | 1996027011 A1 | 9/1996 |
| WO | 1998050431 A2 | 11/1998 |
| WO | 00/63403 A2 | 10/2000 |
| WO | 03/004704 A2 | 1/2003 |
| WO | 2003/107218 A1 | 12/2003 |
| WO | 04/009618 A2 | 1/2004 |
| WO | 2004/061104 A1 | 7/2004 |
| WO | 2005/000894 A2 | 1/2005 |
| WO | 2005/118635 A2 | 12/2005 |
| WO | 2006/028936 A2 | 3/2006 |
| WO | 2006106905 A1 | 10/2006 |
| WO | 2007110205 A2 | 10/2007 |
| WO | 2007147901 A1 | 12/2007 |
| WO | 2008/027236 A2 | 3/2008 |
| WO | 2008/100624 A2 | 8/2008 |
| WO | 2008/119353 A1 | 10/2008 |
| WO | 2008/140493 A2 | 11/2008 |
| WO | 2009051974 A1 | 4/2009 |
| WO | 2009/080251 A1 | 7/2009 |
| WO | 2009/080252 A1 | 7/2009 |
| WO | 2009/080253 A1 | 7/2009 |
| WO | 2009/089004 A1 | 7/2009 |
| WO | 2009/098596 A2 | 8/2009 |
| WO | 2009/157771 A2 | 12/2009 |
| WO | 2010/084197 A1 | 7/2010 |
| WO | 2010/108127 A1 | 9/2010 |
| WO | WO-2010108127 A1 * 9/2010 ......... C07K 16/2863 |
| WO | 2010/129304 A2 | 11/2010 |
| WO | 2010/151792 A1 | 12/2010 |
| WO | 2011/028952 A1 | 3/2011 |
| WO | 2011/028953 A1 | 3/2011 |
| WO | 2011/143545 A1 | 11/2011 |
| WO | 2012023053 A2 | 2/2012 |
| WO | 2012/058768 A1 | 5/2012 |
| WO | 2012/125864 A2 | 9/2012 |
| WO | 2012/131555 A2 | 10/2012 |
| WO | 2013/107218 A1 | 7/2013 |
| WO | 2013/134686 A1 | 9/2013 |
| WO | 2013/157953 A1 | 10/2013 |
| WO | 2013/157954 A1 | 10/2013 |
| WO | 2014/051433 A1 | 4/2014 |
| WO | 2014/060365 A1 | 4/2014 |
| WO | 2014/159580 A1 | 10/2014 |
| WO | 2014/165855 A1 | 10/2014 |
| WO | 2015/130172 A1 | 9/2015 |
| WO | 2015/130173 A1 | 9/2015 |

OTHER PUBLICATIONS

Choi et al., 2011, Molecular BioSystems, 2011, 7:3327-334.*
Griffiths et al. (The EMBO Journal, 1993, 12:725-734).*
Klimka et al., British Journal of Cancer, 2000, 83:252-260.*
Beiboer et al. (Journal of Molecular Biology, 2000, 296:833-849).*
Freeman et al. (Journal of Clinical Oncology, 2008, 26: abstract 14536).*
May et al. (Biochemical Pharmacology, 2012, 84:1105-1112).*
Shiraiwa et al. (Methods, 2019, 154:10-20).*
U.S. Appl. No. 13/866,747, filed Apr. 19, 2013, Cornelis A. de Kruif.
U.S. Appl. No. 14/081,848, filed Nov. 15, 2013, Cornelis A. de Kruif.
U.S. Appl. No. 13/866,756, filed Apr. 19, 2013, Cornelis A. de Kruif.
U.S. Appl. No. 14/974,581, filed Dec. 18, 2015, Cornelis A. de Kruif.
U.S. Appl. No. 14/040,023, filed Sep. 27, 2013, Alexander Berthold Hendrik Bakker.
U.S. Appl. No. 14/395,330, filed Oct. 17, 2014, Cornelis A. de Kruif.
U.S. Appl. No. 14/395,325, filed Oct. 17, 2014, Cornelis A. de Kruif.
U.S. Appl. No. 15/205,629, filed Jul. 8, 2016, Alexander Berthold Hendrik Bakker.
U.S. Appl. No. 15/121,623, filed Aug. 25, 2016, Cecilia Anna Wilhelmina Geuijen.
U.S. Appl. No. 13/866,747, Sep. 29, 2015.
U.S. Appl. No. 13/866,747, Apr. 10, 2015.
U.S. Appl. No. 14/081,848, Feb. 12, 2016.
U.S. Appl. No. 14/081,848, Apr. 10, 2015.
U.S. Appl. No. 13/866,756, Sep. 18, 2015.
U.S. Appl. No. 13/866,756, Apr. 10, 2015.
U.S. Appl. No. 14/974,581, Jan. 25, 2017.
U.S. Appl. No. 14/974,581, Sep. 28, 2016.
U.S. Appl. No. 14/974,581, May 10, 2016.
U.S. Appl. No. 14/040,023, Nov. 28, 2016.
U.S. Appl. No. 14/040,023, Dec. 3, 2015.
U.S. Appl. No. 14/395,330, Apr. 10, 2015.
U.S. Appl. No. 15/205,629, Nov. 1, 2016.
Bendig, Mm., The production of foreign proteins in mammalian cells, Genet Eng., vol. 7:91-127 (1988).
Bogan, Aa. et al., "Anatomy of hot spots in protein interfaces," J Mol Biol, vol. 280 (1): 1-9 (1998).
Bostrom, J., "Variants of the antibody herceptin that interact with HER2 and VEGF at the antigen binding site," Science, vol. 323(5921)1610-1614 (2009).
Gunasekaran, K. et al., "Enhancing Antibody Fc Heterodimer Formation Through Electrostatic Steering Effects, Applications to Bispecific Molecules and Monovalent," JBC, vol. 285(25):19637-19646 (2010).
Gussow, D. et al., "Humanization of monoclonal antibodies," Methods Enzymol., vol. 203(5): 99-121 (1991).
Haagen, Ia, et al., "The efficacy of CD3 x CD19 bispecific monoclonal antibody (BsAb) in a clonogenic assay: the effect of repeated addition of BsAb and interleukin-2," Blood, vol. 85(11): 3208-3212 (1995).
Han, Y. et al., "KLRL1, a novel killer cell lectinlike receptor, inhibits natural killer cell cytotoxicity," Blood, vol. 104(9): 2856-2866 (2004).
Hao, Hx., et al, "ZNRF3 promotes Wnt receptor turnover in an R-spondin-sensitive manner," Nature, vol. 485 (7397):195-200 (2012).
Hendsch, Z. et al., "Preferential heterodimer formation via undercompensated electrostatic interactions," J Am Chem Soc, vol. 123(6): 1264-1265 (2001).
Idusogie, Ee, "Mapping of the C1q binding site on rituxan, a chimeric antibody with a human IgG1 Fc," J Immunol., vol. 164(8):4178-4184 (2000).
Ionescu, Rm. et al, "Contribution of variable domains to the; stability of humanized IgG1 monoclonal antibodies," J. Pharm Sci., vol. 97(4):1414-1426 (2008).
Capelle, Ma et al., "Spectroscopic characterization of antibodies adsorbed to aluminium adjuvants: correlation with antibody vaccine immunogenicity," Vaccine, 23(14): 1686-1694 (2005).
Carmon, K. et al., "R-spondins function as ligands of the orphan receptors LGR4 and LGR5 to regulate Wnt/β-catenin signaling," PNAS, vol. 108(28): 11452-11457 (2011).
Carter, P. J.,"Bispecific Human IgG by Design," Immunol. Methods, vol. 248: 7-15 (2001).
Cartron, G. et al., "Therapeutic activity of humanized anti-CD20 monoclonal antibody and polymorphism in IgG Fc receptor FcγRIIIa gene," Blood, vol. 99(3): 754-758 (2002).
Kabat, Ea., et al., "Identical V region amino acid; sequences and segments of sequences in antibodies of different specificities. Relative contributions of VH and VL genes, minigenes, and complementarity-determining regions to binding of antibody-combining sites," J Immunol., vol. 147(5): 1709-1719 (1991).
Coligan Je, "Commonly used detergents," Curr Protoc Protein Sci., Appendix 1:Appendix 1B (2001).
Kipriyanov, Sm. et al., "Bispecific CD3 x CD19 diabody for T cell-mediated lysis of malignant human B cells," Int. J. Cancer, vol. 77(5): 763-772 (1998).
Kontermann, R.E.,"Dual targeting strategies with bispecific antibodies,"MAbs, vol. 4(2): 182-197 (2012).
Davies, J. et al., "Antibody VH domains as small recognition units," Biotech., vol. 13(5): 475-479 (1995).

(56) References Cited

OTHER PUBLICATIONS

Kumar, R. et al., The Second PDZ Domain of INAD Is a Type I Domain Involved in Binding to Eye Protein Kinase C., J Biol Chem, vol. 276 (27): 24971-24977 (2001).
Lakowicz, Jr., "Principles of Fluorescence Spectroscopy," 3rd edition, Kluwer Academic/Plenum Publisher, ISBN-10: 0-387-31278-1, 469 pages (2006).
Davis, Jh. et al., "SEEDbodies: fusion proteins based on strand-exchange engineered domain (SEED) CH3 heterodimers in an Fc analogue platform for asymmetric binders or immunofusions and bispecific antibodies,", Protein Eng Des Sel., vol. 23(4):195-202 (2010).
Lanzavecchia, A. et al., "Lysis of nonnucleated red blood cells by cytotoxic T lymphocytes," Eur.J.Imm., vol. 17(7): 1073-1074 (1987).
De Kruif, J. et al., "Human immunoglobulin repertoires against Tetanus toxoid contain a large and diverse fraction of high-affinity VH genes" J. Mol. Biol., 387: 548-558 (2009).
Lee, B. et al., "The interpretation of protein structures: estimation of static accessibility," J Mol Biol., vol. 55(3), 379-400 (1971).
De Kruif, J. et al., "Generation of stable cell clones expressing mixtures of human antibodies," Biotechnol Bioeng, vol. 106(5): 741-750 (2010).
Armour, K.L. et al., "Differential binding to human FcgammaRIIa and FcgammaRIIb receptors by human IgG wildtype and mutant antibodies," Mol.Immunol., vol. 40(9): 585-593 (2003).
Liesveld, Jl., "Expression of IgG Fc receptors in myeloid leukemic cell lines. Effect of colony-stimulating factors and cytokines," J. Immunol., vol. 140(5):1527-1533 (1988).
De Lau, W., et al., "The R-spondin/Lgr5/Rnf43 module: regulator of Wnt signal strength," Genes Dev, vol. 28:305-316 (2014).
Liu, H. et al., "Heterogeneity of Monoclonal Antibodies," J Pharm Sci. vol. 97(7): 2426-2447 (2008).
Liu, Ma., et al., "Heteroantibody duplexes target cells for lysis by cytotoxic T lymphocytes," PNAS, vol. 82(24): 8648-8652 (1985).
Loeffler A. et al., "A recombinant bispecific single-chain antibody, CD19 X CD3, induces rapid and high lymphoma-directed cytotoxicity by unstimulated T lymphocytes," Blood, vol. 95(6) 2098-2103 (2000).
Bakker, Ab et al., "C-type lectin-like molecule-1: a novel myeloid cell surface marker associated with acute myeloid leukemia," Cancer Research, vol. 64(22): 8443-8450 (2004).
Mariuzza, Ra. et al., "The Structural Basis of Antigen-Antibody Recognition," Annu Rev Biophys Biophys Chem., vol. 116:139-159 (1987).
De Lau, W., et al., "Lgr5 homologues associate with Wnt receptors and mediate R-spondin signalling," Nature, vol. 476: 293-298 (2011).
Marshall, A.S. et al. "Identification and Characterization of a Novel Human MyeloidInhibitory C-type Lectin-like Receptor (MICL) That Is Predominantly Expressed on Granulocytes and Monocytes," J Biol Chem, vol. 279(15): 14792-14802 (2004).
Marvin, Js. et al., "Redesigning an antibody fragment for faster association with its antigen," Biochemistry, vol. 42 (23): 7077-7083 (2003).
Mcphee, F. et al., "Engineering human immunodeficiency virus 1 protease heterodimers as macromolecular inhibitors of viral maturation," PNAS, vol. 93(21):11477-11481 (1996).
Merchant, Am. et al., "An efficient route to human bispecific IgC," Nat. Biotechn., vol. 16 : 677-681 (1998).
Bluemel, C. et al., "Epitope distance to the target cell membrane and antigen size determine the potency of T cell-mediated lysis by BiTE antibodies specific for a large melanoma surface antigen," Cancer Immunol.Immunother., vol. 59 (8):1197-1209 (2010).
Merus, Press Release Jun. 17, 2013.
Merus, Press Release Jan. 7, 2013.
De Vries, Sj. et al, The Haddock web server for data driven biomolecular docking, Nature Protocols, vol. 5 (5):883-897 (2010).
Miller, S., "Protein-protein recognition and the association of immunoglobulin constant domains," J Mol Biol., vol. 216(4):965-973 (1990).
Moore, Pa. et al., "Application of dual affinity retargeting molecules to achieve optimal redirected T-cell killing of B-cell lymphoma," Blood, vol. 117(17):4542-4551 (2011).
Moshaver, B. et al., "Identification of a small subpopulation of candidate leukemia-initiating cells in the side population of patients with acute myeloid leukemia," Stem Cells, vol. 26(12): 3059-3067 (2008).
Nieba L. et al., "Disrupting the hydrophobic patches at the antibody variable/constant domain interface: improved in vivo folding and physical characterization of an engineered scFv fragment," Protein Eng., vol. 10(4): 435-444 (1997).
Nissim, A. et al., "Antibody fragments from a 'single pot' phage display library as immunochemical reagents," EMBO J., vol. 13(3): 692-698 (1994).
Nohaile, Mj. et al., "Altering dimerization specificity by changes in surface electrostatics," PNAS, USA, vol. 98(6): 3109-3114 (2001).
Almagro, Jc et al., "Humanization of antibodies," Front Biosci., vol. 13:1619-1633 (2008).
Arteaga, Cl et al., "Treatment of HER2-positive breast cancer: current status and future perspectives," Nat Rev Clin Oncol., vol. 9(1):16-32 (2011).
Balko, Jm et al., "The receptor tyrosine kinase ErbB3 maintains the balance between luminal and basal breast epithelium," Proc Natl Acad Sci U S A., vol. 109(1):221-226 (2012).
Baselga, J. et al., "Pertuzumab plus Trastuzumab plus Docetaxel for Metastatic Breast Cancer," N Engl J Med. vol. 366(21):2018-2026 (2012).
Devash, Y. et al, "Vertical transmission of human immunodeficiency virus is correlated with the absence of high-affinity/avidity maternal antibodies to the gp120 principal neutralizing domain," Proc Natl Acad Sci USA, vol. 87, pp. 3445-3449 (1990).
Ewer, MS, et al., "Cardiotoxicity of anticancer treatments: what the cardiologist needs to know," Nat Rev Cardiol., vol. 7(10):564-575 (2010).
Greco, Wr et al., "The search for synergy: a critical review from a response surface perspective," Pharmacol Rev., vol. 47(2):331-385 (1995).
Jain, Kk. et al,"A Prospective Randomized Comparison of Epirubicin and Doxorubicin in Patients With Advanced Breast Cancer," J Clin Oncol., vol. 3(6):818-820 (1985).
Junttila, Tt., et al, "Ligand-Independent HER2/HER3/PI3K Complex Is Disrupted by Trastuzumab and Is Effectively Inhibited by the PI3K Inhibitor GDC-0941," Cancer Cell, vol. 15, 429-440 (2009).
Junttila, Tt., et al,., "Superior in vivo Efficacy of Afucosylated Trastuzumab in the Treatment of HER2-Amplified Breast Cancer," Cancer Res; 70(11):4481-4489 (2010).
Kang, Jc. et al., "Engineering multivalent antibodies to target heregulin-induced HER3 signaling in breast cancer cells," MAbs, vol. 6(2):340-353 (2014).
Landgraf, R., "HER2 therapy. HER2 (ERBB2): functional diversity from structurally conserved building blocks," Breast Cancer Res. , vol. 9(1):202 (2007).
Liu, C. et al., "ADCC Enhancement Technologies for Next Generation TherapeuticAntibody," Trends in Bio/Pharmaceutcial Industry, 9 pages (2009).
Ocana, A. et al., "HER3 Overexpression and Survival in Solid Tumors: A Meta-analysis," J Natl Cancer Inst., vol. 105 (4):266-273 (2013).
Robinson, Mk. et al, "Targeting ErbB2 and ErbB3 with a bispecific single-chain Fv enhances targeting selectivity and induces a therapeutic effect in vitro," Br J Cancer, vol. 99(9):1415-1425 (2008).
Schoeberl, B. et al, "An ErbB3 antibody, MM-121, is active in cancers with ligand dependent activation," Cancer Res., 70(6): 2485-2494 (2010).
Sergina, Nv. et al, "Escape from HER-family tyrosine kinase inhibitor therapy by the kinase-inactive HER3," Nature, vol. 445(7126):437-441(2007).
Shames, Ds. et al., "High Heregulin Expression Is Associated with Activated HER3 and May Define an Actionable Biomarker in Patients with Squamous Cell Carcinomas of the Head and Neck," PLoS One, vol. 8(2): e56765, 10 pages (2013).

(56) References Cited

OTHER PUBLICATIONS

Tanner, M. et al., "Characterization of a novel cell line established from a patient with Herceptin-resistant breast cancer," Mol Cancer Ther., vol. 3(12): 1585-1592 (2004).
Thery, Jc. et al., "Resistance to human epidermal growth factor receptor type 2-targeted therapies," European Journal of Cancer, vol. 50: 892-901(2014).
Wadhwa, D. et al., "Trastuzumab mediated cardiotoxicity in the setting of adjuvant chemotherapy for breast cancer: a retrospective study," Breast Cancer Res Treat, vol. 117: 357-364 (2009).
Wehrman Ts. et al., "A system for quantifying dynamic protein interactions defines a role for Herceptin in modulating ErbB2 interactions," Proc Natl Acad Sci USA, vol. 103(50): 19063-19068 (2006).
Weidle, Uh. et al., "The Intriguing Options of Multispecific Antibody Formats for Treatment of Cancer," Cancer Genomics & Proteomics, vol. 10: 1-18 (2013).
Wilson Tr. et al., "Widespread potential for growth-factor-driven resistance to anticancer kinase inhibitors," Nature, vol. 487(7408): 505-509 (2012).
Yarden, Y. et al., "The ERBB network: at last, cancer therapy meets systems biology," Nat Rev Cancer, vol. 12: 553-563 (2012).
Yonesaka, K. et al.,., "Activation of ERBB2 signaling causes resistance to the EGFR directed therapeutic antibody cetuximab," Sci Transl Med., vol. 3(99): 19 pages (2011).
Zhang, H. et al., "ErbB receptors: from oncogenes to targeted cancer therapies," J. Clin. Invest. 117:2051-2058 (2007).
Buday, L. et al., "Epidermal Growth Factor Regulates the Exchange Rate of Guanine Nucleotides on p21ras in Fibroblasts," Molecular and Cellular Biology, vol. 13(3):1903-1910 (1993).
Cochran, Jr. et al., "Domain-level antibody epitope mapping through yeast surface display of epidermal growth factor receptor fragments," J Immunol Methods, vol. 287(1-2): 147-158 (2004).
De Haard, Hj. et al., "A Large Non-immunized Human Fab Fragment Phage Library That Permits Rapid Isolation and Kinetic Analysis of High Affinity Antibodies*," The Journal of Biological Chemistry, vol. 274(26): 18218-18230 (1999).
Ferguson, Km., "A structure-based view of Epidermal Growth Factor Receptor regulation," Annu Rev Biophys., vol. 37: 353-373 (2008).
Gale, Nw. et al., "Grb2 mediates the EGF-dependent activation of guanine nucleotide exchange on Ras," Nature, vol. 363(6424):88-92 (1993).
Garrett, Tp. et al., "Crystal structure of a truncated epidermal growth factor receptor extracellular domain bound to transforming growth factor alpha," Cell, vol. 110 (6): 763-773 (2002).
Giard, Dj. et al, "In Vitro Cultivation of Human Tumors: Establishment of Cell Lines Derived From a Series of Solid Tumors," J Natl Cancer Inst., vol. 51, 1417-1423 (1973).
Gulli, Lf. et al, "Epidermal growth factor-induced apoptosis in A431 cells can be reversed by reducing the tyrosine kinase activity,"Cell Growth Differ., vol. 7(2):173-178 (1996).
Jorissen, Rn. et al., "Epidermal growth factor receptor: mechanisms of activation and signalling," Exp Cell Res. vol. 284(1):31-53 (2003).
Kubota, T. et al, "Engineered therapeutic antibodies with improved effector functions," Cancer Sci., vol. 100: 1566-1572 (2009).
Ledón, N. et al, "Comparative analysis of binding affinities to epidermal growth factor receptor of monoclonal antibodies nimotuzumab and cetuximab using different experimental animal models," Placenta, vol. 32: 531-534 (2011).
Lichtenberger, Bm. et al., "Epidermal EGFR controls cutaneous host defense and prevents inflammation," Sci Transl Med., vol. 5 (199): 14 pages (2013).
Marks, Jd. et al., "By-passing Immunization Human Antibodies from V-gene Libraries Displayed on Phage," J Mol Biol., vol. 222 :581-597 (1991).
Merlino, Gt. et al, "Amplification and Enhanced Expression of the Epidermal Growth Factor Receptor Gene in A431 Human Carcinoma Cells," Science, vol. 224(4647): 417-419 (1984).

Meulemans, Ev. et al., "Selection of phage-displayed antibodies specific for a cytoskeletal antigen by competitive elution with a monoclonal antibody," J Mol Biol., vol. 244(4):353-360 (1994).
Ogiso, H. et al., "Crystal Structure of the Complex of Human Epidermal Growth Factor and Receptor Extracellular Domains," Cell, vol. 110: 775-787 (2002).
Olayioye, Ma et al., "The ErbB signaling network: receptor heterodimerization in development and cancer," EMBO J., vol. 19(13):3159-3167 (2000).
Pastore, S. et al., "ERK1/2 Regulates Epidermal Chemokine Expression and Skin Inflammation," J. Immunol., vol. 174:5047-5056 (2005).
Patel, Dk., "Clinical use of anti-epidermal growth factor receptor monoclonal antibodies in metastatic colorectal cancer," Pharmacotherapy, vol. 28(11 Pt 2):31S-41S (2008).
Prigent, S et al., "Identification of c-erbB-3 binding sites for phosphatidylinositol 3'-kinase and SHC using an EGF receptor/c-erbB-3 chimera," EMBO J., vol. 13(12):2831-2841(1994).
Robertson, Sc. et al., "RTK mutations and human syndromes when good receptors turn bad," Trends Genet., vol. 16(6):265-271 (2000).
Schmitz, K. et al., "Interaction of antibodies with ErbB receptor extracellular regions," Exp Cell Res., vol. 315(4): 559-670 (2009).
Soltoff, Sp. et al., "ErbB3 Is Involved in Activation of Phosphatidylinositol 3-Kinase by Epidermal Growth Factor," Mol Cell Biol., vol. 14(6): 3550-3558 (1994).
Zhu, Z. et al., "Remodeling domain interfaces to enhance heterodimer formation," Protein Sci., vol. 6(4): 781-788 (1997).
Yarden, Y. et al., "The EGFR family and its ligands in human cancer: signalling mechanisms and therapeutic opportunities," European Journal of Cancer, vol. 37: S3-S8 (2001).
Chatenoud, L. et al., "In vivo cell activation following OKT3 administration. Systemic cytokine release and modulation by corticosteroids", Transplantation, vol. 49(4): 697-702 (1990).
Zebisch, M. et al., "Crystal structure of R-spondin 2 in complex with the ectodomains of its receptors LGR5 and ZNRF3," J Struct Biol., vol. 191: 149-155 (2015).
Zebisch, M. et al., "ZNRF3/RNF43 e a direct linkage of extracellular recognition and E3 ligase activity to modulate cell surface signalling," Prog Biophys Mol Biol., vol. 118: 112-118 (2015).
Zeidler, R. et al., "Simultaneous activation of T cells and accessory cells by a new class of intact bispecific antibody results in efficient tumor cell killing,", J. Immunol., vol. 163(3): 1246-1252 (1999).
Zhang, W. et al., "Homo sapiens C-type lectin protein CLL-1 mRNA, complete cds," GenBank: AF247788.1, 1 page (2002).
Zhao, X., et al., "Targeting C-type lectin-like molecule-1 for antibody-mediated immunotherapy in acute myeloid leukemia," Haematologica, vol. 95(1): 71-78 (2009).
Chen, C.H.et al., "Effect of Duration of Osmotherapy on blood-brain barrier disruption and regional cerebral edema after experiental stroke," Blood, Journal of Cerebral Blood Flow & Metabolism, vol. 26: 951-958 (2006).
Cui, H. et al., "Chemically Programmed Bispecific Antibodies That Recruit and Activate T Cells," The Journal of Biological Chemistry, vol. 287(34): 28206-28214 (2012).
Dewildt, Rm et al.,"Analysis of Heavy and Light Chain Pairings Indicates the Receptor Editing Shapes the Human Antibody Repertoire," J. Mol. Biol., vol. 285: 895-901 (1999).
Dreier, T. et al., "Extremely potent, rapid and costimulation-independent cytotoxic T-cell response against lymphoma cells catalyzed by a single-chain bispecific antibody," Int. J.Canc., vol. 100(6): 690-697 (2002).
Geginat, J., A. et al, "Proliferation and differentiation potential of human CD8+ memory T-cell subsets in response to antigen or homeostatic cytokines," Blood, vol. 101(11): 4260-4266 (2003).
Dekruif, J. et al., "Selection and application of human single chain Fv antibody fragments from a semi-synthetic phage antibody display library with designed CDR3 regions," J. Mol Biol., vol. 248(1): 97-105 (1995.
Legall, F. et al., "Effect of linker sequences between the antibody variable domains on the formation, stability and biological activity of a bispecific tandem diabody," Protein Eng Des Sel., vol. 17(4):357-366 (2004).

(56) References Cited

OTHER PUBLICATIONS

Norde, Wj. et al., "Myeloid leukemic progenitor cells can be specifically targeted by minor histocompatibility antigen LRH-1-reactive cytotoxic T cells," Blood, vol. 113(10): 2312-2123 (2009).
Deisenhofer, J., "Crystallographic refinement and atomic models of a human Fc fragment and its complex with fragment B of protein A from Staphylococcus aureus at 2.9- and 2.8-A resolution," Biochemistry, vol. 20(9): 2361-2370 (1981).
Offner, S. et al., "Induction of regular cytolytic T cell synapses by bispecific single-chain antibody constructs on MHC class I-negative tumor cells," Molecular Immunology, vol. 43(6):763-771( 2006).
Oganesyan, V. et al., "Structural characterization of a human Fc fragment engineered for lack of effector functions," Acta Crystallogr D Biol Crystallogr., vol. 64(Pt. 6):700-704 (2008).
Demeule, B. et al., "Detection and characterization of protein aggregates by fluorescence microscopy," Int J Pharm, vol. 329(1-2):37-45 (2007).
Demeule, B., "Characterization of protein aggregation: the case of a therapeutic immunoglobulin," Biochim Biophys Acta, vol. 1774(1): 146-153 (2007).
Padlan, Ea., "X-ray crystallography of antibodies," Adv Protein Chem, vol. 49: 57-133 (1996).
Papadea, Ea, "Human immunoglobulin G and immunoglobulin G subclasses: biochemical, genetic, and clinical aspects.," Crit Rev Clin Lab Sci., vol. 27(1): 27-58 (1989).
Di, Z. et al., "Ultra High Content Image Analysis and Phenotype Profiling of 3D Cultured Micro-Tissues," PLoS One, PLoS One 9(10): e109688, 10 pages (2014).
Ellerson, Jr. et al., "Structure and function of immunoglobulin domains. III. Isolation and characterization of a fagment corresponding to the Cgamma2 homology region of human immunoglobin G1," J. Immunol, vol. 116 (2):510-517 (1976).
Peng, R., et al., "Bleomycin Induces Molecular Changes Directly Relevant to Idiopathic Pulmonary Fibrosis: A Model for "Active," Disease," Plos One, 8(4): e59348, 15 pages (2013).
Farnan, D. et al., "Multiproduct high-resolution monoclonal antibody charge variant separations by pH gradient ion-exchange chromatography," Anal Chem, vol. 81(21): 8846-8857 (2009).
Raffen, R. et al.., "Reengineering immunoglobulin domain interactions by introduction of charged residues," Protein Eng., vol. 11(4): 303-309 (1998).
Reusch, U. et al., "Beyond mAbs with TandAbs," Innovations in Pharmaceutical Technology, pp. 51-60 (Jun. 2011).
Ridgway, Jb. et al., "Knobs-into-holes' engineering of antibody CH3 domains for heavy chain heterodimerization," Protein Eng., vol. 9(7):617-621 (1996).
Logtenberg, T. "Hub for Organoids", Poster Presentation, www.innovationforhealth.nl/index.php/page/getFileUID/uid/82364b177dfed9754d785aaffb21363/cr_usedb/25, 29 pages, Mar. 22, 2016.
Carter, P., et al., "Toward the Production of Bispecific Antibody Fragments for Clinical Applications," Journal of Hematotherapy, vol. 4, pp. 463-470 (1995).
Sal-Man, N. et al., "Arginine Mutations within a Transmembrane Domain of Tar, an Escherichia coli Aspartate Receptor, Can Drive Homodimer Dissociation and Heterodimer Association in Vivo," Journal of Biochemistry, vol. 385: 29-36 (2005).
Sali, A. et al, "Comparative protein modelling by satisfaction of spatial restraints," J. Mol. Biol., vol. 234(3):779-815 (1993).
Sandercock, Am. et al., "Identification of anti-tumour biologics using primary tumour models, 3-D phenotypic screening and image-based multi-parametric profiling," Mol Cancer., vol. 14:147, 18 pages (2015).
Sato, T. et al., "Long-term Expansion of Epithelial Organoids From Human Colon, Adenoma, Adenocarcinoma, and Barrett's Epithelium," Gastroenterology, vol. 141: 1762-1772 (2011).
Schaefer, G. et al, "A two-in-one antibody against HER3 and EGFR has superior inhibitory activity compared with monospecific antibodies," Cancer Cell, vol. 20(4): 472-486 (2011).
Schiffer, M. et al., "Analysis of Immunoglobulin Domain Interactions Evidence for a Dominant Role of Salt Bridges," JMB, vol. 203:799-802 (1988).
Chames, P. et al., "Bispecific antibodies for cancer therapy: the light at the end of the tunnel?," MAbs, vol. 1(6): 539-547 (2009).
Atwell,S. et al., "Stable heterodimers from remodeling the domain interface of a homodimer using a phage display library," J Mol Biol, vol. 270(1): 26-35 (1997).
Selzer, T. et al., "Rational design of faster associating and tighter binding protein complexes," Nature Structural Biology, vol. 7, p. 537-541 (2000).
Bargou, R. et al., "Tumor regression in cancer patients by very low doses of a T cell-engaging antibody," Science, vol. 321 (5891) 974-977 (2008).
Seshagiri, S., et al., "Recurrent R-spondin fusions in colon cancer," Nature, vol. 488(7413): 660-664 (2012).
Baeuerle, Pa. et al, "Multiple myeloma and monoclonal gammopathy of undetermined significance: importance of whole-body versus spinal MR imaging," Cancer Research, vol. 252(2): 477-485 (2009).
Sheinerman, F., et al., " Electrostatic aspects of protein-protein interactions," Current Opinion in Structural Biology, vol. 10:153-159 (2000).
Sheridan, C., "Amgen swallows Micromet to BiTE into All market," Nat Biotechnol., vol. 30(4):300-301 (2012).
Shields, Rl. et al., "High resolution mapping of the binding site on human IgG1 for Fc gamma RI, Fc gamma RII, Fc gamma RIII, and FcRn and design of IgG1 variants with improved binding to the Fc gamma R," JBC, vol. 276(9): 6591-6604 (2001).
Sinha, N. et al., "Difference in Electrostatic Properties at Antibody-Antigen Binding Sites: Implications for Specificity and Cross-Reactivity," Biophysical Journal, vol. 83: 2946-2968 (2002).
Sinha, N., et al. "Electrostatics in Protein Binding and Function," Current Protein and Peptide Science, vol. 3:601-614 (2002).
Sluijter, B.J., et al., "4-1BB-mediated expansion affords superior detection of in vivo primed effector memory CD8+ T cells from melanoma sentinel lymph nodes ," Clin Immunol, vol. 137(2): 221-233 (2010).
Von Horsten, Hh. et al., "Production of non-fucosylated antibodies by co-expression of heterologous GDP-6-deoxy-D-lyxo-4-hexulose reductase," Glycobiology, vol. 20 (12):1607-1618 ( 2010).
Spiess, C., et al., "Alternative molecular formats and therapeutic applications for bispecific antibodies," Mol. Immunol., vol. 67(2 Pt A):95-106 (2015).
Staerz, Ud. et al., "Hybrid hybridoma producing a bispecific monoclonal antibody that can focus effector T-cell activity," PNAS, vol. 83(5):1453-1457 (1986).
Strelkauskas, A. et al., "Human Monoclonal Antibody: 2. Simultaneous Expression of IgG and IgM with Similar Binding Specificities by a Human Hybrid Clone," Hybridoma, vol. 6 (5): 479-488 (1987).
Suntharalingam, G. et al., "Cytokine storm in a phase 1 trial of the anti-CD28 monoclonal antibody TGN1412," N Engl J Med, vol. 355 (10): 1018-10128 (2006).
Tahallah, N."The effect of the source pressure on the abundance of ions of noncovalent protein assemblies in an electrospray ionization orthogonal time-of-flight instrument," Rapid Commun Mass Spectrom, vol. 15(8):596-601 (2001).
Van Rhenen, A. et al., "The novel AML stem cell associated antigen CLL-1 aids in discrimination between normal and leukemic stem cells," Blood, vol. 110(7): 2659-2666 (2007).
Van De Wetering, M. et al., "Prospective Derivation of a Living Organoid Biobank of Colorectal Cancer Patients," Cell, vol. 161: 933-945 (2015).
Uberall, I. et al.,"The status and role of ErbB receptors in human cancer," Exp Mol Pathol., vol. 84:79-89 (2008).
UniProt Entry Q5QGZ9, UniProt, retrieved Jan. 21, 2015, from <http://www.uniprot.org/uniprotlQ5QGZ9.

* cited by examiner

FIG. 1
(SEQ ID NOS: 1 and 2)

```
GCTAGCacc atggggcccagcggcaccgccggcgccgccctgctggccctgctggcc
      A  S  T  M  G  P  S  G  T  A  G  A  A  L  L  A  L  L  A
Gccctgtgccccgccagccgggcc ctggaggagaagaaggtgtgccagggcaccagcaac
   A  L  C  P  A  S  R  A  L  E  E  K  K  V  C  Q  G  T  S  N
aagctgacccagctgggcaccttcgaggaccacttcctgagcctgcagcggatgttcaac
   K  L  T  Q  L  G  T  F  E  D  H  F  L  S  L  Q  R  M  F  N
aactgcgaggtggtgctgggcaacctggagatcacctacgtgcagcggaactacgacctg
   N  C  E  V  V  L  G  N  L  E  I  T  Y  V  Q  R  N  Y  D  L
agcttcctgaagaccatccaggaggtggccggctacgtgctgatcgccctgaacaccgtg
   S  F  L  K  T  I  Q  E  V  A  G  Y  V  L  I  A  L  N  T  V
gagcggatccccctggagaacctgcagatcatccggggcaacatgtactacgagaacagc
   E  R  I  P  L  E  N  L  Q  I  I  R  G  N  M  Y  Y  E  N  S
tacgccctggccgtgctgagcaactacgacgccaacaagaccggcctgaaggagctgccc
   Y  A  L  A  V  L  S  N  Y  D  A  N  K  T  G  L  K  E  L  P
atgcggaacctgcaggagatcctgcacggcgccgtgcggttcagcaacaaccccgccctg
   M  R  N  L  Q  E  I  L  H  G  A  V  R  F  S  N  N  P  A  L
tgcaacgtggagagcatccagtggcgggacatcgtgagcagcgagttcctgagcaacatg
   C  N  V  E  S  I  Q  W  R  D  I  V  S  S  E  F  L  S  N  M
agcatggacttccagaaccacctgggcagctgccagaagtgcgaccccagctgccccaac
   S  M  D  F  Q  N  H  L  G  S  C  Q  K  C  D  P  S  C  P  N
ggcagctgctggggcgccggcgaggagaactgccagaagctgaccaagatcatctgcgcc
   G  S  C  W  G  A  G  E  E  N  C  Q  K  L  T  K  I  I  C  A
cagcagtgcagcggccggtgccggggcaagagccccagcgactgctgccacaaccagtgc
   Q  Q  C  S  G  R  C  R  G  K  S  P  S  D  C  C  H  N  Q  C
gccgccggctgcaccggcccccgggagagcgactgcctggtgtgccggaagttccgggac
   A  A  G  C  T  G  P  R  E  S  D  C  L  V  C  R  K  F  R  D
gaggccacctgcaaggacacctgccccccccctgatgctgtacaaccccaccacctaccag
   E  A  T  C  K  D  T  C  P  P  L  M  L  Y  N  P  T  T  Y  Q
atggacgtgaaccccgagggcaagtacagcttcggcgccacctgcgtgaagaagtgcccc
   M  D  V  N  P  E  G  K  Y  S  F  G  A  T  C  V  K  K  C  P
cggaactacgtggtgaccgaccacggcagctgcgtgcgggcctgcggcgccgacagctac
   R  N  Y  V  V  T  D  H  G  S  C  V  R  A  C  G  A  D  S  Y
gagatggaggaggacggcgtgcggaagtgcaagaagtgcgagggcccctgccggaaggtg
   E  M  E  E  D  G  V  R  K  C  K  K  C  E  G  P  C  R  K  V
tgcaacggcatcggcatcggcgagttcaaggacaccctgagcatcaacgccaccaacatc
   C  N  G  I  G  I  G  E  F  K  D  T  L  S  I  N  A  T  N  I
aagcacttcaagaactgcaccagcatcagcggcgacctgcacatcctgcccgtggccttc
   K  H  F  K  N  C  T  S  I  S  G  D  L  H  I  L  P  V  A  F
cggggcgacagcttcacccacacccccccctggaccccaggagctggacatcctgaag
   R  G  D  S  F  T  H  T  P  P  L  D  P  Q  E  L  D  I  L  K
accgtgaaggagatcaccggcttcctgctgatccaggcctggcccgagaaccggaccgac
   T  V  K  E  I  T  G  F  L  L  I  Q  A  W  P  E  N  R  T  D
ctgcacgccttcgagaacctggagatcatccggggccggaccaagcagcacggccagttc
   L  H  A  F  E  N  L  E  I  I  R  G  R  T  K  Q  H  G  Q  F
agcctggccgtggtgagcctgaacatcaccagcctgggcctgcggagcctgaaggagatc
   S  L  A  V  V  S  L  N  I  T  S  L  G  L  R  S  L  K  E  I
```

FIG. 1, Cont'd

```
agcgacggcgacgtgatcatcagcggcaacaagaacctgtgctacgccaacaccatcaac
 S  D  G  D  V  I  I  S  G  N  K  N  L  C  Y  A  N  T  I  N
tggaagaagctgttcggcaccagcagccagaagaccaagatcatcagcaaccggggcgag
 W  K  K  L  F  G  T  S  S  Q  K  T  K  I  I  S  N  R  G  E
aacagctgcaaggccaccggccaggtgtgccacgccctgtgcagccccgagggctgctgg
 N  S  C  K  A  T  G  Q  V  C  H  A  L  C  S  P  E  G  C  W
ggccccgagccccgggactgcgtgagctgccagaacgtgagccggggccgggagtgcgtg
 G  P  E  P  R  D  C  V  S  C  Q  N  V  S  R  G  R  E  C  V
gacaagtgcaacatcctggagggcgagccccggggagttcgtggagaacagcgagtgcatc
 D  K  C  N  I  L  E  G  E  P  R  E  F  V  E  N  S  E  C  I
cagtgccacccgagtgcctgccccaggtgatgaacatcacctgcaccggccgggccccc
 Q  C  H  P  E  C  L  P  Q  V  M  N  I  T  C  T  G  R  G  P
gacaactgcatccagtgcgcccactacatcgacggccccactgcgtgaagacctgcccc
 D  N  C  I  Q  C  A  H  Y  I  D  G  P  H  C  V  K  T  C  P
gccggcgtgatgggcgagaacaacaccctggtgtggaagtacgccgacgccggccacgtg
 A  G  V  M  G  E  N  N  T  L  V  W  K  Y  A  D  A  G  H  V
tgccacctgtgccacccaactgcacctacggctgcaccggccccggcctggagggctgc
 C  H  L  C  H  P  N  C  T  Y  G  C  T  G  P  G  L  E  G  C
gccggaacggccccaagatccccagcatcgccaccggcatgctgggcgccctgctgctg
 A  R  N  G  P  K  I  P  S  I  A  T  *G  M  L  G  A  L  L  L*
ctgctggtggtggccctgggcatcggcctgttcatgcggcggcggcacatcgtgcggaag
 *L  L  V  V  A  L  G  I  G  L  F  M*  R  R  R  H  I  V  R  K
cggaccctgcggcggctgctgcaggagcgggagctggtggagcccctgaccccagcggc
 R  T  L  R  R  L  L  Q  E  R  E  L  V  E  P  L  T  P  S  G
gaggcccccaaccaggccctgctgcggatcctgaaggagaccgagttcaagaagatcaag
 E  A  P  N  Q  A  L  L  R  I  L  K  E  T  E  F  K  K  I  K
gtgctgggcagcggcgccttcggcaccgtgtacaagggcctgtggatccccgagggcgag
 V  L  G  S  G  A  F  G  T  V  Y  K  G  L  W  I  P  E  G  E
aaggtgaagatccccgtggccatcaaggagctgcgggaggccaccagccccaaggccaac
 K  V  K  I  P  V  A  I  K  E  L  R  E  A  T  S  P  K  A  N
aaggagatcctggacgaggcctacgtgatggccagcgtggacaaccccacgtgtgccgg
 K  E  I  L  D  E  A  Y  V  M  A  S  V  D  N  P  H  V  C  R
ctgctgggcatctgcctgaccagcaccgtgcagctgatcacccagctgatgcccttcggc
 L  L  G  I  C  L  T  S  T  V  Q  L  I  T  Q  L  M  P  F  G
tgcctgctggactacgtgcgggagcacaaggacaacatcggcagccagtacctgctgaac
 C  L  L  D  Y  V  R  E  H  K  D  N  I  G  S  Q  Y  L  L  N
tggtgcgtgcagatcgccaagggcatgaactacctggaggaccggcggctggtgcaccgg
 W  C  V  Q  I  A  K  G  M  N  Y  L  E  D  R  R  L  V  H  R
gacctggccgcccggaacgtgctggtgaagacccccagcacgtgaagatcaccgacttc
 D  L  A  A  R  N  V  L  V  K  T  P  Q  H  V  K  I  T  D  F
ggcctggccaagctgctgggcgccgaggagaaggagtaccacgccgagggcggcaaggtg
 G  L  A  K  L  L  G  A  E  E  K  E  Y  H  A  E  G  G  K  V
cccatcaagtggatggccctggagagcatcctgcaccggatctacacccaccagagcgac
 P  I  K  W  M  A  L  E  S  I  L  H  R  I  Y  T  H  Q  S  D
gtgtggagctacggcgtgaccgtgtgggagctgatgaccttcggcagcaagccctacgac
 V  W  S  Y  G  V  T  V  W  E  L  M  T  F  G  S  K  P  Y  D
```

FIG. 1, Cont'd

```
ggcatccccgccagcgagatcagcagcatcctggagaagggcgagcggctgccccagccc
 G  I  P  A  S  E  I  S  S  I  L  E  K  G  E  R  L  P  Q  P
cccatctgcaccatcgacgtgtacatgatcatggtgaagtgctggatgatcgacgccgac
 P  I  C  T  I  D  V  Y  M  I  M  V  K  C  W  M  I  D  A  D
agccggcccaagttccggggagctgatcatcgagttcagcaagatggcccgggacccccag
 S  R  P  K  F  R  E  L  I  I  E  F  S  K  M  A  R  D  P  Q
cggtacctggtgatccagggcgacgagcggatgcacctgcccagccccaccgacagcaac
 R  Y  L  V  I  Q  G  D  E  R  M  H  L  P  S  P  T  D  S  N
ttctaccgggccctgatggacgaggaggacatggacgacgtggtggacgccgacgagtac
 F  Y  R  A  L  M  D  E  E  D  M  D  D  V  V  D  A  D  E  Y
ctgatccccagcagggcttcttcagcagccccagcaccagccggacccccctgctgagc
 L  I  P  Q  Q  G  F  F  S  S  P  S  T  S  R  T  P  L  L  S
agcctgagcgccaccagcaacaacagcaccgtggcctgcatcgaccggaacggcctgcag
 S  L  S  A  T  S  N  N  S  T  V  A  C  I  D  R  N  G  L  Q
agctgccccatcaaggaggacagcttcctgcagcggtacagcagcgaccccaccggcgcc
 S  C  P  I  K  E  D  S  F  L  Q  R  Y  S  S  D  P  T  G  A
ctgaccgaggacagcatcgacgacaccttcctgcccgtgcccgagtacatcaaccagagc
 L  T  E  D  S  I  D  D  T  F  L  P  V  P  E  Y  I  N  Q  S
gtgcccaagcggcccgccggcagcgtgcagaacccgtgtaccacaaccagcccctgaac
 V  P  K  R  P  A  G  S  V  Q  N  P  V  Y  H  N  Q  P  L  N
cccgcccagccgggaccccactaccaggaccccacagcaccgccgtgggcaacccc
 P  A  P  S  R  D  P  H  Y  Q  D  P  H  S  T  A  V  G  N  P
gagtacctgaacaccgtgcagcccacctgcgtgaacagcaccttcgacagccccgccac
 E  Y  L  N  T  V  Q  P  T  C  V  N  S  T  F  D  S  P  A  H
tgggcccagaagggcagccaccagatcagcctggacaaccccgactaccagcaggacttc
 W  A  Q  K  G  S  H  Q  I  S  L  D  N  P  D  Y  Q  Q  D  F
ttccccaaggaggccaagcccaacggcatcttcaagggcagcaccgccgagaacgccgag
 F  P  K  E  A  K  P  N  G  I  F  K  G  S  T  A  E  N  A  E
tacctgcgggtggccccccagagcagcgagttcatcggcgcctgaGCGGCCGC
 Y  L  R  V  A  P  Q  S  S  E  F  I  G  A  -  A  A  A
```

FIG. 2

*EGFR HER3 swap varII ECD* (SEQ ID NO: 3)

LEEKKVCQGTSNKLTQLGTFEDHFLSLQRMFNNCEVVLGNLEITYVQRNYDLSFLKTIQEVAGYVLIALNTVERIPLEN
LQIIRGNMYYENSYALAVLSNYDANKTGLKELPMRNLQEILHGAVRFSNNPALCNVESIQWRDIVSSDFLSNMSMD
FQNHLCPPCHEVCKGRCWGPGSEDCQTLTKTICAPQCNGHCFGPNPNQCCHDECAGGCSGPQDTDCFACRHFN
DSGACVPRCPQPLVYNKLTFQLEPNPHTKYQYGGVCVASCPHNFVVDQTSCVRACPPDKMEVDKNGLKMCEPCG
GLCPKACEGIGIGEFKDSLSINATNIKHFKNCTSISGDLHILPVAFRGDSFTHTPPLDPQELDILKTVKEITGFLLIQAWP
ENRTDLHAFENLEIIRGRTKQHGQFSLAVVSLNITSLGLRSLKEISDGDVIISGNKNLCYANTINWKKLFGTSGQKTKIIS
NRGENSCKATGQVCHALCSPEGCWGPEPRDCVSCRNVSRGRECVDKCNLLEGEPREFVENSECIQCHPECLPQAM
NITCTGRGPDNCIQCAHYIDGPHCVKTCPAGVMGENNTLVWKYADAGHVCHLCHPNCTYGCTGPGLEGCPTNGP
KIPS

*EGFR HER3 swap varIII ECD* (SEQ ID NO: 4)

LEEKKVCQGTSNKLTQLGTFEDHFLSLQRMFNNCEVVLGNLEITYVQRNYDLSFLKTIQEVAGYVLIALNTVERIPLEN
LQIIRGNMYYENSYALAVLSNYDANKTGLKELPMRNLQEILHGAVRFSNNPALCNVESIQWRDIVSSDFLSNMSMD
FQNHLGSCQKCDPSCPNGSCWGAGEENCQKLTKIICAQQCSGRCRGKSPSDCCHNQCAAGCTGPRESDCLVCRKF
RDEATCKDTCPPLMLYNPTTYQMDVNPEGKYSFGATCVKKCPRNYVVTDHGSCVRACGADSYEMEEDGVRKCKK
CEGPCRKVCNGIGIGEFKDSLSINATNIKHFKNCTKILGNLDFLITGLNGDPWHKIPALDPEKLNVFRTVREITGYLNIQ
SWPPHMHNFSVFSNLTTIGGRSLYNRGFSLLIMKNLNVTSLGFRSLKEISAGRIYISANRQLCYHHSLNWTKVLGTSG
QKTKIISNRGENSCKATGQVCHALCSPEGCWGPEPRDCVSCRNVSRGRECVDKCNLLEGEPREFVENSECIQCHPE
CLPQAMNITCTGRGPDNCIQCAHYIDGPHCVKTCPAGVMGENNTLVWKYADAGHVCHLCHPNCTYGCTGPGLE
GCPTNGPKIPS

*EGFR HER3 swap varV ECD* (SEQ ID NO: 5)

LEEKKVCQGTSNKLTQLGTFEDHFLSLQRMFNNCEVVLGNLEITYVQRNYDLSFLKTIQEVAGYVLIALNTVERIPLEN
LQIIRGNMYYENSYALAVLSNYDANKTGLKELPMRNLQEILHGAVRFSNNPALCNVESIQWRDIVSSDFLSNMSMD
FQNHLGSCQKCDPSCPNGSCWGAGEENCQKLTKIICAQQCSGRCRGKSPSDCCHNQCAAGCTGPRESDCLVCRKF
RDEATCKDTCPPLMLYNPTTYQMDVNPEGKYSFGATCVKKCPRNYVVTDHGSCVRACGADSYEMEEDGVRKCKK
CEGPCRKVCNGIGIGEFKDSLSINATNIKHFKNCTSISGDLHILPVAFRGDSFTHTPPLDPQELDILKTVKEITGFLLIQA
WPENRTDLHAFENLEIIRGRTKQHGQFSLAVVSLNITSLGLRSLKEISDGDVIISGNKNLCYANTINWKKLFGTSGQKT
KIISNRGENSCKATGQVCHALCSPEGCWGPEPRDCVSCRNVSRGRECVDKCNLLEGEPREFVEECFSCHPECQPME
GTATCNGSGSDTCAQCAHFRDGPHCVSSCPHGVMGENNTLVWKYADAGHVCHLCHPNCTYGCTGPGLEGCPTN
GPKIPS

FIG. 3

| Cluster nr. | MF tested | Competition of phages with | | | | |
|---|---|---|---|---|---|---|
| | | no IgG | Domain I ICR10 | Domain II EGFR.1 | Domain III Cetuximab | Domain III MatuzuMab |
| 1 | 3998 | 2.494 | 2.227 | 2.343 | 0.101 | 0.671 |
| 2 | 4289 | 2.278 | 2.046 | 2.226 | 2.222 | 2.356 |
| 3 | 4000 | 2.597 | 1.736 | 2.604 | 2.533 | 0.345 |
| 4 | 4016 | 2.184 | 0.088 | 2.129 | 2.135 | 2.133 |
| 5 | 4029 | 1.898 | 2.193 | 1.256 | 1.235 | 1.938 |
| 6 | 4034 | 1.747 | 1.42 | 0.108 | 1.62 | 1.776 |
| 7 | 4035 | 1.594 | 0.951 | 1.554 | 1.079 | 1.309 |
| 8 | 4032 | 2.276 | 2.145 | 2.057 | 1.996 | 0.099 |
| 9 | 4284 | 2.04 | 2.212 | 1.776 | 2.08 | 1.226 |
| 10 | 4358 | 1.631 | 1.704 | 1.833 | 1.991 | 0.066 |
| 11 | 4280 | 2.549 | 2.302 | 2.135 | 1.141 | 0.613 |
| 12 | 4283 | 2.827 | 2.336 | 2.889 | 0.265 | 0.122 |
| 13 | 4281 | 2.107 | 2.195 | 1.968 | 1.589 | 1.255 |
| 14 | 4286 | 1.589 | 1.723 | 1.66 | 0.272 | 0.247 |
| 15 | 4285 | 2.176 | 2.332 | 1.599 | 2.369 | 2.285 |
| 16 | 4287 | 2.052 | 1.825 | 1.711 | 1.187 | 1.705 |
| 17 | 4359 | ND | ND | ND | ND | ND |

FIG. 11A

MF4280: heavy chain variable region sequence of an EGFR binding antibody

Complete VH sequence (SEQ ID NO: 7)

QVQLVQSGAEVKKPGASVKVSCKVSGYTLTELSMHWVRQAPGKGLEWMGGFDPEY
GKTFFAQNFQGRVTMTEDTSADTAYMELSSLRSEDTAVYYCATEGYYETTTYYYNLF
DSWGQGTLVTVSS

FR1 (SEQ ID NO: 8): QVQLVQSGAEVKKPGASVKVSCKVSGYTLT

CDR1 (SEQ ID NO: 9): ELSMH

FR2 (SEQ ID NO: 10): WVRQAPGKGLEWMG

CDR2 (SEQ ID NO: 11): GFDPEYGKTFFAQNFQG

FR3 (SEQ ID NO: 12): RVTMTEDTSADTAYMELSSLRSEDTAVYYCAT

CDR3 (SEQ ID NO: 13): EGYYETTTYYYNLFDS

FR4 (SEQ ID NO: 14): WGQGTLVTVSS

Annotated nucleotide sequence (SEQ ID NOS: 6 and 7)

```
CAGGTGCAGCTG
  Q   V   Q   L
GTGCAGTCTGGGGCTGAGGTGAAGAAGCCTGGGGCCTCAGTGAAGGTCTCCTGCAAGGTT
  V   Q   S   G   A   E   V   K   K   P   G   A   S   V   K   V   S   C   K   V
TCCGGATACACCCTCACTGAATTATCCATGCACTGGGTGCGACAGGCTCCTGGTAAAGGG
  S   G   Y   T   L   T   E   L   S   M   H   W   V   R   Q   A   P   G   K   G
CTTGAATGGATGGGAGGCTTTGATCCTGAGTATGGTAAAACATTCTTCGCACAGAACTTC
  L   E   W   M   G   G   F   D   P   E   Y   G   K   T   F   F   A   Q   N   F
CAGGGCAGAGTCACCATGACCGAGGACACATCTGCAGACACAGCCTACATGGAGCTAAGC
  Q   G   R   V   T   M   T   E   D   T   S   A   D   T   A   Y   M   E   L   S
AGCCTGAGATCTGAGGACACGGCCGTGTATTACTGTGCAACAGAGGGGTATTATGAGACT
  S   L   R   S   E   D   T   A   V   Y   Y   C   A   T   E   G   Y   Y   E   T
ACTACTTATTACTACAACCTTTTTGACTCCTGGGGCCAGGGAACCCTGGTCACCGTCTCA
  T   T   Y   Y   Y   N   L   F   D   S   W   G   Q   G   T   L   V   T   V   S
AGC
  S
```

FIG. 11A, Cont'd

MF3998: heavy chain variable region sequence of an EGFR binding antibody

Complete VH sequence (SEQ ID NO: 16):

QVQLVQSGSELKKPGASVKVSCKASGYTFTNNAINWVRQAPGQGLEWMGWINTITG
DPTYAQGFTGRFVFSLDTSVSTAYLQISSLKAEDTGVYYCAREEFLEWLFFDYWGQG
TLVTVSS

FR1 (SEQ ID NO: 17):

QVQLVQSGSELKKPGASVKVSCKASGYTFT

CDR1 (SEQ ID NO: 18): NNAIN

FR2 (SEQ ID NO: 19): WVRQAPGQGLEWMG

CDR2 (SEQ ID NO: 20): WINTITGDPTYAQGFTG

FR3 (SEQ ID NO: 21):

RFVFSLDTSVSTAYLQISSLKAEDTGVYYCAR

CDR3 (SEQ ID NO: 22): EEFLEWLFFDY

FR4 (SEQ ID NO: 23): WGQGTLVTVSS

Annotated nucleotide sequence (SEQ ID NOS: 15 and 16)

```
CAGGTGCAGCTGGTGCAGTCTGGGTCTGAGTTGAAGAAG
  Q  V  Q  L  V  Q  S  G  S  E  L  K  K
CCTGGGGCCTCAGTGAAGGTTTCCTGCAAGGCTTCTGGATACACCTTCACTAACAATGCC
  P  G  A  S  V  K  V  S  C  K  A  S  G  Y  T  F  T  N  N  A
ATAAATTGGGTGCGACAGGCCCCTGGACAAGGGCTTGAGTGGATGGGATGGATCAACACC
  I  N  W  V  R  Q  A  P  G  Q  G  L  E  W  M  G  W  I  N  T
ATCACTGGGGACCCAACGTATGCCCAGGGCTTCACAGGACGGTTTGTCTTCTCCTTGGAC
  I  T  G  D  P  T  Y  A  Q  G  F  T  G  R  F  V  F  S  L  D
ACCTCTGTCAGCACGGCATATCTGCAGATCAGCAGCCTGAAGGCTGAGGACACTGGCGTG
  T  S  V  S  T  A  Y  L  Q  I  S  S  L  K  A  E  D  T  G  V
TATTACTGTGCGAGAGAGGAATTTTTGGAGTGGTTATTCTTTGACTACTGGGGCCAGGGA
  Y  Y  C  A  R  E  E  F  L  E  W  L  F  F  D  Y  W  G  Q
ACCCTGGTCACCGTCTCAAGC
  T  L  V  T  V  S  S
```

FIG. 11A, Cont'd

MF4010: heavy chain variable region sequence of an EGFR binding antibody

Complete VH sequence (SEQ ID NO: 25):

QVQLVQSGSELKKPGASVKVSCKASGYTFTNNAMNWVRQAPGQGLEWMGWINTIT
GDPSYAQGFTGRFVFSLDTSVNTAYLQISSLKAEDTAVYYCAREEFLEWLFFDYWGQ
GTLVTVSS

FR1 (SEQ ID NO: 26): QVQLVQSGSELKKPGASVKVSCKASGYTFT

CDR1 (SEQ ID NO: 27): NNAMN

FR2 (SEQ ID NO: 28): WVRQAPGQGLEWMG

CDR2 (SEQ ID NO: 29): WINTITGDPSYAQGFTG

FR3 (SEQ ID NO: 30): RFVFSLDTSVNTAYLQISSLKAEDTAVYYCAR

CDR3 (SEQ ID NO: 31): EEFLEWLFFDY

FR4 (SEQ ID NO: 32): WGQGTLVTVSS

Annotated nucleotide sequence (SEQ ID NOS: 24 and 25):

```
caggtgcagctggtgcagtctgggtctgagttgaagaagcct
  Q  V  Q  L  V  Q  S  G  S  E  L  K  K  P
ggggcctcagtgaaggtttcctgcaaggcttctggatacaccttcactaacaatgccatg
 G  A  S  V  K  V  S  C  K  A  S  G  Y  T  F  T  N  N  A  M
aattgggtgcgacaggcccctggacaagggcttgagtggatgggatggatcaacaccatc
 N  W  V  R  Q  A  P  G  Q  G  L  E  W  M  G  W  I  N  T  I
actggggacccatcgtatgcccagggcttcacaggacggtttgtcttctccctggacacc
 T  G  D  P  S  Y  A  Q  G  F  T  G  R  F  V  F  S  L  D  T
tctgtcaacacggcatatctgcagatcagcagcctgaaggctgaggacactgccgtatat
 S  V  N  T  A  Y  L  Q  I  S  S  L  K  A  E  D  T  A  V  Y
tactgtgcgagagaggaattttggagtggttattctttgactactggggccagggaacc
 Y  C  A  R  E  E  F  L  E  W  L  F  F  D  Y  W  G  Q  G  T
ctggtcaccgtctcaagcgtctccagt
 L  V  T  V  S  S  V  S  S
```

FIG. 11A, Cont'd

MF4003: heavy chain variable region sequence of an EGFR binding antibody

Complete VH sequence (SEQ ID NO: 34):

QVQLVQSGSELKKPGASVKVSCKASGYTFPSFAMNWLRQAPGQGLEWMGWITTNTG
DPTYAQGFSGRFVFSLDTSVSTAYLQISSLKAEDTAVYYCARVYNWIRGFDYWGQGTL
VTVSS

FR1 (SEQ ID NO: 35): QVQLVQSGSELKKPGASVKVSCKASGYTFP CDR1

(SEQ ID NO: 36): SFAMN

FR2 (SEQ ID NO: 37): WLRQAPGQGLEWMG

CDR2 (SEQ ID NO: 38): WITTNTGDPTYAQGFSG

FR3 (SEQ ID NO: 39): RFVFSLDTSVSTAYLQISSLKAEDTAVYYCAR

CDR3 (EQ ID NO: 40): VYNWIRGFDY

FR4 (SEQ ID NO: 41): WGQGTLVTVSS

Annotated nucleotide sequence (SEQ ID NOS: 33 and 34):

```
caggtgcagctggtgcaatctgggtctgagttgaagaagcct
  Q  V  Q  L  V  Q  S  G  S  E  L  K  K  P
ggggcctcagtgaaggtttcctgcaaggcttctggatacaccttccctagttttgctatg
  G  A  S  V  K  V  S  C  K  A  S  G  Y  T  F  P  S  F  A  M
aattggcttcgacaggcccctggacaagggcttgagtggatgggatggatcaccaccaac
  N  W  L  R  Q  A  P  G  Q  G  L  E  W  M  G  W  I  T  T  N
actggggacccaacgtatgcccagggcttctcaggacggtttgtgttctccctggacacc
  T  G  D  P  T  Y  A  Q  G  F  S  G  R  F  V  F  S  L  D  T
tctgtcagcacggcatatctgcagatcagcagcctaaaggctgaggacactgccgtgtat
  S  V  S  T  A  Y  L  Q  I  S  S  L  K  A  E  D  T  A  V  Y
tactgtgcgagagtttataactggataaggggatttgactactggggccagggaaccctg
  Y  C  A  R  V  Y  N  W  I  R  G  F  D  Y  W  G  Q  G  T  L
gtcaccgtctcaagcgtctccagt
  V  T  V  S  S  V  S  S
```

FIG. 11A, Cont'd

MF4289: heavy chain variable region sequence of an EGFR binding antibody:

Complete VH sequence (SEQ ID NO: 44):

QVQLVQSGSELKKPGASVKVSCKTSGYTFTDYAMTWVRQAPGQGLEWMGWITTNTGDPTYAPGFTGRFVFSLDTSVSTAYLQISSLKAEDTAVYYCARVYHWIRGFEFWGQGTLVTVSS

FR1 (SEQ ID NO: 45): QVQLVQSGSELKKPGASVKVSCKTSGYTFT

CDR1 (SEQ ID NO: 46): DYAMT

FR2 (SEQ ID NO: 47): WVRQAPGQGLEWMG

CDR2 (SEQ ID NO: 48): WITTNTGDPTYAPGFTG

FR3 (SEQ ID NO: 49): RFVFSLDTSVSTAYLQISSLKAEDTAVYYCAR

CDR3 (SEQ ID NO: 50): VYHWIRGFEF

FR4 (SEQ ID NO: 51): WGQGTLVTVSS

Annotated nucleotide sequence (SEQ ID NOS: 42 and 43):

```
ggcccagccggccatggcccaggtgcagctggtgcaatctgggtctgaattgaagaagcct
    A  Q  P  A  M  A  Q  V  Q  L  V  Q  S  G  S  E  L  K  K  P
ggggcctcagtgaaggtttcctgcaagacttctggatacaccttcactgactatgctatg
 G  A  S  V  K  V  S  C  K  T  S  G  Y  T  F  T  D  Y  A  M
acttgggtgcgacaggcccctggacaagggcttgaatggatgggatggatcaccaccaac
 T  W  V  R  Q  A  P  G  Q  G  L  E  W  M  G  W  I  T  T  N
actggggacccaacgtatgccccgggcttcacaggacggtttgtcttctccttggacacc
 T  G  D  P  T  Y  A  P  G  F  T  G  R  F  V  F  S  L  D  T
tctgtcagcacggcatatctgcagatcagcagcctaaaggccgaggacactgccgtatat
 S  V  S  T  A  Y  L  Q  I  S  S  L  K  A  E  D  T  A  V  Y
tactgtgcgagagtgtatcattggatacggggatttgagttttggggccagggaaccctg
 Y  C  A  R  V  Y  H  W  I  R  G  F  E  F  W  G  Q  G  T  L
gtcacggtctcaagcgtctccagt
 V  T  V  S  S  V  S  S
```

FIG. 11A, Cont'd

MF3370: heavy chain variable region sequence of an EGFR binding antibody:

Complete VH sequence (SEQ ID NO: 53):

QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCAKDRHWHWWLDAFDYWGQGTLVTVSS

FR1 (SEQ ID NO: 54): QVQLVQSGAEVKKPGASVKVSCKASGYTFT

CDR1 (SEQ ID NO: 55): SYGIS

FR2 (SEQ ID NO: 56): WVRQAPGQGLEWMG

CDR2 (SEQ ID NO: 57): WISAYNGNTNYAQKLQG

FR3 (SEQ ID NO: 58): RVTMTTDTSTSTAYMELRSLRSDDTAVYYCAK

CDR3 (SEQ ID NO: 59): DRHWHWWLDAFDY

FR4 (SEQ ID NO: 60): WGQGTLVTVSS

Annotated nucleotide sequence (SEQ ID NOS: 52 and 53):

```
caggttcagctggtgcagtctggagctgaggtgaagaagcct
 Q  V  Q  L  V  Q  S  G  A  E  V  K  K  P
ggggcctcagtgaaggtctcctgcaaggcttctggttacacctttaccagctatggtatc
 G  A  S  V  K  V  S  C  K  A  S  G  Y  T  F  T  S  Y  G  I
agctgggtgcgacaggcccctggacaagggcttgagtggatgggatggatcagcgcttac
 S  W  V  R  Q  A  P  G  Q  G  L  E  W  M  G  W  I  S  A  Y
aatggtaacacaaactatgcacagaagctccagggcagagtcaccatgaccacagacaca
 N  G  N  T  N  Y  A  Q  K  L  Q  G  R  V  T  M  T  T  D  T
tccacgagcacagcctacatggagctgaggagcctgagatctgacgacacggctgtgtat
 S  T  S  T  A  Y  M  E  L  R  S  L  R  S  D  D  T  A  V  Y
tactgtgcaaaagatcgtcattggcattggtggctggacgcctttgattattggggccaa
 Y  C  A  K  D  R  H  W  H  W  W  L  D  A  F  D  Y  W  G  Q
ggtaccctggtcaccgtctccagt
 G  T  L  V  T  V  S  S
```

FIG. 11A, Cont'd

MF4002: heavy chain variable region sequence of an EGFR binding antibody

Complete VH sequence (SEQ ID NO: 62):

QVQLVQSGSELKKPGSSVKVSCKASGYTFTNYAMNWVRQAPGQGLEWMGWITTNTGDPTYAQGFTGRFVFSLDTSVSTAYLQISSLKAEDTAVYYCVRVYNWIRGFDYWGQGTLVTVSS

FR1 (SEQ ID NO: 63): QVQLVQSGSELKKPGSSVKVSCKASGYTFT

CDR1 (SEQ ID NO: 64): NYAMN

FR2 (SEQ ID NO: 65): WVRQAPGQGLEWMG

CDR2 (SEQ ID NO: 66): WITTNTGDPTYAQGFTG

FR3 (SEQ ID NO: 67): RFVFSLDTSVSTAYLQISSLKAEDTAVYYCVR

CDR3 (SEQ ID NO: 68): VYNWIRGFDY

FR4 (SEQ ID NO: 69): WGQGTLVTVSS

Annotated nucleotide sequence (SEQ ID NO: 61 and 62):

```
caggtgcagctggtgcaatctgggtctgagttgaagaagcct
 Q  V  Q  L  V  Q  S  G  S  E  L  K  K  P
gggtcctcagtgaaggtttcctgcaaggcttctggatacaccttcactaactatgctatg
 G  S  S  V  K  V  S  C  K  A  S  G  Y  T  F  T  N  Y  A  M
aattgggtgcgacaggcccctggacaagggcttgagtggatgggatggatcaccaccaac
 N  W  V  R  Q  A  P  G  Q  G  L  E  W  M  G  W  I  T  T  N
actggggacccaacgtatgcccagggcttcacaggacgttttgtcttctccttggacacc
 T  G  D  P  T  Y  A  Q  G  F  T  G  R  F  V  F  S  L  D  T
tctgtcagtacggcatatctgcagatcagcagcctaaaggctgaggacactgccgtatat
 S  V  S  T  A  Y  L  Q  I  S  S  L  K  A  E  D  T  A  V  Y
tactgtgtgagagtgtataactggataagggggatttgactactggggccagggaaccctg
 Y  C  V  R  V  Y  N  W  I  R  G  F  D  Y  W  G  Q  G  T  L
gtcaccgtctcaagcgtctccagt
 V  T  V  S  S  V  S  S
```

FIG. 11A, Cont'd

MF3751: heavy chain variable region sequence of an EGFR binding antibody

Complete VH sequence (SEQ ID NO: 71):

QVQLVQSGAEVKKPGASVKVSCKASGYTFTGYYMHWVRQAPGQGLEWMGTINPSGGSTYYAQKFQGRVTMTRDTSTSTVYMELSSLRSEDTAVYYCARDRNWGWDFDYWGQGTLVTVSS

FR1 (SEQ ID NO: 72): QVQLVQSGAEVKKPGASVKVSCKASGYTFT

CDR1 (SEQ ID NO: 73): GYYMH

FR2 (SEQ ID NO: 74): WVRQAPGQGLEWMG

CDR2 (SEQ ID NO: 75): TINPSGGSTYYAQKFQG

FR3 (SEQ ID NO: 76): RVTMTRDTSTSTVYMELSSLRSEDTAVYYCAR

CDR3 (SEQ ID NO: 77): DRNWGWDFDY

FR4 (SEQ ID NO: 78): WGQGTLVTVSS

Annotated nucleotide sequence (SEQ ID NO: 70 and 71):

```
caggtgcagctg
  Q  V  Q  L
gtacagtctggggctgaggtgaagaagcctggggcctcagtgaaggtttcctgcaaggca
  V  Q  S  G  A  E  V  K  K  P  G  A  S  V  K  V  S  C  K  A
tctggatacaccttcaccggctactatatgcactgggtgcgacaggcccctggacaaggg
  S  G  Y  T  F  T  G  Y  Y  M  H  W  V  R  Q  A  P  G  Q  G
cttgagtggatgggaacaatcaaccctagtggtggtagcacatactacgcacagaagttc
  L  E  W  M  G  T  I  N  P  S  G  G  S  T  Y  Y  A  Q  K  F
cagggcagagtcaccatgaccagggacacgtccacgagcacagtctacatggagctgagc
  Q  G  R  V  T  M  T  R  D  T  S  T  S  T  V  Y  M  E  L  S
agcctgagatctgaggacacggccgtgtattactgtgcgagagatcggaactggggatgg
  S  L  R  S  E  D  T  A  V  Y  Y  C  A  R  D  R  N  W  G  W
Gactttgactactggggccagggaaccctggtcaccgtctccagt
  D  F  D  Y  W  G  Q  G  T  L  V  T  V  S  S
```

FIG. 11A, Cont'd

MF3752: heavy chain variable region sequence of an EGFR binding antibody

Complete VH sequence (SEQ ID NO: 80):

EVQLVESGPEVKKPGASVKVSCKASGYTFTSYYMHWVRQAPGQGLEWMGTINPSGG
STYYAQKFQGRVTLTRDTSTSTVYMVLSSLRSEDTAVYYCARDRNWGWDFDYWGQG
TLVTVSS

FR1 (SEQ ID NO: 81): EVQLVESGPEVKKPGASVKVSCKASGYTFT

CDR1 (SEQ ID NO: 82): SYYMH

FR2 (SEQ ID NO: 83): WVRQAPGQGLEWMG

CDR2 (SEQ ID NO: 84): TINPSGGSTYYAQKFQG

FR3 (SEQ ID NO: 85): RVTLTRDTSTSTVYMVLSSLRSEDTAVYYCAR

CDR3 (SEQ ID NO: 86): DRNWGWDFDY

FR4 (SEQ ID NO: 87): WGQGTLVTVSS

Annotated nucleotide sequence (SEQ ID NOS: 79 and 80):

```
  gaggtgcagctggtggagtctgggcctgaggtgaagaagcct
   E   V   Q   L   V   E   S   G   P   E   V   K   K   P
  ggggcctcagtgaaggtttcctgcaaggcatctggatacaccttcaccagctactatatg
   G   A   S   V   K   V   S   C   K   A   S   G   Y   T   F   T   S   Y   Y   M
  cactgggtgcgacaggcccctggacaagggcttgagtggatgggaacaatcaaccctagt
   H   W   V   R   Q   A   P   G   Q   G   L   E   W   M   G   T   I   N   P   S
  ggtggtagcacatactacgcacagaagttccagggcagagtcaccctgaccagggacacg
   G   G   S   T   Y   Y   A   Q   K   F   Q   G   R   V   T   L   T   R   D   T
  tccacgagcacagtctacatggtgctgagcagcctgagatctgaggacacggccgtgtat
   S   T   S   T   V   Y   M   V   L   S   S   L   R   S   E   D   T   A   V   Y
  tactgtgcgagagatcggaactggggatgggactttgactactggggccagggaaccctg
   Y   C   A   R   D   R   N   W   G   W   D   F   D   Y   W   G   Q   G   T   L
  gtcaccgtctcaagcgtctccagt
   V   T   V   S   S   V   S   S
```

FIG. 11B

MF3178: heavy chain variable region sequence of an erbB-3 binding antibody

Nucleic acid sequence (underlined sequence encodes end of leader peptide) (SEQ ID NO: 88):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 GCACTGGGTG CGACAGGCCC CTGGACAAGG GCTTGAGTGG ATGGGATGGA TCAACCCTAA
181 CAGTGGTGGC ACAAACTATG CACAGAAGTT TCAGGGCAGG GTCACGATGA CCAGGGACAC
241 GTCCATCAGC ACAGCCTACA TGGAGCTGAG CAGGCTGAGA TCTGACGACA CGGCTGTGTA
301 TTACTGTGCA AGAGATCATG GTTCTCGTCA TTTCTGGTCT TACTGGGGCT TTGATTATTG
361 GGGCCAAGGT ACCCTGGTCA CCGTCTCCAG T
```

Amino acid sequence (SEQ ID NO: 89):

QVQLVQSGAEVKKPGASVKVSCKASGYTFTGYYMHWVRQAPGQGLEWMGWINPNS
GGTNYAQKFQGRVTMTRDTSISTAYMELSRLRSDDTAVYYCARDHGSRHFWSYWGF
DYWGQGTLVTVSS

CDR1 (SEQ ID NO: 90):   GYYMH

CDR2 (SEQ ID NO: 91):   WINPNSGGTNYAQKFQG

CDR3 (SEQ ID NO: 92):   DHGSRHFWSYWGFDY

FIG. 11B, Cont'd

MF3176: heavy chain variable region sequence of an erbB-3 binding antibody

Nucleic acid sequence (underlined sequence encodes end of leader peptide) (SEQ ID NO: 93):

```
  1 GGCCCAGCCG GCCATGGCCG AGGTGCAGCT GTTGGAGTCT GGGGGAGGCT TGGTACAGCC
 61 TGGGGGGTCC CTGAGACTCT CCTGTGCAGC CTCTGGATTC ACCTTTAGCA GCTATGCCAT
121 GAGCTGGGTC CGCCAGGCTC CAGGGAAGGG GCTGGAGTGG GTCTCAGCTA TTAGTGGTAG
181 TGGTGGTAGC ACATACTACG CAGACTCCGT GAAGGGCCGG TTCACCATCT CCAGAGACAA
241 TTCCAAGAAC ACGCTGTATC TGCAAATGAA CAGCCTGAGA GCCGAGGACA CGGCTGTGTA
301 TTACTGTGCA AGAGATTGGT GGTACCCGCC GTACTACTGG GGCTTTGATT ATTGGGGCCA
361 AGGTACCCTG GTCACCGTCT CCAGT
```

Amino acid sequence (SEQ ID NO: 94):

EVQLLESGGGLVQPGGSLRLSCAASGFTFSSYAMSWVRQAPGKGLEWVSAISGSGGS
TYYADSVKGRFTISRDNSKNTLYLQMNSLRAEDTAVYYCARDWWYPPYYWGFDYWG
QGTLVTVSS

| | |
|---|---|
| CDR1 (SEQ ID NO: 95): | SYAMS |
| CDR2 (SEQ ID NO: 96): | AISGSGGSTYYADSVKG |
| CDR3 (SEQ ID NO: 97): | DWWYPPYYWGFDY |

FIG. 11B, Cont'd

MF3163: heavy chain variable region sequence of an erbB-3 binding antibody

Nucleic acid sequence (underlined sequence encodes end of leader peptide) (SEQ ID NO: 98):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 GCACTGGGTG CGACAGGCCC CTGGACAAGG GCTTGAGTGG ATGGGATGGA TCAACCCTAA
181 CAGTGGTGGC ACAAACTATG CACAGAAGTT TCAGGGCAGG GTCACGATGA CCAGGGACAC
241 GTCCATCAGC ACAGCCTACA TGGAGCTGAG CAGGCTGAGA TCTGACGACA CGGCCGTGTA
301 TTACTGTGCA AAAGATTCTT ACTCTCGTCA TTTCTACTCT TGGTGGGCCT TTGATTATTG
361 GGGCCAAGGT ACCCTGGTCA CCGTCTCCAG T
```

Amino acid sequence (SEQ ID NO: 99):

QVQLVQSGAEVKKPGASVKVSCKASGYTFTGYYMHWVRQAPGQGLEWMGWINPNS
GGTNYAQKFQGRVTMTRDTSISTAYMELSRLRSDDTAVYYCAKDSYSRHFYSWWAF
DYWGQGTLVTVSS

| | |
|---|---|
| CDR1 (SEQ ID NO: 100): | GYYMH |
| CDR2 (SEQ ID NO: 101): | WINPNSGGTNYAQKFQG |
| CDR3 (SEQ ID NO: 102): | DSYSRHFYSWWAFDY |

FIG. 11B, Cont'd

MF3307: heavy chain variable region sequence of an erbB-3 binding antibody

Nucleic acid sequence (underlined sequence encodes end of leader peptide) (SEQ ID NO: 108):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 GCACTGGGTG CGACAGGCCC CTGGACAAGG GCTTGAGTGG ATGGGATGGA TCAACCCTAA
181 CAGTGGTGGC ACAAACTATG CACAGAAGTT TCAGGGCAGG GTCACGATGA CCAGGGACAC
241 GTCCATCAGC ACAGCCTACA TGGAGCTGAG CAGGCTGAGA TCTGACGACA CGGCCGTGTA
301 TTACTGTGCA AGAGGTTCTC GTAAACGTCT GTCTAACTAC TTCAACGCCT TTGATTATTG
361 GGGCCAAGGT ACCCTGGTCA CCGTCTCCAG T
```

<u>Amino acid sequence</u> (SEQ ID NO: 109):

<u>QVQLVQSGAEVKKPGASVKVSCKASGYTFTGYYMHWVRQAPGQGLEWMGWINPNS
GGTNYAQKFQGRVTMTRDTSISTAYMELSRLRSDDTAVYYCARGSRKRLSNYFNAFD
YWGQGTLVTVSS</u>

| | |
|---|---|
| <u>CDR1</u> (SEQ ID NO: 110): | GYYMH |
| <u>CDR2</u> (SEQ ID NO: 111): | WINPNSGGTNYAQKFQG |
| <u>CDR3</u> (SEQ ID NO: 112): | GSRKRLSNYFNAFDY |

FIG. 11B, Cont'd

```
                                               CDR1           CDR2
         1         10        20        30        40        50        60
MF3178  QVQLVQSGAEVKKPGASVKVSCKASGYTFT GYYMH WVRQAPGQGLEWMG WINPNSGGTNYAQKFQG
MF6055  .........D....................  .....  .........A.....  ....S.......K....
MF6056  .........D............T.......  .....  .........A.....  ....S.......K....
MF6057  .........D............T.......  .....  ...............  ....Q............
MF6058  .........D............T.......  .....  .........A.....  ....Q............
MF6059  ..............................  .....  ...............  ....G..S.........
MF6060  .........D....................  .....  .........A.....  ....Q.......K....
MF6061  ..............................  .....  ...............  ....Q..........K.
MF6062  ..............................  .....  ...............  ....G..S.........
MF6063  ..............................  .....  ...............  ....Q.......K....
MF6064  ..............................  .....  ..........K....  ....Q............
MF6065  ..............................  S....  ...............  ....QG.S.........
MF6066  ..............................  .....  ...............  ....Q..S.........
MF6067  ..............................  .....  ...............  ....Q............
MF6068  ..............................  .....  ...............  ....Q............
MF6069  ..............................  .....  ...............  ....Q............
MF6070  ..............................  S....  ...............  ....SG.S.........
MF6071  ..............................  .....  ...............  ....S..S.........
MF6072  ..............................  .....  ...............  ....S............
MF6073  ..............................  .....  ...............  ....S............
MF6074  ..............................  .....  ...............  ....S............

CDR3
         70        80        90        100       110       120     SEQ ID NO:
MF3178  RVTMTRDTSISTAYMELSRLRSDDTAVYYCAR DHGSRHFWSYWGFDY WGQGTLVTVSS     89
MF6055  ......E..T...................T..  ...............  ...........    114
MF6056  ..S...E..T.....Q.............T..  ...............  ...........    116
MF6057  .........T.....Q................  ...............  ...........    118
MF6058  ..S...E..T.....Q.............T..  ...............  ...........    120
MF6059  ................................  ...............  ...........    122
MF6060  ......E..T...................T..  ...............  ...........    124
MF6061  .........T......................  ...............  ...........    126
MF6062  .........T......................  ...............  ...........    128
MF6063  .........T......................  ...............  ...........    130
MF6064  .........T......................  ...............  ...........    132
MF6065  .........T..V........E..........  ...............  ...........    134
MF6066  .........T......S...E...........  ...............  ...........    136
MF6067  .........T..V.....S.............  ...............  ...........    138
MF6068  .........T......................  ...............  ...........    140
MF6069  ................................  ...............  ...........    142
MF6070  .........T..V........E..........  ...............  ...........    144
MF6071  .........T......S...E...........  ...............  ...........    146
MF6072  .........T..V.....S.............  ...............  ...........    148
MF6073  .........T......................  ...............  ...........    150
MF6074  ................................  ...............  ...........    152
```

FIG. 11B, Cont'd

DNA sequences of MF3178 variants (without sequence encoding leader peptide)

>MF6055_VH (SEQ ID NO: 113)

caggtgcagctggtgcagtctggggctgacgtgaagaagcctggggcctcagtgaaggtctcctgcaagg cttctggatacaccttcaccggctactatatgcactgggtgcgacaggcccctggacaagctcttgagtg gatgggatggatcaaccottctagtggtggcacaaactatgcaaagaagtttcagggcagggtcacgatg accagggagacgtccacaagcacagcctacatggagctgagcaggctgagatctgacgacacggctacgt attactgtgcaagagatcatggttctcgtcatttctggtcttactggggctttgattattggggccaagg taccc tggtc accgt ctcca gt

>MF6056_VH (SEQ ID NO:115)

caggtgcagctggtgcagtctggggctgacgtgaagaagcctggggcctcagtgaaggtcacgtgcaagg cttctggatacaccttcaccggctactatatgcactgggtgcgacaggcccctggacaagctcttgagtg gatgggatggatcaaccottctagtggtggcacaaactatgcaaagaagtttcagggcagggtctctatg accagggagacgtccacaagcacagcctacatgcagctgagcaggctgagatctgacgacacggctacgt attactgtgcaagagatcatggttctcgtcatttctggtcttactggggctttgattattggggccaagg taccctggtcaccgtctccagt

>MF6057_VH (SEQ ID NO: 117)

caggtgcagctggtgcagtctggggctgatgtgaagaagcctggggcctcagtgaaggtcacgtgcaagg cttctggatacaccttcaccggctactatatgcactgggtgcgacaggcccctggacaagggcttgagtg gatgggatggatcaaccctcagagtggtggcacaaactatgcacagaagtttcagggcagggtcacgatg accagggacacgtccatcagcacagcctacatgcagctgagcaggctgagatctgacgacacggctgtgt attactgtgcaagagatcatggttctcgtcatttctggtcttactggggctttgattattggggccaagg taccctggtcaccgtctccagt

FIG. 11B, Cont'd

>MF6058_VH (SEQ ID NO:118)

caggtgcagctggtgcagtctggggctgacgtgaagaagcctggggcctcagtgaaggtcacgtgcaagg cttctggatacaccttcaccggctactatatgcactgggtgcgacaggcccctggacaagctcttgagtg gatgggatggatcaaccctcaaagtggtggcacaaactatgcaaagaagtttcagggcagggtctctatg accagggagacgtccacaagcacagcctacatgcagctgagcaggctgagatctgacgacacggctacgt attactgtgcaagagatcatggttctcgtcatttctggtcttactggggctttgattattggggccaagg tacectggtcacegtctccagt

>MF6059_VH (SEQ ID NO: 119)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccctggcagtggttctacaaactatgcacagaagtttcagggcagggtcacgatg accagggacacgtccatcagcacagcctacatggagctgagcaggctgagatctgacgacacggctgtgt attactgtgcaagagatcatggttctcgtcatttctggtcttactggggctttgattattggggccaagg tacectggtcacegtctccagt

>MF6060_VH (SEQ ID NO: 123)

caggtgcagctggtgcagtctggggctgacgtgaagaagcctggggcctcagtgaaggtctcctgcaagg cttctggatacaccttcaccggctactatatgcactgggtgcgacaggcccctggacaagctcttgagtg gatgggatggatcaaccctcaaagtggtggcacaaactatgcaaagaagtttcagggcagggtcacgatg accagggagacgtccacaagcacagcctacatggagctgagcaggctgagatctgacgacacggctacgt attactgtgcaagagatcatggttctcgtcatttctggtcttactggggctttgattattggggccaagg tacectggtcacegtctccagt

FIG. 11B, Cont'd

>MF6061_VH (SEQ ID NO: 125)
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcacagaagtttaagggcagggtcacgatg
accagggacacgtccaccagcacagcctacatggagctgagcaggctgagatctgacgacacggctgtgt
attactgtgcaagagatcatggttctcgtcatttctggtcttactggggctttgattattggggccaagg
taccctggtcaccgtctccagt >MF6062_VH (SEQ ID NO: 127)
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctggcagtggttctacaaactatgcacagaagtttcagggcagggtcacgatg
accagggacacgtccacaagcacagcctacatggagctgagcaggctgagatctgacgacacggctgtgt
attactgtgcaagagatcatggttctcgtcatttctggtcttactggggctttgattattggggccaagg
taccctggtcaccgtctccagt >MF6063_VH (SEQ ID NO: 128)
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcaaagaagtttcagggcagggtcacgatg
accagggacacgtccaccagcacagcctacatggagctgagcaggctgagatctgacgacacggctgtgt
attactgtgcaagagatcatggttctcgtcatttctggtcttactggggctttgattattggggccaagg
taccctggtcaccgtctccagt

FIG. 11B, Cont'd

>MF6064_VH (SEQ ID NO: 131)

caggtgcagctggtgcagtctggggctgaggtgaagaagcctggggcctcagtgaaggtctcctgcaagg cttctggatacaccttcaccggctactatatgcactgggtgcgacaggcccctggaaaggggcttgagtg gatgggatggatcaaccctcagagtggtggcacaaactatgcacagaagtttcagggcagggtcacgatg accagggacacgtccacgagcacagcctacatggagctgagcaggctgagatctgacgacacggctgtgt attactgtgcaagagatcatggttctcgtcatttctggtcttactggggctttgattattggggccaagg taccctggtcaccgtctccagt

>MF6065_VH (SEQ ID NO: 133)

caggtgcagctggtgcagtctggggctgaggtgaagaagcctggggcctcagtgaaggtctcctgcaagg cttctggatacaccttcacctcttactatatgcactgggtgcgacaggcccctggacaagggcttgagtg gatgggatggatcaaccctcagggggttctacaaactatgcacagaagtttcagggcagggtcacgatg accagggacacgtccaccagcacagtgtacatggagctgagcaggctgagatctgaggacacggctgtgt attactgtgcaagagatcatggttctcgtcatttctggtcttactggggctttgattattggggccaagg taccctggtcaccgtctccagt

>MF6066_VH (SEQ ID NO: 135)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccctcagagtggttctacaaactatgcacagaagtttcagggcagggtcacgatg accagggacacgtccaccagcacagcctacatggagctgagctctctgagatctgaggacacggctgtgt attactgtgcaagagatcatggttctcgtcatttctggtcttactggggctttgattattggggccaagg taccctggtcaccgtctccagt

FIG. 11B, Cont'd

>MF6067_VH (SEQ ID NO: 137)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccctcagagtggtggcacaaactatgcacagaagtttcagggcagggtcacgatg accagggacacgtccaccagcacagtctacatggagctgagctctctgagatctgacgacacggctgtgt attactgtgcaagagatcatggttctcgtcatttctggtcttactggggcttttgattattggggccaagg taccctggtcaccgtctccagt

>MF6068_VH (SEQ ID NO: 139)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccctcagagtggtggcacaaactatgcacagaagtttcagggcagggtcacgatg accagggacacgtccaccagcacagcctacatggagctgagcaggctgagatctgacgacacggctgtgt attactgtgcaagagatcatggttctcgtcatttctggtcttactggggcttttgattattggggccaagg taccctggtcaccgtctccagt

>MF6069_VH (SEQ ID NO: 141)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccctcagagtggtggcacaaactatgcacagaagtttcagggcagggtcacgatg accagggacacgtccatcagcacagcctacatggagctgagcaggctgagatctgacgacacggctgtgt attactgtgcaagagatcatggttctcgtcatttctggtcttactggggcttttgattattggggccaagg taccctggtcaccgtctccagt

FIG. 11B, Cont'd

>MF6070_VH (SEQ ID NO: 143)

caggtgcagctggtgcagtctggggctgaggtgaagaagcctggggcctcagtgaaggtctcctgcaagg cttctggatacaccttcacctcttactatatgcactgggtgcgacaggcccctggacaagggcttgagtg gatgggatggatcaaccttctgggggttctacaaactatgcacagaagtttcagggcagggtcacgatg accagggacacgtccaccagcacagtgtacatggagctgagcaggctgagatctgaggacacggctgtgt attactgtgcaagagatcatggttctcgtcatttctggtcttactggggctttgattattggggccaagg taccctggtcaccgtctccagt

>MF6071_VH (SEQ ID NO: 145)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccttctagtggttctacaaactatgcacagaagtttcagggcagggtcacgatg accagggacacgtccaccagcacagcctacatggagctgagctctctgagatctgaggacacggctgtgt attactgtgcaagagatcatggttctcgtcatttctggtcttactggggctttgattattggggccaagg taccctggtcaccgtctccagt

>MF6072_VH (SEQ ID NO: 147)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccttctagtggtggcacaaactatgcacagaagtttcagggcagggtcacgatg accagggacacgtccaccagcacagtctacatggagctgagctctctgagatctgacgacacggctgtgt attactgtgcaagagatcatggttctcgtcatttctggtcttactggggctttgattattggggccaagg taccctggtcaccgtctccagt

FIG. 11B, Cont'd

>MF6073_VH (SEQ ID NO: 149)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccttctagtggtggcacaaactatgcacagaagtttcagggcagggtcacgatg accagggacacgtccaccagcacagcctacatggagctgagcaggctgagatctgacgacacggctgtgt attactgtgcaagagatcatggttctcgtcatttctggtcttactggggctttgattattggggccaagg taccctggtcaccgtctccagt

>MF6074_VH (SEQ ID NO: 151)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccttctagtggtggcacaaactatgcacagaagtttcagggcagggtcacgatg accagggacacgtccatcagcacagcctacatggagctgagcaggctgagatctgacgacacggctgtgt attactgtgcaagagatcatggttctcgtcatttctggtcttactggggctttgattattggggccaagg taccctggtcaccgtctccagt

FIG. 11B, Cont'd

Nucleic acid alignment (*without* end of leader sequence)

```
MF3178  CAGGTGCAGCTGGTGCAGTCTGGGGCTGAGGTGAAGAAGCCTGGGGCCTCAGTGAAGGTCTCCTGCAAG
MF6058  .............................C............................A.G......
MF6061  ....................................................................
MF6065  ....................................................................
                                          CDR1
MF3178  GCTTCTGGATACACCTTCACC GGCTACTATATGCAC TGGGTGCGACAGGCCCCTGGACAAGGGCTTG
MF6058  ..................... ............... ...........................CT....
MF6061  ..................... ............... ....................................
MF6065  ..................... TCT............ ....................................
                                          CDR2
MF3178  AGTGGATGGGA TGGATCAACCCTAACAGTGGTGGCACAAACTATGCACAGAAGTTTCAGGGC AGGGT
MF6058  ........... ...........C.A..................A............... ......
MF6061  ........... ...........C.G..................A............... ......
MF6065  ........... ...........C.GG.G...TCT.......................... ......

MF3178  CACGATGACCAGGGACACGTCCATCAGCACAGCCTACATGGAGCTGAGCAGGCTGAGATCTGACGACAC
MF6058  .T.T.........G.......CA............C................................
MF6061  ....................C................................................
MF6065  ....................C.......TG......................................G.....
                                          CDR3
MF3178  GGCTGTGTATTACTGTGCAAGA GATCATGGTTCTCGTCATTTCTGGTCTTACTGGGGCTTTGATTAT
MF6058  ....AC................ ..................................................
MF6061  ...................... ..................................................
MF6065  ...................... ..................................................

MF3178  TGGGGCCAAGGTACCCTGGTCACCGTCTCCAGT  (Nucleotides 20 - 391 of SEQ ID NO: 88)
MF6058  .................................  (SEQ ID NO: 119)
MF6061  .................................  (SEQ ID NO: 125)
MF6065  .................................  (SEQ ID NO: 133)
```

FIG. 11C a) Common Light Chain (SEQ ID NO: 153)

DIQMTQSPSSLSASVGDRVTITCRASQSISSYLNWYQQKPGKAPKLLIYAASSLQSGVP
SRFSGSGSGTDFTLTISSLQPEDFATYYCQQSYSTPPTFGQGTKVEIKRTVAAPSVFIFP
PSDEQLKSGTASVVCLLNNFYPREAKVQWKVDNALQSGNSQESVTEQDSKDSTYSLS
STLTLSKADYEKHKVYACEVTHQGLSSPVTKSFNRGEC

FIG. 11D heavy chain for EGFR binding (SEQ ID NO: 154)

QVQLVQSGAEVKKPGASVKVSCKVSGYTLTELSMHWVRQAPGKGLEWMGGFDPEY
GKTFFAQNFQGRVTMTEDTSADTAYMELSSLRSEDTAVYYCATEGYYETTTYYYNLF
DSWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPI
EKTISKAKGQPREPQVYTDPPSREEMTKNQVSLTCEVKGFYPSDIAVEWESNGQPEN
NYKTTPPVLDSDGSFFLYSKLTVDKSRWQQGNVFSCSVMHEALHNHYTQKSLSLSPG heavy chain for erbB-3 binding (SEQ ID NO: 155)

QVQLVQSGAEVKKPGASVKVSCKASGYTFTGYYMHWVRQAPGQGLEWMGWINPNS
GGTNYAQKFQGRVTMTRDTSISTAYMELSRLRSDDTAVYYCARDHGSRHFWSYWGF
DYWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPI
EKTISKAKGQPREPQVYTKPPSREEMTKNQVSLKCLVKGFYPSDIAVEWESNGQPEN
NYKTTPPVLDSDGSFFLYSKLTVDKSRWQQGNVFSCSVMHEALHNHYTQKSLSLSPG

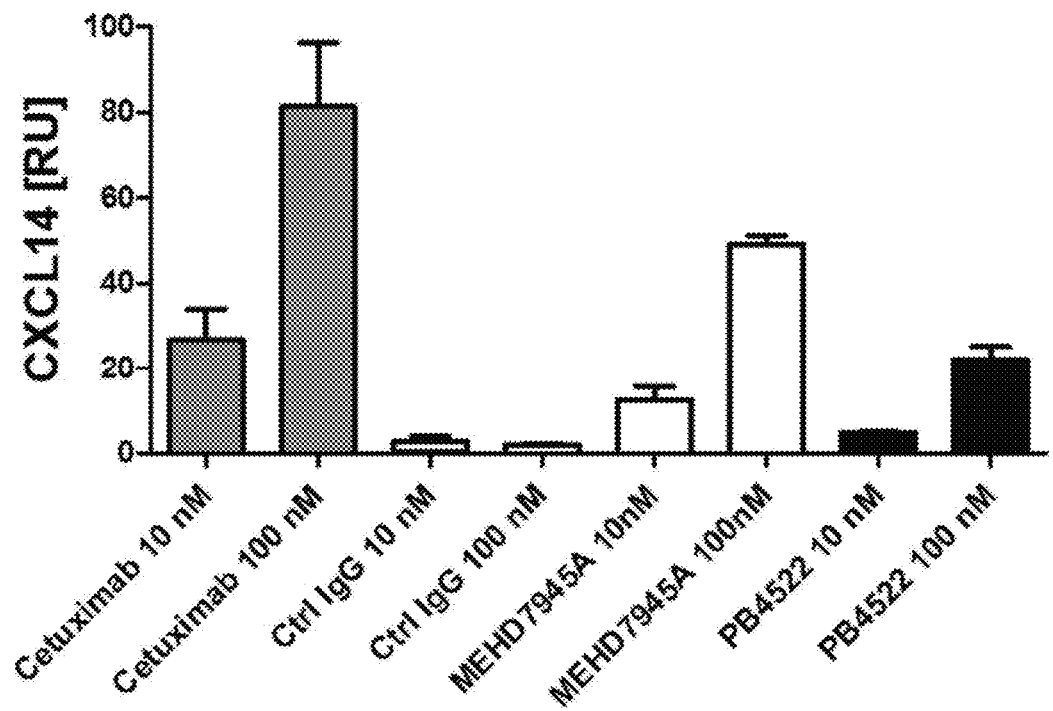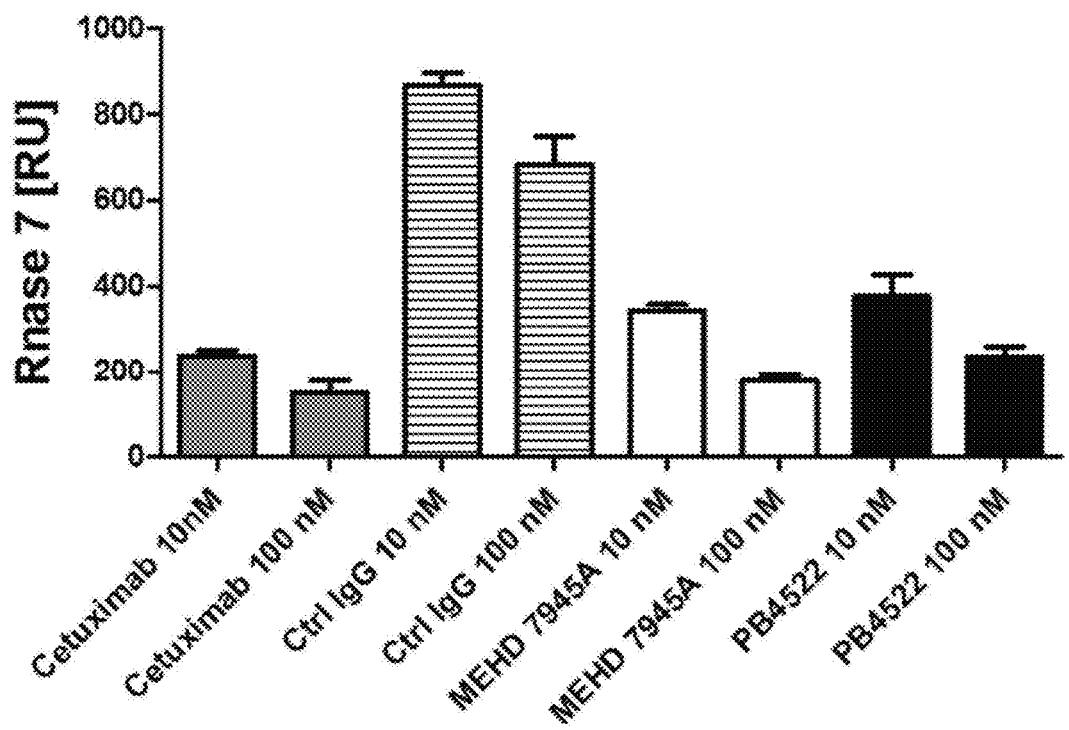
FIG. 12

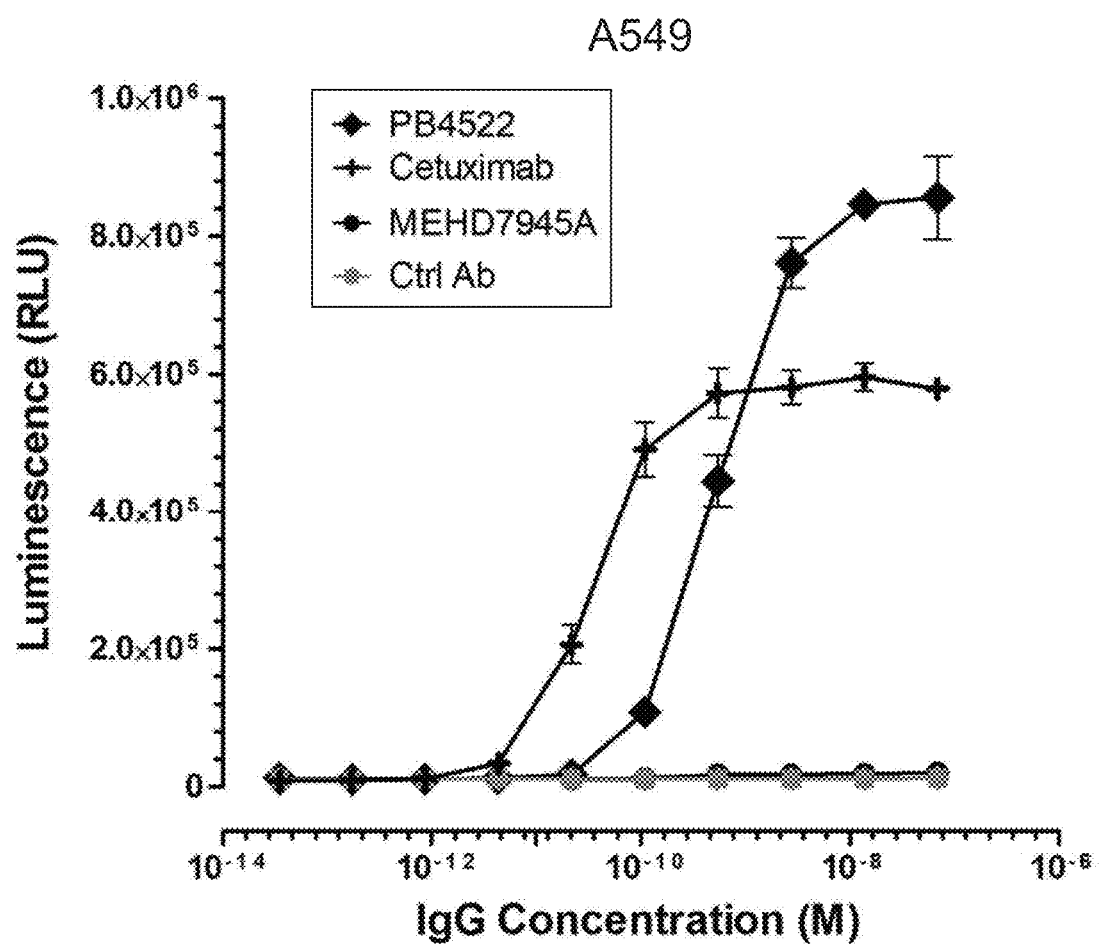
FIG. 13, Cont'd

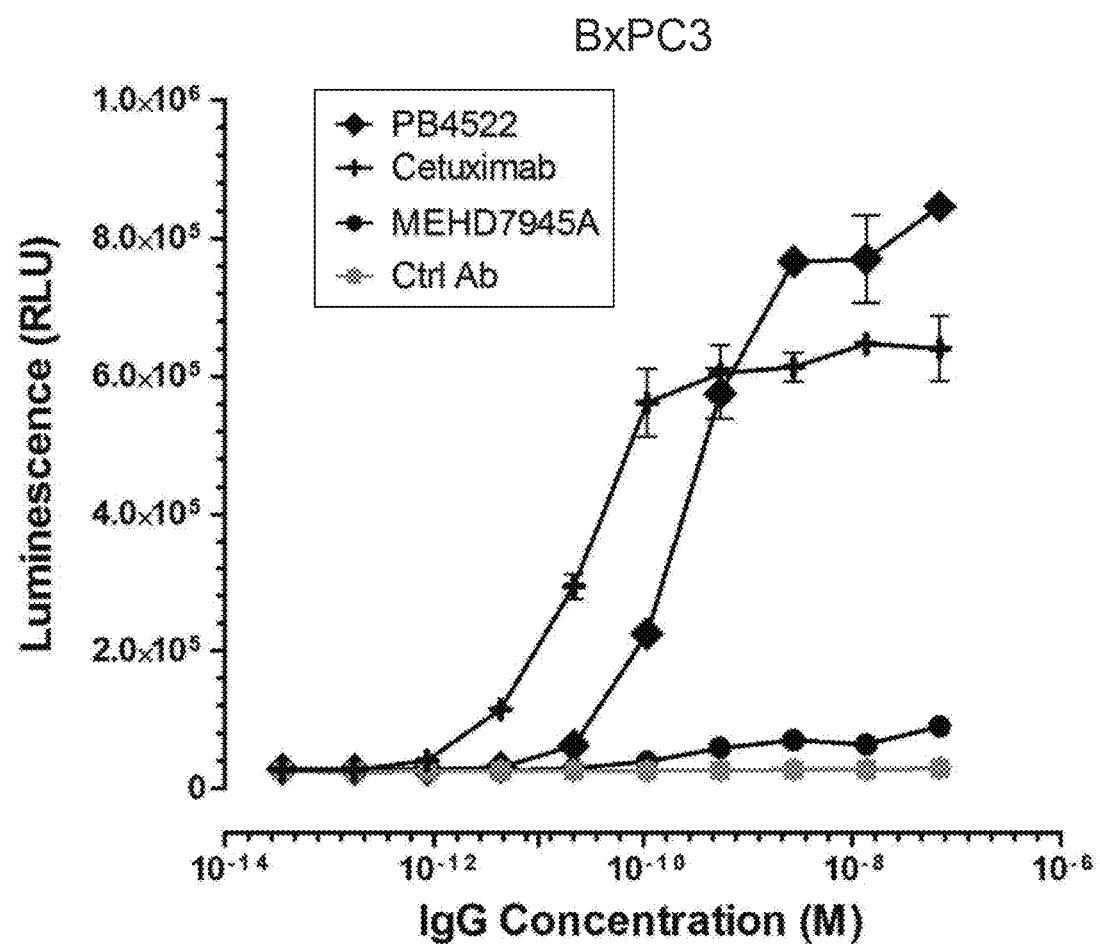
FIG. 13, Cont'd

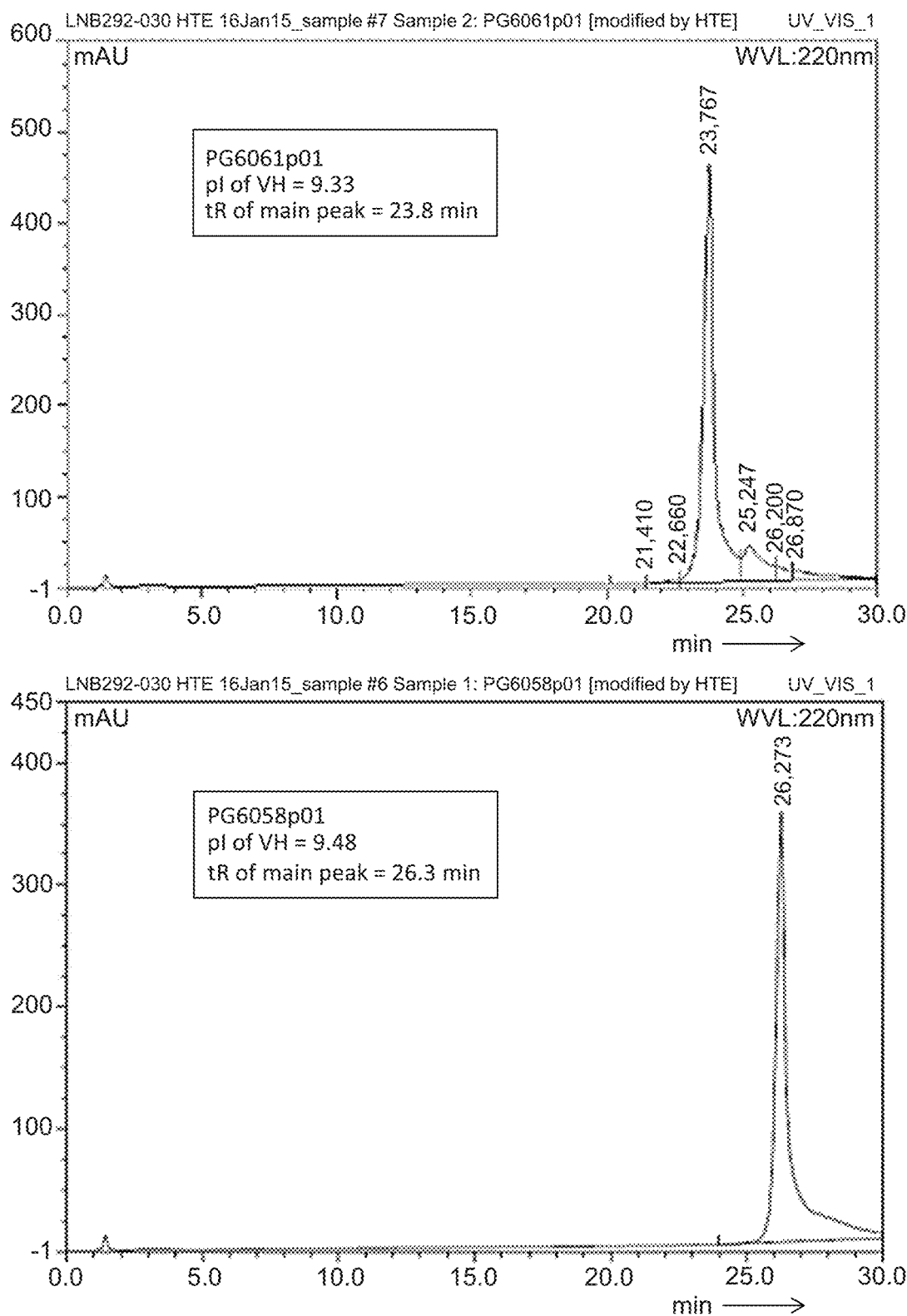
FIG. 15, Cont'd

SEQUENCE LISTING

```
<160> NUMBER OF SEQ ID NOS: 156

<210> SEQ ID NO 1
<211> LENGTH: 3650
<212> TYPE: DNA
<213> ORGANISM: Artificial Sequence
<220> FEATURE:
<223> OTHER INFORMATION: chimeric cynomolgus-human EGFR encoding
      construct
<220> FEATURE:
<221> NAME/KEY: CDS
<222> LOCATION: (1)..(3639)
<220> FEATURE:
<221> NAME/KEY: mat_peptide
<222> LOCATION: (82)..(3639)

<400> SEQUENCE: 1 gct agc acc atg ggg ccc agc ggc acc gcc ggc gcc gcc ctg ctg gcc      48
Ala Ser Thr Met Gly Pro Ser Gly Thr Ala Gly Ala Ala Leu Leu Ala
        -25              -20              -15 ctg ctg gcc gcc ctg tgc ccc gcc agc cgg gcc ctg gag gag aag aag      96
Leu Leu Ala Ala Leu Cys Pro Ala Ser Arg Ala Leu Glu Glu Lys Lys
    -10              -5              -1   1               5 gtg tgc cag ggc acc agc aac aag ctg acc cag ctg ggc acc ttc gag     144
Val Cys Gln Gly Thr Ser Asn Lys Leu Thr Gln Leu Gly Thr Phe Glu
                    10                  15                  20 gac cac ttc ctg agc ctg cag cgg atg ttc aac aac tgc gag gtg gtg     192
Asp His Phe Leu Ser Leu Gln Arg Met Phe Asn Asn Cys Glu Val Val
                25                  30                  35 ctg ggc aac ctg gag atc acc tac gtg cag cgg aac tac gac ctg agc     240
Leu Gly Asn Leu Glu Ile Thr Tyr Val Gln Arg Asn Tyr Asp Leu Ser
            40                  45                  50 ttc ctg aag acc atc cag gag gtg gcc ggc tac gtg ctg atc gcc ctg     288
Phe Leu Lys Thr Ile Gln Glu Val Ala Gly Tyr Val Leu Ile Ala Leu
        55                  60                  65 aac acc gtg gag cgg atc ccc ctg gag aac ctg cag atc atc cgg ggc     336
Asn Thr Val Glu Arg Ile Pro Leu Glu Asn Leu Gln Ile Ile Arg Gly
70                  75                  80                  85 aac atg tac tac gag aac agc tac gcc ctg gcc gtg ctg agc aac tac     384
Asn Met Tyr Tyr Glu Asn Ser Tyr Ala Leu Ala Val Leu Ser Asn Tyr
                    90                  95                 100 gac gcc aac aag acc ggc ctg aag gag ctg ccc atg cgg aac ctg cag     432
Asp Ala Asn Lys Thr Gly Leu Lys Glu Leu Pro Met Arg Asn Leu Gln
                105                 110                 115 gag atc ctg cac ggc gcc gtg cgg ttc agc aac aac ccc gcc ctg tgc     480
Glu Ile Leu His Gly Ala Val Arg Phe Ser Asn Asn Pro Ala Leu Cys
            120                 125                 130 aac gtg gag agc atc cag tgg cgg gac atc gtg agc agc gag ttc ctg     528
Asn Val Glu Ser Ile Gln Trp Arg Asp Ile Val Ser Ser Glu Phe Leu
        135                 140                 145 agc aac atg agc atg gac ttc cag aac cac ctg ggc agc tgc cag aag     576
Ser Asn Met Ser Met Asp Phe Gln Asn His Leu Gly Ser Cys Gln Lys
150                 155                 160                 165
```

-continued

| | | |
|---|---|---|
| tgc gac ccc agc tgc ccc aac ggc agc tgc tgg ggc gcc ggc gag gag<br>Cys Asp Pro Ser Cys Pro Asn Gly Ser Cys Trp Gly Ala Gly Glu Glu<br>           170                        175                         180 | 624 | |
| aac tgc cag aag ctg acc aag atc atc tgc gcc cag cag tgc agc ggc<br>Asn Cys Gln Lys Leu Thr Lys Ile Ile Cys Ala Gln Gln Cys Ser Gly<br>           185                        190                         195 | 672 | |
| cgg tgc cgg ggc aag agc ccc agc gac tgc tgc cac aac cag tgc gcc<br>Arg Cys Arg Gly Lys Ser Pro Ser Asp Cys Cys His Asn Gln Cys Ala<br>           200                        205                        210 | 720 | |
| gcc ggc tgc acc ggc ccc cgg gag agc gac tgc ctg gtg tgc cgg aag<br>Ala Gly Cys Thr Gly Pro Arg Glu Ser Asp Cys Leu Val Cys Arg Lys<br>          215                        220                        225 | 768 | |
| ttc cgg gac gag gcc acc tgc aag gac acc tgc ccc ccc ctg atg ctg<br>Phe Arg Asp Glu Ala Thr Cys Lys Asp Thr Cys Pro Pro Leu Met Leu<br>230                        235                        240                        245 | 816 | |
| tac aac ccc acc acc tac cag atg gac gtg aac ccc gag ggc aag tac<br>Tyr Asn Pro Thr Thr Tyr Gln Met Asp Val Asn Pro Glu Gly Lys Tyr<br>                    250                        255                        260 | 864 | |
| agc ttc ggc gcc acc tgc gtg aag aag tgc ccc cgg aac tac gtg gtg<br>Ser Phe Gly Ala Thr Cys Val Lys Lys Cys Pro Arg Asn Tyr Val Val<br>           265                        270                        275 | 912 | |
| acc gac cac ggc agc tgc gtg cgg gcc tgc ggc gcc gac agc tac gag<br>Thr Asp His Gly Ser Cys Val Arg Ala Cys Gly Ala Asp Ser Tyr Glu<br>           280                        285                        290 | 960 | |
| atg gag gag gac ggc gtg cgg aag tgc aag aag tgc gag ggc ccc tgc<br>Met Glu Glu Asp Gly Val Arg Lys Cys Lys Lys Cys Glu Gly Pro Cys<br>295                        300                        305 | 1008 | |
| cgg aag gtg tgc aac ggc atc ggc atc ggc gag ttc aag gac acc ctg<br>Arg Lys Val Cys Asn Gly Ile Gly Ile Gly Glu Phe Lys Asp Thr Leu<br>310                        315                        320                        325 | 1056 | |
| agc atc aac gcc acc aac atc aag cac ttc aag aac tgc acc agc atc<br>Ser Ile Asn Ala Thr Asn Ile Lys His Phe Lys Asn Cys Thr Ser Ile<br>                    330                        335                        340 | 1104 | |
| agc ggc gac ctg cac atc ctg ccc gtg gcc ttc cgg ggc gac agc ttc<br>Ser Gly Asp Leu His Ile Leu Pro Val Ala Phe Arg Gly Asp Ser Phe<br>          345                        350                        355 | 1152 | |
| acc cac acc ccc ccc ctg gac ccc cag gag ctg gac atc ctg aag acc<br>Thr His Thr Pro Pro Leu Asp Pro Gln Glu Leu Asp Ile Leu Lys Thr<br>           360                        365                        370 | 1200 | |
| gtg aag gag atc acc ggc ttc ctg ctg atc cag gcc tgg ccc gag aac<br>Val Lys Glu Ile Thr Gly Phe Leu Leu Ile Gln Ala Trp Pro Glu Asn<br>375                        380                        385 | 1248 | |
| cgg acc gac ctg cac gcc ttc gag aac ctg gag atc atc cgg ggc cgg<br>Arg Thr Asp Leu His Ala Phe Glu Asn Leu Glu Ile Ile Arg Gly Arg<br>390                        395                        400                        405 | 1296 | |
| acc aag cag cac ggc cag ttc agc ctg gcc gtg gtg agc ctg aac atc<br>Thr Lys Gln His Gly Gln Phe Ser Leu Ala Val Val Ser Leu Asn Ile<br>                    410                        415                        420 | 1344 | |
| acc agc ctg ggc ctg cgg agc ctg aag gag atc agc gac ggc gac gtg<br>Thr Ser Leu Gly Leu Arg Ser Leu Lys Glu Ile Ser Asp Gly Asp Val<br>          425                        430                        435 | 1392 | |
| atc atc agc ggc aac aag aac ctg tgc tac gcc aac acc atc aac tgg<br>Ile Ile Ser Gly Asn Lys Asn Leu Cys Tyr Ala Asn Thr Ile Asn Trp<br>                    440                        445                        450 | 1440 | |
| aag aag ctg ttc ggc acc agc agc cag aag acc aag atc atc agc aac<br>Lys Lys Leu Phe Gly Thr Ser Ser Gln Lys Thr Lys Ile Ile Ser Asn<br>          455                        460                        465 | 1488 | |
| cgg ggc gag aac agc tgc aag gcc acc ggc cag gtg tgc cac gcc ctg<br>Arg Gly Glu Asn Ser Cys Lys Ala Thr Gly Gln Val Cys His Ala Leu<br>470                        475                        480                        485 | 1536 | |

-continued

| | |
|---|---|
| tgc agc ccc gag ggc tgc tgg ggc ccc gag ccc cgg gac tgc gtg agc<br>Cys Ser Pro Glu Gly Cys Trp Gly Pro Glu Pro Arg Asp Cys Val Ser<br>490                    495                    500 | 1584 |
| tgc cag aac gtg agc cgg ggc cgg gag tgc gtg gac aag tgc aac atc<br>Cys Gln Asn Val Ser Arg Gly Arg Glu Cys Val Asp Lys Cys Asn Ile<br>505                    510                    515 | 1632 |
| ctg gag ggc gag ccc cgg gag ttc gtg gag aac agc gag tgc atc cag<br>Leu Glu Gly Glu Pro Arg Glu Phe Val Glu Asn Ser Glu Cys Ile Gln<br>520                    525                    530 | 1680 |
| tgc cac ccc gag tgc ctg ccc cag gtg atg aac atc acc tgc acc ggc<br>Cys His Pro Glu Cys Leu Pro Gln Val Met Asn Ile Thr Cys Thr Gly<br>535                    540                    545 | 1728 |
| cgg ggc ccc gac aac tgc atc cag tgc gcc cac tac atc gac ggc ccc<br>Arg Gly Pro Asp Asn Cys Ile Gln Cys Ala His Tyr Ile Asp Gly Pro<br>550                  555                  560                  565 | 1776 |
| cac tgc gtg aag acc tgc ccc gcc ggc gtg atg ggc gag aac aac acc<br>His Cys Val Lys Thr Cys Pro Ala Gly Val Met Gly Glu Asn Asn Thr<br>570                    575                  580 | 1824 |
| ctg gtg tgg aag tac gcc gac gcc ggc cac gtg tgc cac ctg tgc cac<br>Leu Val Trp Lys Tyr Ala Asp Ala Gly His Val Cys His Leu Cys His<br>585                    590                  595 | 1872 |
| ccc aac tgc acc tac ggc tgc acc ggc ccc ggc ctg gag ggc tgc gcc<br>Pro Asn Cys Thr Tyr Gly Cys Thr Gly Pro Gly Leu Glu Gly Cys Ala<br>600                    605                  610 | 1920 |
| cgg aac ggc ccc aag atc ccc agc atc gcc acc ggc atg ctg ggc gcc<br>Arg Asn Gly Pro Lys Ile Pro Ser Ile Ala Thr Gly Met Leu Gly Ala<br>615                    620                    625 | 1968 |
| ctg ctg ctg ctg gtg gtg gcc ctg ggc atc ggc ctg ttc atg cgg<br>Leu Leu Leu Leu Val Val Ala Leu Gly Ile Gly Leu Phe Met Arg<br>630                    635                  640                  645 | 2016 |
| cgg cgg cac atc gtg cgg aag cgg acc ctg cgg cgg ctg ctg cag gag<br>Arg Arg His Ile Val Arg Lys Arg Thr Leu Arg Arg Leu Leu Gln Glu<br>650                    655                  660 | 2064 |
| cgg gag ctg gtg gag ccc ctg acc ccc agc ggc gag gcc ccc aac cag<br>Arg Glu Leu Val Glu Pro Leu Thr Pro Ser Gly Glu Ala Pro Asn Gln<br>665                    670                    675 | 2112 |
| gcc ctg ctg cgg atc ctg aag gag acc gag ttc aag aag atc aag gtg<br>Ala Leu Leu Arg Ile Leu Lys Glu Thr Glu Phe Lys Lys Ile Lys Val<br>680                    685                    690 | 2160 |
| ctg ggc agc ggc gcc ttc ggc acc gtg tac aag ggc ctg tgg atc ccc<br>Leu Gly Ser Gly Ala Phe Gly Thr Val Tyr Lys Gly Leu Trp Ile Pro<br>695                    700                  705 | 2208 |
| gag ggc gag aag gtg aag atc ccc gtg gcc atc aag gag ctg cgg gag<br>Glu Gly Glu Lys Val Lys Ile Pro Val Ala Ile Lys Glu Leu Arg Glu<br>710                    715                  720                  725 | 2256 |
| gcc acc agc ccc aag gcc aac aag gag atc ctg gac gag gcc tac gtg<br>Ala Thr Ser Pro Lys Ala Asn Lys Glu Ile Leu Asp Glu Ala Tyr Val<br>730                    735                    740 | 2304 |
| atg gcc agc gtg gac aac ccc cac gtg tgc cgg ctg ctg ggc atc tgc<br>Met Ala Ser Val Asp Asn Pro His Val Cys Arg Leu Leu Gly Ile Cys<br>745                    750                    755 | 2352 |
| ctg acc agc acc gtg cag ctg atc acc cag ctg atg ccc ttc ggc tgc<br>Leu Thr Ser Thr Val Gln Leu Ile Thr Gln Leu Met Pro Phe Gly Cys<br>760                    765                    770 | 2400 |
| ctg ctg gac tac gtg cgg gag cac aag gac aac atc ggc agc cag tac<br>Leu Leu Asp Tyr Val Arg Glu His Lys Asp Asn Ile Gly Ser Gln Tyr<br>775                    780                  785 | 2448 |
| ctg ctg aac tgg tgc gtg cag atc gcc aag ggc atg aac tac ctg gag<br>Leu Leu Asn Trp Cys Val Gln Ile Ala Lys Gly Met Asn Tyr Leu Glu | 2496 |

```
                                       -continued
    790              795               800              805
gac cgg cgg ctg gtg cac cgg gac ctg gcc gcc cgg aac gtg ctg gtg      2544
Asp Arg Arg Leu Val His Arg Asp Leu Ala Ala Arg Asn Val Leu Val
                 810              815              820 aag acc ccc cag cac gtg aag atc acc gac ttc ggc ctg gcc aag ctg      2592
Lys Thr Pro Gln His Val Lys Ile Thr Asp Phe Gly Leu Ala Lys Leu
            825              830              835 ctg ggc gcc gag gag aag gag tac cac gcc gag ggc ggc aag gtg ccc      2640
Leu Gly Ala Glu Glu Lys Glu Tyr His Ala Glu Gly Gly Lys Val Pro
        840              845              850 atc aag tgg atg gcc ctg gag agc atc ctg cac cgg atc tac acc cac      2688
Ile Lys Trp Met Ala Leu Glu Ser Ile Leu His Arg Ile Tyr Thr His
    855              860              865 cag agc gac gtg tgg agc tac ggc gtg acc gtg tgg gag ctg atg acc      2736
Gln Ser Asp Val Trp Ser Tyr Gly Val Thr Val Trp Glu Leu Met Thr
870              875              880              885 ttc ggc agc aag ccc tac gac ggc atc ccc gcc agc gag atc agc agc      2784
Phe Gly Ser Lys Pro Tyr Asp Gly Ile Pro Ala Ser Glu Ile Ser Ser
                 890              895              900 atc ctg gag aag ggc gag cgg ctg ccc cag ccc ccc atc tgc acc atc      2832
Ile Leu Glu Lys Gly Glu Arg Leu Pro Gln Pro Pro Ile Cys Thr Ile
            905              910              915 gac gtg tac atg atc atg gtg aag tgc tgg atg atc gac gcc gac agc      2880
Asp Val Tyr Met Ile Met Val Lys Cys Trp Met Ile Asp Ala Asp Ser
        920              925              930 cgg ccc aag ttc cgg gag ctg atc atc gag ttc agc aag atg gcc cgg      2928
Arg Pro Lys Phe Arg Glu Leu Ile Ile Glu Phe Ser Lys Met Ala Arg
    935              940              945 gac ccc cag cgg tac ctg gtg atc cag ggc gac gag cgg atg cac ctg      2976
Asp Pro Gln Arg Tyr Leu Val Ile Gln Gly Asp Glu Arg Met His Leu
950              955              960              965 ccc agc ccc acc gac agc aac ttc tac cgg gcc ctg atg gac gag gag      3024
Pro Ser Pro Thr Asp Ser Asn Phe Tyr Arg Ala Leu Met Asp Glu Glu
                 970              975              980 gac atg gac gac gtg gtg gac gcc gac gag tac ctg atc ccc cag cag      3072
Asp Met Asp Asp Val Val Asp Ala Asp Glu Tyr Leu Ile Pro Gln Gln
            985              990              995 ggc ttc ttc agc agc ccc agc acc agc cgg acc ccc ctg ctg agc          3117
Gly Phe Phe Ser Ser Pro Ser Thr Ser Arg Thr Pro Leu Leu Ser
        1000             1005                 1010 agc ctg agc gcc acc agc aac aac agc acc gtg gcc tgc atc gac          3162
Ser Leu Ser Ala Thr Ser Asn Asn Ser Thr Val Ala Cys Ile Asp
    1015             1020                 1025 cgg aac ggc ctg cag agc tgc ccc atc aag gag gac agc ttc ctg          3207
Arg Asn Gly Leu Gln Ser Cys Pro Ile Lys Glu Asp Ser Phe Leu
    1030             1035                 1040 cag cgg tac agc agc gac ccc acc ggc gcc ctg acc gag gac agc          3252
Gln Arg Tyr Ser Ser Asp Pro Thr Gly Ala Leu Thr Glu Asp Ser
    1045             1050                 1055 atc gac gac acc ttc ctg ccc gtg ccc gag tac atc aac cag agc          3297
Ile Asp Asp Thr Phe Leu Pro Val Pro Glu Tyr Ile Asn Gln Ser
    1060             1065                 1070 gtg ccc aag cgg ccc gcc ggc agc gtg cag aac ccc gtg tac cac          3342
Val Pro Lys Arg Pro Ala Gly Ser Val Gln Asn Pro Val Tyr His
    1075             1080                 1085 aac cag ccc ctg aac ccc gcc ccc agc cgg gac ccc cac tac cag          3387
Asn Gln Pro Leu Asn Pro Ala Pro Ser Arg Asp Pro His Tyr Gln
    1090             1095                 1100 gac ccc cac agc acc gcc gtg ggc aac ccc gag tac ctg aac acc          3432
```

-continued

| | | | | | | | | | | | |
|---|---|---|---|---|---|---|---|---|---|---|---|
| Asp | Pro | His | Ser | Thr | Ala | Val | Gly | Asn | Pro | Glu | Tyr | Leu | Asn | Thr |
| | | 1105 | | | | 1110 | | | | 1115 | |

```
gtg cag ccc acc tgc gtg aac agc acc ttc gac agc ccc gcc cac       3477
Val Gln Pro Thr Cys Val Asn Ser Thr Phe Asp Ser Pro Ala His
    1120                1125                1130 tgg gcc cag aag ggc agc cac cag atc agc ctg gac aac ccc gac       3522
Trp Ala Gln Lys Gly Ser His Gln Ile Ser Leu Asp Asn Pro Asp
    1135                1140                1145 tac cag cag gac ttc ttc ccc aag gag gcc aag ccc aac ggc atc       3567
Tyr Gln Gln Asp Phe Phe Pro Lys Glu Ala Lys Pro Asn Gly Ile
    1150                1155                1160 ttc aag ggc agc acc gcc gag aac gcc gag tac ctg cgg gtg gcc       3612
Phe Lys Gly Ser Thr Ala Glu Asn Ala Glu Tyr Leu Arg Val Ala
    1165                1170                1175 ccc cag agc agc gag ttc atc ggc gcc tgagcggccg c                  3650
Pro Gln Ser Ser Glu Phe Ile Gly Ala
    1180                1185
```

<210> SEQ ID NO 2
<211> LENGTH: 1213
<212> TYPE: PRT
<213> ORGANISM: Artificial Sequence
<220> FEATURE:
<223> OTHER INFORMATION: Synthetic Construct

<400> SEQUENCE: 2

```
Ala Ser Thr Met Gly Pro Ser Gly Thr Ala Gly Ala Ala Leu Leu Ala
        -25                 -20                 -15

Leu Leu Ala Ala Leu Cys Pro Ala Ser Arg Ala Leu Glu Glu Lys Lys
    -10                  -5              -1   1                   5

Val Cys Gln Gly Thr Ser Asn Lys Leu Thr Gln Leu Gly Thr Phe Glu
                 10                  15                  20

Asp His Phe Leu Ser Leu Gln Arg Met Phe Asn Asn Cys Glu Val Val
                 25                  30                  35

Leu Gly Asn Leu Glu Ile Thr Tyr Val Gln Arg Asn Tyr Asp Leu Ser
         40                  45                  50

Phe Leu Lys Thr Ile Gln Glu Val Ala Gly Tyr Val Leu Ile Ala Leu
 55                  60                  65

Asn Thr Val Glu Arg Ile Pro Leu Glu Asn Leu Gln Ile Ile Arg Gly
 70                  75                  80                  85

Asn Met Tyr Tyr Glu Asn Ser Tyr Ala Leu Ala Val Leu Ser Asn Tyr
                 90                  95                 100

Asp Ala Asn Lys Thr Gly Leu Lys Glu Leu Pro Met Arg Asn Leu Gln
             105                 110                 115

Glu Ile Leu His Gly Ala Val Arg Phe Ser Asn Asn Pro Ala Leu Cys
         120                 125                 130

Asn Val Glu Ser Ile Gln Trp Arg Asp Ile Val Ser Ser Glu Phe Leu
 135                 140                 145

Ser Asn Met Ser Met Asp Phe Gln Asn His Leu Gly Ser Cys Gln Lys
 150                 155                 160                 165

Cys Asp Pro Ser Cys Pro Asn Gly Ser Cys Trp Gly Ala Gly Glu Glu
                 170                 175                 180

Asn Cys Gln Lys Leu Thr Lys Ile Ile Cys Ala Gln Gln Cys Ser Gly
             185                 190                 195

Arg Cys Arg Gly Lys Ser Pro Ser Asp Cys Cys His Asn Gln Cys Ala
         200                 205                 210

Ala Gly Cys Thr Gly Pro Arg Glu Ser Asp Cys Leu Val Cys Arg Lys
```

```
            215                 220                 225

Phe Arg Asp Glu Ala Thr Cys Lys Asp Thr Cys Pro Pro Leu Met Leu
230                 235                 240                 245

Tyr Asn Pro Thr Thr Tyr Gln Met Asp Val Asn Pro Glu Gly Lys Tyr
                250                 255                 260

Ser Phe Gly Ala Thr Cys Val Lys Lys Cys Pro Arg Asn Tyr Val Val
                    265                 270                 275

Thr Asp His Gly Ser Cys Val Arg Ala Cys Gly Ala Asp Ser Tyr Glu
            280                 285                 290

Met Glu Glu Asp Gly Val Arg Lys Cys Lys Lys Cys Glu Gly Pro Cys
        295                 300                 305

Arg Lys Val Cys Asn Gly Ile Gly Ile Gly Glu Phe Lys Asp Thr Leu
310                 315                 320                 325

Ser Ile Asn Ala Thr Asn Ile Lys His Phe Lys Asn Cys Thr Ser Ile
                330                 335                 340

Ser Gly Asp Leu His Ile Leu Pro Val Ala Phe Arg Gly Asp Ser Phe
                    345                 350                 355

Thr His Thr Pro Pro Leu Asp Pro Gln Glu Leu Asp Ile Leu Lys Thr
            360                 365                 370

Val Lys Glu Ile Thr Gly Phe Leu Leu Ile Gln Ala Trp Pro Glu Asn
        375                 380                 385

Arg Thr Asp Leu His Ala Phe Glu Asn Leu Glu Ile Ile Arg Gly Arg
390                 395                 400                 405

Thr Lys Gln His Gly Gln Phe Ser Leu Ala Val Val Ser Leu Asn Ile
                410                 415                 420

Thr Ser Leu Gly Leu Arg Ser Leu Lys Glu Ile Ser Asp Gly Asp Val
                    425                 430                 435

Ile Ile Ser Gly Asn Lys Asn Leu Cys Tyr Ala Asn Thr Ile Asn Trp
            440                 445                 450

Lys Lys Leu Phe Gly Thr Ser Ser Gln Lys Thr Lys Ile Ile Ser Asn
        455                 460                 465

Arg Gly Glu Asn Ser Cys Lys Ala Thr Gly Gln Val Cys His Ala Leu
470                 475                 480                 485

Cys Ser Pro Glu Gly Cys Trp Gly Pro Glu Pro Arg Asp Cys Val Ser
                490                 495                 500

Cys Gln Asn Val Ser Arg Gly Arg Glu Cys Val Asp Lys Cys Asn Ile
                    505                 510                 515

Leu Glu Gly Glu Pro Arg Glu Phe Val Glu Asn Ser Glu Cys Ile Gln
            520                 525                 530

Cys His Pro Glu Cys Leu Pro Gln Val Met Asn Ile Thr Cys Thr Gly
        535                 540                 545

Arg Gly Pro Asp Asn Cys Ile Gln Cys Ala His Tyr Ile Asp Gly Pro
550                 555                 560                 565

His Cys Val Lys Thr Cys Pro Ala Gly Val Met Gly Glu Asn Asn Thr
                570                 575                 580

Leu Val Trp Lys Tyr Ala Asp Ala Gly His Val Cys His Leu Cys His
                    585                 590                 595

Pro Asn Cys Thr Tyr Gly Cys Thr Gly Pro Gly Leu Glu Gly Cys Ala
            600                 605                 610

Arg Asn Gly Pro Lys Ile Pro Ser Ile Ala Thr Gly Met Leu Gly Ala
        615                 620                 625

Leu Leu Leu Leu Leu Val Val Ala Leu Gly Ile Gly Leu Phe Met Arg
630                 635                 640                 645
```

-continued

Arg Arg His Ile Val Arg Lys Arg Thr Leu Arg Arg Leu Leu Gln Glu
              650                 655                 660

Arg Glu Leu Val Glu Pro Leu Thr Pro Ser Gly Glu Ala Pro Asn Gln
              665                 670                 675

Ala Leu Leu Arg Ile Leu Lys Glu Thr Glu Phe Lys Lys Ile Lys Val
              680                 685                 690

Leu Gly Ser Gly Ala Phe Gly Thr Val Tyr Lys Gly Leu Trp Ile Pro
695                 700                 705

Glu Gly Glu Lys Val Lys Ile Pro Val Ala Ile Lys Glu Leu Arg Glu
710                 715                 720                 725

Ala Thr Ser Pro Lys Ala Asn Lys Glu Ile Leu Asp Glu Ala Tyr Val
              730                 735                 740

Met Ala Ser Val Asp Asn Pro His Val Cys Arg Leu Leu Gly Ile Cys
              745                 750                 755

Leu Thr Ser Thr Val Gln Leu Ile Thr Gln Leu Met Pro Phe Gly Cys
              760                 765                 770

Leu Leu Asp Tyr Val Arg Glu His Lys Asp Asn Ile Gly Ser Gln Tyr
              775                 780                 785

Leu Leu Asn Trp Cys Val Gln Ile Ala Lys Gly Met Asn Tyr Leu Glu
790                 795                 800                 805

Asp Arg Arg Leu Val His Arg Asp Leu Ala Ala Arg Asn Val Leu Val
              810                 815                 820

Lys Thr Pro Gln His Val Lys Ile Thr Asp Phe Gly Leu Ala Lys Leu
              825                 830                 835

Leu Gly Ala Glu Glu Lys Glu Tyr His Ala Glu Gly Gly Lys Val Pro
              840                 845                 850

Ile Lys Trp Met Ala Leu Glu Ser Ile Leu His Arg Ile Tyr Thr His
              855                 860                 865

Gln Ser Asp Val Trp Ser Tyr Gly Val Thr Val Trp Glu Leu Met Thr
870                 875                 880                 885

Phe Gly Ser Lys Pro Tyr Asp Gly Ile Pro Ala Ser Glu Ile Ser Ser
              890                 895                 900

Ile Leu Glu Lys Gly Glu Arg Leu Pro Gln Pro Pro Ile Cys Thr Ile
              905                 910                 915

Asp Val Tyr Met Ile Met Val Lys Cys Trp Met Ile Asp Ala Asp Ser
              920                 925                 930

Arg Pro Lys Phe Arg Glu Leu Ile Ile Glu Phe Ser Lys Met Ala Arg
935                 940                 945

Asp Pro Gln Arg Tyr Leu Val Ile Gln Gly Asp Glu Arg Met His Leu
950                 955                 960                 965

Pro Ser Pro Thr Asp Ser Asn Phe Tyr Arg Ala Leu Met Asp Glu Glu
              970                 975                 980

Asp Met Asp Asp Val Val Asp Ala Asp Glu Tyr Leu Ile Pro Gln Gln
              985                 990                 995

Gly Phe Phe Ser Ser Pro Ser Thr Ser Arg Thr Pro Leu Leu Ser
              1000                1005                1010

Ser Leu Ser Ala Thr Ser Asn Asn Ser Thr Val Ala Cys Ile Asp
              1015                1020                1025

Arg Asn Gly Leu Gln Ser Cys Pro Ile Lys Glu Asp Ser Phe Leu
              1030                1035                1040

Gln Arg Tyr Ser Ser Asp Pro Thr Gly Ala Leu Thr Glu Asp Ser
              1045                1050                1055

```
Ile Asp Asp Thr Phe Leu Pro Val Pro Glu Tyr Ile Asn Gln Ser
    1060                1065                1070

Val Pro Lys Arg Pro Ala Gly Ser Val Gln Asn Pro Val Tyr His
    1075                1080                1085

Asn Gln Pro Leu Asn Pro Ala Pro Ser Arg Asp Pro His Tyr Gln
    1090                1095                1100

Asp Pro His Ser Thr Ala Val Gly Asn Pro Glu Tyr Leu Asn Thr
    1105                1110                1115

Val Gln Pro Thr Cys Val Asn Ser Thr Phe Asp Ser Pro Ala His
    1120                1125                1130

Trp Ala Gln Lys Gly Ser His Gln Ile Ser Leu Asp Asn Pro Asp
    1135                1140                1145

Tyr Gln Gln Asp Phe Phe Pro Lys Glu Ala Lys Pro Asn Gly Ile
    1150                1155                1160

Phe Lys Gly Ser Thr Ala Glu Asn Ala Glu Tyr Leu Arg Val Ala
    1165                1170                1175

Pro Gln Ser Ser Glu Phe Ile Gly Ala
    1180                1185

<210> SEQ ID NO 3
<211> LENGTH: 617
<212> TYPE: PRT
<213> ORGANISM: Artificial Sequence
<220> FEATURE:
<223> OTHER INFORMATION: EGFR HER3 swap varII ECD

<400> SEQUENCE: 3

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
                20                  25                  30

Asn Cys Glu Val Val Leu Gly Asn Leu Glu Ile Thr Tyr Val Gln Arg
            35                  40                  45

Asn Tyr Asp Leu Ser Phe Leu Lys Thr Ile Gln Glu Val Ala Gly Tyr
        50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Cys Pro Pro Cys His Glu Val Cys Lys Gly Arg Cys Trp Gly Pro Gly
                165                 170                 175

Ser Glu Asp Cys Gln Thr Leu Thr Lys Thr Ile Cys Ala Pro Gln Cys
            180                 185                 190

Asn Gly His Cys Phe Gly Pro Asn Pro Asn Gln Cys Cys His Asp Glu
        195                 200                 205

Cys Ala Gly Gly Cys Ser Gly Pro Gln Asp Thr Asp Cys Phe Ala Cys
    210                 215                 220
```

```
Arg His Phe Asn Asp Ser Gly Ala Cys Val Pro Arg Cys Pro Gln Pro
225                 230                 235                 240

Leu Val Tyr Asn Lys Leu Thr Phe Gln Leu Glu Pro Asn Pro His Thr
            245                 250                 255

Lys Tyr Gln Tyr Gly Gly Val Cys Val Ala Ser Cys Pro His Asn Phe
        260                 265                 270

Val Val Asp Gln Thr Ser Cys Val Arg Ala Cys Pro Pro Asp Lys Met
    275                 280                 285

Glu Val Asp Lys Asn Gly Leu Lys Met Cys Glu Pro Cys Gly Gly Leu
290                 295                 300

Cys Pro Lys Ala Cys Glu Gly Ile Gly Ile Gly Glu Phe Lys Asp Ser
305                 310                 315                 320

Leu Ser Ile Asn Ala Thr Asn Ile Lys His Phe Lys Asn Cys Thr Ser
                325                 330                 335

Ile Ser Gly Asp Leu His Ile Leu Pro Val Ala Phe Arg Gly Asp Ser
            340                 345                 350

Phe Thr His Thr Pro Pro Leu Asp Pro Gln Glu Leu Asp Ile Leu Lys
        355                 360                 365

Thr Val Lys Glu Ile Thr Gly Phe Leu Leu Ile Gln Ala Trp Pro Glu
    370                 375                 380

Asn Arg Thr Asp Leu His Ala Phe Glu Asn Leu Glu Ile Ile Arg Gly
385                 390                 395                 400

Arg Thr Lys Gln His Gly Gln Phe Ser Leu Ala Val Val Ser Leu Asn
                405                 410                 415

Ile Thr Ser Leu Gly Leu Arg Ser Leu Lys Glu Ile Ser Asp Gly Asp
            420                 425                 430

Val Ile Ile Ser Gly Asn Lys Asn Leu Cys Tyr Ala Asn Thr Ile Asn
        435                 440                 445

Trp Lys Lys Leu Phe Gly Thr Ser Gly Gln Lys Thr Lys Ile Ile Ser
450                 455                 460

Asn Arg Gly Glu Asn Ser Cys Lys Ala Thr Gly Gln Val Cys His Ala
465                 470                 475                 480

Leu Cys Ser Pro Glu Gly Cys Trp Gly Pro Glu Pro Arg Asp Cys Val
                485                 490                 495

Ser Cys Arg Asn Val Ser Arg Gly Arg Glu Cys Val Asp Lys Cys Asn
            500                 505                 510

Leu Leu Glu Gly Glu Pro Arg Glu Phe Val Glu Asn Ser Glu Cys Ile
        515                 520                 525

Gln Cys His Pro Glu Cys Leu Pro Gln Ala Met Asn Ile Thr Cys Thr
    530                 535                 540

Gly Arg Gly Pro Asp Asn Cys Ile Gln Cys Ala His Tyr Ile Asp Gly
545                 550                 555                 560

Pro His Cys Val Lys Thr Cys Pro Ala Gly Val Met Gly Glu Asn Asn
                565                 570                 575

Thr Leu Val Trp Lys Tyr Ala Asp Ala Gly His Val Cys His Leu Cys
            580                 585                 590

His Pro Asn Cys Thr Tyr Gly Cys Thr Gly Pro Gly Leu Glu Gly Cys
        595                 600                 605

Pro Thr Asn Gly Pro Lys Ile Pro Ser
    610                 615

<210> SEQ ID NO 4
<211> LENGTH: 622
<212> TYPE: PRT
```

<213> ORGANISM: Artificial Sequence
<220> FEATURE:
<223> OTHER INFORMATION: EGFR HER3 swap varIII ECD

<400> SEQUENCE: 4

```
Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Lys Ile Leu Gly Asn Leu Asp Phe Leu Ile Thr Gly Leu
            340                 345                 350

Asn Gly Asp Pro Trp His Lys Ile Pro Ala Leu Asp Pro Glu Lys Leu
        355                 360                 365

Asn Val Phe Arg Thr Val Arg Glu Ile Thr Gly Tyr Leu Asn Ile Gln
    370                 375                 380

Ser Trp Pro Pro His Met His Asn Phe Ser Val Phe Ser Asn Leu Thr
```

```
                385                 390                 395                 400
        Thr Ile Gly Gly Arg Ser Leu Tyr Asn Arg Gly Phe Ser Leu Leu Ile
                        405                 410                 415

Met Lys Asn Leu Asn Val Thr Ser Leu Gly Phe Arg Ser Leu Lys Glu
                        420                 425                 430

Ile Ser Ala Gly Arg Ile Tyr Ile Ser Ala Asn Arg Gln Leu Cys Tyr
                        435                 440                 445

His His Ser Leu Asn Trp Thr Lys Val Leu Gly Thr Ser Gly Gln Lys
                        450                 455                 460

Thr Lys Ile Ile Ser Asn Arg Gly Glu Asn Ser Cys Lys Ala Thr Gly
        465                 470                 475                 480

Gln Val Cys His Ala Leu Cys Ser Pro Glu Gly Cys Trp Gly Pro Glu
                        485                 490                 495

Pro Arg Asp Cys Val Ser Cys Arg Asn Val Ser Arg Gly Arg Glu Cys
                        500                 505                 510

Val Asp Lys Cys Asn Leu Leu Glu Gly Glu Pro Arg Glu Phe Val Glu
                        515                 520                 525

Asn Ser Glu Cys Ile Gln Cys His Pro Glu Cys Leu Pro Gln Ala Met
                        530                 535                 540

Asn Ile Thr Cys Thr Gly Arg Gly Pro Asp Asn Cys Ile Gln Cys Ala
        545                 550                 555                 560

His Tyr Ile Asp Gly Pro His Cys Val Lys Thr Cys Pro Ala Gly Val
                        565                 570                 575

Met Gly Glu Asn Asn Thr Leu Val Trp Lys Tyr Ala Asp Ala Gly His
                        580                 585                 590

Val Cys His Leu Cys His Pro Asn Cys Thr Tyr Gly Cys Thr Gly Pro
                        595                 600                 605

Gly Leu Glu Gly Cys Pro Thr Asn Gly Pro Lys Ile Pro Ser
                        610                 615                 620

<210> SEQ ID NO 5
<211> LENGTH: 619
<212> TYPE: PRT
<213> ORGANISM: Artificial Sequence
<220> FEATURE:
<223> OTHER INFORMATION: EGFR HER3 swap varIV ECD

<400> SEQUENCE: 5

Leu Glu Glu Lys Lys Val Cys Gln Gly Thr Ser Asn Lys Leu Thr Gln
        1               5                   10                  15

Leu Gly Thr Phe Glu Asp His Phe Leu Ser Leu Gln Arg Met Phe Asn
                        20                  25                  30

Asn Cys Glu Val Val Leu Gly Asn Leu Glu Ile Thr Tyr Val Gln Arg
                        35                  40                  45

Asn Tyr Asp Leu Ser Phe Leu Lys Thr Ile Gln Glu Val Ala Gly Tyr
                50                  55                  60

Val Leu Ile Ala Leu Asn Thr Val Glu Arg Ile Pro Leu Glu Asn Leu
        65                  70                  75                  80

Gln Ile Ile Arg Gly Asn Met Tyr Tyr Glu Asn Ser Tyr Ala Leu Ala
                        85                  90                  95

Val Leu Ser Asn Tyr Asp Ala Asn Lys Thr Gly Leu Lys Glu Leu Pro
                        100                 105                 110

Met Arg Asn Leu Gln Glu Ile Leu His Gly Ala Val Arg Phe Ser Asn
                        115                 120                 125

Asn Pro Ala Leu Cys Asn Val Glu Ser Ile Gln Trp Arg Asp Ile Val
```

```
            130                 135                 140
Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
            165                 170                 175

Gly Ala Gly Glu Glu Asn Cys Gln Lys Leu Thr Lys Ile Ile Cys Ala
                180                 185                 190

Gln Gln Cys Ser Gly Arg Cys Arg Gly Lys Ser Pro Ser Asp Cys Cys
            195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
            275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
            355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
    435                 440                 445

Asn Thr Ile Asn Trp Lys Lys Leu Phe Gly Thr Ser Gly Gln Lys Thr
450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Glu
    515                 520                 525

Cys Phe Ser Cys His Pro Glu Cys Gln Pro Met Glu Gly Thr Ala Thr
530                 535                 540

Cys Asn Gly Ser Gly Ser Asp Thr Cys Ala Gln Cys Ala His Phe Arg
545                 550                 555                 560
```

```
Asp Gly Pro His Cys Val Ser Ser Cys Pro His Gly Val Met Gly Glu
            565                 570                 575

Asn Asn Thr Leu Val Trp Lys Tyr Ala Asp Ala Gly His Val Cys His
            580                 585                 590

Leu Cys His Pro Asn Cys Thr Tyr Gly Cys Thr Gly Pro Gly Leu Glu
            595                 600                 605

Gly Cys Pro Thr Asn Gly Pro Lys Ile Pro Ser
    610                 615

<210> SEQ ID NO 6
<211> LENGTH: 375
<212> TYPE: DNA
<213> ORGANISM: Artificial Sequence
<220> FEATURE:
<223> OTHER INFORMATION: MF4280: heavy chain variable region sequence
      of an EGFR binding antibody
<220> FEATURE:
<221> NAME/KEY: CDS
<222> LOCATION: (1)..(375)

<400> SEQUENCE: 6 cag gtg cag ctg gtg cag tct ggg gct gag gtg aag aag cct ggg gcc     48
Gln Val Gln Leu Val Gln Ser Gly Ala Glu Val Lys Lys Pro Gly Ala
 1               5                  10                  15 tca gtg aag gtc tcc tgc aag gtt tcc gga tac acc ctc act gaa tta     96
Ser Val Lys Val Ser Cys Lys Val Ser Gly Tyr Thr Leu Thr Glu Leu
             20                  25                  30 tcc atg cac tgg gtg cga cag gct cct ggt aaa ggg ctt gaa tgg atg    144
Ser Met His Trp Val Arg Gln Ala Pro Gly Lys Gly Leu Glu Trp Met
         35                  40                  45 gga ggc ttt gat cct gag tat ggt aaa aca ttc ttc gca cag aac ttc    192
Gly Gly Phe Asp Pro Glu Tyr Gly Lys Thr Phe Phe Ala Gln Asn Phe
     50                  55                  60 cag ggc aga gtc acc atg acc gag gac aca tct gca gac aca gcc tac    240
Gln Gly Arg Val Thr Met Thr Glu Asp Thr Ser Ala Asp Thr Ala Tyr
 65                  70                  75                  80 atg gag cta agc agc ctg aga tct gag gac acg gcc gtg tat tac tgt    288
Met Glu Leu Ser Ser Leu Arg Ser Glu Asp Thr Ala Val Tyr Tyr Cys
                 85                  90                  95 gca aca gag ggg tat tat gag act act act tat tac tac aac ctt ttt    336
Ala Thr Glu Gly Tyr Tyr Glu Thr Thr Thr Tyr Tyr Tyr Asn Leu Phe
            100                 105                 110 gac tcc tgg ggc cag gga acc ctg gtc acc gtc tca agc                375
Asp Ser Trp Gly Gln Gly Thr Leu Val Thr Val Ser Ser
        115                 120                 125

<210> SEQ ID NO 7
<211> LENGTH: 125
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
             20                  25                  30

Ser Met His Trp Val Arg Gln Ala Pro Gly Lys Gly Leu Glu Trp Met
         35                  40                  45

Gly Gly Phe Asp Pro Glu Tyr Gly Lys Thr Phe Phe Ala Gln Asn Phe
```

```
                50                  55                  60
Gln Gly Arg Val Thr Met Thr Glu Asp Thr Ser Ala Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Glu Gly Tyr Tyr Glu Thr Thr Tyr Tyr Tyr Asn Leu Phe
                100                 105                 110

Asp Ser Trp Gly Gln Gly Thr Leu Val Thr Val Ser Ser
            115                 120                 125

<210> SEQ ID NO 8
<211> LENGTH: 30
<212> TYPE: PRT
<213> ORGANISM: Artificial Sequence
<220> FEATURE:
<223> OTHER INFORMATION: MF4280 FR1

<400> SEQUENCE: 8

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr
                20                  25                  30

<210> SEQ ID NO 9
<211> LENGTH: 5
<212> TYPE: PRT
<213> ORGANISM: Artificial Sequence
<220> FEATURE:
<223> OTHER INFORMATION: MF4280 CDR1

<400> SEQUENCE: 9

Glu Leu Ser Met His
 1               5

<210> SEQ ID NO 10
<211> LENGTH: 14
<212> TYPE: PRT
<213> ORGANISM: Artificial Sequence
<220> FEATURE:
<223> OTHER INFORMATION: MF4280 FR2

<400> SEQUENCE: 10

Trp Val Arg Gln Ala Pro Gly Lys Gly Leu Glu Trp Met Gly
 1               5                  10

<210> SEQ ID NO 11
<211> LENGTH: 17
<212> TYPE: PRT
<213> ORGANISM: Artificial Sequence
<220> FEATURE:
<223> OTHER INFORMATION: MF4280 CDR2

<400> SEQUENCE: 11

Gly Phe Asp Pro Glu Tyr Gly Lys Thr Phe Phe Ala Gln Asn Phe Gln
 1               5                  10                  15

Gly

<210> SEQ ID NO 12
<211> LENGTH: 32
<212> TYPE: PRT
<213> ORGANISM: Artificial Sequence
<220> FEATURE:
<223> OTHER INFORMATION: MF4280 FR3
```

<400> SEQUENCE: 12

Arg Val Thr Met Thr Glu Asp Thr Ser Ala Asp Thr Ala Tyr Met Glu
1               5                   10                  15

Leu Ser Ser Leu Arg Ser Glu Asp Thr Ala Val Tyr Tyr Cys Ala Thr
                20                  25                  30

<210> SEQ ID NO 13
<211> LENGTH: 16
<212> TYPE: PRT
<213> ORGANISM: Artificial Sequence
<220> FEATURE:
<223> OTHER INFORMATION: MF4280 CDR3

<400> SEQUENCE: 13

Glu Gly Tyr Tyr Glu Thr Thr Thr Tyr Tyr Tyr Asn Leu Phe Asp Ser
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: MF4280 FR4

<400> SEQUENCE: 14

Trp Gly Gln Gly Thr Leu Val Thr Val Ser Ser
1               5                   10

<210> SEQ ID NO 15
<211> LENGTH: 360
<212> TYPE: DNA
<213> ORGANISM: Artificial Sequence
<220> FEATURE:
<223> OTHER INFORMATION: MF3998: heavy chain variable region sequence of
      an EGFR binding antibody
<220> FEATURE:
<221> NAME/KEY: CDS
<222> LOCATION: (1)..(360)

<400> SEQUENCE: 15 cag gtg cag ctg gtg cag tct ggg tct gag ttg aag aag cct ggg gcc         48
Gln Val Gln Leu Val Gln Ser Gly Ser Glu Leu Lys Lys Pro Gly Ala
1               5                   10                  15 tca gtg aag gtt tcc tgc aag gct tct gga tac acc ttc act aac aat         96
Ser Val Lys Val Ser Cys Lys Ala Ser Gly Tyr Thr Phe Thr Asn Asn
                20                  25                  30 gcc ata aat tgg gtg cga cag gcc cct gga caa ggg ctt gag tgg atg        144
Ala Ile Asn Trp Val Arg Gln Ala Pro Gly Gln Gly Leu Glu Trp Met
            35                  40                  45 gga tgg atc aac acc atc act ggg gac cca acg tat gcc cag ggc ttc        192
Gly Trp Ile Asn Thr Ile Thr Gly Asp Pro Thr Tyr Ala Gln Gly Phe
        50                  55                  60 aca gga cgg ttt gtc ttc tcc ttg gac acc tct gtc agc acg gca tat        240
Thr Gly Arg Phe Val Phe Ser Leu Asp Thr Ser Val Ser Thr Ala Tyr
65                  70                  75                  80 ctg cag atc agc agc ctg aag gct gag gac act ggc gtg tat tac tgt        288
Leu Gln Ile Ser Ser Leu Lys Ala Glu Asp Thr Gly Val Tyr Tyr Cys
                85                  90                  95 gcg aga gag gaa ttt ttg gag tgg tta ttc ttt gac tac tgg ggc cag        336
Ala Arg Glu Glu Phe Leu Glu Trp Leu Phe Phe Asp Tyr Trp Gly Gln
            100                 105                 110 gga acc ctg gtc acc gtc tca agc                                        360
Gly Thr Leu Val Thr Val Ser Ser
        115                 120

```
<210> SEQ ID NO 16
<211> LENGTH: 120
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Asn
            20                  25                  30

Ala Ile Asn Trp Val Arg Gln Ala Pro Gly Gln Gly Leu Glu Trp Met
        35                  40                  45

Gly Trp Ile Asn Thr Ile Thr Gly Asp Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Gly Val Tyr Tyr Cys
                85                  90                  95

Ala Arg Glu Glu Phe Leu Glu Trp Leu Phe Phe Asp Tyr Trp Gly Gln
            100                 105                 110

Gly Thr Leu Val Thr Val Ser Ser
        115                 120

<210> SEQ ID NO 17
<211> LENGTH: 30
<212> TYPE: PRT
<213> ORGANISM: Artificial Sequence
<220> FEATURE:
<223> OTHER INFORMATION: MF3998 FR1

<400> SEQUENCE: 17

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 18
<211> LENGTH: 5
<212> TYPE: PRT
<213> ORGANISM: Artificial Sequence
<220> FEATURE:
<223> OTHER INFORMATION: MF3998 CDR1

<400> SEQUENCE: 18

Asn Asn Ala Ile Asn
1               5

<210> SEQ ID NO 19
<211> LENGTH: 14
<212> TYPE: PRT
<213> ORGANISM: Artificial Sequence
<220> FEATURE:
<223> OTHER INFORMATION: MF3998 FR2

<400> SEQUENCE: 19

Trp Val Arg Gln Ala Pro Gly Gln Gly Leu Glu Trp Met Gly
1               5                   10

<210> SEQ ID NO 20
```

```
<211> LENGTH: 17
<212> TYPE: PRT
<213> ORGANISM: Artificial Sequence
<220> FEATURE:
<223> OTHER INFORMATION: MF3998 CDR2

<400> SEQUENCE: 20

Trp Ile Asn Thr Ile Thr Gly Asp Pro Thr Tyr Ala Gln Gly Phe Thr
1               5                   10                  15

Gly

<210> SEQ ID NO 21
<211> LENGTH: 32
<212> TYPE: PRT
<213> ORGANISM: Artificial Sequence
<220> FEATURE:
<223> OTHER INFORMATION: MF3998 FR3

<400> SEQUENCE: 21

Arg Phe Val Phe Ser Leu Asp Thr Ser Val Ser Thr Ala Tyr Leu Gln
1               5                   10                  15

Ile Ser Ser Leu Lys Ala Glu Asp Thr Gly Val Tyr Tyr Cys Ala Arg
            20                  25                  30

<210> SEQ ID NO 22
<211> LENGTH: 11
<212> TYPE: PRT
<213> ORGANISM: Artificial Sequence
<220> FEATURE:
<223> OTHER INFORMATION: MF3998 CDR3

<400> SEQUENCE: 22

Glu Glu Phe Leu Glu Trp Leu Phe Phe Asp Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: MF3998 FR4

<400> SEQUENCE: 23

Trp Gly Gln Gly Thr Leu Val Thr Val Ser Ser
1               5                   10

<210> SEQ ID NO 24
<211> LENGTH: 369
<212> TYPE: DNA
<213> ORGANISM: Artificial Sequence
<220> FEATURE:
<223> OTHER INFORMATION: MF4010: heavy chain variable region sequence of
      an EGFR binding antibody:
<220> FEATURE:
<221> NAME/KEY: CDS
<222> LOCATION: (1)..(369)

<400> SEQUENCE: 24 cag gtg cag ctg gtg cag tct ggg tct gag ttg aag aag cct ggg gcc        48
Gln Val Gln Leu Val Gln Ser Gly Ser Glu Leu Lys Lys Pro Gly Ala
1               5                   10                  15 tca gtg aag gtt tcc tgc aag gct tct gga tac acc ttc act aac aat        96
Ser Val Lys Val Ser Cys Lys Ala Ser Gly Tyr Thr Phe Thr Asn Asn
            20                  25                  30 gcc atg aat tgg gtg cga cag gcc cct gga caa ggg ctt gag tgg atg       144
Ala Met Asn Trp Val Arg Gln Ala Pro Gly Gln Gly Leu Glu Trp Met
```

```
                       35                  40                  45
gga tgg atc aac acc atc act ggg gac cca tcg tat gcc cag ggc ttc      192
Gly Trp Ile Asn Thr Ile Thr Gly Asp Pro Ser Tyr Ala Gln Gly Phe
        50                  55                  60 aca gga cgg ttt gtc ttc tcc ctg gac acc tct gtc aac acg gca tat      240
Thr Gly Arg Phe Val Phe Ser Leu Asp Thr Ser Val Asn Thr Ala Tyr
 65                  70                  75                  80 ctg cag atc agc agc ctg aag gct gag gac act gcc gta tat tac tgt      288
Leu Gln Ile Ser Ser Leu Lys Ala Glu Asp Thr Ala Val Tyr Tyr Cys
                 85                  90                  95 gcg aga gag gaa ttt ttg gag tgg tta ttc ttt gac tac tgg ggc cag      336
Ala Arg Glu Glu Phe Leu Glu Trp Leu Phe Phe Asp Tyr Trp Gly Gln
            100                 105                 110 gga acc ctg gtc acc gtc tca agc gtc tcc agt                          369
Gly Thr Leu Val Thr Val Ser Ser Val Ser Ser
            115                 120

<210> SEQ ID NO 25
<211> LENGTH: 123
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Asn
            20                  25                  30

Ala Met Asn Trp Val Arg Gln Ala Pro Gly Gln Gly Leu Glu Trp Met
        35                  40                  45

Gly Trp Ile Asn Thr Ile Thr Gly Asp Pro Ser Tyr Ala Gln Gly Phe
    50                  55                  60

Thr Gly Arg Phe Val Phe Ser Leu Asp Thr Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Glu Phe Leu Glu Trp Leu Phe Phe Asp Tyr Trp Gly Gln
            100                 105                 110

Gly Thr Leu Val Thr Val Ser Ser Val Ser Ser
        115                 120

<210> SEQ ID NO 26
<211> LENGTH: 30
<212> TYPE: PRT
<213> ORGANISM: Artificial Sequence
<220> FEATURE:
<223> OTHER INFORMATION: MF4010 FR1

<400> SEQUENCE: 26

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 27
<211> LENGTH: 5
<212> TYPE: PRT
<213> ORGANISM: Artificial Sequence
<220> FEATURE:
<223> OTHER INFORMATION: MF40101 FR1
```

<400> SEQUENCE: 27

Asn Asn Ala Met Asn
1               5

<210> SEQ ID NO 28
<211> LENGTH: 14
<212> TYPE: PRT
<213> ORGANISM: Artificial Sequence
<220> FEATURE:
<223> OTHER INFORMATION: MF4010 FR2

<400> SEQUENCE: 28

Trp Val Arg Gln Ala Pro Gly Gln Gly Leu Glu Trp Met Gly
1               5                   10

<210> SEQ ID NO 29
<211> LENGTH: 17
<212> TYPE: PRT
<213> ORGANISM: Artificial Sequence
<220> FEATURE:
<223> OTHER INFORMATION: MF4010 CDR2

<400> SEQUENCE: 29

Trp Ile Asn Thr Ile Thr Gly Asp Pro Ser Tyr Ala Gln Gly Phe Thr
1               5                   10                  15

Gly

<210> SEQ ID NO 30
<211> LENGTH: 32
<212> TYPE: PRT
<213> ORGANISM: Artificial Sequence
<220> FEATURE:
<223> OTHER INFORMATION: MF4010 FR3

<400> SEQUENCE: 30

Arg Phe Val Phe Ser Leu Asp Thr Ser Val Asn Thr Ala Tyr Leu Gln
1               5                   10                  15

Ile Ser Ser Leu Lys Ala Glu Asp Thr Ala Val Tyr Tyr Cys Ala Arg
                20                  25                  30

<210> SEQ ID NO 31
<211> LENGTH: 11
<212> TYPE: PRT
<213> ORGANISM: Artificial Sequence
<220> FEATURE:
<223> OTHER INFORMATION: MF40101 CDR3

<400> SEQUENCE: 31

Glu Glu Phe Leu Glu Trp Leu Phe Phe Asp Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: MF4010 FR4

<400> SEQUENCE: 32

Trp Gly Gln Gly Thr Leu Val Thr Val Ser Ser
1               5                   10

<210> SEQ ID NO 33
<211> LENGTH: 366

```
<212> TYPE: DNA
<213> ORGANISM: Artificial Sequence
<220> FEATURE:
<223> OTHER INFORMATION: MF4003: heavy chain variable region sequence of
      an EGFR binding antibody:
<220> FEATURE:
<221> NAME/KEY: CDS
<222> LOCATION: (1)..(366)

<400> SEQUENCE: 33 cag gtg cag ctg gtg caa tct ggg tct gag ttg aag aag cct ggg gcc      48
Gln Val Gln Leu Val Gln Ser Gly Ser Glu Leu Lys Lys Pro Gly Ala
1               5                   10                  15 tca gtg aag gtt tcc tgc aag gct tct gga tac acc ttc cct agt ttt      96
Ser Val Lys Val Ser Cys Lys Ala Ser Gly Tyr Thr Phe Pro Ser Phe
                20                  25                  30 gct atg aat tgg ctt cga cag gcc cct gga caa ggg ctt gag tgg atg     144
Ala Met Asn Trp Leu Arg Gln Ala Pro Gly Gln Gly Leu Glu Trp Met
            35                  40                  45 gga tgg atc acc acc aac act ggg gac cca acg tat gcc cag ggc ttc     192
Gly Trp Ile Thr Thr Asn Thr Gly Asp Pro Thr Tyr Ala Gln Gly Phe
        50                  55                  60 tca gga cgg ttt gtg ttc tcc ctg gac acc tct gtc agc acg gca tat     240
Ser Gly Arg Phe Val Phe Ser Leu Asp Thr Ser Val Ser Thr Ala Tyr
65                  70                  75                  80 ctg cag atc agc agc cta aag gct gag gac act gcc gtg tat tac tgt     288
Leu Gln Ile Ser Ser Leu Lys Ala Glu Asp Thr Ala Val Tyr Tyr Cys
                85                  90                  95 gcg aga gtt tat aac tgg ata agg gga ttt gac tac tgg ggc cag gga     336
Ala Arg Val Tyr Asn Trp Ile Arg Gly Phe Asp Tyr Trp Gly Gln Gly
                100                 105                 110 acc ctg gtc acc gtc tca agc gtc tcc agt                              366
Thr Leu Val Thr Val Ser Ser Val Ser Ser
            115                 120

<210> SEQ ID NO 34
<211> LENGTH: 122
<212> TYPE: PRT
<213> ORGANISM: Artificial Sequence
<220> FEATURE:
<223> OTHER INFORMATION: Synthetic Construct

<400> SEQUENCE: 34

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Pro Ser Phe
                20                  25                  30

Ala Met Asn Trp Leu Arg Gln Ala Pro Gly Gln Gly Leu Glu Trp Met
            35                  40                  45

Gly Trp Ile Thr Thr Asn Thr Gly Asp Pro Thr Tyr Ala Gln Gly Phe
        50                  55                  60

Ser Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Val Tyr Asn Trp Ile Arg Gly Phe Asp Tyr Trp Gly Gln Gly
                100                 105                 110

Thr Leu Val Thr Val Ser Ser Val Ser Ser
            115                 120

<210> SEQ ID NO 35
```

<211> LENGTH: 30
<212> TYPE: PRT
<213> ORGANISM: Artificial Sequence
<220> FEATURE:
<223> OTHER INFORMATION: MF4003 FR1

<400> SEQUENCE: 35

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Pro
            20                  25                  30

<210> SEQ ID NO 36
<211> LENGTH: 5
<212> TYPE: PRT
<213> ORGANISM: Artificial Sequence
<220> FEATURE:
<223> OTHER INFORMATION: MF4003 CDR1

<400> SEQUENCE: 36

Ser Phe Ala Met Asn
1               5

<210> SEQ ID NO 37
<211> LENGTH: 14
<212> TYPE: PRT
<213> ORGANISM: Artificial Sequence
<220> FEATURE:
<223> OTHER INFORMATION: MF4003 FR2

<400> SEQUENCE: 37

Trp Leu Arg Gln Ala Pro Gly Gln Gly Leu Glu Trp Met Gly
1               5                   10

<210> SEQ ID NO 38
<211> LENGTH: 17
<212> TYPE: PRT
<213> ORGANISM: Artificial Sequence
<220> FEATURE:
<223> OTHER INFORMATION: MF4003 CDR2

<400> SEQUENCE: 38

Trp Ile Thr Thr Asn Thr Gly Asp Pro Thr Tyr Ala Gln Gly Phe Ser
1               5                   10                  15
Gly

<210> SEQ ID NO 39
<211> LENGTH: 32
<212> TYPE: PRT
<213> ORGANISM: Artificial Sequence
<220> FEATURE:
<223> OTHER INFORMATION: MF4003 FR3

<400> SEQUENCE: 39

Arg Phe Val Phe Ser Leu Asp Thr Ser Val Ser Thr Ala Tyr Leu Gln
1               5                   10                  15
Ile Ser Ser Leu Lys Ala Glu Asp Thr Ala Val Tyr Tyr Cys Ala Arg
            20                  25                  30

<210> SEQ ID NO 40
<211> LENGTH: 10
<212> TYPE: PRT
<213> ORGANISM: Artificial Sequence
<220> FEATURE:
<223> OTHER INFORMATION: MF4003 CDR3

-continued

<400> SEQUENCE: 40

Val Tyr Asn Trp Ile Arg Gly Phe Asp Tyr
1               5                   10

<210> SEQ ID NO 41
<211> LENGTH: 11
<212> TYPE: PRT
<213> ORGANISM: Artificial Sequence
<220> FEATURE:
<223> OTHER INFORMATION: MF4003 FR4

<400> SEQUENCE: 41

Trp Gly Gln Gly Thr Leu Val Thr Val Ser Ser
1               5                   10

<210> SEQ ID NO 42
<211> LENGTH: 385
<212> TYPE: DNA
<213> ORGANISM: Artificial Sequence
<220> FEATURE:
<223> OTHER INFORMATION: MF4289: heavy chain variable region sequence of
      an EGFR binding antibody:
<220> FEATURE:
<221> NAME/KEY: CDS
<222> LOCATION: (2)..(385)

<400> SEQUENCE: 42 g gcc cag ccg gcc atg gcc cag gtg cag ctg gtg caa tct ggg tct gaa      49
  Ala Gln Pro Ala Met Ala Gln Val Gln Leu Val Gln Ser Gly Ser Glu
  1               5                   10                  15 ttg aag aag cct ggg gcc tca gtg aag gtt tcc tgc aag act tct gga        97
Leu Lys Lys Pro Gly Ala Ser Val Lys Val Ser Cys Lys Thr Ser Gly
             20                  25                  30 tac acc ttc act gac tat gct atg act tgg gtg cga cag gcc cct gga       145
Tyr Thr Phe Thr Asp Tyr Ala Met Thr Trp Val Arg Gln Ala Pro Gly
         35                  40                  45 caa ggg ctt gaa tgg atg gga tgg atc acc acc aac act ggg gac cca       193
Gln Gly Leu Glu Trp Met Gly Trp Ile Thr Thr Asn Thr Gly Asp Pro
 50                  55                  60 acg tat gcc ccg ggc ttc aca gga cgg ttt gtc ttc tcc ttg gac acc       241
Thr Tyr Ala Pro Gly Phe Thr Gly Arg Phe Val Phe Ser Leu Asp Thr
 65                  70                  75                  80 tct gtc agc acg gca tat ctg cag atc agc agc cta aag gcc gag gac       289
Ser Val Ser Thr Ala Tyr Leu Gln Ile Ser Ser Leu Lys Ala Glu Asp
                 85                  90                  95 act gcc gta tat tac tgt gcg aga gtg tat cat tgg ata cgg gga ttt       337
Thr Ala Val Tyr Tyr Cys Ala Arg Val Tyr His Trp Ile Arg Gly Phe
            100                 105                 110 gag ttt tgg ggc cag gga acc ctg gtc acc gtc tca agc gtc tcc agt       385
Glu Phe Trp Gly Gln Gly Thr Leu Val Thr Val Ser Ser Val Ser Ser
        115                 120                 125

<210> SEQ ID NO 43
<211> LENGTH: 128
<212> TYPE: PRT
<213> ORGANISM: Artificial Sequence
<220> FEATURE:
<223> OTHER INFORMATION: Synthetic Construct

<400> SEQUENCE: 43

Ala Gln Pro Ala Met Ala Gln Val Gln Leu Val Gln Ser Gly Ser Glu
1               5                   10                  15

Leu Lys Lys Pro Gly Ala Ser Val Lys Val Ser Cys Lys Thr Ser Gly
             20                  25                  30

```
Tyr Thr Phe Thr Asp Tyr Ala Met Thr Trp Val Arg Gln Ala Pro Gly
            35                  40                  45

Gln Gly Leu Glu Trp Met Gly Trp Ile Thr Thr Asn Thr Gly Asp Pro
 50                  55                  60

Thr Tyr Ala Pro Gly Phe Thr Gly Arg Phe Val Phe Ser Leu Asp Thr
 65                  70                  75                  80

Ser Val Ser Thr Ala Tyr Leu Gln Ile Ser Ser Leu Lys Ala Glu Asp
                 85                  90                  95

Thr Ala Val Tyr Tyr Cys Ala Arg Val Tyr His Trp Ile Arg Gly Phe
                100                 105                 110

Glu Phe Trp Gly Gln Gly Thr Leu Val Thr Val Ser Ser Val Ser Ser
            115                 120                 125
```

```
<210> SEQ ID NO 44
<211> LENGTH: 119
<212> TYPE: PRT
<213> ORGANISM: Artificial Sequence
<220> FEATURE:
<223> OTHER INFORMATION: MF4289 complete VH sequence

<400> SEQUENCE: 44

Gln Val Gln Leu Val Gln Ser Gly Ser Glu Leu Lys Lys Pro Gly Ala
 1               5                  10                  15

Ser Val Lys Val Ser Cys Lys Thr Ser Gly Tyr Thr Phe Thr Asp Tyr
                20                  25                  30

Ala Met Thr Trp Val Arg Gln Ala Pro Gly Gln Gly Leu Glu Trp Met
            35                  40                  45

Gly Trp Ile Thr Thr Asn Thr Gly Asp Pro Thr Tyr Ala Pro Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Val Tyr His Trp Ile Arg Gly Phe Glu Phe Trp Gly Gln Gly
                100                 105                 110

Thr Leu Val Thr Val Ser Ser
            115
```

```
<210> SEQ ID NO 45
<211> LENGTH: 30
<212> TYPE: PRT
<213> ORGANISM: Artificial Sequence
<220> FEATURE:
<223> OTHER INFORMATION: MF4289 FR1

<400> SEQUENCE: 45

Gln Val Gln Leu Val Gln Ser Gly Ser Glu Leu Lys Lys Pro Gly Ala
 1               5                  10                  15

Ser Val Lys Val Ser Cys Lys Thr Ser Gly Tyr Thr Phe Thr
                20                  25                  30
```

```
<210> SEQ ID NO 46
<211> LENGTH: 5
<212> TYPE: PRT
<213> ORGANISM: Artificial Sequence
<220> FEATURE:
<223> OTHER INFORMATION: MF4289 CDR1

<400> SEQUENCE: 46
```

Asp Tyr Ala Met Thr
1               5

<210> SEQ ID NO 47
<211> LENGTH: 14
<212> TYPE: PRT
<213> ORGANISM: Artificial Sequence
<220> FEATURE:
<223> OTHER INFORMATION: MF4289 FR2

<400> SEQUENCE: 47

Trp Val Arg Gln Ala Pro Gly Gln Gly Leu Glu Trp Met Gly
1               5                   10

<210> SEQ ID NO 48
<211> LENGTH: 17
<212> TYPE: PRT
<213> ORGANISM: Artificial Sequence
<220> FEATURE:
<223> OTHER INFORMATION: MF4289 CDR2

<400> SEQUENCE: 48

Trp Ile Thr Thr Asn Thr Gly Asp Pro Thr Tyr Ala Pro Gly Phe Thr
1               5                   10                  15

Gly

<210> SEQ ID NO 49
<211> LENGTH: 32
<212> TYPE: PRT
<213> ORGANISM: Artificial Sequence
<220> FEATURE:
<223> OTHER INFORMATION: MF4289 FR3

<400> SEQUENCE: 49

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Ala Arg
            20                  25                  30

<210> SEQ ID NO 50
<211> LENGTH: 10
<212> TYPE: PRT
<213> ORGANISM: Artificial Sequence
<220> FEATURE:
<223> OTHER INFORMATION: MF4289 CDR3

<400> SEQUENCE: 50

Val Tyr His Trp Ile Arg Gly Phe Glu Phe
1               5                   10

<210> SEQ ID NO 51
<211> LENGTH: 11
<212> TYPE: PRT
<213> ORGANISM: Artificial Sequence
<220> FEATURE:
<223> OTHER INFORMATION: MF4289 FR4

<400> SEQUENCE: 51

Trp Gly Gln Gly Thr Leu Val Thr Val Ser Ser
1               5                   10

<210> SEQ ID NO 52
<211> LENGTH: 366
<212> TYPE: DNA
<213> ORGANISM: Artificial Sequence
<220> FEATURE:

<223> OTHER INFORMATION: MF3370: heavy chain variable region sequence of
      an EGFR binding antibody:
<220> FEATURE:
<221> NAME/KEY: CDS
<222> LOCATION: (1)..(366)

<400> SEQUENCE: 52

| cag | gtt | cag | ctg | gtg | cag | tct | gga | gct | gag | gtg | aag | aag | cct | ggg | gcc | 48 |
| Gln | Val | Gln | Leu | Val | Gln | Ser | Gly | Ala | Glu | Val | Lys | Lys | Pro | Gly | Ala | |
| 1   |     |     |     | 5   |     |     |     |     | 10  |     |     |     |     | 15  |     | |

| tca | gtg | aag | gtc | tcc | tgc | aag | gct | tct | ggt | tac | acc | ttt | acc | agc | tat | 96 |
| Ser | Val | Lys | Val | Ser | Cys | Lys | Ala | Ser | Gly | Tyr | Thr | Phe | Thr | Ser | Tyr | |
|     |     |     | 20  |     |     |     |     | 25  |     |     |     |     | 30  |     |     | |

| ggt | atc | agc | tgg | gtg | cga | cag | gcc | cct | gga | caa | ggg | ctt | gag | tgg | atg | 144 |
| Gly | Ile | Ser | Trp | Val | Arg | Gln | Ala | Pro | Gly | Gln | Gly | Leu | Glu | Trp | Met | |
|     |     | 35  |     |     |     |     | 40  |     |     |     |     | 45  |     |     |     | |

| gga | tgg | atc | agc | gct | tac | aat | ggt | aac | aca | aac | tat | gca | cag | aag | ctc | 192 |
| Gly | Trp | Ile | Ser | Ala | Tyr | Asn | Gly | Asn | Thr | Asn | Tyr | Ala | Gln | Lys | Leu | |
| 50  |     |     |     |     | 55  |     |     |     |     | 60  |     |     |     |     |     | |

| cag | ggc | aga | gtc | acc | atg | acc | aca | gac | aca | tcc | acg | agc | aca | gcc | tac | 240 |
| Gln | Gly | Arg | Val | Thr | Met | Thr | Thr | Asp | Thr | Ser | Thr | Ser | Thr | Ala | Tyr | |
| 65  |     |     |     |     | 70  |     |     |     |     | 75  |     |     |     |     | 80  | |

| atg | gag | ctg | agg | agc | ctg | aga | tct | gac | gac | acg | gct | gtg | tat | tac | tgt | 288 |
| Met | Glu | Leu | Arg | Ser | Leu | Arg | Ser | Asp | Asp | Thr | Ala | Val | Tyr | Tyr | Cys | |
|     |     |     |     | 85  |     |     |     |     | 90  |     |     |     |     | 95  |     | |

| gca | aaa | gat | cgt | cat | tgg | cat | tgg | tgg | ctg | gac | gcc | ttt | gat | tat | tgg | 336 |
| Ala | Lys | Asp | Arg | His | Trp | His | Trp | Trp | Leu | Asp | Ala | Phe | Asp | Tyr | Trp | |
|     |     |     | 100 |     |     |     |     | 105 |     |     |     |     | 110 |     |     | |

| ggc | caa | ggt | acc | ctg | gtc | acc | gtc | tcc | agt |  |  |  |  |  |  | 366 |
| Gly | Gln | Gly | Thr | Leu | Val | Thr | Val | Ser | Ser |  |  |  |  |  |  | |
|     |     |     | 115 |     |     |     |     | 120 |     |  |  |  |  |  |  | |

<210> SEQ ID NO 53
<211> LENGTH: 122
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Arg His Trp His Trp Trp Leu Asp Ala Phe Asp Tyr Trp
            100                 105                 110

Gly Gln Gly Thr Leu Val Thr Val Ser Ser
        115                 120

<210> SEQ ID NO 54
<211> LENGTH: 30
<212> TYPE: PRT
<213> ORGANISM: Artificial Sequence

```
<220> FEATURE:
<223> OTHER INFORMATION: MF3370 FR1

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 55
<211> LENGTH: 5
<212> TYPE: PRT
<213> ORGANISM: Artificial Sequence
<220> FEATURE:
<223> OTHER INFORMATION: MF3370 CDR1

<400> SEQUENCE: 55

Ser Tyr Gly Ile Ser
1               5

<210> SEQ ID NO 56
<211> LENGTH: 14
<212> TYPE: PRT
<213> ORGANISM: Artificial Sequence
<220> FEATURE:
<223> OTHER INFORMATION: MF3370 FR2

<400> SEQUENCE: 56

Trp Val Arg Gln Ala Pro Gly Gln Gly Leu Glu Trp Met Gly
1               5                   10

<210> SEQ ID NO 57
<211> LENGTH: 17
<212> TYPE: PRT
<213> ORGANISM: Artificial Sequence
<220> FEATURE:
<223> OTHER INFORMATION: MF3370 CDR2

<400> SEQUENCE: 57

Trp Ile Ser Ala Tyr Asn Gly Asn Thr Asn Tyr Ala Gln Lys Leu Gln
1               5                   10                  15

Gly

<210> SEQ ID NO 58
<211> LENGTH: 32
<212> TYPE: PRT
<213> ORGANISM: Artificial Sequence
<220> FEATURE:
<223> OTHER INFORMATION: MF3370 FR3

<400> SEQUENCE: 58

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Lys
            20                  25                  30

<210> SEQ ID NO 59
<211> LENGTH: 13
<212> TYPE: PRT
<213> ORGANISM: Artificial Sequence
<220> FEATURE:
<223> OTHER INFORMATION: MF3370 CDR3

<400> SEQUENCE: 59

Asp Arg His Trp His Trp Trp Leu Asp Ala Phe Asp Tyr
```

<210> SEQ ID NO 60
<211> LENGTH: 11
<212> TYPE: PRT
<213> ORGANISM: Artificial Sequence
<220> FEATURE:
<223> OTHER INFORMATION: MF3370 FR4

<400> SEQUENCE: 60

```
Trp Gly Gln Gly Thr Leu Val Thr Val Ser Ser
1               5                   10
```

<210> SEQ ID NO 61
<211> LENGTH: 366
<212> TYPE: DNA
<213> ORGANISM: Artificial Sequence
<220> FEATURE:
<223> OTHER INFORMATION: MF4002: heavy chain variable region sequence of
      an EGFR binding antibody:
<220> FEATURE:
<221> NAME/KEY: CDS
<222> LOCATION: (1)..(366)

<400> SEQUENCE: 61

```
cag gtg cag ctg gtg caa tct ggg tct gag ttg aag aag cct ggg tcc      48
Gln Val Gln Leu Val Gln Ser Gly Ser Glu Leu Lys Lys Pro Gly Ser
1               5                   10                  15 tca gtg aag gtt tcc tgc aag gct tct gga tac acc ttc act aac tat      96
Ser Val Lys Val Ser Cys Lys Ala Ser Gly Tyr Thr Phe Thr Asn Tyr
                20                  25                  30 gct atg aat tgg gtg cga cag gcc cct gga caa ggg ctt gag tgg atg     144
Ala Met Asn Trp Val Arg Gln Ala Pro Gly Gln Gly Leu Glu Trp Met
            35                  40                  45 gga tgg atc acc acc aac act ggg gac cca acg tat gcc cag ggc ttc     192
Gly Trp Ile Thr Thr Asn Thr Gly Asp Pro Thr Tyr Ala Gln Gly Phe
        50                  55                  60 aca gga cgt ttt gtc ttc tcc ttg gac acc tct gtc agt acg gca tat     240
Thr Gly Arg Phe Val Phe Ser Leu Asp Thr Ser Val Ser Thr Ala Tyr
65                  70                  75                  80 ctg cag atc agc agc cta aag gct gag gac act gcc gta tat tac tgt     288
Leu Gln Ile Ser Ser Leu Lys Ala Glu Asp Thr Ala Val Tyr Tyr Cys
                85                  90                  95 gtg aga gtg tat aac tgg ata agg gga ttt gac tac tgg ggc cag gga     336
Val Arg Val Tyr Asn Trp Ile Arg Gly Phe Asp Tyr Trp Gly Gln Gly
                100                 105                 110 acc ctg gtc acc gtc tca agc gtc tcc agt                             366
Thr Leu Val Thr Val Ser Ser Val Ser Ser
            115                 120
```

<210> SEQ ID NO 62
<211> LENGTH: 122
<212> TYPE: PRT
<213> ORGANISM: Artificial Sequence
<220> FEATURE:
<223> OTHER INFORMATION: Synthetic Construct

<400> SEQUENCE: 62

```
Gln Val Gln Leu Val Gln Ser Gly Ser Glu Leu Lys Lys Pro Gly Ser
1               5                   10                  15

Ser Val Lys Val Ser Cys Lys Ala Ser Gly Tyr Thr Phe Thr Asn Tyr
                20                  25                  30

Ala Met Asn Trp Val Arg Gln Ala Pro Gly Gln Gly Leu Glu Trp Met
            35                  40                  45
```

```
Gly Trp Ile Thr Thr Asn Thr Gly Asp Pro Thr Tyr Ala Gln Gly Phe
        50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Val Arg Val Tyr Asn Trp Ile Arg Gly Phe Asp Tyr Trp Gly Gln Gly
            100                 105                 110

Thr Leu Val Thr Val Ser Ser Val Ser Ser
            115                 120

<210> SEQ ID NO 63
<211> LENGTH: 30
<212> TYPE: PRT
<213> ORGANISM: Artificial Sequence
<220> FEATURE:
<223> OTHER INFORMATION: MF4002 FR1

<400> SEQUENCE: 63

Gln Val Gln Leu Val Gln Ser Gly Ser Glu Leu Lys Lys Pro Gly Ser
 1               5                  10                  15

Ser Val Lys Val Ser Cys Lys Ala Ser Gly Tyr Thr Phe Thr
            20                  25                  30

<210> SEQ ID NO 64
<211> LENGTH: 5
<212> TYPE: PRT
<213> ORGANISM: Artificial Sequence
<220> FEATURE:
<223> OTHER INFORMATION: MF4002 CDR1

<400> SEQUENCE: 64

Asn Tyr Ala Met Asn
 1               5

<210> SEQ ID NO 65
<211> LENGTH: 14
<212> TYPE: PRT
<213> ORGANISM: Artificial Sequence
<220> FEATURE:
<223> OTHER INFORMATION: MF4002 FR2

<400> SEQUENCE: 65

Trp Val Arg Gln Ala Pro Gly Gln Gly Leu Glu Trp Met Gly
 1               5                  10

<210> SEQ ID NO 66
<211> LENGTH: 17
<212> TYPE: PRT
<213> ORGANISM: Artificial Sequence
<220> FEATURE:
<223> OTHER INFORMATION: MF4002 CDR2

<400> SEQUENCE: 66

Trp Ile Thr Thr Asn Thr Gly Asp Pro Thr Tyr Ala Gln Gly Phe Thr
 1               5                  10                  15

Gly

<210> SEQ ID NO 67
<211> LENGTH: 32
<212> TYPE: PRT
<213> ORGANISM: Artificial Sequence
<220> FEATURE:
```

<223> OTHER INFORMATION: MF4002 FR3

<400> SEQUENCE: 67

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Val Arg
            20                  25                  30

<210> SEQ ID NO 68
<211> LENGTH: 10
<212> TYPE: PRT
<213> ORGANISM: Artificial Sequence
<220> FEATURE:
<223> OTHER INFORMATION: MF4002 CDR3

<400> SEQUENCE: 68

Val Tyr Asn Trp Ile Arg Gly Phe Asp Tyr
1               5                   10

<210> SEQ ID NO 69
<211> LENGTH: 11
<212> TYPE: PRT
<213> ORGANISM: Artificial Sequence
<220> FEATURE:
<223> OTHER INFORMATION: MF4002 FR4

<400> SEQUENCE: 69

Trp Gly Gln Gly Thr Leu Val Thr Val Ser Ser
1               5                   10

<210> SEQ ID NO 70
<211> LENGTH: 357
<212> TYPE: DNA
<213> ORGANISM: Artificial Sequence
<220> FEATURE:
<223> OTHER INFORMATION: MF3751: heavy chain variable region sequence of
      an EGFR binding antibody:
<220> FEATURE:
<221> NAME/KEY: CDS
<222> LOCATION: (1)..(357)

<400> SEQUENCE: 70 cag gtg cag ctg gta cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtt tcc tgc aag gca tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga aca atc aac cct agt ggt ggt agc aca tac tac gca cag aag ttc     192
Gly Thr Ile Asn Pro Ser Gly Gly Ser Thr Tyr Tyr Ala Gln Lys Phe
    50                  55                  60 cag ggc aga gtc acc atg acc agg gac acg tcc acg agc aca gtc tac     240
Gln Gly Arg Val Thr Met Thr Arg Asp Thr Ser Thr Ser Thr Val Tyr
65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                85                  90                  95 gcg aga gat cgg aac tgg gga tgg gac ttt gac tac tgg ggc cag gga     336
Ala Arg Asp Arg Asn Trp Gly Trp Asp Phe Asp Tyr Trp Gly Gln Gly
            100                 105                 110 acc ctg gtc acc gtc tcc agt                                          357

Thr Leu Val Thr Val Ser Ser
        115

<210> SEQ ID NO 71
<211> LENGTH: 119
<212> TYPE: PRT
<213> ORGANISM: Artificial Sequence
<220> FEATURE:
<223> OTHER INFORMATION: Synthetic Construct

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Thr Ile Asn Pro Ser Gly Gly Ser Thr Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Asn Trp Gly Trp Asp Phe Asp Tyr Trp Gly Gln Gly
            100                 105                 110

Thr Leu Val Thr Val Ser Ser
        115

<210> SEQ ID NO 72
<211> LENGTH: 30
<212> TYPE: PRT
<213> ORGANISM: Artificial Sequence
<220> FEATURE:
<223> OTHER INFORMATION: MF3751 FR1

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 73
<211> LENGTH: 5
<212> TYPE: PRT
<213> ORGANISM: Artificial Sequence
<220> FEATURE:
<223> OTHER INFORMATION: MF3751 CDR1

<400> SEQUENCE: 73

Gly Tyr Tyr Met His
1               5

<210> SEQ ID NO 74
<211> LENGTH: 14
<212> TYPE: PRT
<213> ORGANISM: Artificial Sequence
<220> FEATURE:
<223> OTHER INFORMATION: MF3751 FR2

<400> SEQUENCE: 74

Trp Val Arg Gln Ala Pro Gly Gln Gly Leu Glu Trp Met Gly
1               5                   10

<210> SEQ ID NO 75
<211> LENGTH: 17
<212> TYPE: PRT
<213> ORGANISM: Artificial Sequence
<220> FEATURE:
<223> OTHER INFORMATION: MF3751 CDR2

<400> SEQUENCE: 75

Thr Ile Asn Pro Ser Gly Gly Ser Thr Tyr Tyr Ala Gln Lys Phe Gln
1               5                   10                  15

Gly

<210> SEQ ID NO 76
<211> LENGTH: 32
<212> TYPE: PRT
<213> ORGANISM: Artificial Sequence
<220> FEATURE:
<223> OTHER INFORMATION: MF3751 FR3

<400> SEQUENCE: 76

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 77
<211> LENGTH: 10
<212> TYPE: PRT
<213> ORGANISM: Artificial Sequence
<220> FEATURE:
<223> OTHER INFORMATION: MF3751 CDR3

<400> SEQUENCE: 77

Asp Arg Asn Trp Gly Trp Asp Phe Asp Tyr
1               5                   10

<210> SEQ ID NO 78
<211> LENGTH: 11
<212> TYPE: PRT
<213> ORGANISM: Artificial Sequence
<220> FEATURE:
<223> OTHER INFORMATION: MF3751 FR4

<400> SEQUENCE: 78

Trp Gly Gln Gly Thr Leu Val Thr Val Ser Ser
1               5                   10

<210> SEQ ID NO 79
<211> LENGTH: 366
<212> TYPE: DNA
<213> ORGANISM: Artificial Sequence
<220> FEATURE:
<223> OTHER INFORMATION: MF3752: heavy chain variable region sequence of
      an EGFR binding antibody:
<220> FEATURE:
<221> NAME/KEY: CDS
<222> LOCATION: (1)..(366)

<400> SEQUENCE: 79 gag gtg cag ctg gtg gag tct ggg cct gag gtg aag aag cct ggg gcc      48
Glu Val Gln Leu Val Glu Ser Gly Pro Glu Val Lys Lys Pro Gly Ala
1               5                   10                  15 tca gtg aag gtt tcc tgc aag gca tct gga tac acc ttc acc agc tac      96
Ser Val Lys Val Ser Cys Lys Ala Ser Gly Tyr Thr Phe Thr Ser Tyr
            20                  25                  30

```
tat atg cac tgg gtg cga cag gcc cct gga caa ggg ctt gag tgg atg        144
Tyr Met His Trp Val Arg Gln Ala Pro Gly Gln Gly Leu Glu Trp Met
        35                  40                  45 gga aca atc aac cct agt ggt ggt agc aca tac tac gca cag aag ttc        192
Gly Thr Ile Asn Pro Ser Gly Gly Ser Thr Tyr Tyr Ala Gln Lys Phe
 50                  55                  60 cag ggc aga gtc acc ctg acc agg gac acg tcc acg agc aca gtc tac        240
Gln Gly Arg Val Thr Leu Thr Arg Asp Thr Ser Thr Ser Thr Val Tyr
 65                  70                  75                  80 atg gtg ctg agc agc ctg aga tct gag gac acg gcc gtg tat tac tgt        288
Met Val Leu Ser Ser Leu Arg Ser Glu Asp Thr Ala Val Tyr Tyr Cys
                 85                  90                  95 gcg aga gat cgg aac tgg gga tgg gac ttt gac tac tgg ggc cag gga        336
Ala Arg Asp Arg Asn Trp Gly Trp Asp Phe Asp Tyr Trp Gly Gln Gly
            100                 105                 110 acc ctg gtc acc gtc tca agc gtc tcc agt                                366
Thr Leu Val Thr Val Ser Ser Val Ser Ser
        115                 120
```

<210> SEQ ID NO 80
<211> LENGTH: 122
<212> TYPE: PRT
<213> ORGANISM: Artificial Sequence
<220> FEATURE:
<223> OTHER INFORMATION: Synthetic Construct

<400> SEQUENCE: 80

```
Glu Val Gln Leu Val Glu Ser Gly Pro Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Thr Ile Asn Pro Ser Gly Gly Ser Thr Tyr Tyr Ala Gln Lys Phe
 50                  55                  60

Gln Gly Arg Val Thr Leu Thr Arg Asp Thr Ser Thr Ser Thr Val Tyr
 65                  70                  75                  80

Met Val Leu Ser Ser Leu Arg Ser Glu Asp Thr Ala Val Tyr Tyr Cys
                 85                  90                  95

Ala Arg Asp Arg Asn Trp Gly Trp Asp Phe Asp Tyr Trp Gly Gln Gly
            100                 105                 110

Thr Leu Val Thr Val Ser Ser Val Ser Ser
        115                 120
```

<210> SEQ ID NO 81
<211> LENGTH: 30
<212> TYPE: PRT
<213> ORGANISM: Artificial Sequence
<220> FEATURE:
<223> OTHER INFORMATION: MF3752 FR1

<400> SEQUENCE: 81

```
Glu Val Gln Leu Val Glu Ser Gly Pro Glu Val Lys Lys Pro Gly Ala
1               5                   10                  15

Ser Val Lys Val Ser Cys Lys Ala Ser Gly Tyr Thr Phe Thr
            20                  25                  30
```

<210> SEQ ID NO 82
<211> LENGTH: 5
<212> TYPE: PRT
<213> ORGANISM: Artificial Sequence

```
<220> FEATURE:
<223> OTHER INFORMATION: FR3752 CDR1

<400> SEQUENCE: 82

Ser Tyr Tyr Met His
1               5

<210> SEQ ID NO 83
<211> LENGTH: 14
<212> TYPE: PRT
<213> ORGANISM: Artificial Sequence
<220> FEATURE:
<223> OTHER INFORMATION: MF3752 FR2

<400> SEQUENCE: 83

Trp Val Arg Gln Ala Pro Gly Gln Gly Leu Glu Trp Met Gly
1               5                   10

<210> SEQ ID NO 84
<211> LENGTH: 17
<212> TYPE: PRT
<213> ORGANISM: Artificial Sequence
<220> FEATURE:
<223> OTHER INFORMATION: MF3752 CDR2

<400> SEQUENCE: 84

Thr Ile Asn Pro Ser Gly Gly Ser Thr Tyr Tyr Ala Gln Lys Phe Gln
1               5                   10                  15

Gly

<210> SEQ ID NO 85
<211> LENGTH: 32
<212> TYPE: PRT
<213> ORGANISM: Artificial Sequence
<220> FEATURE:
<223> OTHER INFORMATION: MF3752 FR3

<400> SEQUENCE: 85

Arg Val Thr Leu Thr Arg Asp Thr Ser Thr Ser Thr Val Tyr Met Val
1               5                   10                  15

Leu Ser Ser Leu Arg Ser Glu Asp Thr Ala Val Tyr Tyr Cys Ala Arg
                20                  25                  30

<210> SEQ ID NO 86
<211> LENGTH: 10
<212> TYPE: PRT
<213> ORGANISM: Artificial Sequence
<220> FEATURE:
<223> OTHER INFORMATION: MF3752 CDR3

<400> SEQUENCE: 86

Asp Arg Asn Trp Gly Trp Asp Phe Asp Tyr
1               5                   10

<210> SEQ ID NO 87
<211> LENGTH: 11
<212> TYPE: PRT
<213> ORGANISM: Artificial Sequence
<220> FEATURE:
<223> OTHER INFORMATION: MF3752 FR4

<400> SEQUENCE: 87

Trp Gly Gln Gly Thr Leu Val Thr Val Ser Ser
1               5                   10
```

<210> SEQ ID NO 88
<211> LENGTH: 391
<212> TYPE: DNA
<213> ORGANISM: Artificial Sequence
<220> FEATURE:
<223> OTHER INFORMATION: MF3178: heavy chain variable region sequence of an erbB-3 binding antibody
<220> FEATURE:
<221> NAME/KEY: CDS
<222> LOCATION: (20)..(391)

<400> SEQUENCE: 88

```
ggcccagccg gccatggcc cag gtg cag ctg gtg cag tct ggg gct gag gtg        52
                      Gln Val Gln Leu Val Gln Ser Gly Ala Glu Val
                       1               5                  10 aag aag cct ggg gcc tca gtg aag gtc tcc tgc aag gct tct gga tac        100
Lys Lys Pro Gly Ala Ser Val Lys Val Ser Cys Lys Ala Ser Gly Tyr
             15                  20                  25 acc ttc acc ggc tac tat atg cac tgg gtg cga cag gcc cct gga caa        148
Thr Phe Thr Gly Tyr Tyr Met His Trp Val Arg Gln Ala Pro Gly Gln
         30                  35                  40 ggg ctt gag tgg atg gga tgg atc aac cct aac agt ggt ggc aca aac        196
Gly Leu Glu Trp Met Gly Trp Ile Asn Pro Asn Ser Gly Gly Thr Asn
     45                  50                  55 tat gca cag aag ttt cag ggc agg gtc acg atg acc agg gac acg tcc        244
Tyr Ala Gln Lys Phe Gln Gly Arg Val Thr Met Thr Arg Asp Thr Ser
 60                  65                  70                  75 atc agc aca gcc tac atg gag ctg agc agg ctg aga tct gac gac acg        292
Ile Ser Thr Ala Tyr Met Glu Leu Ser Arg Leu Arg Ser Asp Asp Thr
                 80                  85                  90 gct gtg tat tac tgt gca aga gat cat ggt tct cgt cat ttc tgg tct        340
Ala Val Tyr Tyr Cys Ala Arg Asp His Gly Ser Arg His Phe Trp Ser
             95                 100                 105 tac tgg ggc ttt gat tat tgg ggc caa ggt acc ctg gtc acc gtc tcc        388
Tyr Trp Gly Phe Asp Tyr Trp Gly Gln Gly Thr Leu Val Thr Val Ser
         110                 115                 120 agt                                                                    391
Ser
```

<210> SEQ ID NO 89
<211> LENGTH: 124
<212> TYPE: PRT
<213> ORGANISM: Artificial Sequence
<220> FEATURE:
<223> OTHER INFORMATION: Synthetic Construct

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

```
Tyr Trp Gly Gln Gly Thr Leu Val Thr Val Ser Ser
        115                 120

<210> SEQ ID NO 90
<211> LENGTH: 5
<212> TYPE: PRT
<213> ORGANISM: Artificial Sequence
<220> FEATURE:
<223> OTHER INFORMATION: MF3178 CDR1

<400> SEQUENCE: 90

Gly Tyr Tyr Met His
1               5

<210> SEQ ID NO 91
<211> LENGTH: 17
<212> TYPE: PRT
<213> ORGANISM: Artificial Sequence
<220> FEATURE:
<223> OTHER INFORMATION: MF3178 CDR2

<400> SEQUENCE: 91

Trp Ile Asn Pro Asn Ser Gly Gly Thr Asn Tyr Ala Gln Lys Phe Gln
1               5                   10                  15

Gly

<210> SEQ ID NO 92
<211> LENGTH: 15
<212> TYPE: PRT
<213> ORGANISM: Artificial Sequence
<220> FEATURE:
<223> OTHER INFORMATION: MF3178 CDR3

<400> SEQUENCE: 92

Asp His Gly Ser Arg His Phe Trp Ser Tyr Trp Gly Phe Asp Tyr
1               5                   10                  15

<210> SEQ ID NO 93
<211> LENGTH: 385
<212> TYPE: DNA
<213> ORGANISM: Artificial Sequence
<220> FEATURE:
<223> OTHER INFORMATION: MF3176: heavy chain variable region sequence of
      an erbB-3 binding antibody
<220> FEATURE:
<221> NAME/KEY: CDS
<222> LOCATION: (20)..(385)

<400> SEQUENCE: 93
ggcccagccg gccatggcc gag gtg cag ctg ttg gag tct ggg gga ggc ttg      52
                     Glu Val Gln Leu Leu Glu Ser Gly Gly Gly Leu
                     1               5                   10 gta cag cct ggg ggg tcc ctg aga ctc tcc tgt gca gcc tct gga ttc     100
Val Gln Pro Gly Gly Ser Leu Arg Leu Ser Cys Ala Ala Ser Gly Phe
            15                  20                  25 acc ttt agc agc tat gcc atg agc tgg gtc cgc cag gct cca ggg aag     148
Thr Phe Ser Ser Tyr Ala Met Ser Trp Val Arg Gln Ala Pro Gly Lys
        30                  35                  40 ggg ctg gag tgg gtc tca gct att agt ggt agt ggt ggt agc aca tac     196
Gly Leu Glu Trp Val Ser Ala Ile Ser Gly Ser Gly Gly Ser Thr Tyr
    45                  50                  55 tac gca gac tcc gtg aag ggc cgg ttc acc atc tcc aga gac aat tcc     244
Tyr Ala Asp Ser Val Lys Gly Arg Phe Thr Ile Ser Arg Asp Asn Ser
60                  65                  70                  75 aag aac acg ctg tat ctg caa atg aac agc ctg aga gcc gag gac acg     292
```

```
                Lys Asn Thr Leu Tyr Leu Gln Met Asn Ser Leu Arg Ala Glu Asp Thr
                                 80                  85                  90 gct gtg tat tac tgt gca aga gat tgg tgg tac ccg ccg tac tac tgg           340
Ala Val Tyr Tyr Cys Ala Arg Asp Trp Trp Tyr Pro Pro Tyr Tyr Trp
             95                 100                 105 ggc ttt gat tat tgg ggc caa ggt acc ctg gtc acc gtc tcc agt               385
Gly Phe Asp Tyr Trp Gly Gln Gly Thr Leu Val Thr Val Ser Ser
        110                 115                 120
```

<210> SEQ ID NO 94
<211> LENGTH: 122
<212> TYPE: PRT
<213> ORGANISM: Artificial Sequence
<220> FEATURE:
<223> OTHER INFORMATION: Synthetic Construct

<400> SEQUENCE: 94

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Trp Tyr Pro Pro Tyr Tyr Trp Gly Phe Asp Tyr Trp
            100                 105                 110

Gly Gln Gly Thr Leu Val Thr Val Ser Ser
        115                 120
```

<210> SEQ ID NO 95
<211> LENGTH: 5
<212> TYPE: PRT
<213> ORGANISM: Artificial Sequence
<220> FEATURE:
<223> OTHER INFORMATION: MF3176 CDR1

<400> SEQUENCE: 95

```
Ser Tyr Ala Met Ser
1               5
```

<210> SEQ ID NO 96
<211> LENGTH: 17
<212> TYPE: PRT
<213> ORGANISM: Artificial Sequence
<220> FEATURE:
<223> OTHER INFORMATION: MF3176 CDR2

<400> SEQUENCE: 96

```
Ala Ile Ser Gly Ser Gly Gly Ser Thr Tyr Tyr Ala Asp Ser Val Lys
1               5                   10                  15

Gly
```

<210> SEQ ID NO 97
<211> LENGTH: 13
<212> TYPE: PRT
<213> ORGANISM: Artificial Sequence
<220> FEATURE:

<223> OTHER INFORMATION: MF3176 CDR3

<400> SEQUENCE: 97

Asp Trp Trp Tyr Pro Pro Tyr Tyr Trp Gly Phe Asp Tyr
1               5                   10

<210> SEQ ID NO 98
<211> LENGTH: 391
<212> TYPE: DNA
<213> ORGANISM: Artificial Sequence
<220> FEATURE:
<223> OTHER INFORMATION: MF3163: heavy chain variable region sequence of
      an erbB-3 binding antibody
<220> FEATURE:
<221> NAME/KEY: CDS
<222> LOCATION: (20)..(391)

<400> SEQUENCE: 98

```
ggcccagccg gccatggcc cag gtg cag ctg gtg cag tct ggg gct gag gtg      52
                     Gln Val Gln Leu Val Gln Ser Gly Ala Glu Val
                      1               5                  10 aag aag cct ggg gcc tca gtg aag gtc tcc tgc aag gct tct gga tac     100
Lys Lys Pro Gly Ala Ser Val Lys Val Ser Cys Lys Ala Ser Gly Tyr
             15                  20                  25 acc ttc acc ggc tac tat atg cac tgg gtg cga cag gcc cct gga caa    148
Thr Phe Thr Gly Tyr Tyr Met His Trp Val Arg Gln Ala Pro Gly Gln
         30                  35                  40 ggg ctt gag tgg atg gga tgg atc aac cct aac agt ggt ggc aca aac    196
Gly Leu Glu Trp Met Gly Trp Ile Asn Pro Asn Ser Gly Gly Thr Asn
 45                  50                  55 tat gca cag aag ttt cag ggc agg gtc acg atg acc agg gac acg tcc    244
Tyr Ala Gln Lys Phe Gln Gly Arg Val Thr Met Thr Arg Asp Thr Ser
 60                  65                  70                  75 atc agc aca gcc tac atg gag ctg agc agg ctg aga tct gac gac acg    292
Ile Ser Thr Ala Tyr Met Glu Leu Ser Arg Leu Arg Ser Asp Asp Thr
             80                  85                  90 gcc gtg tat tac tgt gca aaa gat tct tac tct cgt cat ttc tac tct    340
Ala Val Tyr Tyr Cys Ala Lys Asp Ser Tyr Ser Arg His Phe Tyr Ser
         95                  100                 105 tgg tgg gcc ttt gat tat tgg ggc caa ggt acc ctg gtc acc gtc tcc    388
Trp Trp Ala Phe Asp Tyr Trp Gly Gln Gly Thr Leu Val Thr Val Ser
     110                 115                 120 agt                                                                  391
Ser
```

<210> SEQ ID NO 99
<211> LENGTH: 124
<212> TYPE: PRT
<213> ORGANISM: Artificial Sequence
<220> FEATURE:
<223> OTHER INFORMATION: Synthetic Construct

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr

```
                65                  70                  75                  80
Met Glu Leu Ser Arg Leu Arg Ser Asp Asp Thr Ala Val Tyr Tyr Cys
                        85                  90                  95

Ala Lys Asp Ser Tyr Ser Arg His Phe Tyr Ser Trp Trp Ala Phe Asp
                    100                 105                 110

Tyr Trp Gly Gln Gly Thr Leu Val Thr Val Ser Ser
        115                 120

<210> SEQ ID NO 100
<211> LENGTH: 5
<212> TYPE: PRT
<213> ORGANISM: Artificial Sequence
<220> FEATURE:
<223> OTHER INFORMATION: MF3163 CDR1

<400> SEQUENCE: 100

Gly Tyr Tyr Met His
1               5

<210> SEQ ID NO 101
<211> LENGTH: 17
<212> TYPE: PRT
<213> ORGANISM: Artificial Sequence
<220> FEATURE:
<223> OTHER INFORMATION: MF3163 CDR2

<400> SEQUENCE: 101

Trp Ile Asn Pro Asn Ser Gly Gly Thr Asn Tyr Ala Gln Lys Phe Gln
1               5                   10                  15

Gly

<210> SEQ ID NO 102
<211> LENGTH: 15
<212> TYPE: PRT
<213> ORGANISM: Artificial Sequence
<220> FEATURE:
<223> OTHER INFORMATION: MF3163 CDR3

<400> SEQUENCE: 102

Asp Ser Tyr Ser Arg His Phe Tyr Ser Trp Trp Ala Phe Asp Tyr
1               5                   10                  15

<210> SEQ ID NO 103
<211> LENGTH: 382
<212> TYPE: DNA
<213> ORGANISM: Artificial Sequence
<220> FEATURE:
<223> OTHER INFORMATION: MF3099: heavy chain variable region sequence of
      an erbB-3 binding antibody
<220> FEATURE:
<221> NAME/KEY: CDS
<222> LOCATION: (20)..(382)

<400> SEQUENCE: 103
ggcccagccg gccatggcc gag gtc cag ctg cag cag cct ggg gct gag ctg      52
                     Glu Val Gln Leu Gln Gln Pro Gly Ala Glu Leu
                      1               5                  10 gtg agg cct ggg act tca gtg aag ttg tcc tgc aag gct tct ggc tac     100
Val Arg Pro Gly Thr Ser Val Lys Leu Ser Cys Lys Ala Ser Gly Tyr
             15                  20                  25 acc ttc acc agc tac tgg atg cac tgg gta aag cag agg cct gga caa     148
Thr Phe Thr Ser Tyr Trp Met His Trp Val Lys Gln Arg Pro Gly Gln
         30                  35                  40 ggc ctt gag tgg atc gga att ctt gat cct tct gat agt tat act acc     196
```

```
Gly Leu Glu Trp Ile Gly Ile Leu Asp Pro Ser Asp Ser Tyr Thr Thr
        45              50              55 tac aat caa aag ttc aag ggc aag gcc aca tta aca gta gac aca tcc    244
Tyr Asn Gln Lys Phe Lys Gly Lys Ala Thr Leu Thr Val Asp Thr Ser
 60              65              70              75 tcc agc ata gcc tac atg cag ctc agc agc ctg aca tct gag gac tct    292
Ser Ser Ile Ala Tyr Met Gln Leu Ser Ser Leu Thr Ser Glu Asp Ser
             80              85              90 gcg ctc tat tac tgt gca aga ggg gga gat tac gac gag gga ggt gct    340
Ala Leu Tyr Tyr Cys Ala Arg Gly Gly Asp Tyr Asp Glu Gly Gly Ala
             95             100             105 atg gac tac tgg ggt caa gga acc tcg gtc acc gtc tcc agt            382
Met Asp Tyr Trp Gly Gln Gly Thr Ser Val Thr Val Ser Ser
        110             115             120

<210> SEQ ID NO 104
<211> LENGTH: 121
<212> TYPE: PRT
<213> ORGANISM: Artificial Sequence
<220> FEATURE:
<223> OTHER INFORMATION: Synthetic Construct

<400> SEQUENCE: 104

Glu Val Gln Leu Gln Gln Pro Gly Ala Glu Leu Val Arg Pro Gly Thr
 1               5                  10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Gln Gly Leu Glu Trp Ile
         35                  40                  45

Gly Ile Leu Asp Pro Ser Asp Ser Tyr Thr Thr Tyr Asn Gln Lys Phe
     50                  55                  60

Lys Gly Lys Ala Thr Leu Thr Val Asp Thr Ser Ser Ser Ile Ala Tyr
 65                  70                  75                  80

Met Gln Leu Ser Ser Leu Thr Ser Glu Asp Ser Ala Leu Tyr Tyr Cys
                 85                  90                  95

Ala Arg Gly Gly Asp Tyr Asp Glu Gly Gly Ala Met Asp Tyr Trp Gly
            100                 105                 110

Gln Gly Thr Ser Val Thr Val Ser Ser
        115                 120

<210> SEQ ID NO 105
<211> LENGTH: 5
<212> TYPE: PRT
<213> ORGANISM: Artificial Sequence
<220> FEATURE:
<223> OTHER INFORMATION: MF3099 CDR1

<400> SEQUENCE: 105

Ser Tyr Trp Met His
 1               5

<210> SEQ ID NO 106
<211> LENGTH: 17
<212> TYPE: PRT
<213> ORGANISM: Artificial Sequence
<220> FEATURE:
<223> OTHER INFORMATION: MF3099 CDR2

<400> SEQUENCE: 106

Ile Leu Asp Pro Ser Asp Ser Tyr Thr Thr Tyr Asn Gln Lys Phe Lys
 1               5                  10                  15
```

<210> SEQ ID NO 107
<211> LENGTH: 12
<212> TYPE: PRT
<213> ORGANISM: Artificial Sequence
<220> FEATURE:
<223> OTHER INFORMATION: MF3099 CDR3

<400> SEQUENCE: 107

Gly Gly Asp Tyr Asp Glu Gly Gly Ala Met Asp Tyr
1               5                   10

<210> SEQ ID NO 108
<211> LENGTH: 391
<212> TYPE: DNA
<213> ORGANISM: Artificial Sequence
<220> FEATURE:
<223> OTHER INFORMATION: MF3307: heavy chain variable region sequence of an erbB-3 binding antibody
<220> FEATURE:
<221> NAME/KEY: CDS
<222> LOCATION: (20)..(391)

<400> SEQUENCE: 108

```
ggcccagccg gccatggcc cag gtg cag ctg gtg cag tct ggg gct gag gtg      52
                      Gln Val Gln Leu Val Gln Ser Gly Ala Glu Val
                        1               5                  10 aag aag cct ggg gcc tca gtg aag gtc tcc tgc aag gct tct gga tac     100
Lys Lys Pro Gly Ala Ser Val Lys Val Ser Cys Lys Ala Ser Gly Tyr
             15                  20                  25 acc ttc acc ggc tac tat atg cac tgg gtg cga cag gcc cct gga caa     148
Thr Phe Thr Gly Tyr Tyr Met His Trp Val Arg Gln Ala Pro Gly Gln
         30                  35                  40 ggg ctt gag tgg atg gga tgg atc aac cct aac agt ggt ggc aca aac     196
Gly Leu Glu Trp Met Gly Trp Ile Asn Pro Asn Ser Gly Gly Thr Asn
     45                  50                  55 tat gca cag aag ttt cag ggc agg gtc acg atg acc agg gac acg tcc     244
Tyr Ala Gln Lys Phe Gln Gly Arg Val Thr Met Thr Arg Asp Thr Ser
 60                  65                  70                  75 atc agc aca gcc tac atg gag ctg agc agg ctg aga tct gac gac acg     292
Ile Ser Thr Ala Tyr Met Glu Leu Ser Arg Leu Arg Ser Asp Asp Thr
                 80                  85                  90 gcc gtg tat tac tgt gca aga ggt tct cgt aaa cgt ctg tct aac tac     340
Ala Val Tyr Tyr Cys Ala Arg Gly Ser Arg Lys Arg Leu Ser Asn Tyr
             95                 100                 105 ttc aac gcc ttt gat tat tgg ggc caa ggt acc ctg gtc acc gtc tcc     388
Phe Asn Ala Phe Asp Tyr Trp Gly Gln Gly Thr Leu Val Thr Val Ser
        110                 115                 120 agt                                                                  391
Ser
```

<210> SEQ ID NO 109
<211> LENGTH: 124
<212> TYPE: PRT
<213> ORGANISM: Artificial Sequence
<220> FEATURE:
<223> OTHER INFORMATION: Synthetic Construct

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

```
Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ser Arg Lys Arg Leu Ser Asn Tyr Phe Asn Ala Phe Asp
            100                 105                 110

Tyr Trp Gly Gln Gly Thr Leu Val Thr Val Ser Ser
        115                 120

<210> SEQ ID NO 110
<211> LENGTH: 5
<212> TYPE: PRT
<213> ORGANISM: Artificial Sequence
<220> FEATURE:
<223> OTHER INFORMATION: MF3307 CDR1

<400> SEQUENCE: 110

Gly Tyr Tyr Met His
1               5

<210> SEQ ID NO 111
<211> LENGTH: 17
<212> TYPE: PRT
<213> ORGANISM: Artificial Sequence
<220> FEATURE:
<223> OTHER INFORMATION: MF3307 CDR2

<400> SEQUENCE: 111

Trp Ile Asn Pro Asn Ser Gly Gly Thr Asn Tyr Ala Gln Lys Phe Gln
1               5                   10                  15

Gly

<210> SEQ ID NO 112
<211> LENGTH: 15
<212> TYPE: PRT
<213> ORGANISM: Artificial Sequence
<220> FEATURE:
<223> OTHER INFORMATION: MF3307 CDR3

<400> SEQUENCE: 112

Gly Ser Arg Lys Arg Leu Ser Asn Tyr Phe Asn Ala Phe Asp Tyr
1               5                   10                  15

<210> SEQ ID NO 113
<211> LENGTH: 372
<212> TYPE: DNA
<213> ORGANISM: Artificial Sequence
<220> FEATURE:
<223> OTHER INFORMATION: MF6055_VH
<220> FEATURE:
<221> NAME/KEY: CDS
<222> LOCATION: (1)..(372)

<400> SEQUENCE: 113 cag gtg cag ctg gtg cag tct ggg gct gac gtg aag aag cct ggg gcc      48
Gln Val Gln Leu Val Gln Ser Gly Ala Asp Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
```

```
                   20                  25                  30
tat atg cac tgg gtg cga cag gcc cct gga caa gct ctt gag tgg atg      144
Tyr Met His Trp Val Arg Gln Ala Pro Gly Gln Ala Leu Glu Trp Met
         35                  40                  45 gga tgg atc aac cct tct agt ggt ggc aca aac tat gca aag aag ttt      192
Gly Trp Ile Asn Pro Ser Ser Gly Gly Thr Asn Tyr Ala Lys Lys Phe
 50                  55                  60 cag ggc agg gtc acg atg acc agg gag acg tcc aca agc aca gcc tac      240
Gln Gly Arg Val Thr Met Thr Arg Glu Thr Ser Thr Ser Thr Ala Tyr
 65                  70                  75                  80 atg gag ctg agc agg ctg aga tct gac gac acg gct acg tat tac tgt      288
Met Glu Leu Ser Arg Leu Arg Ser Asp Asp Thr Ala Thr Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
                100                 105                 110 tat tgg ggc caa ggt acc ctg gtc acc gtc tcc agt                      372
Tyr Trp Gly Gln Gly Thr Leu Val Thr Val Ser Ser
        115                 120

<210> SEQ ID NO 114
<211> LENGTH: 124
<212> TYPE: PRT
<213> ORGANISM: Artificial Sequence
<220> FEATURE:
<223> OTHER INFORMATION: Synthetic Construct

<400> SEQUENCE: 114

Gln Val Gln Leu Val Gln Ser Gly Ala Asp Val Lys Lys Pro Gly Ala
1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
         35                  40                  45

Gly Trp Ile Asn Pro Ser Ser Gly Gly Thr Asn Tyr Ala Lys Lys Phe
 50                  55                  60

Gln Gly Arg Val Thr Met Thr Arg Glu Thr Ser Thr Ser Thr Ala Tyr
 65                  70                  75                  80

Met Glu Leu Ser Arg Leu Arg Ser Asp Asp Thr Ala Thr Tyr Tyr Cys
                 85                  90                  95

Ala Arg Asp His Gly Ser Arg His Phe Trp Ser Tyr Trp Gly Phe Asp
                100                 105                 110

Tyr Trp Gly Gln Gly Thr Leu Val Thr Val Ser Ser
        115                 120

<210> SEQ ID NO 115
<211> LENGTH: 372
<212> TYPE: DNA
<213> ORGANISM: Artificial Sequence
<220> FEATURE:
<223> OTHER INFORMATION: MF6056_VH
<220> FEATURE:
<221> NAME/KEY: CDS
<222> LOCATION: (1)..(372)

<400> SEQUENCE: 115 cag gtg cag ctg gtg cag tct ggg gct gac gtg aag aag cct ggg gcc       48
Gln Val Gln Leu Val Gln Ser Gly Ala Asp Val Lys Lys Pro Gly Ala
1               5                  10                  15 tca gtg aag gtc acg tgc aag gct tct gga tac acc ttc acc ggc tac       96
Ser Val Lys Val Thr Cys Lys Ala Ser Gly Tyr Thr Phe Thr Gly Tyr
```

```
tat atg cac tgg gtg cga cag gcc cct gga caa gct ctt gag tgg atg      144
Tyr Met His Trp Val Arg Gln Ala Pro Gly Gln Ala Leu Glu Trp Met
         35                  40                  45 gga tgg atc aac cct tct agt ggt ggc aca aac tat gca aag aag ttt      192
Gly Trp Ile Asn Pro Ser Ser Gly Gly Thr Asn Tyr Ala Lys Lys Phe
 50                  55                  60 cag ggc agg gtc tct atg acc agg gag acg tcc aca agc aca gcc tac      240
Gln Gly Arg Val Ser Met Thr Arg Glu Thr Ser Thr Ser Thr Ala Tyr
 65                  70                  75                  80 atg cag ctg agc agg ctg aga tct gac gac acg gct acg tat tac tgt      288
Met Gln Leu Ser Arg Leu Arg Ser Asp Asp Thr Ala Thr Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
             100                 105                 110 tat tgg ggc caa ggt acc ctg gtc acc gtc tcc agt                      372
Tyr Trp Gly Gln Gly Thr Leu Val Thr Val Ser Ser
         115                 120

<210> SEQ ID NO 116
<211> LENGTH: 124
<212> TYPE: PRT
<213> ORGANISM: Artificial Sequence
<220> FEATURE:
<223> OTHER INFORMATION: Synthetic Construct

<400> SEQUENCE: 116

Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
        35                  40                  45

Gly Trp Ile Asn Pro Ser Ser Gly Gly Thr Asn Tyr Ala Lys Lys Phe
 50                 55                  60

Gln Gly Arg Val Ser Met Thr Arg Glu Thr Ser Thr Ser Thr Ala Tyr
 65                 70                  75                  80

Met Gln Leu Ser Arg Leu Arg Ser Asp Asp Thr Ala Thr Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 117
<211> LENGTH: 372
<212> TYPE: DNA
<213> ORGANISM: Artificial Sequence
<220> FEATURE:
<223> OTHER INFORMATION: MF6057_VH
<220> FEATURE:
<221> NAME/KEY: CDS
<222> LOCATION: (1)..(372)

<400> SEQUENCE: 117 cag gtg cag ctg gtg cag tct ggg gct gat gtg aag aag cct ggg gcc      48
Gln Val Gln Leu Val Gln Ser Gly Ala Asp Val Lys Lys Pro Gly Ala
1               5                   10                  15 tca gtg aag gtc acg tgc aag gct tct gga tac acc ttc acc ggc tac      96
Ser Val Lys Val Thr Cys Lys Ala Ser Gly Tyr Thr Phe Thr Gly Tyr
            20                  25                  30
```

```
              20                  25                  30
tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc aac cct cag agt ggt ggc aca aac tat gca cag aag ttt      192
Gly Trp Ile Asn Pro Gln Ser Gly Gly Thr Asn Tyr Ala Gln Lys Phe
 50                  55                  60 cag ggc agg gtc acg atg acc agg gac acg tcc atc agc aca gcc tac      240
Gln Gly Arg Val Thr Met Thr Arg Asp Thr Ser Ile Ser Thr Ala Tyr
 65                  70                  75                  80 atg cag ctg agc agg ctg aga tct gac gac acg gct gtg tat tac tgt      288
Met Gln Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
             100                 105                 110 tat tgg ggc caa ggt acc ctg gtc acc gtc tcc agt                       372
Tyr Trp Gly Gln Gly Thr Leu Val Thr Val Ser Ser
         115                 120

<210> SEQ ID NO 118
<211> LENGTH: 124
<212> TYPE: PRT
<213> ORGANISM: Artificial Sequence
<220> FEATURE:
<223> OTHER INFORMATION: Synthetic Construct

<400> SEQUENCE: 118

Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 119
<211> LENGTH: 372
<212> TYPE: DNA
<213> ORGANISM: Artificial Sequence
<220> FEATURE:
<223> OTHER INFORMATION: MF6058_VH
<220> FEATURE:
<221> NAME/KEY: CDS
<222> LOCATION: (1)..(372)

<400> SEQUENCE: 119 cag gtg cag ctg gtg cag tct ggg gct gac gtg aag aag cct ggg gcc       48
Gln Val Gln Leu Val Gln Ser Gly Ala Asp Val Lys Lys Pro Gly Ala
1               5                   10                  15 tca gtg aag gtc acg tgc aag gct tct gga tac acc ttc acc ggc tac       96
Ser Val Lys Val Thr Cys Lys Ala Ser Gly Tyr Thr Phe Thr Gly Tyr
```

```
                   20                  25                  30
tat atg cac tgg gtg cga cag gcc cct gga caa gct ctt gag tgg atg       144
Tyr Met His Trp Val Arg Gln Ala Pro Gly Gln Ala Leu Glu Trp Met
         35                  40                  45 gga tgg atc aac cct caa agt ggt ggc aca aac tat gca aag aag ttt       192
Gly Trp Ile Asn Pro Gln Ser Gly Gly Thr Asn Tyr Ala Lys Lys Phe
 50                  55                  60 cag ggc agg gtc tct atg acc agg gag acg tcc aca agc aca gcc tac       240
Gln Gly Arg Val Ser Met Thr Arg Glu Thr Ser Thr Ser Thr Ala Tyr
 65                  70                  75                  80 atg cag ctg agc agg ctg aga tct gac gac acg gct acg tat tac tgt       288
Met Gln Leu Ser Arg Leu Arg Ser Asp Asp Thr Ala Thr Tyr Tyr Cys
                 85                  90                  95 gca aga gat cat ggt tct cgt cat ttc tgg tct tac tgg ggc ttt gat       336
Ala Arg Asp His Gly Ser Arg His Phe Trp Ser Tyr Trp Gly Phe Asp
                100                 105                 110 tat tgg ggc caa ggt acc ctg gtc acc gtc tcc agt                       372
Tyr Trp Gly Gln Gly Thr Leu Val Thr Val Ser Ser
            115                 120

<210> SEQ ID NO 120
<211> LENGTH: 124
<212> TYPE: PRT
<213> ORGANISM: Artificial Sequence
<220> FEATURE:
<223> OTHER INFORMATION: Synthetic Construct

<400> SEQUENCE: 120

Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
         35                  40                  45

Gly Trp Ile Asn Pro Gln Ser Gly Gly Thr Asn Tyr Ala Lys Lys Phe
 50                  55                  60

Gln Gly Arg Val Ser Met Thr Arg Glu Thr Ser Thr Ser Thr Ala Tyr
 65                  70                  75                  80

Met Gln Leu Ser Arg Leu Arg Ser Asp Asp Thr Ala Thr Tyr Tyr Cys
                 85                  90                  95

Ala Arg Asp His Gly Ser Arg His Phe Trp Ser Tyr Trp Gly Phe Asp
                100                 105                 110

Tyr Trp Gly Gln Gly Thr Leu Val Thr Val Ser Ser
            115                 120

<210> SEQ ID NO 121
<211> LENGTH: 372
<212> TYPE: DNA
<213> ORGANISM: Artificial Sequence
<220> FEATURE:
<223> OTHER INFORMATION: MF6059_VH
<220> FEATURE:
<221> NAME/KEY: CDS
<222> LOCATION: (1)..(372)

<400> SEQUENCE: 121 cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
```

```
tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45 gga tgg atc aac cct ggc agt ggt tct aca aac tat gca cag aag ttt      192
Gly Trp Ile Asn Pro Gly Ser Gly Ser Thr Asn Tyr Ala Gln Lys Phe
 50                  55                  60 cag ggc agg gtc acg atg acc agg gac acg tcc atc agc aca gcc tac      240
Gln Gly Arg Val Thr Met Thr Arg Asp Thr Ser Ile Ser Thr Ala Tyr
 65                  70                  75                  80 atg gag ctg agc agg ctg aga tct gac gac acg gct gtg tat tac tgt      288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
             100                 105                 110 tat tgg ggc caa ggt acc ctg gtc acc gtc tcc agt                      372
Tyr Trp Gly Gln Gly Thr Leu Val Thr Val Ser Ser
         115                 120
```

<210> SEQ ID NO 122
<211> LENGTH: 124
<212> TYPE: PRT
<213> ORGANISM: Artificial Sequence
<220> FEATURE:
<223> OTHER INFORMATION: Synthetic Construct

<400> SEQUENCE: 122

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gly Ser Gly Ser Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp His Gly Ser Arg His Phe Trp Ser Tyr Trp Gly Phe Asp
             100                 105                 110

Tyr Trp Gly Gln Gly Thr Leu Val Thr Val Ser Ser
         115                 120
```

<210> SEQ ID NO 123
<211> LENGTH: 372
<212> TYPE: DNA
<213> ORGANISM: Artificial Sequence
<220> FEATURE:
<223> OTHER INFORMATION: MF6060_VH
<220> FEATURE:
<221> NAME/KEY: CDS
<222> LOCATION: (1)..(372)

<400> SEQUENCE: 123

```
cag gtg cag ctg gtg cag tct ggg gct gac gtg aag aag cct ggg gcc      48
Gln Val Gln Leu Val Gln Ser Gly Ala Asp Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
```

```
tat atg cac tgg gtg cga cag gcc cct gga caa gct ctt gag tgg atg      144
Tyr Met His Trp Val Arg Gln Ala Pro Gly Gln Ala Leu Glu Trp Met
        35                  40                  45 gga tgg atc aac cct caa agt ggt ggc aca aac tat gca aag aag ttt      192
Gly Trp Ile Asn Pro Gln Ser Gly Gly Thr Asn Tyr Ala Lys Lys Phe
 50                  55                  60 cag ggc agg gtc acg atg acc agg gag acg tcc aca agc aca gcc tac      240
Gln Gly Arg Val Thr Met Thr Arg Glu Thr Ser Thr Ser Thr Ala Tyr
65                  70                  75                  80 atg gag ctg agc agg ctg aga tct gac gac acg gct acg tat tac tgt      288
Met Glu Leu Ser Arg Leu Arg Ser Asp Asp Thr Ala Thr Tyr Tyr Cys
                85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
            100                 105                 110 tat tgg ggc caa ggt acc ctg gtc acc gtc tcc agt                      372
Tyr Trp Gly Gln Gly Thr Leu Val Thr Val Ser Ser
        115                 120
```

<210> SEQ ID NO 124
<211> LENGTH: 124
<212> TYPE: PRT
<213> ORGANISM: Artificial Sequence
<220> FEATURE:
<223> OTHER INFORMATION: Synthetic Construct

<400> SEQUENCE: 124

```
Gln Val Gln Leu Val Gln Ser Gly Ala Asp Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
        35                  40                  45

Gly Trp Ile Asn Pro Gln Ser Gly Gly Thr Asn Tyr Ala Lys Lys Phe
 50                  55                  60

Gln Gly Arg Val Thr Met Thr Arg Glu Thr Ser Thr Ser Thr Ala Tyr
65                  70                  75                  80

Met Glu Leu Ser Arg Leu Arg Ser Asp Asp Thr Ala Thr Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 125
<211> LENGTH: 372
<212> TYPE: DNA
<213> ORGANISM: Artificial Sequence
<220> FEATURE:
<223> OTHER INFORMATION: MF6061_VH
<220> FEATURE:
<221> NAME/KEY: CDS
<222> LOCATION: (1)..(372)

<400> SEQUENCE: 125

```
cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
```

```
tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt      192
Gly Trp Ile Asn Pro Gln Ser Gly Gly Thr Asn Tyr Ala Gln Lys Phe
 50                  55                  60 aag ggc agg gtc acg atg acc agg gac acg tcc acc agc aca gcc tac      240
Lys Gly Arg Val Thr Met Thr Arg Asp Thr Ser Thr Ser Thr Ala Tyr
 65                  70                  75                  80 atg gag ctg agc agg ctg aga tct gac gac acg gct gtg tat tac tgt      288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
            100                 105                 110 tat tgg ggc caa ggt acc ctg gtc acc gtc tcc agt                      372
Tyr Trp Gly Gln Gly Thr Leu Val Thr Val Ser Ser
        115                 120
```

<210> SEQ ID NO 126
<211> LENGTH: 124
<212> TYPE: PRT
<213> ORGANISM: Artificial Sequence
<220> FEATURE:
<223> OTHER INFORMATION: Synthetic Construct

<400> SEQUENCE: 126

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Gln Ser Gly Gly Thr Asn Tyr Ala Gln Lys Phe
 50                  55                  60

Lys Gly Arg Val Thr Met Thr Arg Asp Thr Ser Thr Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 127
<211> LENGTH: 372
<212> TYPE: DNA
<213> ORGANISM: Artificial Sequence
<220> FEATURE:
<223> OTHER INFORMATION: MF6062_VH
<220> FEATURE:
<221> NAME/KEY: CDS
<222> LOCATION: (1)..(372)

<400> SEQUENCE: 127

```
cag gtg cag ctg gtg cag tct ggg gct gag gtg aag aag cct ggg gcc       48
Gln Val Gln Leu Val Gln Ser Gly Ala Glu Val Lys Lys Pro Gly Ala
  1               5                  10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
```

```
                     20                  25                  30
tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc aac cct ggc agt ggt tct aca aac tat gca cag aag ttt      192
Gly Trp Ile Asn Pro Gly Ser Gly Ser Thr Asn Tyr Ala Gln Lys Phe
 50                  55                  60 cag ggc agg gtc acg atg acc agg gac acg tcc aca agc aca gcc tac      240
Gln Gly Arg Val Thr Met Thr Arg Asp Thr Ser Thr Ser Thr Ala Tyr
 65                  70                  75                  80 atg gag ctg agc agg ctg aga tct gac gac acg gct gtg tat tac tgt      288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
                 100                 105                 110 tat tgg ggc caa ggt acc ctg gtc acc gtc tcc agt                      372
Tyr Trp Gly Gln Gly Thr Leu Val Thr Val Ser Ser
        115                 120

<210> SEQ ID NO 128
<211> LENGTH: 124
<212> TYPE: PRT
<213> ORGANISM: Artificial Sequence
<220> FEATURE:
<223> OTHER INFORMATION: Synthetic Construct

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gly Ser Gly Ser Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 129
<211> LENGTH: 372
<212> TYPE: DNA
<213> ORGANISM: Artificial Sequence
<220> FEATURE:
<223> OTHER INFORMATION: MF6063_VH
<220> FEATURE:
<221> NAME/KEY: CDS
<222> LOCATION: (1)..(372)

<400> SEQUENCE: 129 cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
```

```
                20                  25                  30
tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc aac cct cag agt ggt ggc aca aac tat gca aag aag ttt      192
Gly Trp Ile Asn Pro Gln Ser Gly Gly Thr Asn Tyr Ala Lys Lys Phe
 50                  55                  60 cag ggc agg gtc acg atg acc agg gac acg tcc acc agc aca gcc tac      240
Gln Gly Arg Val Thr Met Thr Arg Asp Thr Ser Thr Ser Thr Ala Tyr
 65                  70                  75                  80 atg gag ctg agc agg ctg aga tct gac gac acg gct gtg tat tac tgt      288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
             100                 105                 110 tat tgg ggc caa ggt acc ctg gtc acc gtc tcc agt                      372
Tyr Trp Gly Gln Gly Thr Leu Val Thr Val Ser Ser
         115                 120
```

<210> SEQ ID NO 130
<211> LENGTH: 124
<212> TYPE: PRT
<213> ORGANISM: Artificial Sequence
<220> FEATURE:
<223> OTHER INFORMATION: Synthetic Construct

<400> SEQUENCE: 130

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
         35                  40                  45

Gly Trp Ile Asn Pro Gln Ser Gly Gly Thr Asn Tyr Ala Lys Lys Phe
 50                  55                  60

Gln Gly Arg Val Thr Met Thr Arg Asp Thr Ser Thr Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp His Gly Ser Arg His Phe Trp Ser Tyr Trp Gly Phe Asp
             100                 105                 110

Tyr Trp Gly Gln Gly Thr Leu Val Thr Val Ser Ser
         115                 120
```

<210> SEQ ID NO 131
<211> LENGTH: 372
<212> TYPE: DNA
<213> ORGANISM: Artificial Sequence
<220> FEATURE:
<223> OTHER INFORMATION: MF6064_VH
<220> FEATURE:
<221> NAME/KEY: CDS
<222> LOCATION: (1)..(372)

<400> SEQUENCE: 131

```
cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
```

```
                    20                  25                  30
tat atg cac tgg gtg cga cag gcc cct gga aag ggg ctt gag tgg atg        144
Tyr Met His Trp Val Arg Gln Ala Pro Gly Lys Gly Leu Glu Trp Met
         35                  40                  45 gga tgg atc aac cct cag agt ggt ggc aca aac tat gca cag aag ttt        192
Gly Trp Ile Asn Pro Gln Ser Gly Gly Thr Asn Tyr Ala Gln Lys Phe
 50                  55                  60 cag ggc agg gtc acg atg acc agg gac acg tcc acg agc aca gcc tac        240
Gln Gly Arg Val Thr Met Thr Arg Asp Thr Ser Thr Ser Thr Ala Tyr
 65                  70                  75                  80 atg gag ctg agc agg ctg aga tct gac gac acg gct gtg tat tac tgt        288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat        336
Ala Arg Asp His Gly Ser Arg His Phe Trp Ser Tyr Trp Gly Phe Asp
                100                 105                 110 tat tgg ggc caa ggt acc ctg gtc acc gtc tcc agt                        372
Tyr Trp Gly Gln Gly Thr Leu Val Thr Val Ser Ser
        115                 120

<210> SEQ ID NO 132
<211> LENGTH: 124
<212> TYPE: PRT
<213> ORGANISM: Artificial Sequence
<220> FEATURE:
<223> OTHER INFORMATION: Synthetic Construct

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Lys Gly Leu Glu Trp Met
        35                  40                  45

Gly Trp Ile Asn Pro Gln Ser Gly Gly Thr Asn Tyr Ala Gln Lys Phe
 50                 55                  60

Gln Gly Arg Val Thr Met Thr Arg Asp Thr Ser Thr Ser Thr Ala Tyr
 65                 70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 133
<211> LENGTH: 372
<212> TYPE: DNA
<213> ORGANISM: Artificial Sequence
<220> FEATURE:
<223> OTHER INFORMATION: MF6065_VH
<220> FEATURE:
<221> NAME/KEY: CDS
<222> LOCATION: (1)..(372)

<400> SEQUENCE: 133 cag gtg cag ctg gtg cag tct ggg gct gag gtg aag aag cct ggg gcc         48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc tct tac         96
Ser Val Lys Val Ser Cys Lys Ala Ser Gly Tyr Thr Phe Thr Ser Tyr
            20                  25                  30
```

```
tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45 gga tgg atc aac cct cag ggg ggt tct aca aac tat gca cag aag ttt      192
Gly Trp Ile Asn Pro Gln Gly Gly Ser Thr Asn Tyr Ala Gln Lys Phe
 50                  55                  60 cag ggc agg gtc acg atg acc agg gac acg tcc acc agc aca gtg tac      240
Gln Gly Arg Val Thr Met Thr Arg Asp Thr Ser Thr Ser Thr Val Tyr
 65                  70                  75                  80 atg gag ctg agc agg ctg aga tct gag gac acg gct gtg tat tac tgt      288
Met Glu Leu Ser Arg Leu Arg Ser Glu Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
            100                 105                 110 tat tgg ggc caa ggt acc ctg gtc acc gtc tcc agt                      372
Tyr Trp Gly Gln Gly Thr Leu Val Thr Val Ser Ser
        115                 120
```

<210> SEQ ID NO 134
<211> LENGTH: 124
<212> TYPE: PRT
<213> ORGANISM: Artificial Sequence
<220> FEATURE:
<223> OTHER INFORMATION: Synthetic Construct

<400> SEQUENCE: 134

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Gln Gly Gly Ser Thr Asn Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Arg Leu Arg Ser Glu Asp Thr Ala Val Tyr Tyr Cys
                 85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 135
<211> LENGTH: 372
<212> TYPE: DNA
<213> ORGANISM: Artificial Sequence
<220> FEATURE:
<223> OTHER INFORMATION: MF6066_VH
<220> FEATURE:
<221> NAME/KEY: CDS
<222> LOCATION: (1)..(372)

<400> SEQUENCE: 135

```
cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
```

```
                       20                  25                  30
tat atg cac tgg gtg cga cag gcc cct gga caa ggg ctt gag tgg atg        144
Tyr Met His Trp Val Arg Gln Ala Pro Gly Gln Gly Leu Glu Trp Met
             35                  40                  45 gga tgg atc aac cct cag agt ggt tct aca aac tat gca cag aag ttt        192
Gly Trp Ile Asn Pro Gln Ser Gly Ser Thr Asn Tyr Ala Gln Lys Phe
     50                  55                  60 cag ggc agg gtc acg atg acc agg gac acg tcc acc agc aca gcc tac        240
Gln Gly Arg Val Thr Met Thr Arg Asp Thr Ser Thr Ser Thr Ala Tyr
 65                  70                  75                  80 atg gag ctg agc tct ctg aga tct gag gac acg gct gtg tat tac tgt        288
Met Glu Leu Ser Ser Leu Arg Ser Glu Asp Thr Ala Val Tyr Tyr Cys
                 85                  90                  95 gca aga gat cat ggt tct cgt cat ttc tgg tct tac tgg ggc ttt gat        336
Ala Arg Asp His Gly Ser Arg His Phe Trp Ser Tyr Trp Gly Phe Asp
             100                 105                 110 tat tgg ggc caa ggt acc ctg gtc acc gtc tcc agt                        372
Tyr Trp Gly Gln Gly Thr Leu Val Thr Val Ser Ser
         115                 120

<210> SEQ ID NO 136
<211> LENGTH: 124
<212> TYPE: PRT
<213> ORGANISM: Artificial Sequence
<220> FEATURE:
<223> OTHER INFORMATION: Synthetic Construct

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Ser Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 137
<211> LENGTH: 372
<212> TYPE: DNA
<213> ORGANISM: Artificial Sequence
<220> FEATURE:
<223> OTHER INFORMATION: MF6067_VH
<220> FEATURE:
<221> NAME/KEY: CDS
<222> LOCATION: (1)..(372)

<400> SEQUENCE: 137 cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac        96
Ser Val Lys Val Ser Cys Lys Ala Ser Gly Tyr Thr Phe Thr Gly Tyr
```

```
                20                  25                  30
tat atg cac tgg gtg cga cag gcc cct gga caa ggg ctt gag tgg atg        144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt        192
Gly Trp Ile Asn Pro Gln Ser Gly Gly Thr Asn Tyr Ala Gln Lys Phe
 50                  55                  60 cag ggc agg gtc acg atg acc agg gac acg tcc acc agc aca gtc tac        240
Gln Gly Arg Val Thr Met Thr Arg Asp Thr Ser Thr Ser Thr Val Tyr
 65                  70                  75                  80 atg gag ctg agc tct ctg aga tct gac gac acg gct gtg tat tac tgt        288
Met Glu Leu Ser Ser Leu Arg Ser Asp Asp Thr Ala Val Tyr Tyr Cys
                85                  90                  95 gca aga gat cat ggt tct cgt cat ttc tgg tct tac tgg ggc ttt gat        336
Ala Arg Asp His Gly Ser Arg His Phe Trp Ser Tyr Trp Gly Phe Asp
                100                 105                 110 tat tgg ggc caa ggt acc ctg gtc acc gtc tcc agt                        372
Tyr Trp Gly Gln Gly Thr Leu Val Thr Val Ser Ser
        115                 120

<210> SEQ ID NO 138
<211> LENGTH: 124
<212> TYPE: PRT
<213> ORGANISM: Artificial Sequence
<220> FEATURE:
<223> OTHER INFORMATION: Synthetic Construct

<400> SEQUENCE: 138

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Gln Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 139
<211> LENGTH: 372
<212> TYPE: DNA
<213> ORGANISM: Artificial Sequence
<220> FEATURE:
<223> OTHER INFORMATION: MF6068_VH
<220> FEATURE:
<221> NAME/KEY: CDS
<222> LOCATION: (1)..(372)

<400> SEQUENCE: 139 cag gtg cag ctg gtg cag tct ggg gct gag gtg aag aag cct ggg gcc         48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac         96
Ser Val Lys Val Ser Cys Lys Ala Ser Gly Tyr Thr Phe Thr Gly Tyr
```

```
                    20                  25                  30
tat atg cac tgg gtg cga cag gcc cct gga caa ggg ctt gag tgg atg    144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt    192
Gly Trp Ile Asn Pro Gln Ser Gly Gly Thr Asn Tyr Ala Gln Lys Phe
 50                  55                  60 cag ggc agg gtc acg atg acc agg gac acg tcc acc agc aca gcc tac    240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt    288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat    336
Ala Arg Asp His Gly Ser Arg His Phe Trp Ser Tyr Trp Gly Phe Asp
            100                 105                 110 tat tgg ggc caa ggt acc ctg gtc acc gtc tcc agt                    372
Tyr Trp Gly Gln Gly Thr Leu Val Thr Val Ser Ser
        115                 120

<210> SEQ ID NO 140
<211> LENGTH: 124
<212> TYPE: PRT
<213> ORGANISM: Artificial Sequence
<220> FEATURE:
<223> OTHER INFORMATION: Synthetic Construct

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
 50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 141
<211> LENGTH: 372
<212> TYPE: DNA
<213> ORGANISM: Artificial Sequence
<220> FEATURE:
<223> OTHER INFORMATION: MF6069_VH
<220> FEATURE:
<221> NAME/KEY: CDS
<222> LOCATION: (1)..(372)

<400> SEQUENCE: 141 cag gtg cag ctg gtg cag tct ggg gct gag gtg aag aag cct ggg gcc    48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac    96
Ser Val Lys Val Ser Cys Lys Ala Ser Gly Tyr Thr Phe Thr Gly Tyr
```

```
                    20                  25                  30
tat atg cac tgg gtg cga cag gcc cct gga caa ggg ctt gag tgg atg        144
Tyr Met His Trp Val Arg Gln Ala Pro Gly Gln Gly Leu Glu Trp Met
         35                  40                  45 gga tgg atc aac cct cag agt ggt ggc aca aac tat gca cag aag ttt        192
Gly Trp Ile Asn Pro Gln Ser Gly Gly Thr Asn Tyr Ala Gln Lys Phe
 50                  55                  60 cag ggc agg gtc acg atg acc agg gac acg tcc atc agc aca gcc tac        240
Gln Gly Arg Val Thr Met Thr Arg Asp Thr Ser Ile Ser Thr Ala Tyr
 65                  70                  75                  80 atg gag ctg agc agg ctg aga tct gac gac acg gct gtg tat tac tgt        288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat        336
Ala Arg Asp His Gly Ser Arg His Phe Trp Ser Tyr Trp Gly Phe Asp
                100                 105                 110 tat tgg ggc caa ggt acc ctg gtc acc gtc tcc agt                        372
Tyr Trp Gly Gln Gly Thr Leu Val Thr Val Ser Ser
        115                 120

<210> SEQ ID NO 142
<211> LENGTH: 124
<212> TYPE: PRT
<213> ORGANISM: Artificial Sequence
<220> FEATURE:
<223> OTHER INFORMATION: Synthetic Construct

<400> SEQUENCE: 142

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 143
<211> LENGTH: 372
<212> TYPE: DNA
<213> ORGANISM: Artificial Sequence
<220> FEATURE:
<223> OTHER INFORMATION: MF6070_VH
<220> FEATURE:
<221> NAME/KEY: CDS
<222> LOCATION: (1)..(372)

<400> SEQUENCE: 143 cag gtg cag ctg gtg cag tct ggg gct gag gtg aag aag cct ggg gcc         48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc tct tac         96
Ser Val Lys Val Ser Cys Lys Ala Ser Gly Tyr Thr Phe Thr Ser Tyr
            20                  25                  30
```

```
tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc aac cct tct ggg ggt tct aca aac tat gca cag aag ttt      192
Gly Trp Ile Asn Pro Ser Gly Gly Ser Thr Asn Tyr Ala Gln Lys Phe
 50                  55                  60 cag ggc agg gtc acg atg acc agg gac acg tcc acc agc aca gtg tac      240
Gln Gly Arg Val Thr Met Thr Arg Asp Thr Ser Thr Ser Thr Val Tyr
 65                  70                  75                  80 atg gag ctg agc agg ctg aga tct gag gac acg gct gtg tat tac tgt      288
Met Glu Leu Ser Arg Leu Arg Ser Glu Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
             100                 105                 110 tat tgg ggc caa ggt acc ctg gtc acc gtc tcc agt                      372
Tyr Trp Gly Gln Gly Thr Leu Val Thr Val Ser Ser
         115                 120
```

<210> SEQ ID NO 144
<211> LENGTH: 124
<212> TYPE: PRT
<213> ORGANISM: Artificial Sequence
<220> FEATURE:
<223> OTHER INFORMATION: Synthetic Construct

<400> SEQUENCE: 144

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Trp Ile Asn Pro Ser Gly Gly Ser Thr Asn Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Arg Leu Arg Ser Glu Asp Thr Ala Val Tyr Tyr Cys
                 85                  90                  95

Ala Arg Asp His Gly Ser Arg His Phe Trp Ser Tyr Trp Gly Phe Asp
             100                 105                 110

Tyr Trp Gly Gln Gly Thr Leu Val Thr Val Ser Ser
         115                 120
```

<210> SEQ ID NO 145
<211> LENGTH: 372
<212> TYPE: DNA
<213> ORGANISM: Artificial Sequence
<220> FEATURE:
<223> OTHER INFORMATION: MF6071_VH
<220> FEATURE:
<221> NAME/KEY: CDS
<222> LOCATION: (1)..(372)

<400> SEQUENCE: 145

```
cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
```

```
                  20                  25                  30
tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45 gga tgg atc aac cct tct agt ggt tct aca aac tat gca cag aag ttt      192
Gly Trp Ile Asn Pro Ser Ser Gly Ser Thr Asn Tyr Ala Gln Lys Phe
 50                  55                  60 cag ggc agg gtc acg atg acc agg gac acg tcc acc agc aca gcc tac      240
Gln Gly Arg Val Thr Met Thr Arg Asp Thr Ser Thr Ser Thr Ala Tyr
 65                  70                  75                  80 atg gag ctg agc tct ctg aga tct gag gac acg gct gtg tat tac tgt      288
Met Glu Leu Ser Ser Leu Arg Ser Glu Asp Thr Ala Val Tyr Tyr Cys
                85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
            100                 105                 110 tat tgg ggc caa ggt acc ctg gtc acc gtc tcc agt                      372
Tyr Trp Gly Gln Gly Thr Leu Val Thr Val Ser Ser
        115                 120
```

<210> SEQ ID NO 146
<211> LENGTH: 124
<212> TYPE: PRT
<213> ORGANISM: Artificial Sequence
<220> FEATURE:
<223> OTHER INFORMATION: Synthetic Construct

<400> SEQUENCE: 146

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Ser Ser Gly Ser Thr Asn Tyr Ala Gln Lys Phe
     50                  55                  60

Gln Gly Arg Val Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 147
<211> LENGTH: 372
<212> TYPE: DNA
<213> ORGANISM: Artificial Sequence
<220> FEATURE:
<223> OTHER INFORMATION: MF6072_VH
<220> FEATURE:
<221> NAME/KEY: CDS
<222> LOCATION: (1)..(372)

<400> SEQUENCE: 147

```
cag gtg cag ctg gtg cag tct ggg gct gag gtg aag aag cct ggg gcc       48
Gln Val Gln Leu Val Gln Ser Gly Ala Glu Val Lys Lys Pro Gly Ala
  1               5                  10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
```

```
                    20                  25                  30
tat atg cac tgg gtg cga cag gcc cct gga caa ggg ctt gag tgg atg        144
Tyr Met His Trp Val Arg Gln Ala Pro Gly Gln Gly Leu Glu Trp Met
         35                  40                  45 gga tgg atc aac cct tct agt ggt ggc aca aac tat gca cag aag ttt        192
Gly Trp Ile Asn Pro Ser Ser Gly Gly Thr Asn Tyr Ala Gln Lys Phe
 50                  55                  60 cag ggc agg gtc acg atg acc agg gac acg tcc acc agc aca gtc tac        240
Gln Gly Arg Val Thr Met Thr Arg Asp Thr Ser Thr Ser Thr Val Tyr
 65                  70                  75                  80 atg gag ctg agc tct ctg aga tct gac gac acg gct gtg tat tac tgt        288
Met Glu Leu Ser Ser Leu Arg Ser Asp Asp Thr Ala Val Tyr Tyr Cys
             85                  90                  95 gca aga gat cat ggt tct cgt cat ttc tgg tct tac tgg ggc ttt gat        336
Ala Arg Asp His Gly Ser Arg His Phe Trp Ser Tyr Trp Gly Phe Asp
             100                 105                 110 tat tgg ggc caa ggt acc ctg gtc acc gtc tcc agt                        372
Tyr Trp Gly Gln Gly Thr Leu Val Thr Val Ser Ser
         115                 120

<210> SEQ ID NO 148
<211> LENGTH: 124
<212> TYPE: PRT
<213> ORGANISM: Artificial Sequence
<220> FEATURE:
<223> OTHER INFORMATION: Synthetic Construct

<400> SEQUENCE: 148

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ser Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 149
<211> LENGTH: 372
<212> TYPE: DNA
<213> ORGANISM: Artificial Sequence
<220> FEATURE:
<223> OTHER INFORMATION: MF6073_VH
<220> FEATURE:
<221> NAME/KEY: CDS
<222> LOCATION: (1)..(372)

<400> SEQUENCE: 149 cag gtg cag ctg gtg cag tct ggg gct gag gtg aag aag cct ggg gcc         48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac         96
Ser Val Lys Val Ser Cys Lys Ala Ser Gly Tyr Thr Phe Thr Gly Tyr
```

```
                    20                  25                  30
tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc aac cct tct agt ggt ggc aca aac tat gca cag aag ttt      192
Gly Trp Ile Asn Pro Ser Ser Gly Gly Thr Asn Tyr Ala Gln Lys Phe
 50                  55                  60 cag ggc agg gtc acg atg acc agg gac acg tcc acc agc aca gcc tac      240
Gln Gly Arg Val Thr Met Thr Arg Asp Thr Ser Thr Ser Thr Ala Tyr
 65                  70                  75                  80 atg gag ctg agc agg ctg aga tct gac gac acg gct gtg tat tac tgt      288
Met Glu Leu Ser Arg Leu Arg Ser Asp Asp Thr Ala Val Tyr Tyr Cys
             85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
                100                 105                 110 tat tgg ggc caa ggt acc ctg gtc acc gtc tcc agt                      372
Tyr Trp Gly Gln Gly Thr Leu Val Thr Val Ser Ser
        115                 120

<210> SEQ ID NO 150
<211> LENGTH: 124
<212> TYPE: PRT
<213> ORGANISM: Artificial Sequence
<220> FEATURE:
<223> OTHER INFORMATION: Synthetic Construct

<400> SEQUENCE: 150

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ser Ser Gly Gly Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 151
<211> LENGTH: 372
<212> TYPE: DNA
<213> ORGANISM: Artificial Sequence
<220> FEATURE:
<223> OTHER INFORMATION: MF6074_VH
<220> FEATURE:
<221> NAME/KEY: CDS
<222> LOCATION: (1)..(372)

<400> SEQUENCE: 151 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30
```

```
                      20                  25                  30 tat atg cac tgg gtg cga cag gcc cct gga caa ggg ctt gag tgg atg          144
Tyr Met His Trp Val Arg Gln Ala Pro Gly Gln Gly Leu Glu Trp Met
         35                  40                  45 gga tgg atc aac cct tct agt ggt ggc aca aac tat gca cag aag ttt          192
Gly Trp Ile Asn Pro Ser Ser Gly Gly Thr Asn Tyr Ala Gln Lys Phe
 50                  55                  60 cag ggc agg gtc acg atg acc agg gac acg tcc atc agc aca gcc tac          240
Gln Gly Arg Val Thr Met Thr Arg Asp Thr Ser Ile Ser Thr Ala Tyr
 65                  70                  75                  80 atg gag ctg agc agg ctg aga tct gac gac acg gct gtg tat tac tgt          288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat          336
Ala Arg Asp His Gly Ser Arg His Phe Trp Ser Tyr Trp Gly Phe Asp
                100                 105                 110 tat tgg ggc caa ggt acc ctg gtc acc gtc tcc agt                          372
Tyr Trp Gly Gln Gly Thr Leu Val Thr Val Ser Ser
            115                 120

<210> SEQ ID NO 152
<211> LENGTH: 124
<212> TYPE: PRT
<213> ORGANISM: Artificial Sequence
<220> FEATURE:
<223> OTHER INFORMATION: Synthetic Construct

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
         35                  40                  45

Gly Trp Ile Asn Pro Ser Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp His Gly Ser Arg His Phe Trp Ser Tyr Trp Gly Phe Asp
                100                 105                 110

Tyr Trp Gly Gln Gly Thr Leu Val Thr Val Ser Ser
            115                 120

<210> SEQ ID NO 153
<211> LENGTH: 214
<212> TYPE: PRT
<213> ORGANISM: Artificial Sequence
<220> FEATURE:
<223> OTHER INFORMATION: Common Light Chain

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
         35                  40                  45
```

```
Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 154
<211> LENGTH: 454
<212> TYPE: PRT
<213> ORGANISM: Artificial Sequence
<220> FEATURE:
<223> OTHER INFORMATION: heavy chain for EGFR binding

<400> SEQUENCE: 154

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Tyr Gly Lys Thr Phe Phe Ala Gln Asn Phe
     50                  55                  60

Gln Gly Arg Val Thr Met Thr Glu Asp Thr Ser Ala Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Gly Tyr Tyr Glu Thr Thr Thr Tyr Tyr Asn Leu Phe
            100                 105                 110

Asp Ser Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190
```

```
Val Val Thr Val Pro Ser Ser Leu Gly Thr Gln Thr Tyr Ile Cys
            195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Asp Pro Pro Ser Arg Glu Glu Met Thr Lys
            355                 360                 365

Asn Gln Val Ser Leu Thr Cys Glu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly
    450

<210> SEQ ID NO 155
<211> LENGTH: 453
<212> TYPE: PRT
<213> ORGANISM: Artificial Sequence
<220> FEATURE:
<223> OTHER INFORMATION: heavy chain for erbB-3 binding

<400> SEQUENCE: 155

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Lys Pro Pro Ser Arg Glu Glu Met Thr Lys Asn
        355                 360                 365

Gln Val Ser Leu Lys Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 156
<211> LENGTH: 17
<212> TYPE: PRT
<213> ORGANISM: Artificial Sequence
<220> FEATURE:
<223> OTHER INFORMATION: MF6058 CDR2

<400> SEQUENCE: 156

-continued

```
Trp Ile Asn Pro Gln Ser Gly Gly Thr Asn Tyr Ala Lys Lys Phe Gln
1               5                   10                  15
Gly
```

ANTIBODIES THAT BIND EGFR AND ERBB3

SEQUENCE LISTING

The instant application contains a Sequence Listing which has been submitted in ASCII format via EFS-Web, and is hereby incorporated by reference in its entirety. Said ASCII copy, created on Nov. 9, 2016, is named MRX5-016US_Sequence_Listing.txt and is 184,223 bytes in size.

The invention relates to the field of antibodies. In particular it relates to the field of therapeutic (human) antibodies for the treatment of diseases involving aberrant cells. More in particular it relates to antibodies that bind EGFR and ErbB-3 and their use in the binding of EGFR and ErbB-3 positive cells, particularly tumor cells.

The epidermal growth factor (EGF) receptor (EGFR) is the prototype cell-surface receptor for members of the epidermal growth factor family (EGF-family) of extracellular protein ligands. EGFR is also known as the ErbB-1 receptor. The receptor has been given various names in the past (EGFR; ERBB; ERBB1; HER1; PIG61; mENA). In the present invention the names ErbB-1, EGFR or HER1 in humans will be used interchangeably. EGFR is a member of the ErbB family of receptors, a subfamily of four closely related receptor tyrosine kinases: ErbB-1 (EGFR), ErbB-2 (HER2/c-neu; Her2), ErbB-3 (Her 3) and ErbB-4 (Her 4).

EGFR exists on the cell surface and is activated by binding of its specific ligands, including epidermal growth factor and transforming growth factor α (TGFα). Upon activation by its growth factor ligands, the receptor undergoes a transition from an inactive mostly monomeric form to an active homo-dimer. In addition to forming homo-dimers after ligand binding, EGFR may pair with another member of the ErbB receptor family, such as ErbB2, to create an activated hetero-dimer There is also evidence to suggest that dimers form in the absence of ligand-binding and clusters of activated EGFRs form after ligand binding.

EGFR dimerization stimulates its intrinsic intracellular protein-tyrosine kinase (PTK) activity. This activity induces several signal transduction cascades that lead to cell proliferation and differentiation. The kinase domain of EGFR can cross-phosphorylate tyrosine residues of other receptors it is complexed with, and can itself be activated in that manner.

Mutations involving EGFR have been identified in several types of cancer, and it is the target of an expanding class of anticancer therapies. These include EGFR targeted small molecules as gefitinib and erlotinib for lung cancer, and antibodies as cetuximab and panitumab for colon cancer and head and neck cancer.

Cetuximab and panitumumab are monoclonal antibodies that inhibit the receptor. Other monoclonals in clinical development are zalutumumab, nimotuzumab, and matuzumab. The monoclonal antibodies aim to block the extracellular ligand-induced receptor activation, mostly by blocking ligand binding to the receptor. With the binding site blocked, signal-inducing molecules cannot attach effectively and thereby also not activate downstream signaling. However, ligand-induced receptor activation may also be inhibited by stabilization of the inactive receptor conformation (matuzumab).

Although there is some success with the EGFR targeted antibody therapy, most are associated with the development of treatment resistance over time. One of the ways in which EGFR positive tumors can escape the targeted therapy is by signaling through another receptor(dimer). For instance, increased signaling by EGFR/ErbB-3 (HER1/HER3) dimers due to increased HER3 expression or heregulin expression is associated with EGFR related drug resistance in lung cancers and head and neck cancers. Apart from the induction of treatment resistance, some side effects of EGFR-targeting antibodies have been observed. One example is the development of a skin rash, associated with efficient EGFR inhibition. When extreme, such rashes can lead to a reduction in treatment cycles and/or premature termination of treatment.

ErbB-3 does not have inherent kinase inactivity. Therefore, effective inhibition of ErbB-3 receptor signaling cannot be achieved with small molecule tyrosine kinase inhibitors (TKI's). Recently a monoclonal antibody termed MEHD7945A was found to show promise in a pre-clinical setting of EGFR positive tumors. MEHD7945A is a monoclonal antibody with two identical antigen-binding sites. MEHD7945A has the unique property that it has two identical antigen-binding arms that each individually have the capacity to bind either EGFR or ErbB-3, but not to other receptors. Once an antigen is bound, the antigen-binding site is blocked for the other antigen. Therefore, MEHD7945A (called a 'two in one' antibody) can be regarded both as an EGFR-targeting antibody, as well as a HER5 targeting antibody.

SUMMARY OF THE INVENTION

The invention provides a bispecific antibody comprising a first antigen-binding site that binds EGFR and a second antigen-binding site that binds ErbB-3 and wherein the antibody has a half maximal growth inhibitory concentration (IC50) of less than 200 pM for inhibiting EGFR and/or ErbB-3 ligand induced growth of BxPC3 cells (ATCC CRL-1687) or BxPC3-luc2 cells (Perkin Elmer 125058).

Further provided is an antibody that comprises an antigen-binding site that binds EGFR, wherein the antibody comprises an immunoglobulin heavy chain with a heavy chain variable region that binds EGFR and that comprises the amino acid sequence of VH chain MF3998; MF4280; MF4002; MF4003; MF4010; MF4289; MF3370; MF3751; MF3752 as depicted in FIG. 11A, preferably wherein the immunoglobulin light chain variable region comprises the amino acid sequence of FIG. 11C The invention further provides an antibody that comprises an antigen-binding site that binds ErbB-3, comprising an immunoglobulin heavy chain with a heavy chain variable region that binds ErbB-3 and that comprises the amino acid sequence of VH chain MF3178; MF3176; MF3163; MF3307, MF6055-MF6074, preferably MF3178, MF3176, MF3163, MF6058, MF6061 or MF6065 as depicted in FIG. 11B, preferably wherein the immunoglobulin light chain variable region comprises the amino acid sequence of FIG. 11C.

An antibody of the invention is, unless otherwise specifically specified, preferably a bispecific antibody.

The invention further provides a pharmaceutical composition comprising an antibody according to the invention.

Also provided is an antibody of the invention that further comprises a label, preferably a label for in vivo imaging.

The invention further provides a method for the treatment of a subject having a EGFR, ErbB-3 or EGFR/ErbB-3 positive tumor or at risk of having said tumor comprising administering to the subject a bispecific antibody according to the invention. Also provided is a bispecific antibody according to the invention for use in the treatment of a subject having or at risk of having an EGFR, ErbB-3 or EGFR/ErbB-3 positive tumor.

DETAILED DESCRIPTION OF THE INVENTION

As used herein, the term "antigen-binding site" refers to a site on an antibody which is capable of binding to antigen. The unmodified antigen-binding site is typically formed by and present in the variable domain of the antibody. In one embodiment an antibody variable domain of the invention comprises a heavy chain variable region (VH) and a light chain variable region (VL). The antigen-binding site can be present in the combined VH/VL variable domain, or in only the VH region or only the VL region. When the antigen-binding site is present in only one of the two regions of the variable domain, the counterpart variable region can contribute to the folding and/or stability of the binding variable region, but does not significantly contribute to the binding of the antigen itself.

Antigen binding by an antibody is typically mediated through the complementarity determining regions (CDR's) of the antibody and the specific three-dimensional structure of both the antigen and the variable domain allowing these two structures to bind together with precision (an interaction similar to a lock and key), as opposed to random, non-specific sticking of antibodies. As an antibody typically recognizes only part of an antigen (called the epitope), and as such epitope may be present in other, but preferably non-human, compounds as well, antibodies according to the present invention that bind EGFR and/or ErbB-3 may recognize other proteins as well, but preferably not other human proteins, if such other compounds contain the same epitope. Hence, the term "binding" does not exclude binding of the antibodies to another protein or protein(s) that contain the same epitope. Such other protein(s) is preferably not a human protein. Instead, cross-reactivity is allowed. An EGFR antigen-binding site and an ErbB-3 antigen-binding site as defined in the present invention typically do not bind to other proteins on the membrane of cells in a post-natal, preferably adult human. An antibody according to the present invention is typically capable of binding EGFR and ErbB-3 with a binding affinity (i.e. equilibrium dissociation constant KD) of at least $1 \times 10e-6$ M, as outlined in more detail below.

As used herein, antigen-binding refers to the typical binding capacity of an antibody to its antigen. An antibody comprising an antigen-binding site that binds to EGFR, binds to EGFR and, under otherwise identical conditions, at least 100-fold lower to the homologous receptors ErbB-2 and ErbB-4 of the same species. An antibody comprising an antigen-binding site that binds to ErbB-3, binds to ErbB-3 and, under otherwise identical conditions, not to the homologous receptors ErbB-2 and ErbB-4 of the same species. Considering that the ErbB-family is a family of cell surface receptors, the binding is typically assessed on cells that express the receptor(s). Binding of an antibody to an antigen can be assessed in various ways.

The term "interferes with binding" as used herein means that the antibody is directed to an epitope on ErbB-3 and the antibody competes with ligand for binding to ErbB-3. The antibody may diminish ligand binding, displace ligand when this is already bound to ErbB-3 or it may, for instance through steric hindrance, at least partially prevent that ligand can bind to ErbB-3. One way to measure binding of an antigen binding site is to incubate the antibody with the antigen (preferably cells expressing the antigen), removing unbound antibody (preferably by a wash step) and detecting bound antibody by means of a labeled antibody that binds to the bound antibody constant domain. The measurement is preferably compared with a positive and negative reference. In case of cells the negative reference is a cell that does not express the antigen.

The term "antibody" as used herein means a proteinaceous molecule preferably belonging to the immunoglobulin class of proteins, containing one or more variable domains that bind an epitope on an antigen, where such domains are derived from or share sequence homology with the variable domain of an antibody. Antibodies of the invention preferably comprise two variable domains. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Specific binding, is defined as binding with affinities (KD) of at least $1 \times 10e-6$ M, more preferably $1 \times 10e-7$ M, more preferably higher than $1 \times 10e-9$ M. Typically, antibodies for therapeutic applications have affinities of up to $1 \times 10e-10$ M or higher. Antibodies such as bispecific antibodies of the present invention comprise the constant domains (Fc part) of a natural antibody. An antibody of the invention is typically a bispecific full length antibody, preferably of the human IgG subclass. Preferably, the antibodies of the present invention are of the human IgG1 subclass. Such antibodies of the invention have good ADCC properties, have favorable half life upon in vivo administration to humans and CH3 engineering technology exists that can provide for modified heavy chains that preferentially form hetero-dimers over homo-dimers upon co-expression in clonal cells For instance, ADCC activity of an antibody can be improved when the antibody itself has a low ADCC activity, by slightly modifying the constant region of the antibody (Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489)

An antibody of the invention is preferably a "full length" antibody. The term 'full length' according to the invention is defined as comprising an essentially complete antibody, which however does not necessarily have all functions of an intact antibody. For the avoidance of doubt, a full length antibody contains two heavy and two light chains. Each chain contains constant (C) and variable (V) regions, which can be broken down into domains designated CH1, CH2, CH3, VH, and CL, VL. An antibody binds to antigen via the variable domains contained in the Fab portion, and after binding can interact with molecules and cells of the immune system through the constant domains, mostly through the Fc portion. The terms 'variable domain', 'VH/VL pair', 'VH/VL' are used herein interchangeably. Full length antibodies according to the invention encompass antibodies wherein mutations may be present that provide desired characteristics. Such mutations should not be deletions of substantial portions of any of the regions. However, antibodies wherein one or several amino acid residues are deleted, without essentially altering the binding characteristics of the resulting antibody are embraced within the term "full length antibody". For instance, an IgG antibody can have 1-20 amino acid residue insertions, deletions or a combination thereof in the constant region.

Full length IgG antibodies are preferred because of their favorable half life and the need to stay as close to fully autologous (human) molecules for reasons of immunogenicity. An antibody of the invention is preferably a bispecific IgG antibody, preferably a bispecific full length IgG1 antibody. IgG1 is favored based on its long circulatory half life in man. It is preferred that the bispecific IgG antibody according to the invention is a human IgG1.

The term 'bispecific' (bs) means that one part of the antibody (as defined above) binds to one epitope on an antigen whereas the second part binds to a different epitope on the antigen, or on a different antigen. The different epitope is typically present on a different antigen. According to the present invention, said first and second antigens are in fact two different proteins. A preferred bispecific antibody is an antibody that comprises parts of two different monoclonal antibodies and consequently binds to two different types of antigen. One arm of the bispecific antibody typically contains a variable domain of one antibody and the other arm contains a variable domain of another antibody. The heavy chain variable regions of the bispecific antibody of the invention are different from each other, whereas the light chain variable regions are preferably the same in the bispecific antibodies of the invention, i.e. the bispecific antibodies of the invention are preferably composed of two parental antibodies that have the same light chain (i.e. common light chain antibodies). A bispecific antibody wherein the different heavy chain variable regions are associated with the same, or a common, light chain is also referred to as a bispecific antibody with a common light chain. Further provided is therefore a bispecific antibody according to the invention, wherein both arms comprise a common light chain.

Preferred bispecific antibodies can be obtained by co-expression of two different heavy chains and a common light chain in a single cell. When wildtype CH3 domains are used, co-expression of two different heavy chains and a common light chain will result in three different species, AA, AB and BB. To increase the percentage of the desired bispecific product (AB) CH3 engineering can be employed, or in other words, one can use heavy chains with compatible hetero-dimerization domains as defined hereunder.

The term 'compatible hetero-dimerization domains' as used herein refers to protein domains that are engineered such that engineered domain A' will preferentially form hetero-dimers with engineered domain B' and vice versa, whereas homo-dimerization between A'-A' and B'-B' is disfavoured.

The term 'common light chain' according to the invention refers to light chains which may be identical or have some amino acid sequence differences while the binding specificity of the full-length antibody is not affected. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common VL', 'single light chain', 'single VL', with or without the addition of the term 'rearranged' are all used herein interchangeably. It is an aspect of the present invention to use as common light chain a human light chain that can combine with different heavy chains to form antibodies with functional antigen binding domains (WO2004/009618, WO02/009157771, Merchant et al. 1998, Nissim et al. 1994). Preferably, the common light chain has a germline sequence. A preferred germline sequence is a light chain variable region that is frequently used in the human repertoire and has good thermodynamic stability, yield and solubility. A preferred germline light chain is based on O12, preferably it is the rearranged germline human kappa light chain IgV$_K$1-39*01/IGJ$_K$1*01 or a fragment or a functional equivalent (i.e. same IgV$_K$1-39 gene segment but different IGJ$_K$ gene segment) thereof (nomenclature according to the IMGT database worldwide web at imgt.org). Further provided is therefore a bispecific antibody according to the invention, wherein said common light chain is a germline light chain, preferably a rearranged germline human kappa light chain comprising the IgVK1-39 gene segment, most preferably the rearranged germline human kappa light chain IgVK1-39*01/IGJK1*01. The terms rearranged germline human kappa light chain IgV$_K$1-39*01/IGJ$_K$1*01, IGKV1-39/IGKJ1, huV$_K$1-39 light chain or in short huV$_K$1-39 are used interchangeably throughout the application. Obviously, those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions. The light chain of the present invention can also be a light chain as specified herein above, having 1-5 amino acid insertions, deletions, substitutions or a combination thereof.

Also contemplated are antibodies wherein a VH is capable of specifically recognizing a first antigen and the VL, paired with the VH in a immunoglobulin variable domain, is capable of specifically recognizing a second antigen. The resulting VH/VL pair will bind either antigen 1 or antigen 2. Such so called "two-in-one antibodies", described in for instance WO 2008/027236, WO 2010/108127 and Schaefer et al (Cancer Cell 20, 472-486, October 2011), are different from bispecific antibodies of the invention and are further referred to as "two-in-one antibodies". Such "two-in-one" antibodies have identical arms and are not antibodies of the present invention.

EGFR is a member of a family of four receptor tyrosine kinases (RTKs), named Her- or cErbB-1, -2, -3 and -4. The EGFR has an extracellular domain (ECD) that is composed of four sub-domains, two of which are involved in ligand binding and one of which is involved in homo-dimerisation and hetero-dimerisation[1,2] (for review, see Ref. 3). The reference numbers used in this section refer to the numbering of the references in the list headed "References cited in the specification". EGFR integrates extracellular signals from a variety of ligands to yield diverse intracellular responses.[4,5] The major signal transduction pathway activated by EGFR is composed of the Ras-mitogen-activated protein kinase (MAPK) mitogenic signalling cascade. Activation of this pathway is initiated by the recruitment of Grb2 to tyrosine phosphorylated EGFR.[6,7] This leads to activation of Ras through the Grb2-bound Ras-guanine nucleotide exchange factor Son of Sevenless (SOS). In addition, the PI3-kinase-Akt signal transduction pathway is also activated by EGFR, although this activation is much stronger in case there is co-expression of Her3.[8,9] The EGFR is implicated in several human epithelial malignancies, notably cancers of the breast, bladder, non-small cell lung cancer lung, colon, ovarian head and neck and brain.[10] Activating mutations in the gene have been found, as well as over-expression of the receptor and of its ligands, giving rise to autocrine activation loops (for review, see Ref. 11). This RTK has therefore been extensively used as target for cancer therapy. Both small-molecule inhibitors targeting the RTK and monoclonal antibodies (mAbs) directed to the extracellular ligand-binding domains have been developed and have shown hitherto several clinical successes, albeit mostly for a select group of patients.[12] Database accession numbers for the human EGFR protein and the gene encoding it are (GenBank NM_005228.3). The accession number is primarily given to provide a further method of identification of EGFR protein as a target, the actual sequence of the EGFR protein bound by an antibody may vary, for instance because of a mutation in the encoding gene such as those occurring in some cancers or the like. Where reference herein is made to EGFR, the reference refers to human EGFR unless otherwise stated. The antigen-binding site that binds EGFR, binds EGFR and a variety of variants thereof such as those expressed on some EGFR positive tumors.

The term 'ErbB-3' as used herein refers to the protein that in humans is encoded by the ERBB3 gene. Alternative names for the gene or protein are HER3; LCCS2; MDA-BF-1; c-ErbB-3; c-ErbB3; ErbB3-S; p180-ErbB3; p45-sErbB3; and p85-sErbB3. Where reference is made herein to ErbB-3, the reference refers to human ErbB-3. An antibody comprising an antigen-binding site that binds ErbB-3, binds human ErbB-3. The ErbB-3 antigen-binding site may, due to sequence and tertiary structure similarity between human and other mammalian orthologs, also bind such an ortholog but not necessarily so. Database accession numbers for the human ErbB-3 protein and the gene encoding it are (NP_001005915.1 NP_001973.2, NC_000012.11, NC_018923.2, NT_029419.12). The accession numbers are primarily given to provide a further method of identification of ErbB-3 as a target, the actual sequence of the ErbB-3 protein bound by an antibody may vary, for instance because of a mutation in the encoding gene such as those occurring in some cancers or the like. The ErbB-3 antigen binding site binds ErbB-3 and a variety of variants thereof, such as those expressed by some ErbB-2 positive tumor cells. The antigen-binding site that binds ErbB-3 preferably binds domain III of ErbB-3. In a preferred embodiment the affinity (KD) of an antigen-binding site for an ErbB-3 positive cell is lower than or equal to 2.0 nM, more preferably lower than or equal to 1.5 nM, more preferably lower than or equal to 1.39 nM, more preferably lower than or equal to 0.99 nM. In a preferred embodiment, an antibody according to the invention preferably comprises an antigen-binding site that binds at least one amino acid of domain III of ErbB-3 selected from the group consisting of R426 and surface-exposed amino acid residues that are located within 11.2 Å from R426 in the native ErbB-3 protein. In one preferred embodiment, the affinity (KD) of an antigen-binding site for ErbB-3 on SK-BR-3 cells is lower than or equal to 2.0 nM, more preferably lower than or equal to 1.5 nM, more preferably lower than or equal to 1.39 nM, preferably lower than or equal to 0.99 nM. In one embodiment, said affinity (KD) is within the range of 1.39-0.59 nM. In one preferred embodiment, the affinity (KD) an antigen-binding site for ErbB-3 on BT-474 cells is lower than or equal to 2.0 nM, more preferably lower than or equal to 1.5 nM, more preferably lower than or equal to 1.0 nM, more preferably lower than 0.5 nM, more preferably lower than or equal to 0.31 nM, more preferably lower than or equal to 0.23 nM. In one embodiment, said affinity (KD) is within the range of 0.31-0.15 nM. The above-mentioned affinities are preferably as measured using steady state cell affinity measurements, wherein cells are incubated at 4° C. using radioactively labeled antibody, where after cell-bound radioactivity is measured, as described in the Examples.

An antigen-binding site that binds at least one amino acid of domain III of ErbB-3 preferably binds an amino acid selected from the group consisting of R426 and surface-exposed amino acid residues that are located within 11.2 Å from R426 in the native ErbB-3 protein. The amino acid residue numbering is that of Protein Data Bank (PDB) ID #4P59. As shown in the Examples, antibodies binding this region of domain III of ErbB-3 exhibit particularly good binding characteristics and they are capable of counteracting an activity of ErbB-3 on ErbB-3 positive cells. The term "surface-exposed amino acid residues that are located within 11.2 Å from R426 in the native ErbB-3 protein" refers to amino acid residues that are in the tertiary structure of the ErbB-3 protein spationally positioned within 11.2 Å from R426 and that are at least in part exposed to the outside of the protein, so that they can be reached by antibodies. Preferably, said amino acid residues that are located within 11.2 Å from R426 in the native ErbB-3 protein are selected from the group consisting of L423, Y424, N425, G427, G452, R453, Y455, E480, R481, L482, D483 and K485 (see for instance FIG. 16 and Table 8). In one preferred embodiment, a bispecific antibody according to the invention is provided, wherein said antibody comprises an antigen-binding site that binds at least R426 of domain III of ErbB-3. Preferably, said antibody comprises an antigen-binding site that binds at least R426 of domain III of ErbB-3.

The invention further provides a bispecific antibody comprising an antigen-binding site that binds at least R426 of domain III of ErbB-3. Preferably, said antibody comprises an antigen-binding site that binds at least R426 of domain III of ErbB-3. Preferably said antibody further comprises a variable region as depicted in FIG. 11B. In a preferred embodiment the antibody further comprises a binding site for EGFR. The variable region preferably comprises a sequence as depicted in FIG. 11a.

A bispecific antibody of the invention preferably has improved ADCC activity. One technique for enhancing ADCC of an antibody is afucosylation. (See for instance Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489). Further provided is therefore a bispecific antibody according to the invention, which is afucosylated. Alternatively, or additionally, multiple other strategies can be used to achieve ADCC enhancement, for instance including glycoengineering (Kyowa Hakko/Biowa, GlycArt (Roche) and Eureka Therapeutics) and mutagenesis (Xencor and Macrogenics), all of which seek to improve Fc binding to low-affinity activating FcγRIIIa, and/or to reduce binding to the low affinity inhibitory FcγRIIb. A bispecific antibody of the invention is preferably afucosylated in order to enhance ADCC activity. A bispecific antibody of the invention preferably comprises a reduced amount of fucosylation of the N-linked carbohydrate structure in the Fc region, when compared to the same antibody produced in a normal CHO cell.

The invention provides a bispecific antibody comprising a first antigen-binding site that binds EGFR and a second antigen-binding site that binds ErbB-3, wherein the antibody has a half maximal growth inhibitory concentration (IC50) of less than 200 pM for inhibiting EGFR and/or ErbB-3 ligand induced growth of BxPC3 cells (ATCC CRL-1687) or BxPC3-luc2 cells (Perkin Elmer 125058). Said antibody preferably has an IC50 for inhibiting EGFR and/or ErbB-3 ligand induced growth of BxPC3 cells (ATCC CRL 1687) or BxPC3-luc2 cells (Perkin Elmer 125058) of less than 100 pM, preferably less than 50 pM, more preferably less than 20 pM. An antibody of the invention preferably has an IC50 of more than 1 pM for inhibiting EGFR and/or ErbB-3 ligand induced growth of BxPC3 cells (ATCC CRL 1687) or BxPC3-luc2 cells (Perkin Elmer 125058).

The invention further provides a bispecific comprising a first antigen-binding site that binds EGFR and a second antigen-binding site that binds ErbB-3, wherein the antibody has a half maximal growth inhibitory concentration (IC50) for inhibiting EGFR and/or ErbB-3 ligand induced growth of BxPC3 cells (ATCC CRL-1687) or BxPC3-luc2 cells (Perkin Elmer 125058) that is lower than the IC50 of the antibody MEHD7945A for inhibiting growth of these cells under otherwise the same conditions. The anti-EGFR/anti-HER3 antibody MEHD7945A is described in WO2010/108127. Preferably the IC50 for inhibiting EGFR and/or ErbB-3 ligand induced growth of BxPC3 cells or BxPC3-luc2 cells of an antibody of the invention is lower than 90% of the IC50 of MEHD7945A for inhibiting growth of these cells under otherwise the same conditions, preferably lower than 80%, more preferably lower than 60%, more preferably lower than 50%, more preferably lower than 40%, more preferably lower than 30%, more preferably lower than 20%, more preferably lower than 10% of the IC50 of the antibody MEHD7945A. An antibody of the invention preferably has an IC50 for inhibiting EGFR and/or ErbB-3 ligand induced growth of BxPC3 cells (ATCC CRL 1687) or BxPC3-luc2 cells (Perkin Elmer 125058) of more than 1% of the IC50 of the antibody MEHD7945A for inhibiting growth of these cells under otherwise the same conditions. An antibody of the invention preferably has the indicated IC50 for inhibiting EGFR and ErbB-3 ligand induced growth of BxPC3 cells (ATCC CRL 1687) or BxPC3-luc2 cells (Perkin Elmer 125058).

An antibody that is effective at relatively low concentrations of the antibody is preferred in the present invention. Such an antibody can be provided in lower amounts and/or with a lower frequency of administration making the utility of the antibody more economic. An antibody that is effective at relatively low concentrations of the antibody more effectively inhibits proliferation of tumor cells in vivo, particularly at lower concentrations. Such an antibody also has a better therapeutic window, and can be administered less frequently or with longer administration intervals.

EGFR and ErbB-3 each can bind a number of ligands and stimulate growth of BxPC3 cells or BxPC3-luc2 cells. In the presence of a ligand for one or both receptors the growth of BxPC3 or BxPC3-luc2 cells is stimulated. EGFR and/or ErbB-3 ligand-induced growth of BxPC3 cells can be measured by comparing the growth of the cells in the absence and presence of the ligand. The preferred EGFR ligand for measuring EGFR ligand-induced growth of BxPC3 or BxPC3-luc2 cells is EGF. The preferred ErbB-3 ligand for measuring ErbB-3 ligand-induced growth of BxPC3 or BxPC3-luc2 cells is NRG1. The ligand-induced growth is preferably measured using saturating amounts of ligand. In a preferred embodiment EGF is used in an amount of 100 ng/ml of culture medium. NRG1 is preferably used in 10 ng/ml of culture medium. It is preferred that the half maximal growth inhibitory concentration (IC50) is measured on EGFR and ErbB-3 ligand induced BxPC3 or BxPC3-luc2 cells. It is preferred that EGF is the EGFR-ligand in this assay and that NRG1 is the ErbB-3 ligand. A suitable test for the IC50 assay is described in the examples.

In the presence of excess ErbB-2, ErbB-2/ErbB-3 hetero-dimers may provide a growth signal to the expressing cell in the absence of detectable ligand for the ErbB-3 chain in the hetero-dimer. This ErbB-3 receptor function is herein referred as a ligand-independent receptor function of ErbB-3. The ErbB-2/ErbB-3 hetero-dimer also provide a growth signal to the expressing cell in the presence an ErbB-3 ligand. This ErbB-3 receptor function is herein referred to as a ligand-induced receptor function of ErbB-3.

EGF and NRG1 are preferably the EGF and NRG1 of R&D systems, cat. nr. 396-HB and 236-EG as described in the examples.

An antibody of the invention comprising an antigen-binding site that binds ErbB-3 preferably can reduce a ligand-induced receptor function of ErbB-3 on a ErbB-3 positive cell. The antibody is capable of reducing ErbB-3 signaling via dimerization with EGFR. The antibody is capable of reducing ErbB-3 signaling via ErbB-2. The ErbB-3 positive cell is preferably also positive for ErbB-2. The ErbB-3 positive cell is preferably also positive for EGFR. The ligand-induced receptor function of ErbB-3 is preferably ErbB-3 ligand-induced growth of an ErbB-2 and ErbB-3 positive cell. In a preferred embodiment the ErbB-2 and ErbB-3 positive cell comprises at least 50.000 ErbB-2 receptors on the cell surface. In a preferred embodiment at least 100.000 ErbB-2 receptors. In a preferred embodiment the ErbB-2 and ErbB-3 positive cell comprises no more than 1.000.000 ErbB-2 receptors on the cell surface. In a preferred embodiment the ErbB-2 and ErbB-3 positive cell comprises more than 1.000.000 ErbB-2 receptors on the cell surface. In a preferred embodiment said ErbB-2 and ErbB-3 positive cell is an BxPC3 cell (ATCC CRL-1687), a or BxPC3-luc2 cell (Perkin Elmer 125058); an MCF-7 cell (ATCC® HTB-22™), an SKBR3 cell (ATCC® HTB-30™) an NCI-87 cell (ATCC® CRL-5822™) or an A431 cell (ATCC® CRL-1555™). Preferably said ErbB-2 and ErbB-3 positive cell is also EGFR positive. Said ErbB-2 and ErbB-3 positive cell is preferably a BxPC3 or BxPC3-luc2 cell as indicated herein above.

As used herein the ligand-induced receptor function is reduced by at least 20%, preferably at least 30, 40, 50 60, or at least 70% in a particularly preferred embodiment the ligand-induced receptor function is reduced by 80, more preferably by 90%. The reduction is preferably determined by determining a ligand-induced receptor function in the presence of a bispecific antibody of the invention, and comparing it with the same function in the absence of the antibody, under otherwise identical conditions. The conditions comprise at least the presence of an ErbB-3 ligand. The amount of ligand present is preferably an amount that induces half of the maximum growth of an ErbB-2 and ErbB-3 positive cell line. The ErbB-2 and ErbB-3 positive cell line for this test is preferably the BxPC3 or BxPC3-luc2 cell as indicated herein above. The test and/or the ligand for determining ErbB-3 ligand-induced receptor function is preferably a test for ErbB-3 ligand induced growth reduction as specified in the examples.

An antibody of the invention comprising an antigen-binding site that binds ErbB-3, preferably interferes with binding of an ErbB-3 ligand to ErbB-3. Such antibodies are more effective in reducing ligand induced growth of BxPC3 or BxPC3-luc2 cells particularly in the context of an antibody that also comprises an antigen-binding site that binds EGFR.

The term "ErbB-3 ligand" as used herein refers to polypeptides which bind and activate ErbB-3. Examples of ErbB-3 ligands include, but are not limited to neuregulin 1 (NRG1) and neuregulin 2 (NRG2) (for review Olayioye M A et al.; EMBO J (2000) Vol 19: pp 3159-3167). The term includes biologically active fragments and/or variants of a naturally occurring polypeptide.

The term "EGFR ligand" as used herein refers to polypeptides which bind and activate EGFR. Examples of EGFR ligands include, but are not limited to EGF, TGF-α, HB-EGF, amphiregulin, betacellulin and epiregulin (for review Olayioye M A et al.; EMBO J (2000) Vol 19: pp 3159-3167). The term includes biologically active fragments and/or variants of a naturally occurring polypeptide The first antigen-binding site of an antibody of the invention preferably binds domain I or domain III of EGFR. Preferably said antibody binds domain III of EGFR. The antibody preferably inhibits EGF induced proliferation of BxPC3 or BxPC3-luc2 cells.

A bispecific antibody of the invention preferably comprises antibody-dependent cell-mediated cytotoxicity (ADCC). An antibody that has a low intrinsic ADCC activity can be provided with additional ADCC activity. The antibody can be engineered to enhance the ADCC activity (for review, see Cancer Sci. 2009 September; 100(9):1566-72. Engineered therapeutic antibodies with improved effector functions. Kubota T, Niwa R, Satoh M, Akinaga S, shitara K, Hanai N). Several in vitro methods exist for determining the efficacy of antibodies or effector cells in eliciting ADCC. Among these are chromium-51 [Cr51] release assays, europium [Eu] release assays, and sulfur-35 [S35] release assays. Usually, a labeled target cell line expressing a certain surface-exposed antigen is incubated with antibody specific for that antigen. After washing, effector cells expressing Fc receptor CD16 are co-incubated with the antibody-labeled target cells. Target cell lysis is subsequently measured by release of intracellular label by a scintillation counter or spectrophotometry. A preferred test is detailed in the examples. A bispecific antibody of the invention is preferably afucosylated. A bispecific antibody of the invention preferably comprises a reduced amount of fucosylation of the N-linked carbohydrate structure in the Fc region, when compared to the same antibody produced in a normal CHO cell.

A bispecific antibody of the present invention is preferably used in humans. To this end an antibody of the invention is preferably a human or humanized antibody. Tolerance of a human to a polypeptide is governed by many different aspects. Immunity, be it T-cell mediated, B-cell mediated or other is one of the variables that are encompassed in tolerance of the human for a polypeptide. The constant region of a bispecific antibody of the present invention is preferably a human constant region. The constant region may contain one or more, preferably not more than 10, preferably not more than 5 amino-acid differences with the constant region of a naturally occurring human antibody. It is preferred that the constant part is entirely derived from a naturally occurring human antibody. Various antibodies produced herein are derived from a human antibody variable domain library. As such these variable domains are human. The unique CDR regions may be derived from humans, be synthetic or derived from another organism. The variable region is considered a human variable region when it has an amino acid sequence that is identical to an amino acid sequence of the variable region of a naturally occurring human antibody, but for the CDR regions. The variable region of an EGFR binding VH, an ErbB-3 binding VH, or a light chain in an antibody of the invention may contain one or more, preferably not more than 10, preferably not more than 5 amino-acid differences with the variable region of a naturally occurring human antibody, not counting possible differences in the amino acid sequence of the CDR regions. Such mutations also occur in nature in the context of somatic hypermutation.

Antibodies may be derived from various animal species, at least with regard to the heavy chain variable region. It is common practice to humanize such e.g. murine heavy chain variable regions. There are various ways in which this can be achieved among which there are CDR-grafting into a human heavy chain variable region with a 3D-structure that matches the 3-D structure of the murine heavy chain variable region; deimmunization of the murine heavy chain variable region, preferably done by removing known or suspected T- or B-cell epitopes from the murine heavy chain variable region. The removal is typically by substituting one or more of the amino acids in the epitope for another (typically conservative) amino acid, such that the sequence of the epitope is modified such that it is no longer a T- or B-cell epitope.

Deimmunized murine heavy chain variable regions are less immunogenic in humans than the original murine heavy chain variable region. Preferably a variable region or domain of the invention is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in the invention is preferably a mammal, more preferably a primate, most preferably a human.

A bispecific antibody according to the invention preferably comprises a constant region of a human antibody. According to differences in their heavy chain constant domains, antibodies are grouped into five classes, or isotypes: IgG, IgA, IgM, IgD, and IgE. These classes or isotypes comprise at least one of said heavy chains that is named with a corresponding Greek letter. In a preferred embodiment the invention provides an antibody according to the invention wherein said constant region is selected from the group of IgG, IgA, IgM, IgD, and IgE constant regions, more preferably said constant region comprises an IgG constant region, more preferably an IgG1 constant region, preferably a mutated IgG1 constant region. Some variation in the constant region of IgG1 occurs in nature and/or is allowed without changing the immunological properties of the resulting antibody. Typically between about 1-10 amino acid insertions, deletions, substitutions or a combination thereof are allowed in the constant region.

The invention in one embodiment provides an antibody comprising a variable domain that binds EGFR, wherein said antibody comprises at least the CDR3 sequence of an EGFR specific heavy chain variable region selected from the group consisting of MF3998; MF4280; MF4002; MF4003; MF4010; MF4289; MF3370; MF3751; MF3752 as depicted in FIG. 11A, or wherein said antibody comprises a heavy chain CDR3 sequence that differs in at most three, preferably in at most two, preferably in no more than one amino acid from a CDR3 sequence of a VH selected from the group consisting of MF3998; MF4280; MF4002; MF4003; MF4010; MF4289; MF3370; MF3751; MF3752 as depicted in FIG. 11A. Said antibody preferably comprises at least the CDR3 sequence of MF3998; MF4280; MF4003; MF4010; MF4289; or MF3370 as depicted in FIG. 11A. Said antibody preferably comprises at least the CDR1, CDR2 and CDR3 sequences of an EGFR specific heavy chain variable region selected from the group consisting of MF3998; MF4280; MF4002; MF4003; MF4010; MF4289; MF3370; MF3751; MF3752 as depicted in FIG. 11A, or heavy chain CDR1, CDR2 and CDR3 sequences that differ in at most three, preferably in at most two, preferably in at most one amino acid from the CDR1, CDR2 and CDR3 sequences of EGFR specific heavy chain variable region selected from the group consisting of MF3998; MF4280; MF4002; MF4003; MF4010; MF4289; MF3370; MF3751; MF3752 as depicted in FIG. 11A. Said antibody preferably comprises at least the CDR1, CDR2 and CDR3 sequences of MF3998; MF4280; MF4003; MF4010; MF4289; or MF3370 as depicted in FIG. 11A.

The invention also provides an antibody comprising a variable domain that binds ErbB-3, wherein said antibody comprises at least the CDR3 sequence of an ErbB-3 specific heavy chain variable region selected from the group consisting of MF3178, MF3176, MF3163, MF3307, MF6055-MF6074, preferably MF3178, MF3176, MF3163, MF6058, MF6061 or MF6065 as depicted in FIG. 11B, or wherein said antibody comprises a heavy chain CDR3 sequence that differs in at most three, preferably in at most two, preferably in no more than one amino acid from a CDR3 sequence of a VH selected from the group consisting of MF3178, MF3176, MF3163, MF3307, MF6055-MF6074, preferably MF3178, MF3176, MF3163, MF6058, MF6061 or MF6065 as depicted in FIG. 11B. Said antibody preferably comprises at least the CDR3 sequence of MF3178, MF3176 or MF3163, most preferably at least the CDR3 sequence of MF3178. Said antibody preferably comprises at least the CDR1, CDR2 and CDR3 sequences of an ErbB 3 specific heavy chain variable region selected from the group consisting of MF3178, MF3176, MF3163, MF3307, MF6055-MF6074, preferably MF3178, MF3176, MF3163, MF6058, MF6061 or MF6065 as depicted in FIG. 11B, or heavy chain CDR1, CDR2 and CDR3 sequences that differ in at most three, preferably in at most two, preferably in at most one amino acid from the CDR1, CDR2 and CDR3 sequences of MF3178, MF3176, MF3163, MF3307, MF6055-MF6074, preferably MF3178, MF3176, MF3163, MF6058, MF6061 or MF6065. Said antibody preferably comprises at least the CDR1, CDR2 and CDR3 sequences of MF3178, MF3176 or MF3163, most preferably at least the CDR1, CDR2 and CDR3 sequence of MF3178.

The invention in one embodiment provides a bispecific antibody comprising a first antigen-binding site that binds EGFR and a second antigen-binding site that binds ErbB-3, wherein said first antigen-binding site comprises at least the CDR3 sequence of an EGFR specific heavy chain variable region selected from the group consisting of MF3998; MF4280; MF4002; MF4003; MF4010; MF4289; MF3370; MF3751; MF3752 as depicted in FIG. 11A, or a heavy chain CDR3 sequence that differs in at most three, preferably in at most two, preferably in no more than one amino acid from a CDR3 sequence of a VH selected from the group consisting of MF3998; MF4280; MF4002; MF4003; MF4010; MF4289; MF3370; MF3751; MF3752 as depicted in FIG. 11A, and wherein said second antigen-binding site comprises at least the CDR3 sequence of an ErbB 3 specific heavy chain variable region selected from the group consisting of MF3178, MF3176, MF3163, MF3307, MF6055-MF6074, preferably MF3178, MF3176, MF3163, MF6058, MF6061 or MF6065 as depicted in FIG. 16B or FIG. 16E, or a heavy chain CDR3 sequence that differs in at most three, preferably in at most two, preferably in no more than one amino acid from a CDR3 sequence of a VH selected from the group consisting of MF3178, MF3176, MF3163, MF3307, MF6055-MF6074, preferably MF3178, MF3176, MF3163, MF6058, MF6061 or MF6065 as depicted in FIG. 11B. Said first antigen-binding site preferably comprises at least the CDR3 sequence of MF3998; MF4280; MF4003; MF4010; MF4289; or MF3370 as depicted in FIG. 11A and said second antigen-binding site preferably comprises at least the CDR3 sequence of MF3178, MF3176 or MF3163, most preferably at least the CDR3 sequence of MF3178 of FIG. 11B. Said first antigen-binding site preferably comprises at least the CDR1, CDR2 and CDR3 sequences of an EGFR specific heavy chain variable region selected from the group consisting of MF3998; MF4280; MF4003; MF4010; MF4289; or MF3370 as depicted in FIG. 11A, or heavy chain CDR1, CDR2 and CDR3 sequences that differ in at most three, preferably in at most two, preferably in at most one amino acid from the CDR1, CDR2 and CDR3 sequences of MF3998; MF4280; MF4003; MF4010; MF4289; or MF3370 as depicted in FIG. 11A, and said second antigen-binding site preferably comprises at least the CDR1, CDR2 and CDR3 sequences of an ErbB 3 specific heavy chain variable region selected from the group consisting of MF3178, MF3176, MF3163, MF3307, MF6055-MF6074, preferably MF3178, MF3176, MF3163, MF6058, MF6061 or MF6065 as depicted in FIG. 11B, or heavy chain CDR1, CDR2 and CDR3 sequences that differ in at most three, preferably in at most two, preferably in at most one amino acid from the CDR1, CDR2 and CDR3 sequences of MF3178, MF3176, MF3163, MF3307, MF6055-MF6074, preferably MF3178, MF3176, MF3163, MF6058, MF6061 or MF6065. Said first antigen-binding site preferably comprises at least the CDR1, CDR2 and CDR3 sequences of MF3998; MF4280; MF4003; MF4010; MF4289; or MF3370 as depicted in FIG. 11A, and said second antigen-binding site preferably comprises at least the CDR1, CDR2 and CDR3 sequences of MF3178, MF3176 or MF3163, most preferably at least the CDR1, CDR2 and CDR3 sequence of MF3178.

A preferred embodiment provides a bispecific antibody comprising a first antigen-binding site that binds EGFR and a second antigen-binding site that binds ErbB-3, wherein said first antigen-binding site comprises at least the CDR3 sequence of MF3998 as depicted in FIG. 11A, or a CDR3 sequence that differs in at most three, preferably in at most two, preferably in no more than one amino acid from the CDR3 sequence of MF3998 as depicted in FIG. 11A, and wherein said second antigen-binding site comprises at least the CDR3 sequence of MF3178, or a CDR3 sequence that differs in at most three, preferably in at most two, preferably in no more than one amino acid from the CDR3 sequence of MF3178.

The invention in one embodiment provides a bispecific antibody comprising a first antigen-binding site that binds EGFR and a second antigen-binding site that binds ErbB-3, wherein said first antigen-binding site comprises at least the CDR1, CDR2 and CDR3 sequences of MF3998, or CDR1, CDR2 and CDR3 sequences that differ in at most three, preferably in at most two, preferably in at most one amino acid from the CDR1, CDR2 and CDR3 sequences of MF3958, and wherein said second antigen-binding site comprises at least the CDR1, CDR2 and CDR3 sequence of MF3178, or CDR1, CDR2 and CDR3 sequences that differ in at most three, preferably in at most two, preferably in at most one amino acid from the CDR1, CDR2 and CDR3 sequences of MF3178.

The invention in one embodiment provides a bispecific antibody comprising a first antigen-binding site that binds EGFR and a second antigen-binding site that binds ErbB-3, wherein said first antigen-binding site comprises at least the CDR3 sequence of MF3998 and wherein said second antigen-binding site comprises at least the CDR3 sequence of MF3178.

The invention in one embodiment provides a bispecific antibody comprising a first antigen-binding site that binds ErbB-2 and a second antigen-binding site that binds ErbB-3, wherein said first antigen-binding site comprises at least the CDR1, CDR2 and CDR3 sequences of MF3998 and wherein said second antigen-binding site comprises at least the CDR1, CDR2 and CDR3 sequence of MF3178.

The invention in one embodiment provides a bispecific antibody comprising a first antigen-binding site that binds EGFR and a second antigen-binding site that binds ErbB-3, wherein said first antigen-binding site comprises at least the CDR3 sequence of MF4280 and wherein said second antigen-binding site comprises at least the CDR3 sequence of MF3178.

The invention in one embodiment provides a bispecific antibody comprising a first antigen-binding site that binds ErbB-2 and a second antigen-binding site that binds ErbB-3, wherein said first antigen-binding site comprises at least the CDR1, CDR2 and CDR3 sequences of MF4280 and wherein said second antigen-binding site comprises at least the CDR1, CDR2 and CDR3 sequence of MF3178.

CDR sequences are for instance varied for optimization purposes, preferably in order to improve binding efficacy or the stability of the antibody. Optimization is for instance performed by mutagenesis procedures where after the stability and/or binding affinity of the resulting antibodies are preferably tested and an improved EGFR or ErbB 3-specific CDR sequence is preferably selected. A skilled person is well capable of generating antibody variants comprising at least one altered CDR sequence according to the invention. For instance, conservative amino acid substitution is applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine.

The invention in one embodiment provides an antibody comprising a variable domain that binds EGFR, wherein the VH chain of said variable domain comprises the amino acid sequence of VH chain MF3998; MF4280; MF4002; MF4003; MF4010; MF4289; MF3370; MF3751; MF3752 as depicted in FIG. 11A; or comprises the amino acid sequence of VH chain MF3998; MF4280; MF4002; MF4003; MF4010; MF4289; MF3370; MF3751; MF3752 depicted in FIG. 11A having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11A. Said antibody preferably comprises a variable domain that binds EGFR, wherein the VH chain of said variable domain comprises the amino acid sequence of VH chain MF3998; MF4280; MF4003; MF4010; MF4289; or MF3370 as depicted in FIG. 11A; or comprises the amino acid sequence of VH chain MF3998; MF4280; MF4003; MF4010; MF4289; or MF3370 as depicted in FIG. 11A having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11A. An antibody comprising a variable domain that binds EGFR, preferably further comprises a variable domain that binds ErbB-3. The antibody comprising a variable domain that binds EGFR is preferably a bispecific antibody that preferably further comprises a variable domain that binds ErbB-3. The VH chain of the variable domain that binds Erb-B3 preferably comprises the amino acid sequence of VH chain MF3178; MF3176; MF3163; MF3307, MF6055-MF6074, preferably MF3178, MF3176, MF3163, MF6058, MF6061 or MF6065 as depicted in FIG. 11B; or comprises the amino acid sequence of VH MF3178; MF3176; MF3163; MF3307, MF6055-MF6074, preferably MF3178, MF3176, MF3163, MF6058, MF6061 or MF6065 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11B. The VH chain of the variable domain that binds Erb-B3 preferably comprises the amino acid sequence of MF3178, MF3176 or MF3163; or comprises the amino acid sequence of MF3178, MF3176 or MF3163 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the respective VH chain sequence of FIG. 11A. In a preferred embodiment the VH chain of the variable domain that binds ErbB-3 comprises the amino acid sequence of MF3178; or comprises the amino acid sequence of MF3178 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence.

Preferably, the mentioned amino acid insertions, deletions and substitutions in a VH or VL as specified herein are not present in the CDR3 region. The mentioned amino acid insertions, deletions and substitutions are also preferably not present in the CDR1 and CDR2 regions. The mentioned amino acid insertions, deletions and substitutions are also preferably not present in the FR4 region.

The invention further provides an antibody comprising a variable domain that binds ErbB-3, wherein the VH chain of said variable region comprises the amino acid sequence of VH chain MF3178; MF3176; MF3163 or MF3307 as depicted in FIG. 11B, or comprises the amino acid sequence of VH MF3178; MF3176; MF3163; MF3307; MF6055-MF6074, preferably MF3178, MF3176, MF3163, MF6058, MF6061 or MF6065 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11B. The VH chain of the variable domain that binds ErbB3 preferably comprises the amino acid sequence of VH chain MF3178, MF3176 or MF3163; or comprises the amino acid sequence of VH chain MF3178, MF3176 or MF3163 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11B. In a preferred embodiment the VH chain of the variable domain that binds ErbB-3 comprises the amino acid sequence of VH chain MF3178 depicted in FIG. 11B; or comprises the amino acid sequence of VH chain MF3178 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence. The antibody preferably further comprises a variable domain that binds EGFR. The VH chain of the variable domain that binds EGFR preferably comprises an amino acid sequence of VH chain of FIG. 11A.

Further provided is an antibody according to the invention, wherein said antibody comprises an EGFR specific heavy chain variable region sequence selected from the group consisting of the heavy chain variable region sequences of MF3998; MF4280; MF4002; MF4003; MF4010; MF4289; MF3370; MF3751; MF3752 as depicted in FIG. 11A, or wherein said antibody comprises a heavy chain variable region sequence that differs in at most 15 amino acids from the heavy chain variable region sequences of MF3998; MF4280; MF4002; MF4003; MF4010; MF4289; MF3370; MF3751; MF3752 as depicted in FIG. 11A.

Further provided is an antibody according to the invention, wherein said antibody comprises an ErbB 3 specific heavy chain variable region sequence selected from the group consisting of the heavy chain variable region sequences of MF3178, MF3176, MF3163, MF3307, MF6055-MF6074, preferably MF3178, MF3176, MF3163, MF6058, MF6061 or MF6065 as depicted in FIG. 11B, or wherein said antibody comprises a heavy chain variable region sequence that differs in at most 15 amino acids from the heavy chain variable region sequences of MF3178, MF3176, MF3163, MF3307, MF6055-MF6074, preferably MF3178, MF3176, MF3163, MF6058, MF6061 or MF6065.

The invention further provides an antibody comprising two variable domains that each bind EGFR wherein a VH of the variable domains comprises the amino acid sequence of the VH chain MF3998; MF4280; MF4002; MF4003; MF4010; MF4289; MF3370; MF3751; MF3752 as depicted in FIG. 11A; or comprises the amino acid sequence of the VH chain MF3998; MF4280; MF4002; MF4003; MF4010; MF4289; MF3370; MF3751; MF3752 as depicted in FIG. 11A, wherein said VH-chain has at most 15, preferably 1, 2, 3, 4, 5, 6, 7, 8, 9 or 10 and preferably has 1, 2, 3, 4 or 5 amino acid insertions, deletions, substitutions or a combination thereof with respect to the VH chain sequence of FIG. 11A. Said VH preferably comprises the amino acid sequence of the VH chain MF3998; MF4280; MF4003; MF4010; MF4289; or MF3370 as depicted in FIG. 11A; or the amino acid sequence of the VH chain MF3998; MF4280; MF4003; MF4010; MF4289; or MF3370 as depicted in FIG. 11A, having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11A. The variable domains of the antibody preferably comprise identical VH chains, preferably having a sequence as depicted in FIG. 11A. An antibody with variable domains with identical VH chains is not a bispecific antibody. VH chains are identical for the present invention if they comprise the same VH chain sequence as depicted in FIG. 11, or the same VH chain sequence but for 1, 2, 3, 4 or 5 amino acid insertions, deletions, substitutions or a combination thereof with respect to the VH chain sequence of FIG. 11A.

The invention further provides an antibody comprising two variable domains that each bind ErbB3 wherein a VH of the variable domains comprises the amino acid sequence of VH chain MF3178; MF3176; MF3163 or MF3307 as depicted in FIG. 11B; or comprises the amino acid sequence of VH chain MF3178; MF3176; MF3163 or MF3307 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11B. Said VH preferably comprises the amino acid sequence of VH chain MF3178, MF3176 or MF3163; or comprises the amino acid sequence of VH chain MF3178, MF3176 or MF3163 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11B. Said VH preferably comprises the amino acid sequence of VH chain MF3178; or comprises the amino acid sequence of VH chain MF3178 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11B. The variable domains of the antibody preferably comprise identical VH chains, preferably having a sequence as depicted in FIG. 11B. An antibody with variable domains with identical VH chains is not a bispecific antibody. The VH chains are identical if they comprise the same VH chain sequence as depicted in FIG. 11B, or the same VH chain sequence but for 1, 2, 3, 4 or 5 amino acid insertions, deletions, substitutions or a combination thereof with respect to the VH chain sequence of FIG. 11B.

The invention preferably provides an antibody comprising a variable domain that binds EGFR and a variable domain that binds ErbB-3,
wherein the VH chain of the variable domain that binds EGFR comprises
the amino acid sequence of VH chain MF3998 as depicted in FIG. 11; or
the amino acid sequence of VH chain MF3998 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and
wherein the VH chain of the variable domain that binds ErbB-3 comprises
the amino acid sequence of VH chain MF3178 as depicted in FIG. 11; or
the amino acid sequence of VH chain MF3178 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention preferably provides an antibody comprising a variable domain that binds EGFR and a variable domain that binds ErbB-3,
wherein the VH chain of the variable domain that binds EGFR comprises
the amino acid sequence of VH chain MF4280 as depicted in FIG. 11; or
the amino acid sequence of VH chain MF4280 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and
wherein the VH chain of the variable domain that binds ErbB-3 comprises
the amino acid sequence of VH chain MF3178 as depicted in FIG. 11; or
the amino acid sequence of VH chain MF3178 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention preferably provides an antibody comprising a variable domain that binds EGFR and a variable domain that binds ErbB-3,
wherein the VH chain of the variable domain that binds EGFR comprises
the amino acid sequence of VH chain MF4003 as depicted in FIG. 11; or
the amino acid sequence of VH chain MF4003 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ErbB-3 comprises the amino acid sequence of VH chain MF3178 as depicted in FIG. 11; or the amino acid sequence of VH chain MF3178 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention preferably provides an antibody comprising a variable domain that binds EGFR and a variable domain that binds ErbB-3, wherein the VH chain of the variable domain that binds EGFR comprises the amino acid sequence of VH chain MF4010 as depicted in FIG. 11; or the amino acid sequence of VH chain MF4010 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ErbB-3 comprises the amino acid sequence of VH chain MF3178 as depicted in FIG. 11; or the amino acid sequence of VH chain MF3178 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention preferably provides an antibody comprising a variable domain that binds EGFR and a variable domain that binds ErbB-3, wherein the VH chain of the variable domain that binds EGFR comprises the amino acid sequence of VH chain MF4289 as depicted in FIG. 11; or the amino acid sequence of VH chain MF4289 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ErbB-3 comprises the amino acid sequence of VH chain MF3178 as depicted in FIG. 11; or the amino acid sequence of VH chain MF3178 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention preferably provides an antibody comprising a variable domain that binds EGFR and a variable domain that binds ErbB-3, wherein the VH chain of the variable domain that binds EGFR comprises the amino acid sequence of VH chain MF3370 as depicted in FIG. 11; or the amino acid sequence of VH chain MF3370 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ErbB-3 comprises the amino acid sequence of VH chain MF3163 as depicted in FIG. 11; or the amino acid sequence of VH chain MF3163 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH. This antibody binds to human EGFR and murine EGFR and can be used to study target effects in mice.

When compared to the sequence in FIG. 11, the behavior of a VH chain typically starts to become noticeably different when it has more than 15 amino acid changes with respect to the amino acid sequence of a VH chain as depicted in FIG. 11. A VH chain having at most 15, preferably 1, 2, 3, 4, 5, 6, 7, 8, 9 or 10 amino acid insertions, deletions, substitutions or a combination thereof with respect to the VH chain depicted in FIG. 11, preferably has 1, 2, 3, 4 or 5 amino acid insertions, deletions, substitutions or a combination thereof with respect to the VH chain depicted in FIG. 11, preferably 1, 2, 3 or 4 insertions, deletions, substitutions or a combination thereof, preferably 1, 2 or 3 insertions, deletions, substitutions or a combination thereof, more preferably 1 or 2 insertions, deletions, substitutions or a combination thereof, and preferably 1 insertion, deletion, substitution or a combination thereof with respect to the VH chain depicted in FIG. 11. The one or more amino acid insertions, deletions, substitutions or a combination thereof are preferably not in the CDR1, CDR2 and CDR3 region of the VH chain. They are also preferably not present in the Fr4 region. An amino acid substitution is preferably a conservative amino acid substitution.

In a preferred embodiment the invention provides an antibody that has a heavy chain comprising an amino acid sequence as depicted in FIG. 11D, or an amino acid sequence of FIG. 11D having at most 15, preferably 1, 2, 3, 4, 5, 6, 7, 8, 9 or 10 and preferably having 1, 2, 3, 4 or 5 amino acid insertions, deletions, substitutions or a combination thereof with respect to the sequence of FIG. 11D. In a preferred embodiment the antibody has two heavy chains each comprising an amino acid sequence as depicted in FIG. 11D, or an amino acid sequence of FIG. 11D having at most 15, preferably 1, 2, 3, 4, 5, 6, 7, 8, 9 or 10 and preferably having 1, 2, 3, 4 or 5 amino acid insertions, deletions, substitutions or a combination thereof with respect to the sequence of FIG. 11D. The at most 15, preferably 1, 2, 3, 4, 5, 6, 7, 8, 9 or 10 and preferably 1, 2, 3 4 or 5 amino acid substitutions are preferably conservative amino acid substitutions. The insertions, deletions, substitutions or a combination thereof are preferably not in the CDR3 region of the VH chain, preferably not in the CDR1, CDR2 and CDR3 region of the VH chain and preferably not in the FR4 region.

Rational methods have evolved toward minimizing the content of non-human residues in the human context. Various methods are available to successfully graft the antigen-binding property of an antibody onto another antibody. The binding properties of antibodies rest predominantly in the exact sequence of the CDR3 region, often supported by the sequence of the CDR1 and CDR2 regions in the variable domain combined with the appropriate structure of the variable domain as a whole. Various methods are presently available to graft CDR regions onto a suitable variable domain of another antibody. Some of these methods are reviewed in J. C. Almagrol and J. Fransson (2008) Frontiers in Bioscience 13, 1619-1633, which is included by reference herein. The invention therefore further provides a human or humanized bispecific antibody comprising a first antigen-binding site that binds EGFR and a second antigen-binding site that binds ErbB-3, wherein the variable domain comprising the EGFR binding site comprises a VH CDR3 sequence as depicted in FIG. 11A, and wherein the variable domain comprising the ErbB-3 binding site comprises a VH CDR3 region as depicted in FIG. 11B. The VH variable region comprising the EGFR binding site preferably comprises the sequence of the CDR1 region, CDR2 region and the CDR3 region of a VH chain in FIG. 11A. The VH variable region comprising the ErbB-3 binding site preferably comprises the sequence of the CDR1 region, CDR2 region and the CDR3 region of a VH chain in FIG. 11B. CDR grafting may also be used to produce a VH chain with the CDR regions of a VH of FIG. 11, but having a different framework. The different framework may be of another human VH, or of a different mammal The mentioned at most 15, preferably 1, 2, 3, 4, 5, 6, 7, 8, 9 or 10 and preferably 1, 2, 3, 4 or 5 amino acid substitutions are preferably conservative amino acid substitutions, the insertions, deletions, substitutions or a combination thereof are preferably not in the CDR3 region of the VH chain, preferably not in the CDR1, CDR2 or CDR3 region of the VH chain and preferably not in the FR4 region.

The light chain of a variable domain comprising a variable heavy chain sequence as depicted in FIG. 11, is preferably a germline light chain of or based on O12, preferably the rearranged germline human kappa light chain IgVκ1-39*01/IGJκ1*01 or a fragment or a functional derivative thereof (nomenclature according to the IMGT database worldwide web at imgt.org). The terms rearranged germline human kappa light chain IgVκ1-39*01/IGJκ1*01, IGKV1-39/IGKJ1, huVκ1-39 light chain or in short huVκ1-39 are used. The light chain can have 1, 2, 3, 4 or 5 amino acid insertions, deletions, substitutions or combination thereof. The mentioned 1, 2, 3, 4 or 5 amino acid substitutions are preferably conservative amino acid substitutions, the insertions, deletions, substitutions or combination thereof are preferably not in the CDR3 region of the VL chain, preferably not in the CDR1, CDR2 or CDR3 region or FR4 region of the VL chain.

Various methods are available to produce bispecific antibodies. One method involves the expression of two different heavy chains and two different light chains in a cell and collecting antibody that is produced by the cell. Antibody produced in this way will typically contain a collection of antibodies with different combinations of heavy and light chains, some of which are the desired bispecific antibody. The bispecific antibody can subsequently be purified from the collection. The ratio of bispecific to other antibodies that are produced by the cell can be increased in various ways. In a preferred embodiment of the invention, the ratio is increased by expressing not two different light chains but two essentially identical light chains in the cell. This concept is in the art also referred to as the "common light chain" method. When the essentially identical light chains work together with the two different heavy chains allowing the formation of variable domains with different antigen-binding sites and concomitant different binding properties, the ratio of bispecific antibody to other antibody that is produced by the cell is significantly improved over the expression of two different light chains. The ratio of bispecific antibody that is produced by the cell can be further improved by stimulating the pairing of two different heavy chains with each other over the pairing of two identical heavy chains. The art describes various ways in which such heterodimerization of heavy chains can be achieved. One way is to generate 'knob into hole' bispecific antibodies. See US Patent Application 20030078385 (Arathoon et al.—Genentech). Another method is by using charge engineering as described in Gunasekaran (JBC 2010, vol 285, pp 19637-19646). Another and preferred method is described in U.S. provisional application 61/635,935, which has been followed up by U.S. application Ser. No. 13/866,747 and PCT application No. PCT/NL2013/050294 (WO 2013/157954 A1), which are incorporated herein by reference. Methods and means are disclosed for producing bispecific antibodies (from a single cell), whereby means are provided that favor the formation of bispecific antibodies over the formation of monospecific antibodies. These methods can also be favorably employed in the present invention. Thus the invention provides a method for producing a bispecific antibody according to the invention (from a single cell), wherein said bispecific antibody comprises two CH3 domains that are capable of forming an interface, said method comprising providing in said cell a) a first nucleic acid molecule encoding a 1st CH3 domain comprising heavy chain, b) a second nucleic acid molecule encoding a 2nd CH3 domain comprising heavy chain, wherein said nucleic acid molecules are provided with means for preferential pairing of said 1st and 2nd CH3 domain comprising heavy chains, said method further comprising the step of culturing said host cell and allowing for expression of said two nucleic acid molecules and harvesting said bispecific antibody from the culture. Said first and second nucleic acid molecules may be part of the same nucleic acid molecule, vector or gene delivery vehicle and may be integrated at the same site of the host cell's genome. Alternatively, said first and second nucleic acid molecules are separately provided to said cell.

A preferred embodiment provides a method for producing a bispecific antibody according to the invention from a single cell, wherein said bispecific antibody comprises two CH3 domains that are capable of forming an interface, said method comprising providing:

a cell having a) a first nucleic acid molecule encoding a heavy chain comprising an antigen binding site that binds EGFR and that contains a 1st CH3 domain, and b) a second nucleic acid molecule encoding a heavy chain comprising an antigen-binding site that binds ErbB-3 and that contains a 2nd CH3 domain, wherein said nucleic acid molecules are provided with means for preferential pairing of said 1st and 2nd CH3 domains, said method further comprising the step of culturing said cell and allowing for expression of the proteins encoded by said two nucleic acid molecules and harvesting said bispecific IgG antibody from the culture. In a particularly preferred embodiment, said cell also has a third nucleic acid molecule encoding a common light chain. Said first, second and third nucleic acid molecule may be part of the same nucleic acid molecule, vector or gene delivery vehicle and may be integrated at the same site of the host cell's genome. Alternatively, said first, second and third nucleic acid molecules are separately provided to said cell. A preferred common light chain is based on O12, preferably it is the rearranged germline human kappa light chain IgVκ1 39*01/GJκ1*01, as described above. Means for preferential pairing of said $1^{st}$ and said $2^{nd}$ CH3 domain are preferably the corresponding mutations in the CH3 domain of the heavy chain coding regions. The preferred mutations to produce essentially only bispecific antibodies are the amino acid substitutions L351K and T366K (numbering according to Kabat) in the first CH3 domain and the amino acid substitutions L351D and L368E in the second CH3 domain, or vice versa. Further provided is therefore a method according to the invention for producing a bispecific antibody, wherein said first CH3 domain comprises the amino acid substitutions L351K and T366K (numbering according to Kabat) and wherein said second CH3 domain comprises the amino acid substitutions L351D and L368E, said method further comprising the step of culturing said cell and allowing for expression of proteins encoded by said nucleic acid molecules and harvesting said bispecific antibody from the culture. Also provided is a method according to the invention for producing a bispecific antibody, wherein said first CH3 domain comprises the amino acid substitutions L351D and L368E (numbering according to Kabat) and wherein said second CH3 domain comprises the amino acid substitutions L351K and T366K, said method further comprising the step of culturing said cell and allowing for expression of said nucleic acid molecules and harvesting said bispecific antibody from the culture. Antibodies that can be produced by these methods are also part of the present invention. The CH3 hetero-dimerization domains are preferably IgG1 hetero-dimerization domains. The heavy chain constant regions comprising the CH3 hetero-dimerization domains are preferably IgG1 constant regions.

In one embodiment the invention provides a nucleic acid molecule encoding an antibody heavy chain variable region according to the invention. The nucleic acid molecule (typically an in vitro, isolated or recombinant nucleic acid molecule) preferably encodes a heavy chain variable region as depicted in FIG. 11A or FIG. 11B, or a heavy chain variable region as depicted in FIG. 11A or FIG. 11B having 1, 2, 3, 4 or 5 amino acid insertions, deletions, substitutions or combination thereof. In a preferred embodiment the nucleic acid molecule comprises a sequence as depicted in FIG. 11. In another preferred embodiment the nucleic acid molecule encodes the same amino acid sequence as the nucleic acid depicted in FIG. 11 but has a different sequence because it encodes one or more different codons. The invention further provides a nucleic acid sequence encoding a heavy chain of FIG. 11D.

A nucleic acid molecule as used in the invention is typically but not exclusively a ribonucleic acid (RNA) or a deoxyribonucleic acid (DNA). Alternative nucleic acids are available for a person skilled in the art. A nucleic acid according to the invention is for instance comprised in a cell. When said nucleic acid is expressed in said cell, said cell can produce an antibody according to the invention. Therefore, the invention in one embodiment provides a cell comprising an antibody according to the invention and/or a nucleic acid according to the invention. Said cell is preferably an animal cell, more preferably a mammal cell, more preferably a primate cell, most preferably a human cell. For the purposes of the invention a suitable cell is any cell capable of comprising and preferably of producing an antibody according to the invention and/or a nucleic acid according to the invention.

The invention further provides a cell comprising an antibody according to the invention. Preferably said cell (typically an in vitro, isolated or recombinant cell) produces said antibody. In a preferred embodiment said cell is a hybridoma cell, a Chinese hamster ovary (CHO) cell, an NS0 cell or a PER-C6™ cell. In a particularly preferred embodiment said cell is a CHO cell. Further provided is a cell culture comprising a cell according to the invention. Various institutions and companies have developed cell lines for the large scale production of antibodies, for instance for clinical use. Non-limiting examples of such cell lines are CHO cells, NS0 cells or PER.C6™ cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of antibody for the production of an antibody of the invention. The invention further provides a cell for producing an antibody comprising a nucleic acid molecule that codes for a VH, a VL, and/or a heavy chain as depicted in FIG. 11. Preferably said nucleic acid molecule comprises a sequence as depicted in FIG. 11a or 11b.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, a 293F cell, an NS0 cell or another cell type known for its suitability for antibody production for clinical purposes. In a particularly preferred embodiment said cell is a human cell. Preferably a cell that is transformed by an adenovirus E1 region or a functional equivalent thereof. A preferred example of such a cell line is the PER.C6™ cell line or equivalent thereof. In a particularly preferred embodiment said cell is a CHO cell or a variant thereof. Preferably a variant that makes use of a Glutamine synthetase (GS) vector system for expression of an antibody.

The invention further provides a pharmaceutical composition comprising an antibody according to the invention. The pharmaceutical composition preferably comprises a preferably pharmaceutically acceptable excipient or carrier. In a preferred embodiment the pharmaceutical composition comprises 5-50 mM Histidine, 100-300 mM Trehalose, 0.1-03 g/L PolySorbate20 or a combination thereof. The pH is preferably set at pH=5.5-6.5. In a preferred embodiment the pharmaceutical composition comprises 25 mM Histidine, 220 mM Trehalose, 0.2 g/L PolySorbate20 or a combination thereof. The pH is preferably set at pH=5.5-6.5, most preferably at pH=6.

An antibody of the invention preferably further comprises a label, preferably a label for in vivo imaging. Such a label is typically not necessary for therapeutic applications. In for instance a diagnostic setting, a label can be helpful. For instance in visualizing target cells in the body. Various labels are suited and many are well known in the art. In a preferred embodiment the label is a radioactive label for detection. In another preferred embodiment, the label is an infrared label. Preferably the infrared label is suited for in vivo imaging. Various infrared labels are available to the person skilled in the art. Preferred infrared labels are for instance, IRDye 800; IRDye 680RD; IRDye 680LT; IRDye 750; IRDye 700DX; IRDye 800RS IRDye 650; IRDye 700 phosphoramidite; IRDye 800 phosphoramidite (LI-COR USA; 4647 Superior Street; Lincoln, Nebr.).

The invention further provides a method for the treatment of a subject having an EGFR, ErbB-3 or EGFR/ErbB-3 positive tumor or at risk of having said tumor comprising administering to the subject an antibody or pharmaceutical composition according to the invention. Before start of said treatment, the method preferably comprises determining whether said subject has, or is at risk of, such EGFR, ErbB-3 or EGFR/ErbB-3 positive tumor. The invention further provides an antibody or pharmaceutical composition of the invention for use in the treatment of a subject having or at risk of having an EGFR, ErbB-3 or EGFR/ErbB-3 positive tumor.

To establish whether a tumor is positive for EGFR the skilled person can for instance determine the EGFR amplification and/or staining immune-histochemistry. At least 10% of the tumor cells in a biopt should be positive. The biopt can also contain 20%, 30% 40% 50% 60% 70% or more positive cells. To establish whether a tumor is positive for HER3 the skilled person can for instance determine the HER3 amplification and/or staining in immunohistochemistry. At least 10% tumor cells in a biopt should be positive. The biopt can also contain 20%, 30% 40% 50% 60% 70% or more positive cells.

The tumor is preferably an EGFR, ErbB-3 or EGFR/ErbB-3 positive cancer. Preferably said positive cancer is a breast cancer, such as early-stage breast cancer. However, the invention can be applied to a wide range of EGFR, ErbB-3 or EGFR/ErbB-3 positive cancers, like breast cancer, colon cancer, pancreatic cancer, gastric cancer, ovarian cancer, colorectal cancer, head- and neck cancer, lung cancer including non-small cell lung cancer, bladder cancer and the like. The subject is preferably a human subject. The subject is preferably a subject eligible for antibody therapy using an EGFR specific antibody such as cetuximab. In a preferred embodiment the subject comprises a tumor, preferably an EGFR/ErbB-3 positive cancer, preferably a tumor/cancer with an EGFR monoclonal antibody resistant phenotype.

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred. The dosage can be in range of the dosing regime of cetuximab. The dosage can also be lower.

A bispecific antibody according to the invention preferably induces less skin toxicity as compared to cetuximab under otherwise similar conditions of course. A bispecific antibody according to the invention preferably produces less proinflammatory chemokines, preferably of CXCL14 as compared to cetuximab under otherwise similar conditions of course. A bispecific antibody according to the invention preferably induces less impairment of antimicrobial RNAses, preferably Rnase 7, as compared to cetuximab under otherwise similar conditions of course.

The present invention describes among others antibodies that target the EGFR and ErbB-3 receptors and result in potent proliferation inhibition of cancer cell lines in vitro and tumor growth inhibition in vivo. A diverse panel of human and Fab binding arms specific for either EGFR or ErbB-3 were identified. These were produced as bispecific antibodies by cloning them into complementary expression vectors that contain mutations in the CH3 region that drives hetero-dimerization of heavy chains. Many bispecific antibodies were produced at small scale and tested in binding and functional assays on cancer cell lines. Various bispecific antibodies were selected and tested in an orthotopic xenograft model using the BxPC3-luc2 cell line. This cell line expresses both the EGFR and ErbB-3 receptors and is partially dependent on the presence of an EGFR ligand and an ErbB-3 ligand for growth. BxPC3 models are a robust and stringent screening model. An antibody of the invention, particularly a bispecific antibody of the invention can combine low toxicity profiles with high efficacy. An antibody of the invention can be useful in various types and lines of EGFR-targeted therapies. An antibody of the invention can have an increased therapeutic window when compared to an antibody that binds the same antigen(s) with both arms. A bispecific antibody of the invention can exhibit better growth inhibitory effects in vitro, in vivo or a combination thereof when compared to the MEHD7945A antibody.

Preferred embodiments of the invention provide uses of antibodies according to the invention under heregulin stress conditions. Heregulin is a growth factor that is involved in growth of ErbB-3 positive tumor cells. Typically, when the tumor cells express high levels of heregulin (referred to as heregulin stress), currently known therapies like trastuzumab, pertuzumab and lapatinib are no longer capable of inhibiting tumor growth. This phenomenon is called heregulin resistance. Surprisingly, however, an antibody according to the invention is also capable of counteracting growth of tumor cells that express high levels of heregulin. As used herein, an expression level of heregulin is considered high if a cell has a heregulin expression level that is at least 60%, preferably at least 70%, more preferably at least 80%, more preferably at least 85%, more preferably at least 90% or 95% of the heregulin expression level of BXPC3 or MCF7 cells. Heregulin expression levels are for instance measured using qPCR with tumor RNA (such as for instance described in Shames et al. PLOS ONE, February 2013, Vol. 8, Issue 2, pp 1-10 and in Yonesaka et al., Sci. transl. Med., Vol. 3, Issue 99 (2011); pp 1-11), or using protein detection methods, like for instance ELISA, preferably using blood, plasma or serum samples (such as for instance described in Yonesaka et al., Sci. transl. Med., Vol. 3, Issue 99 (2011); pp 1-11).

Also provided is a method for counteracting the formation of a metastasis in a subject having a EGFR, ErbB-3 or EGFR/ErbB-3 positive tumor, wherein said EGFR, ErbB-3 or EGFR/ErbB-3 positive tumor has a heregulin expression level that is at least 60%, preferably at least 70%, more preferably at least 80%, more preferably at least 85%, more preferably at least 90% or 95% of the heregulin expression level of BXPC3 or MCF7 cells, comprising administering to the subject a bispecific antibody comprising a first antigen-binding site that binds EGFR and a second antigen-binding site that binds ErbB-3. Also provided is a bispecific antibody comprising a first antigen-binding site that binds EGFR and a second antigen-binding site that binds ErbB-3 for use in the treatment or prevention of focal adhesion of a EGFR, ErbB-3 or EGFR/ErbB-3 positive tumor cell, or for use in the treatment or prevention of the formation of metastases, wherein said EGFR, ErbB-3 or EGFR/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Further provided is a use of a bispecific antibody according to the invention for the preparation of a medicament for the treatment or prevention of focal adhesion of a EGFR, ErbB-3 or EGFR/ErbB-3 positive tumor cell, or for the treatment or prevention of the formation of metastases, wherein said EGFR, ErbB-3 or EGFR/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Said EGFR, ErbB-3 or EGFR/ErbB-3 positive tumor is preferably breast cancer, colon cancer, pancreatic cancer, gastric cancer, ovarian cancer, colorectal cancer, head- and neck cancer, lung cancer including non-small cell lung cancer, bladder cancer and the like. Most preferably, said tumor is breast cancer. Further provided is therefore a bispecific antibody according to the invention comprising a first antigen-binding site that binds EGFR and a second antigen-binding site that binds ErbB-3 for use in the treatment or prevention of focal adhesion, or the formation of metastases, of breast cancer, colon cancer, pancreatic cancer, gastric cancer, ovarian cancer, colorectal cancer, head- and neck cancer, lung cancer including non-small cell lung cancer, bladder cancer and the like, preferably breast cancer cells, wherein said cells have a heregulin expression level that is at least 60%, preferably at least 70%, more preferably at least 80%, more preferably at least 85%, more preferably at least 90% or 95% of the heregulin expression level of BXPC3 or MCF7 cells. Said antibody according to the present invention is typically capable of reducing a ligand-induced receptor function, preferably ligand induced growth, of ErbB 3 on a ErbB 2 and ErbB 3 positive cell. Said antibody according to the invention preferably comprises an antigen-binding site that binds domain III of ErbB-3. The affinity (KD) of said ErbB-3 antigen-binding site for an ErbB-3 positive cell is preferably lower than or equal to 2.0 nM, more preferably lower than or equal to 1.39 nM, more preferably lower than or equal to 0.99 nM.

In one preferred embodiment, said antibody according to the invention preferably comprises an antigen-binding site that binds at least one amino acid of domain III of ErbB-3 selected from the group consisting of R426 and surface-exposed amino acid residues that are located within 11.2 Å from R426 in the native ErbB-3 protein.

One preferred embodiment provides a use of an antibody according to the invention for the preparation of a medicament for the treatment of an EGFR, ErbB-3 or EGFR/ErbB-3 positive tumor, wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells. Said EGFR, ErbB-3 or EGFR/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. Further provided is therefore an antibody according to the invention for use in the treatment of a subject having or at risk of having breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma, preferably breast cancer, wherein cells of said cancer have a heregulin expression level that is at least 60%, preferably at least 70%, more preferably at least 80%, more preferably at least 85%, more preferably at least 90% or 95% of the heregulin expression level of BXPC3 or MCF7 cells.

High heregulin levels are typically present during the formation of metastases (i.e. the migration, invasion, growth and/or differentiation of tumor cells or tumor initiating cells). Typically, tumor initiating cells are identified based on stem cell markers such as CD44. These processes can therefore barely be counteracted with currently known therapies like trastuzumab and pertuzumab. Since an antibody according to the invention is capable of counteracting growth and/or differentiation of tumor cells or tumor initiating cells that express high levels of heregulin, such antibody according to the invention is also particularly suitable for counteracting the formation of metastases. Further provided is therefore a method for counteracting the formation of a metastasis in a subject having a EGFR, ErbB-3 or EGFR/ErbB-3 positive tumor, wherein said EGFR, ErbB-3 or EGFR/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells, comprising administering to the subject a bispecific antibody comprising a first antigen-binding site that binds EGFR and a second antigen-binding site that binds ErbB-3. Also provided is a bispecific antibody comprising a first antigen-binding site that binds EGFR and a second antigen-binding site that binds ErbB-3 for use in the treatment or prevention of the formation of metastases, wherein said EGFR, ErbB-3 or EGFR/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Further provided is a use of a bispecific antibody according to the invention for the preparation of a medicament for the treatment or prevention of the formation of metastases, wherein said EGFR, ErbB-3 or EGFR/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Said EGFR, ErbB-3 or EGFR/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. Further provided is therefore a bispecific antibody according to the invention comprising a first antigen-binding site that binds EGFR and a second antigen-binding site that binds ErbB-3 for use in the treatment or prevention of the formation of metastases of breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma cells, preferably breast cancer cells, wherein said cells have a heregulin expression level that is at least 60%, preferably at least 70%, more preferably at least 80%, more preferably at least 85%, more preferably at least 90% or 95% of the heregulin expression level of BXPC3 or MCF7 cells. Said antibody according to the present invention is typically capable of reducing a ligand-induced receptor function, preferably ligand induced growth, of ErbB-3 on a EGFR and ErbB-3 positive cell. Said antibody according to the invention preferably comprises a first antigen-binding site that binds domain I of EGFR and a second antigen-binding site that binds domain III of ErbB-3. The affinity of said second antigen-binding site for an ErbB-3 positive cell is preferably lower than or equal to 2.0 nM, more preferably lower than or equal to 1.39 nM, more preferably lower than or equal to 0.99 nM.

In one embodiment, said bispecific antibody is for use in the treatment of a subject under hereregulin stress conditions, as explained in more detail herein above.

Antibodies of the invention can be produced at levels >50 mg/L after transient transfection in suspension 293F cells. The bispecific antibodies can be purified to greater than 98% purity with yields >70%. Analytical characterization studies show bispecific IgG1 antibody profiles that are comparable to bivalent monospecific IgG1. In terms of functional activity a bispecific antibody of the invention can demonstrate superior potency compared to MEHD7945A in vitro and in vivo.

For the purpose of clarity and a concise description features are described herein as part of the same or separate embodiments, however, it will be appreciated that the scope of the invention may include embodiments having combinations of all or some of the features described.

BRIEF DESCRIPTION OF THE DRAWINGS

FIG. 1 (SEQ ID NOS: 1 and 2): Annotated sequence of the chimeric cynomolgus-human EGFR encoding construct. Restriction sites used for re-cloning (Nhe1-Not1) are indicated in capitals. The start of the mature peptide is underlined and indicated in bold. The trans-membrane region is in bold and italics.

FIG. 2 (SEQ ID NOS: 3-5, respectively): Amino acid sequences of the extra-cellular domain (ECD) of EGFR 'swap-domain variants': the human EGFR ECD was used as backbone and specific domains were swapped for the human HER3 sequence. HER3-derived sequences are indicated. These sequences were cloned in frame with a c-Myc derived epitope tag and the trans-membrane region of the platelet-derived growth factor receptor (PDGFR).

FIG. 3: Epitope mapping of anti-EGFR Fab's (MF number; selected from the 'immune' phage libraries) expressed on phage by competition for binding with known, literature-derived antibodies. Representative OD values obtained after testing of phage binding to immobilized EGFR in ELISA in the presence (or absence) of the indicated antibodies ND: not determined. The domain specificity of the control antibodies is indicated.

Y axis (counts) shows the fluorescence readout of the assay, reminiscent of the number of metabolically active cells, as a function of the concentration of antibody used (X-axis). Antibodies that show functional EGFR blocking activity dose-dependently inhibit the EGF-induced cell death and therefore show enhanced growth of the cells with increasing antibody concentration. The clinically used antibody cetuximab was used in all experiments as an internal standard (diamonds).

Figure 6:
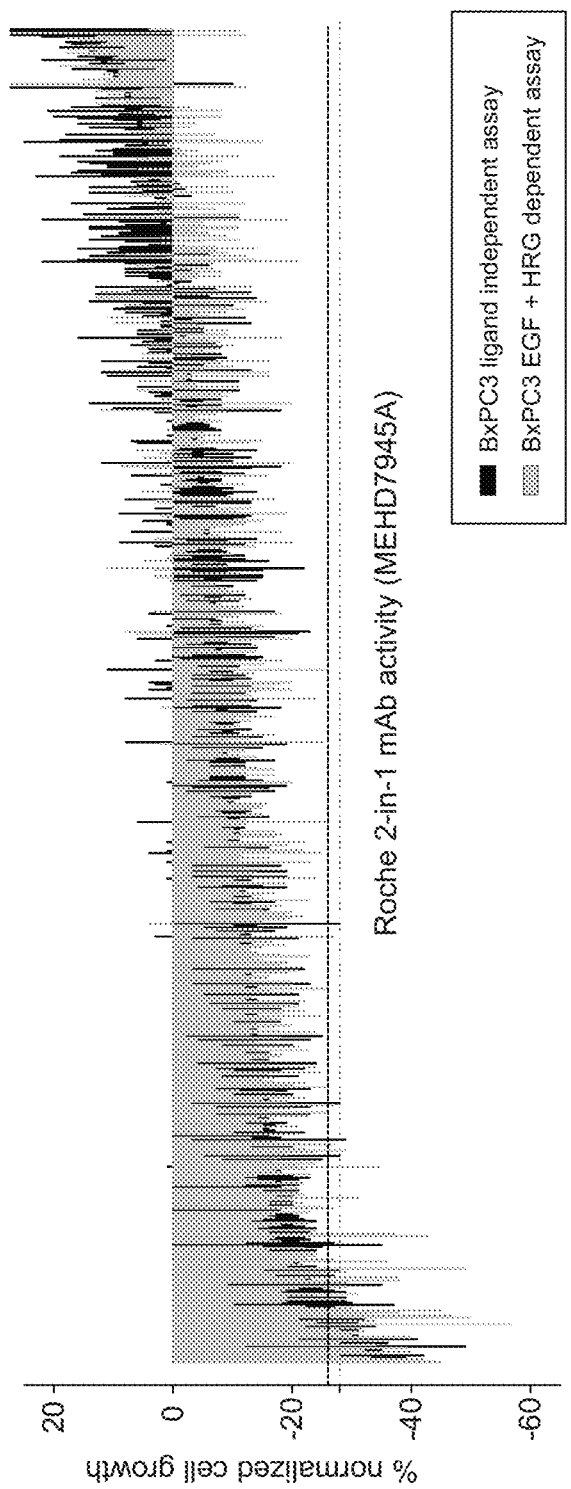

FIG. 6: overview of the screening of anti-EGFRxHER3 bispecifics, compared to the activity of the MEHD7945A antibody. Every bar represents the activity of a bispecific anti-EGFRxHER3 antibody in the BxPC-3 ligand-independent (light bars) and ligand-driven assay (dark bars). The average activity of the MEHD7945A antibody is indicated by a light (upper) and dark (lower) line for the independent and dependent assay respectively. Growth was normalized to untreated controls. Over 800 bispecific anti-EGFRxHER3 antibodies were screened.

Figure 7:
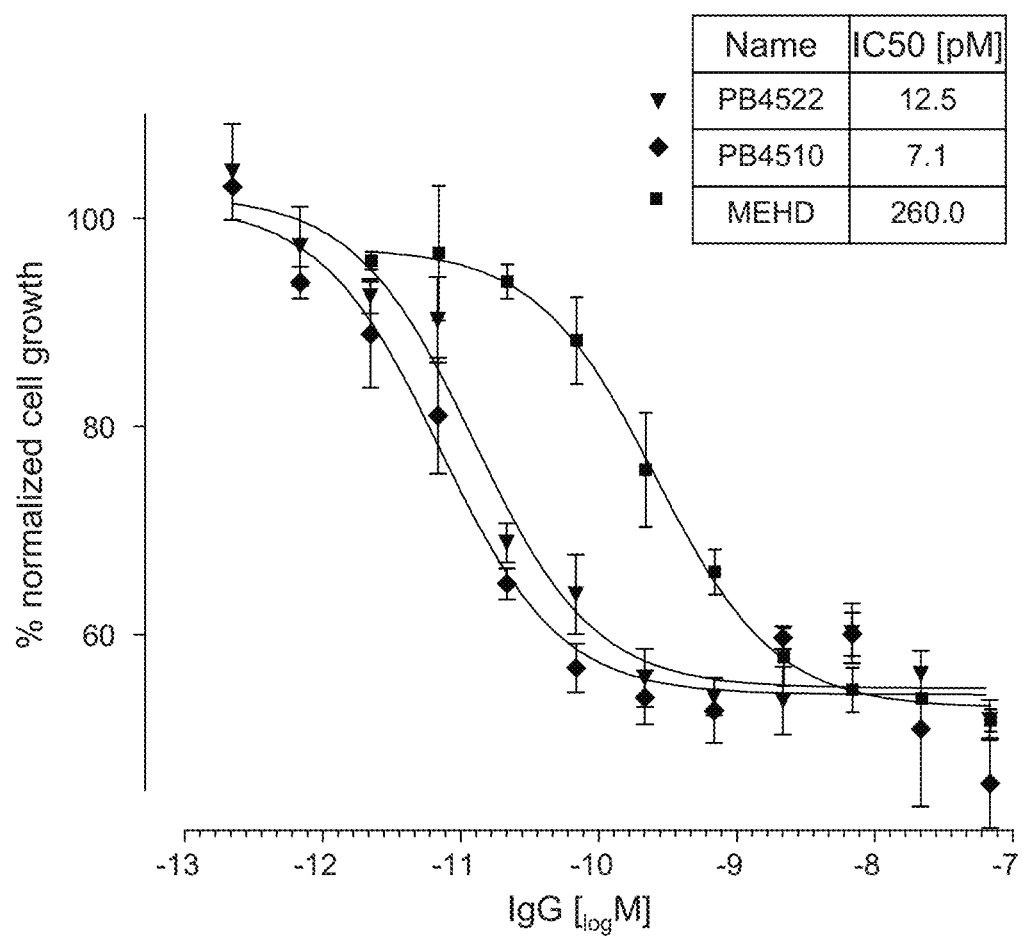

FIG. 7: IC50 determination for BxPC-3 cell proliferation inhibition of the two best performing bispecifics (PB numbers), compared to MEHD7945A. The Y-axis represents the percentage of growth, normalised to the control situation (i.e. uninhibited growth in the presence of both ligands) and the X-axis the antibody concentration used. IC50 values are indicated.

Figure 8:
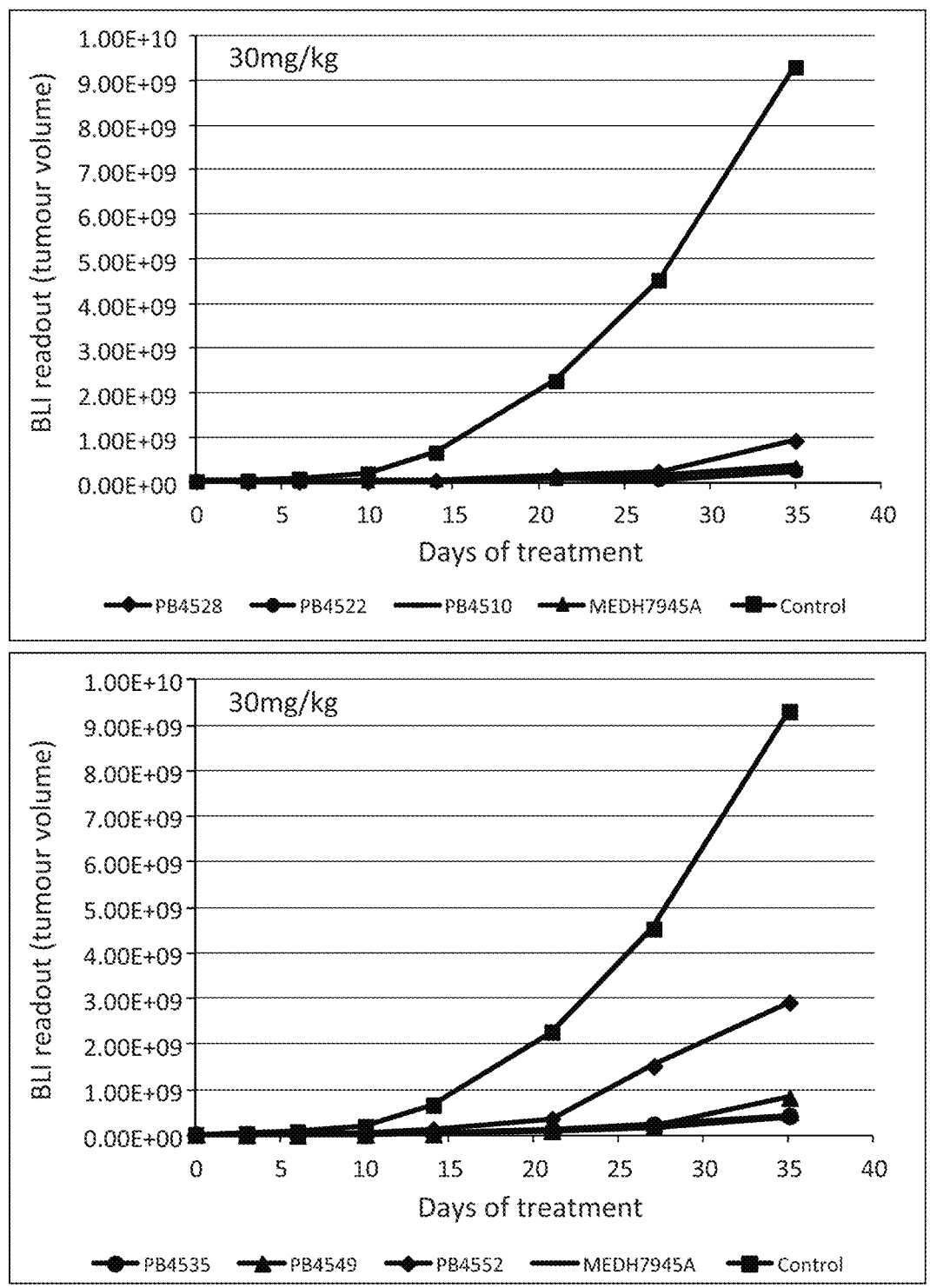

FIG. 8: therapeutic effect of bispecific antibody (PB numbers) treatment on the growth of BxPC-3 cells orthotopically implanted. The Y-axis shows the bioluminescence (BLI) readout (reminiscent of the number of live tumor cells) after injection of luciferin in the mice as a function of time (X-axis). The MEHD7945A antibody was used as reference and an irrelevant (anti-RSV) antibody as a negative control antibody (squares). For the sake of clarity, error bars have been omitted from the Figure.

Figure 9:
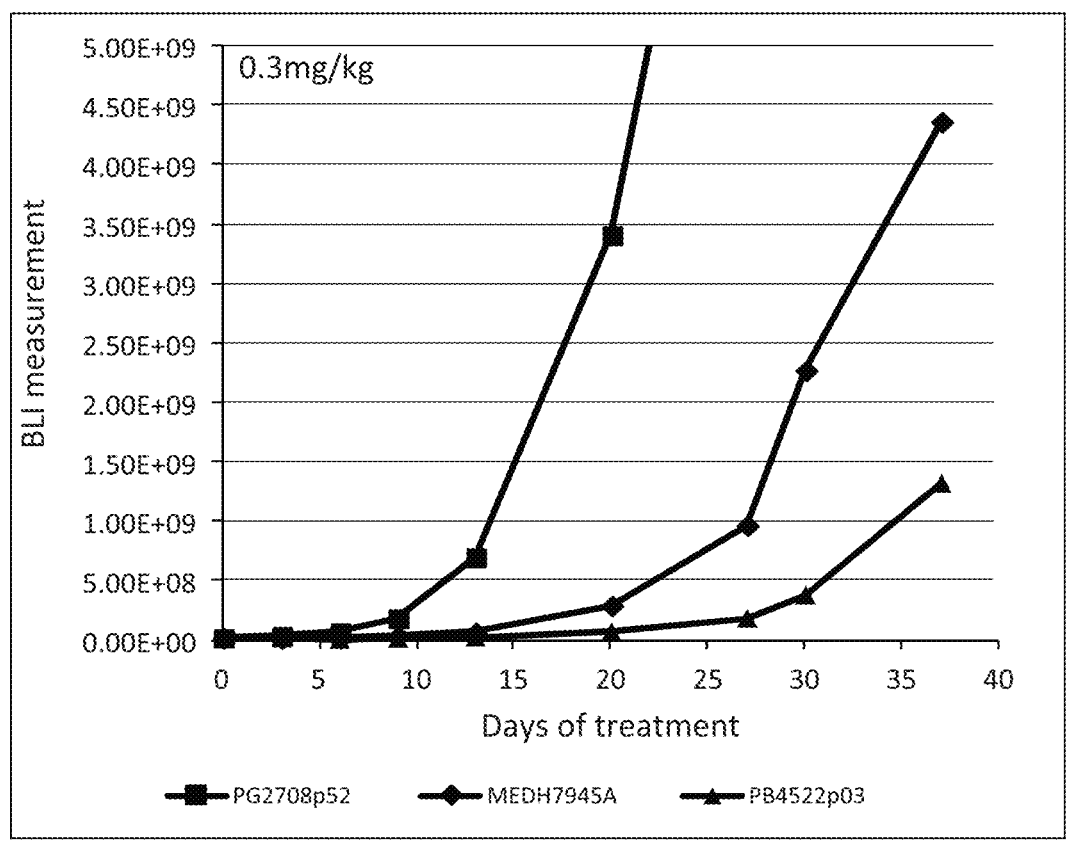

FIG. 9: therapeutic effect of the lead bispecific PB4522 in comparison with that of MEHD7945A at 0.3 mg/kg dose. Y axis shows the in vivo bioluminescence (BLI), reminiscent of the number of live tumor cells as a function of time (X-axis). NC: negative control antibody (anti-RSV, 30 mg/kg dose). For the sake of clarity, error bars have been omitted from the Figure.

Figure 10:
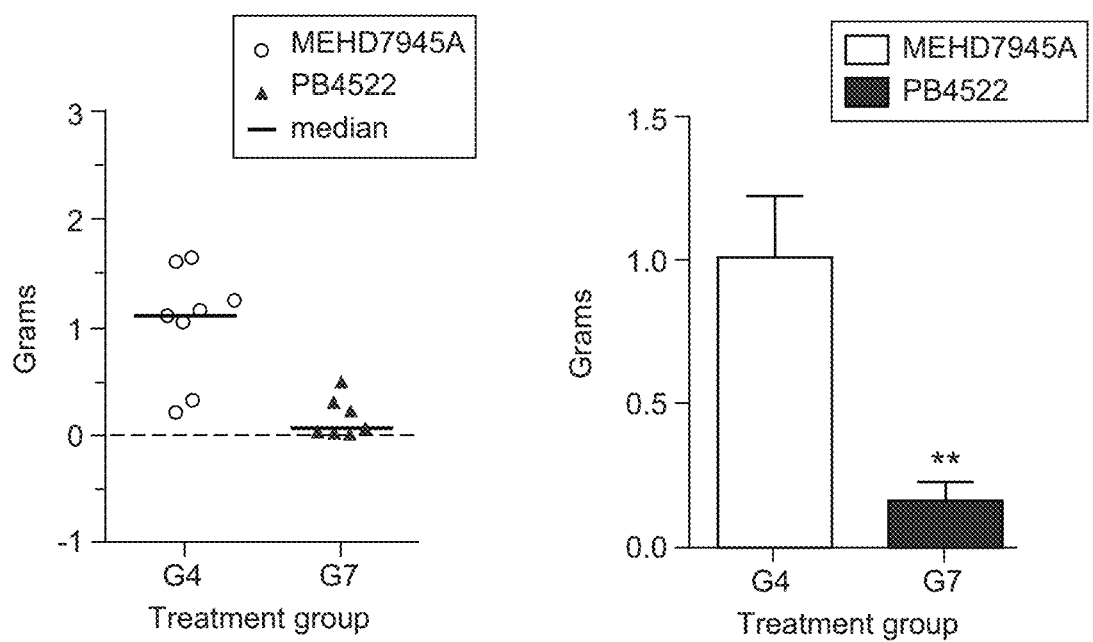

FIG. 10: tumor weights measured ex vivo at day 38 of the study of tumors isolated from mice treated with either MEHD7945A (group G4) or PB4522 (group G7) at 0.3 mg/kg. The left panel shows the weight of the tumor of every individual mouse and the right panel shows the average weight of the 7 mice that were treated. **p<0.05.

FIG. 11 (SEQ ID NOS: 7-155): Nucleic acid and amino acid sequences of VH-chains, common light chain and heavy chains of antibodies of the invention. Where in this Figure a leader sequence is indicated this is not part of the VH chain or antibody, but is typically cleaved of during processing of the protein in the cell that produces the protein. The VH chain sequence of a heavy chain indicated with the capitals MG followed by a number in the text is indicated herein by the same number preceded with the letters VH. FIG. 11b further specifies the amino acid sequences of heavy chain variable region sequences of an erbB-3 binding antibodies MF6055-MF6074. The variable heavy chain sequences are variants of heavy chain variable region MF3178. Dots indicate the same amino acid as in MF3178 at that position. The CDR regions are separated by a space and indicated in bold.

FIG. 12: CXCL14 and Rnase7 expression in primary keratinocytes stimulated with different IgGs. Expression was measured by Q-PCR in the presence of two antibody concentrations.

Figure 13:
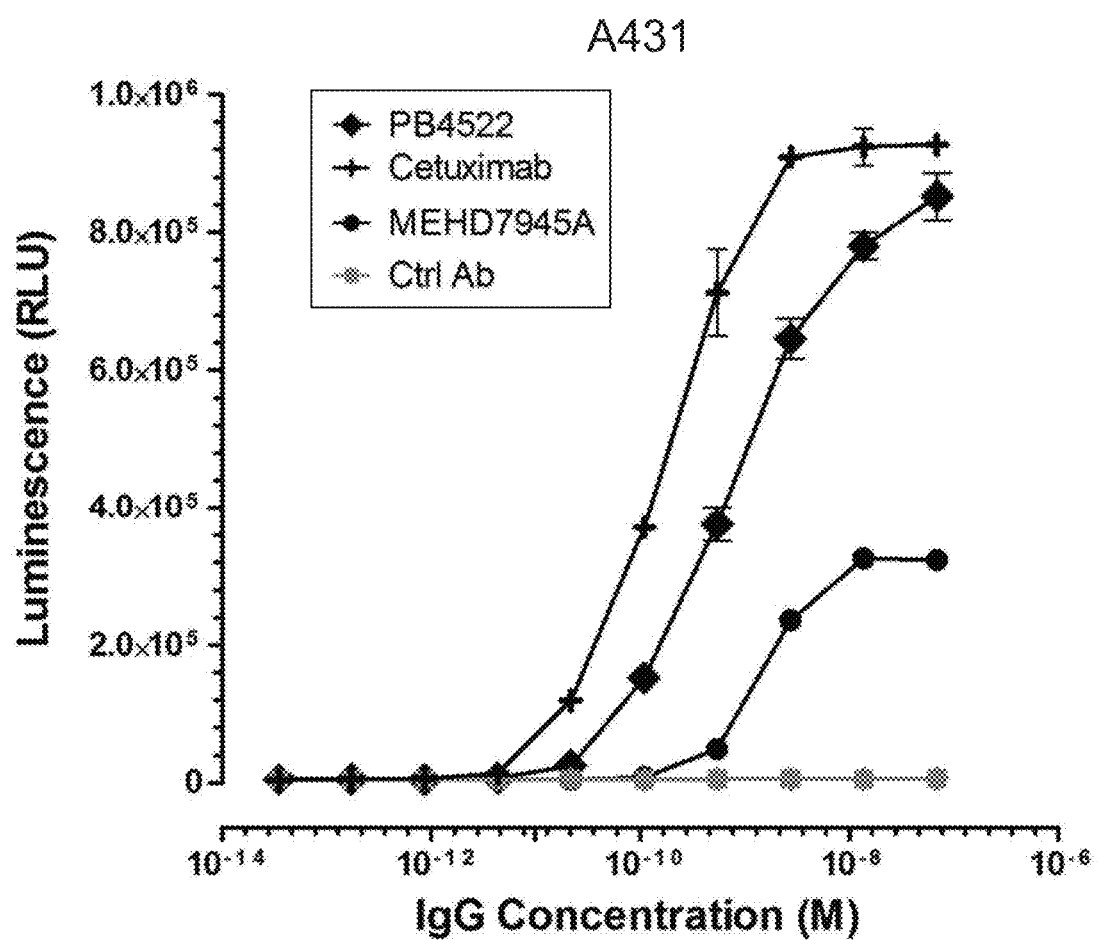
Figure 14:
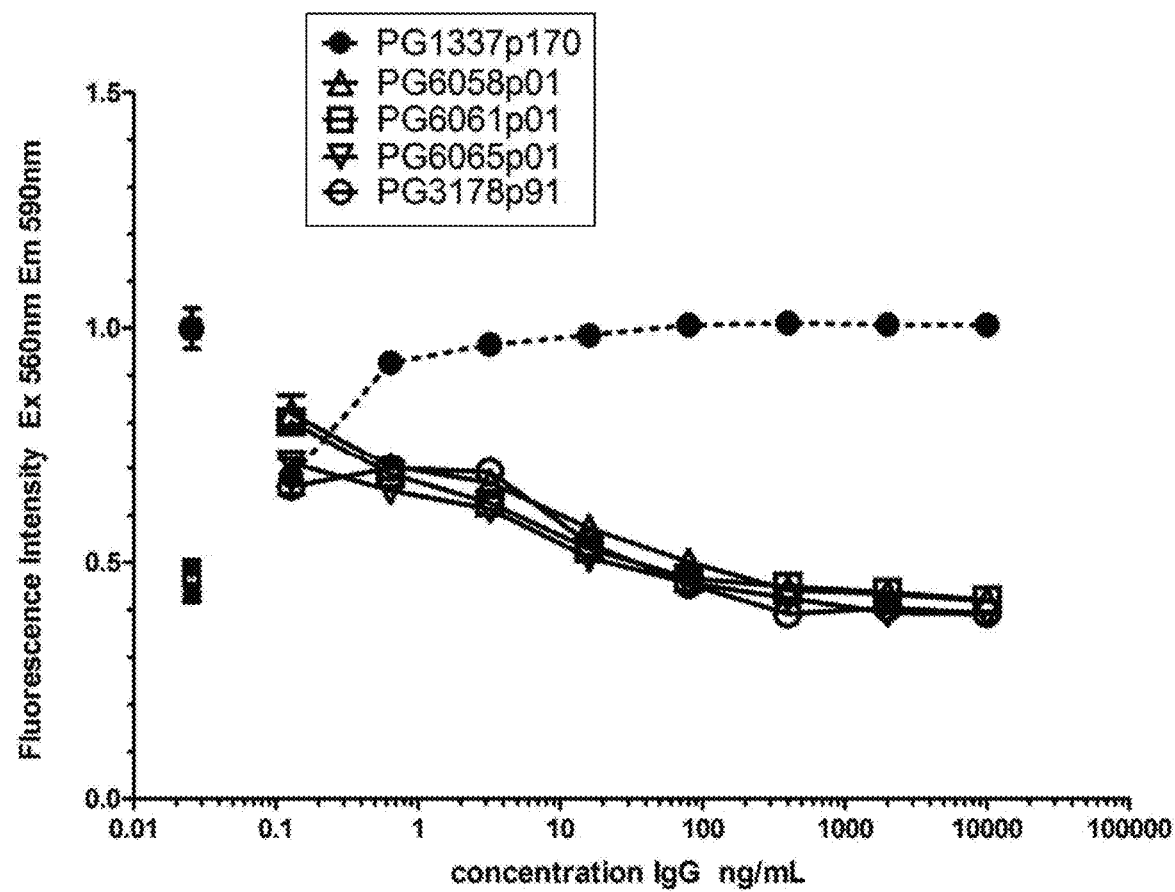

FIG. 13: ADCC activity of afucosylated PB4522 compared to MEHD7945A and cetuximab on high EGFR (A431) and intermediate EGFR (BxPC3 and A549) expressing cells. 'Ctrl Ab' is an IgG directed against Tetanus Toxoid FIG. 14: Titration curves of HER3 monoclonal antibodies in the HRG dependent N87 assay. PG6058, PG6061 and PG6065 are variants of PG3178. PG1337 is a negative control specific for tetanus toxoid. Data were normalized to basal proliferation with ligand present on each plate.

Figure 15:
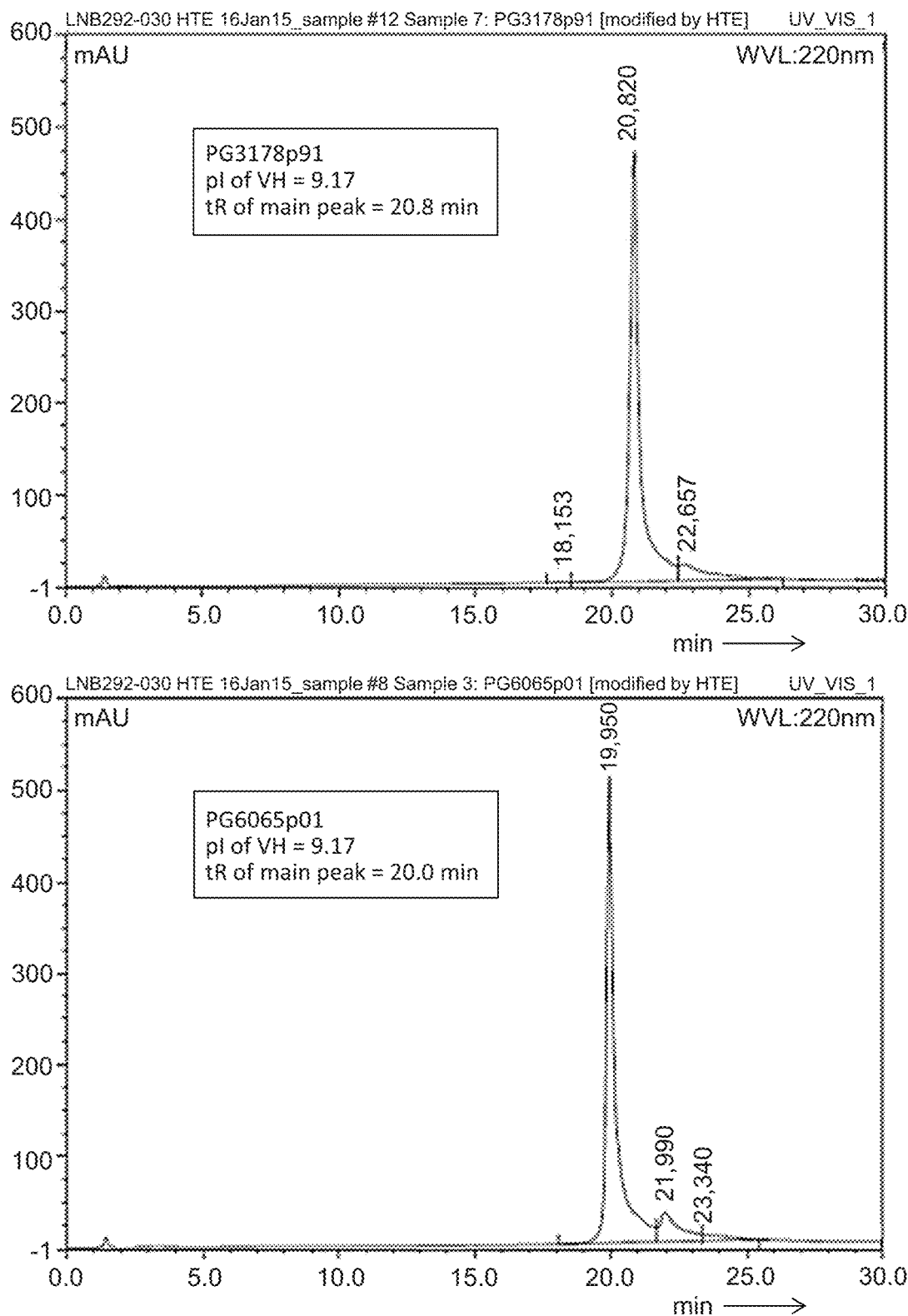
Figure 16A:
Figure 16B:
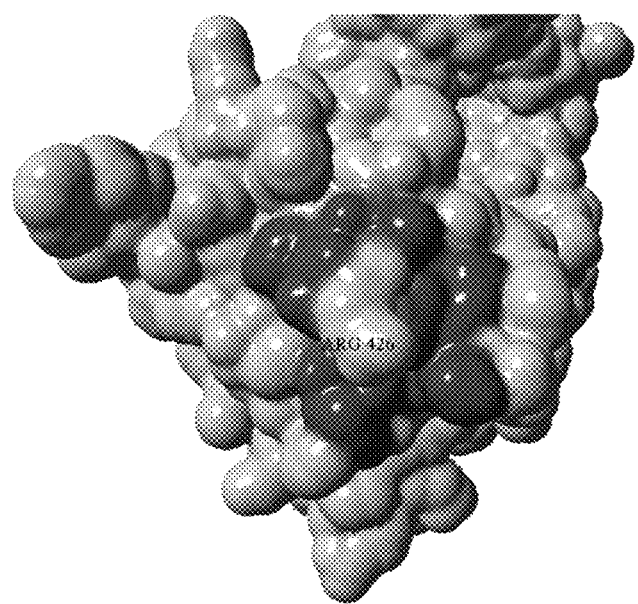
Figure 16C:
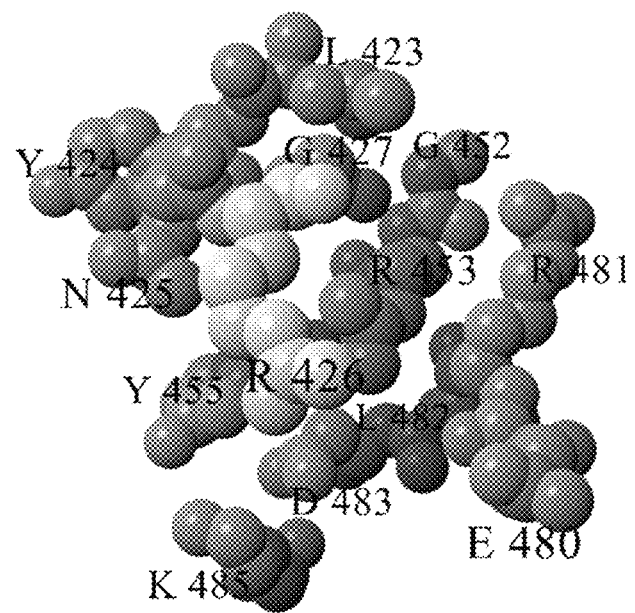

FIG. 15: CIEX-HPLC profiles of HER3 monoclonal antibodies. PG6058, PG6061 and PG6065 are variants of PG3178. The calculated iso-electric point (pI) of the VH region and the retention time (tR) of the main peak are given for each antibody.

FIG. 16:

a) HER3 crystal structure (PDB #4P59) showing epitope residue Arg 426 in gray spheres and all surface exposed residues within an 11.2 Å radius from Arg 426 in black spheres. b) Solvent exposed surface of epitope region with Arg 426 and distant residues shown in gray and all surface exposed residues within a 11.2 Å radius from Arg 426 shown in black. c) Residues in the epitope region Arg 426 in light gray and surrounding residues (all labeled) in dark gray. Figures and analyses were made with Yasara (www.yasara.org).

Figure 17:
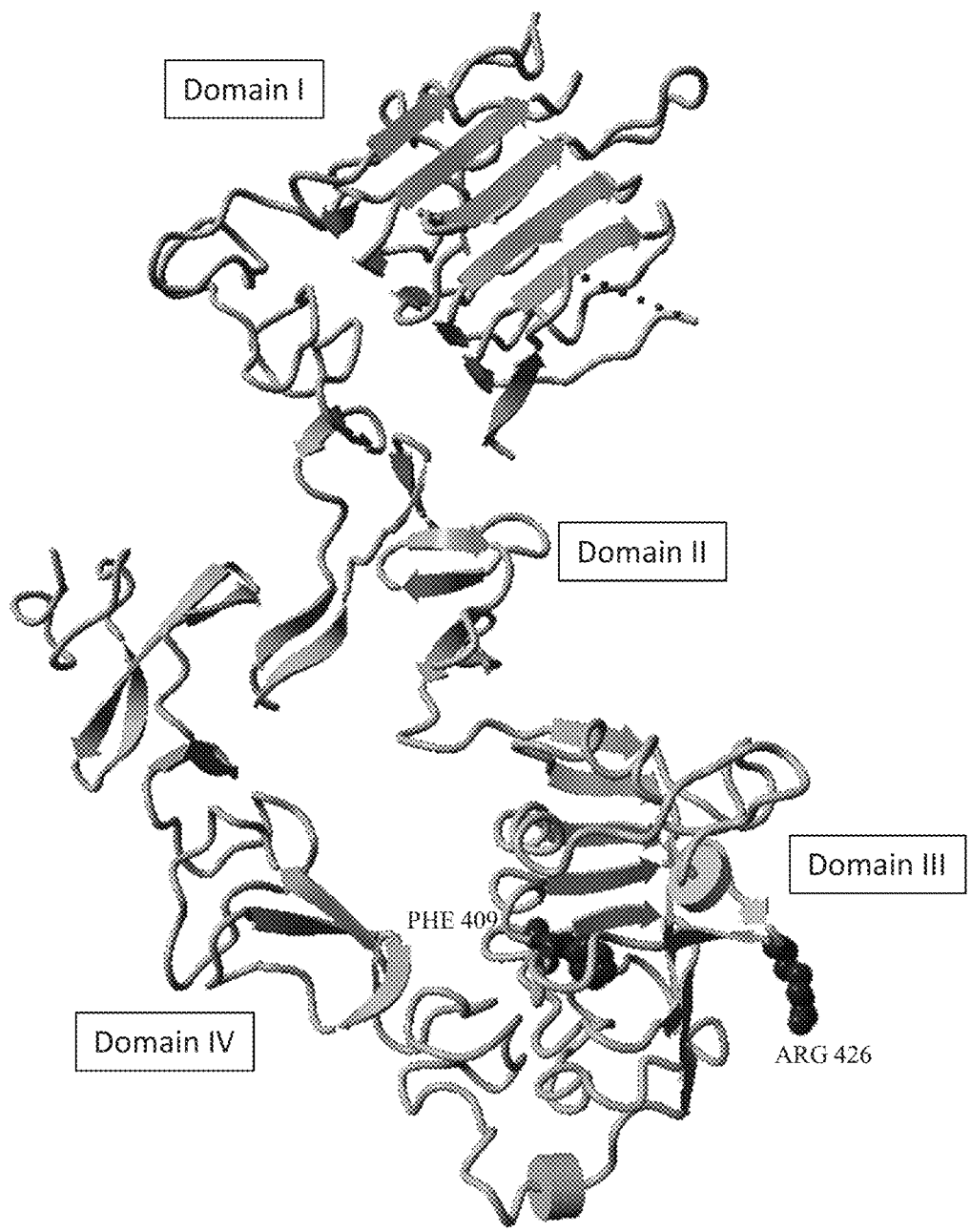

FIG. 17: Critical residues for PG3178 binding represented in the HER3 crystal structure. Critical residues identified for PG3178 binding are represented as black spheres on the HER3 crystal structure (PDB ID #4P59).

Figure 18:
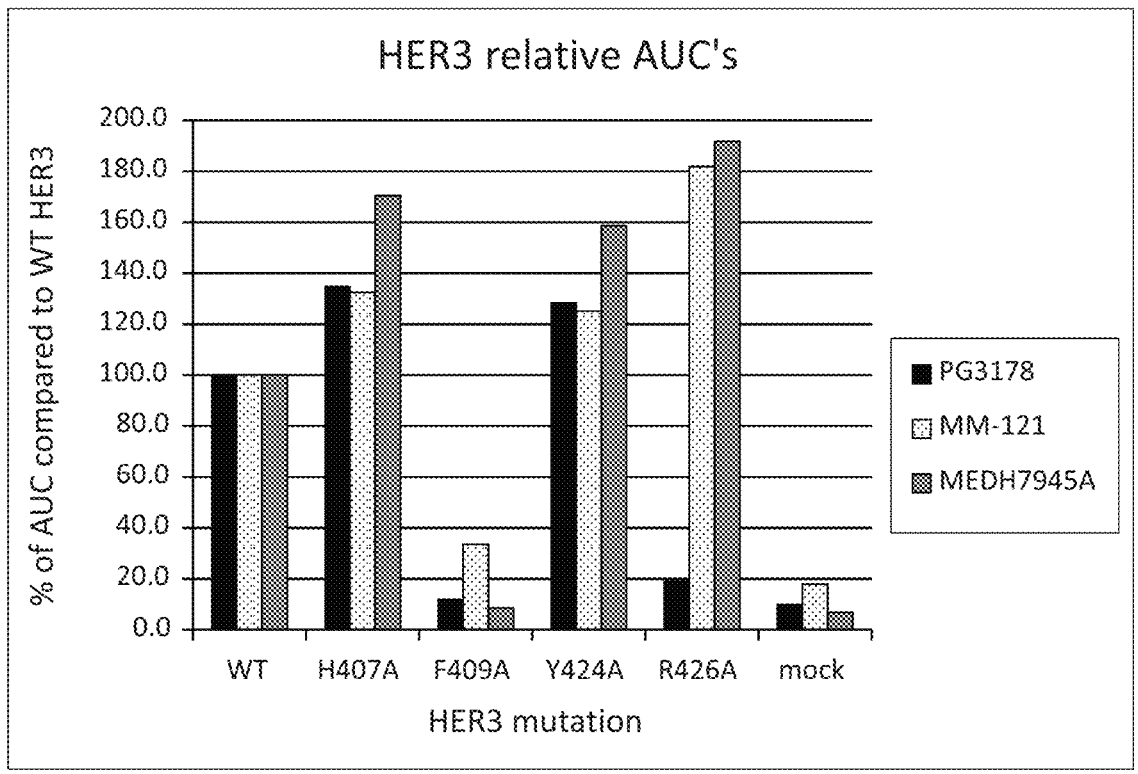

FIG. 18: Confirmation of R426 as a critical binding residue for PG3175 to HER3. Two anti-HER3 antibodies were included as control antibodies. Binding was determined in a FACS titration and binding is expressed as AUC in comparison to binding to WT HER3.

EXAMPLES

Cell Lines:

BxPC-3-luc2 (Perkin Elmer 125058), CHO-K1 (DSMZ ACC110), 293F (Invitrogen R790-07), A549 ATCC® CCL-185™ Homo sapiens lung Carcinoma, BxPC-3 ATCC® CRL-1687™ Homo sapiens pancreas adenocarcinoma, and A431 cells DSMZ ACC 91 were purchased and routinely maintained in growth media supplemented with 10% fetal heat inactivated bovine serum (FBS). 293F Freestyle cells were obtained from Invitrogen and routinely maintained in 293 FreeStyle medium. BxPc-3-luc2 (Bioware® Ultra Light Producing) cell line is a luciferase expressing cell line which was stably transfected with firefly luciferase gene (luc2). The cell line was established by transducing lentivirus (pGL4 luc2) containing luciferase 2 gene under the control of human ubiquitin C promoter. The cell line is commonly referred to as BxPc-3-luc2, it is a human cell pancreas adenocarcinoma cell line derived from BxPC-3 ATCC (CRL-1687™). Bioluminescence In Vitro: Approximately 370 photons/sec/cell. Exact number will vary depending on imaging and culturing conditions.

Cloning of the cDNA Encoding Cynomolgus EGFR and EGFR Swap-Domain Constructs

A construct encoding a chimeric receptor comprising the extra-cellular domain (ECD) of cynomolgus EGFR fused to the human trans-membrane domain and intra-cellular tail was copied from a published patent application by Micromet (US 2010/0183615 A1). The sequence is depicted in FIG. 1. This cDNA was synthetically made by GeneArt and was cloned in the vector pMK-RQ, flanked by the restriction sites NheI and NotI. The cDNA was liberated from this vector using these two enzymes and then cloned into the mammalian expression vector pCDNA3.1. The cDNA was fully sequenced to make sure it matched the designed construct and no mutations were found.

For epitope mapping purposes, constructs were generated in which the different domains in the extra-cellular domain (ECD) of EGFR (L1, CR1, L2 and CR2, also named domains I-IV: [1]) were swapped for the corresponding domains of HER3: FIG. 2. These were then cloned into an expression vector for transient expression in (antigen-negative) CHO cells, in frame with an extra-cellular cMyc-derived epitope tag and the trans-membrane region of the platelet-derived growth factor receptor. Constructs were designed, synthesised by GeneArt and subsequently cloned into pDisplay as Sfi1-Sal1 fragments. All constructs were sequenced, shown to be correct and tested for expression. Only the domain I swap variant (HER3 domain I with HER1 domains II-IV) was shown not to give rise to detectable amounts of protein on the surface of transfected cells (not shown).

The reference numbers used in the Examples refer to the numbering of the references in the list headed "References cited in the Examples".

Immunisations of MeMo with rhEGFR-Fc Fusion Protein and A431 Cells Over-Expressing the Antigen Mice that are transgenic for a rearranged human VL and a divers set of unrearranged human VH, DH and JH gene segments operably linked to murine constant region genes (MeMo®; see also WO2009/157771) were immunized with EGFR-Fc protein (R&D Systems, cat nr. 344-ER) emulsified with TitermaxGold adjuvant (TMG, Sigma Aldrich, cat. nr. T2684) at an interval of 14 days. MeMo produces common light chain (cLC) antibodies upon exposure to an antigen, i.e.: all antibodies coming out of Memo carry essentially the same light chain yet are diversified in their heavy chains. At day 0 and 14 mice were vaccinated subcutaneously (s.c.) to minimize the TMG induced discomfort of the mice. At all later time points mice were immunized via the intra-peritoneal (i.p.) route to insure the antigen is efficiently taken up and presented in the spleen. At day 35, the anti-EGFR serum titer was determined by FACS using the EGFR over-expressing cell line A431. Mice that developed at day 35 a serum titer >1/1,000 received a final i.p. boost with EGFR-Fc protein dissolved in PBS at day 42 followed by collection of spleen and lymph node three days later. Mice with too low EGFR serum titer at day 35 received an additional i.p. boost of EGFR-Fc in TMG at day 49. Subsequently, serum titers were determined at day 56 by ELISA. Those mice that at day 56 had a serum titer above the acceptance criteria received a final i.p. boost with EGFR-Fc protein dissolved in PBS at day 63 followed by collection of spleen and lymph node. Mice were injected with 20 μg EGFR-Fc protein dissolved in 125 μl TMG or 200 μl PBS.

Two MeMo mice immunized with EGFR-Fc received also a boost with A431 cells.

This was because these mice had developed a low a-EGFR-Fc IgG serum titer that was primarily directed against the Fc-tail. To specifically boost the EGFR response were these mice boosted with a single i.p. injection of 2E+6 A431 cells in 200 μl PBS at day 49.

All mice were shown to have mounted a significant response directed to the extra-cellular domain of EGFR, as witnessed by their reactivity with CHO cells stably expressing full length human EGFR and with A431 cells over-expressing EGFR in FACS.

Generation of 'Immune' Phage Antibody Libraries from Immunised Mice

After immunisation, RNA was extracted from lymphoid tissues (lymph nodes, spleen) and the polyclonal pool of VH-encoding cDNA's was amplified using VH family specific primers as previously described (e.g. EP 2604625). Material of two mice was pooled for library construction. The resulting PCR products were then cut with the restriction enzymes SfiI and BstEII and cloned in frame with the bacteriophage gene III for display on filamentous bacteriophage, essentially as described in [2], only the phagemid vector already contained the W1-39 germline VL gene. Phage library ML1155 was generated from the two mice with the highest α-EGFR serum titer (mice E094#12 and E094#18). Library ML1156 was generated from the two mice that received the additional A431 boost (mice E094#14 and E094#16). Characteristics of the libraries are depicted in Table 1.

Phage Selections for EGFR Binding Clones

The (Fc-) immune-fusion of the ecto-domain of EGFR (R&D systems) was diluted in PBS (to 5 µg/ml and in two-fold dilutions thereof) and coated to the wells of Maxisorp immune-plates. Phage were then panned for binding as described [3]. Selection of Fc-reactive clones was avoided by stringent counter-selection using (10 µg of) soluble IgG during the incubation of phage with coated antigen. To direct the selections on EGFR towards the ligand binding (L1) domain I, competition with an excess of the EGFR variant III (vIII) immune-fusion was also performed. In order to obtain cLC antibodies with functionality in inhibiting the receptor, phage selections on immobilised antigens were performed in combination with epitope-specific elution [4] using the either the ligand (EGF), or antibodies copied from literature (Matuzumab, Cetuximab). Elutions of EGFR-reactive phage were also performed using the domain I specific antibody ICR10 (Abcam, nr. ab231) and the domain II-specific antibody EGFR.1 (Thermo Scientific, nr. MS-311). As A431 cells [5] have been shown to carry an amplification of the EGFR gene [6] and therefore express high numbers of the EGFR, these were used for selection of EGFR-reactive phage.

Output phage titers were determined and for every selection where the output phage titer was 1.5 times above background (selection on a non antigen-coated well), 48 different clones were picked and phage were screened for binding to the respective antigens in ELISA. All clones were also tested for binding to human IgG in ELISA to identify binders to the Fc-portion of the immune-fusions used for selection. A high percentage of positive clones (defined as clones recognising the respective immune-fusions in ELISA, but not being IgG-reactive) was found in all selection outputs (up to 0.625 µg/ml) of coated immune-fusion. Clones that scored positive in phage ELISA on EGFR-Fc but not on hIgG were then sequenced and sequences were compared. Sequences were analysed as previously described (EP 2604625) and grouped on the basis of their VH gene segment usage and heavy chain CDR3 (HCDR3) sequence. An antibody cluster was defined as all sequences using the same germline VH segment having an HCDR3 with the same length and over 70% sequence identity in that HCDR3. In total, 17 antibody clusters were identified from immunised MeMo mice.

Using large synthetic cLC repertoires (synthesised in house) and selections on rhEGFR-Fc (as described above) many EGFR-specific clones were isolated, of which only one (MF3370) was later shown to be able to inhibit EGF-induced A431 cell death. This clone was therefore also analysed in more detail and used in subsequent EGFRxHER3 screening assays.

Testing Selected Anti-EGFR Phage Antibodies for Competitive Binding with Control Antibodies To delineate the epitope recognized by representative anti-EGFR Fabs, they were tested (as Fabs expressed on phage: named 'MF') for binding to EGFR in the presence of an excess of control, literature-derived IgG [7]. Control IgG used for these competition experiments are listed in Table 2.

When phage expressing the selected Fabs were tested for binding to the antigen in ELISA in the presence of an excess of these control antibodies, several were found to be competed for binding by one or more of the control antibodies: FIG. 3. These results show the anti-EGFR panel to be diverse in epitope recognition.

Re-cloning of Selected Anti-EGFR cLC Fab's, Expression and Purification of cLC IgG1

EGFR specific phage clones (termed 'MF') were re-cloned as mono-specific, bivalent IgG (termed 'PG') by re-cloning the VH-encoding gene fragment (as Sfi1-BstEII fragment) in an expression vector (named 'MG') for the transient expression of IgG in 293F cells. After production by transient transfection of 293F cells, secreted IgG (termed 'PG') was purified from the culture supernatant by prot. A affinity chromatography using standardised procedures.

Testing of Anti-EGFR Antibodies for Their Cross-Reactivity with Cynomolgus EGFR and Mouse EGFR To test whether anti-EGFR cLC IgG were reactive with cynomolgus EGFR, the constructs encoding full-length human EGFR, as well as the newly synthesized expression construct encoding the chimeric cynomolgus/human EGFR (FIG. 1) were both transfected in (antigen negative) CHO cells and cells were then stained with the anti-EGFR cLC IgG (PG) at 5 µg/ml and finally analysed by FACS. As a positive control for the staining, the clinically used antibody cetuximab was used, as this antibody is known to cross-react with cynomolgus EGFR [8]. The construct encoding the chimeric cyno-human receptor gave rise to high levels of the chimeric construct being expressed on the surface of transfected cells (as judged by the staining using cetuximab). In addition, all cLC IgG were shown to be reactive with cynomolgus EGFR, as the staining of cells expressing human EGFR was virtually indistinguishable from that of cells expressing the chimeric receptor.

To test anti-EGFR cLC IgG for their cross-reactivity with murine EGFR, an ELISA was performed. Purified protein, composed of the mouse EGFR ECD, fused to human IgG1 Fc was bought from Sino Biologicals (cat. nr. 51091-M02H) and a serial 2-fold dilution of this antigen was used to coat wells of an ELISA plate, starting at 5 µg/ml. Binding of the anti-EGFR cLC IgG to this antigen was then tested at a fixed concentration of 5 µg/ml. As a positive control for the immuno-reactivity of the antibodies, the same ELISA setup was performed using the human EGFR ECD-Fc fusion protein as antigen (R&D systems). From all 17 antibody clusters as described above, at least one representative antibody was tested. In addition, clone MF3370 from the synthetic library was also tested as an IgG (PG3370). All but one of the cLC antibodies were shown not to recognise mouse EGFR, as they failed to react with the fusion protein in ELISA. However, antibody PG3370 was shown to recognise murine EGFR, as well as human EGFR with similar affinity (data not shown): Table 3 summarises the data.

Figure 4:
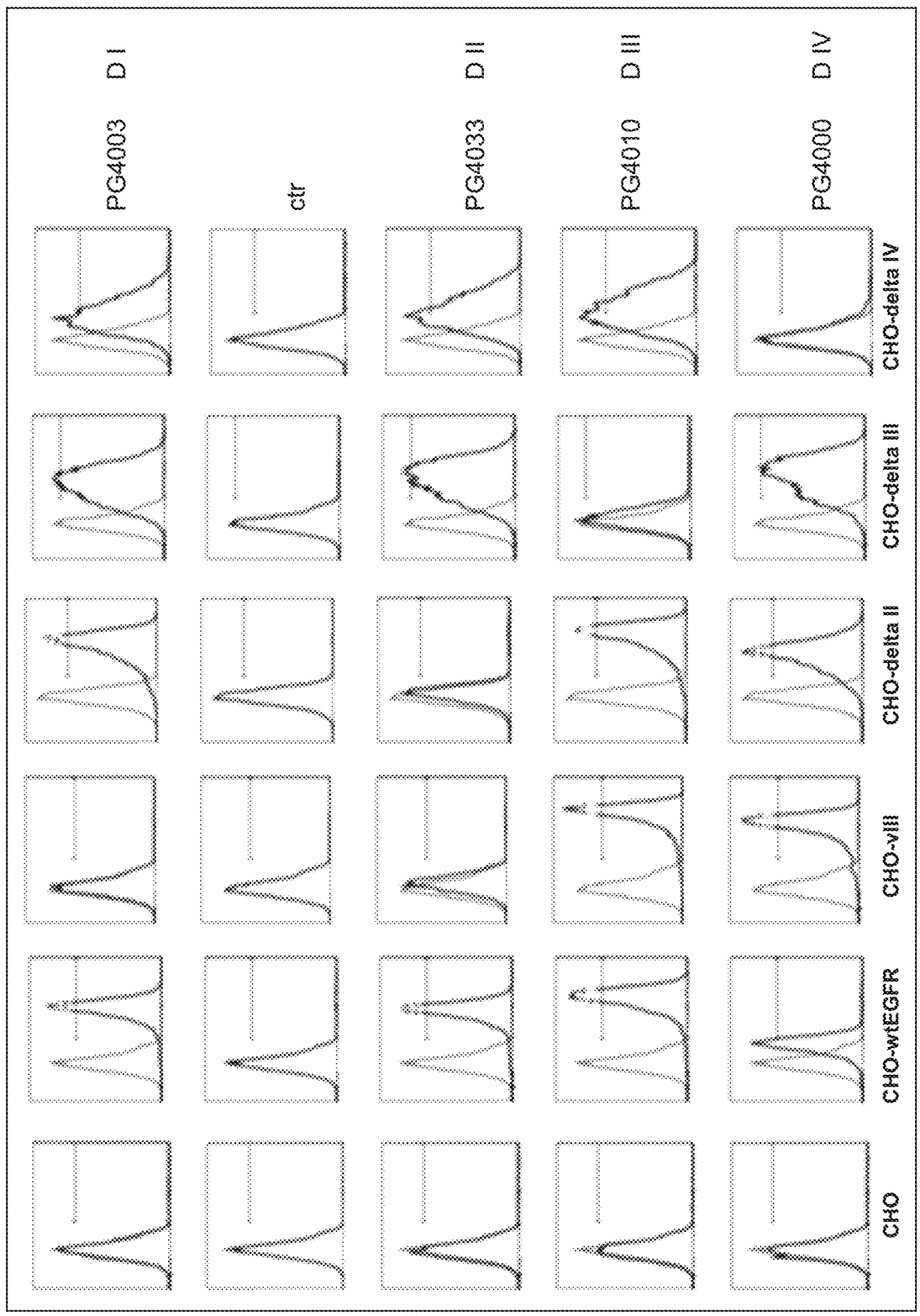
FIG. 4: example of epitope mapping of selected anti-EGFR common light chain (cLC) IgG (PG numbers) by FACS staining using EGFR swap domain mutants. Antibodies were tested for binding to CHO cells stably expressing the indicated EGFR swap mutants (domains in the wtEGFR sequence that were swapped for the corresponding domain of HER3). Light line: negative control (irrelevant antibody) staining; dark line: antibody staining vIII: EGFR variant III, lacking domain I and most of domain II). Ctr: negative control staining (irrelevant primary antibody added). The determined domain specificity is indicated on the right of the Figure.

Testing the Domain Specificity of Anti-EGFR Antibodies using EGFR Swap-Domain Constructs in FACS To unequivocally demonstrate the domain-specificity of the anti-EGFR cLC IgG, they were tested for binding to CHO cells stably expressing 'swap-domain' constructs: i.e. CHO cells expressing mutants of EGFR in which specific domains had been replaced for the corresponding domains of Her3 in FACS (FIG. 2). FIG. 4 gives an example of the FACS data obtained; data are summarizd in Table 3.

Testing Anti-EGFR Antibodies for Their Effect on Ligand-Induced Signalling

Figure 5:
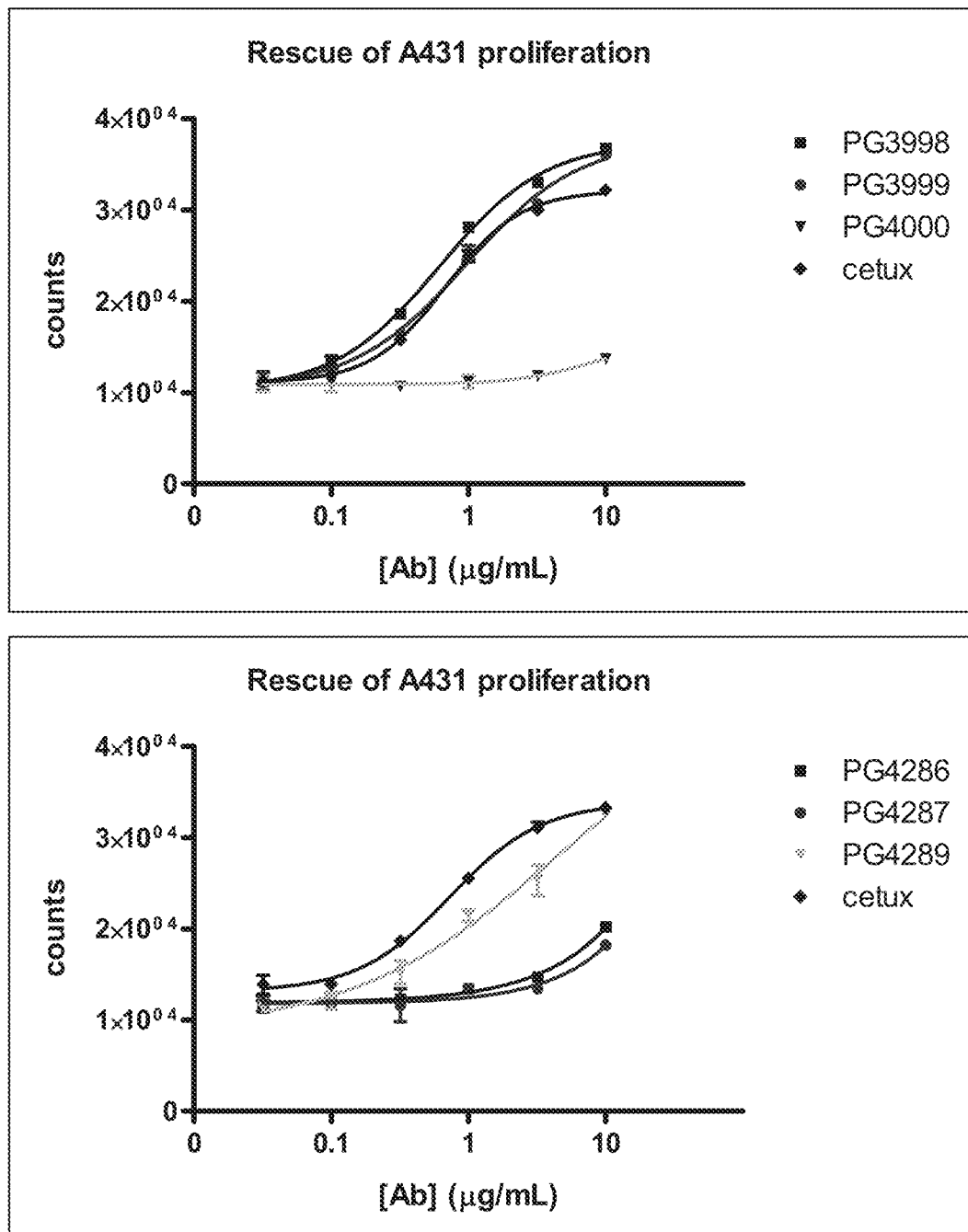
FIG. 5: example of the functionality of anti-EGFR cLC IgG (PG numbers) in inhibiting the EGF-induced death of A431 cells.

To test the selected anti-EGFR cLC IgG for their effects on EGF-induced signalling, they were tested for their ability to prevent the EGF-induced cell death of A431 cells. In brief, high (10 nM) concentrations of EGF induce (apoptotic) cell death in A431 cells [9]. This effect can be dose-dependently reverted by the addition of ligand-blocking anti-EGFR antibodies, such as cetuximab (the murine 225 antibody is the mouse equivalent of cetuximab: [9]) Antibodies were tested in this assay for their effect on receptor inhibition in a serial semi-log dilution from 10 µg/ml onwards. In every assay, the EGFR-blocking and clinically used antibody cetuximab was included as positive control. Anti-EGFR antibodies were found to have varying potencies in inhibiting EGF-induced cell death: some were more potent than cetuximab in rescuing the EGF-induced effect (e.g. PG3998: FIG. 5), some were less potent (e.g. PG4289, FIG. 5) and some had very little to no activity (e.g. PG4000, FIG. 5). Table 3 shows the activity of cLC antibodies directed to EGFR in inhibiting the receptor, compared to that of cetuximab.

Screening of Bispecific Anti-EGFRxHER3 Antibodies for their Capacity to Inhibit BxPC-3 Cell Proliferation VH-encoding cDNA fragments from the EGFR and HER3 antibody panel were re-cloned into vectors encoding charge-engineered CH3 domains that forced the generation of bispecific antibodies (Gunasekaran et al., JBC 2010; PCT/NL2013/050294) after transient transfection into 293F cells (termed 'TB' for bispecific protein). Three different strategies were used in combining EGFR and HER3 arms in bispecific IgG format: I) bispecifics of which both parental antibodies had proven ligand blocking activity for the receptor in respective cellular assays (the A431 assay for EGFR and the MCF-7 assay for Her3) resulting in 120 unique bispecific antibodies (Table 4); II) bispecifics of which only one of the arms (either the anti-Her3 or the anti-EGFR) had functionality in the above-mentioned assays (a total of 440 unique bispecific antibodies, not shown) and III) bispecifics of which both Fab arms had no (or almost no) functionality in these assays (a total of 320 unique bispecific antibodies, not shown). In total, 880 unique bispecific antibodies were tested for their ability to inhibit the growth of BxPC-3 cells.

All 880 bispecific antibodies were produced by co-transfection and transient co-expression in 293F cells; IgG was purified from the culture supernatant and the buffer in which the protein was kept was changed to PBS according to standardised procedures. Purified protein was quantified using Octet analysis. Bispecifics were tested at two concentrations (1 µg/ml and 100 ng/ml) in a ligand- (EGF- and NRG-) dependent assay (addition of 100 ng/ml of EGF, next to 10 ng/ml of NRG), as well as in a ligand-independent assay (no ligand added).

First, antibodies were diluted in chemically defined starvation medium (CDS: RPMI1640 medium, containing 80U penicillin and 80 µg of streptomycin per ml, 0.05% (w/v) BSA and 10 µg/ml holo-transferrin) and 50 µl of diluted antibody was added to the wells of a 96 wells black well clear bottom plate (Costar). Ligand was added (50 µl per well of a stock solution containing 40 ng/ml NRG and 400 ng/ml of EGF, diluted in CDS: R&D systems, cat. nr. 396-HB and 236-EG). In case of the ligand-independent assay, no ligand was added, instead only 50 µl of CDS. BxPC-3 cells were trypsinised, harvested and counted and 8000 cells in 100 µl of CDS were added to each well of the plate. Plates were left for an hour at rt before being put in a container inside a 37° C. cell culture incubator for three days. On the fourth day, Alamar blue (Invitrogen, # DAL1100) was added (20 µl per well) and the fluorescence was measured after 6 hours of incubation (at 37° C.) with Alamar blue using 560 nm excitation and 590 nm readout on a Biotek Synergy 2 Multi-mode microplate reader. Fluorescence values were normalised to uninhibited growth (no antibody, but both ligands added).

IC50 Determination

An overview of the screening data of the 880 bispecific antibodies is given in FIG. 6. MEHD7945A served as a benchmark antibody; the upper dotted line in FIG. 5 represents the average activity observed in the ligand-independent assay and the lower dotted line the average activity of that antibody observed in the ligand-dependent assay. Twenty bispecifics that had a potency in both assays that was at least as good as that of the MEHD7945A antibody were then re-produced, re-purified and tested again in the ligand-driven BxPC-3 proliferation assays to determine IC50 values. Antibodies were serially diluted in CDS from 10 µg/ml downward and 50 µl of antibody solution was added per well. Ligands and cells were added as described above and cells were incubated for three days before the addition of Alamar Blue and fluorescence readout. Again, values were normalised to uninhibited growth and IC50 values were calculated using GraphPad Prism software (non-linear curve fitting). The six best performing bispecifics were selected based on their IC50 being lower than that of the comparator antibody MEHD7945A in both assays. FIG. 7 shows the IC50 determination of two of these best performing antibodies; Table 6 summarises the data for these six bispecifics, as compared to the activity of a mixture of each of the parental monoclonal antibodies (see below).

Testing Anti-EGFRxHER3 Bispecifics for their Effect on the Growth of BxPC-3 Tumours Orthotopically Implanted CB17 SCID female mice, 8-10 weeks old at the beginning of the study were engrafted orthotopically in the pancreas with $1\times10^6$ tumor cells in 20 µl. Therefore mice were anesthetized and laid on the right side to expose the left side and a 0.5 cm incision is made on the left flank region. The pancreas and spleen were exteriorized and $1\times10^6$ tumor cells in 20 µl were injected into the sub-capsulary space of the pancreas tail. One week after implantation, bioluminescence (BLI) data were generated. For BLI imaging (once or twice weekly) left side view, all mice received 15 minutes prior to the imaging all of the mice receive i.p. injections of 150 mg/kg Luciferin (D-Luciferin-EF Potassium Salt, Cat. # E6552, Promega). Outlier animals—based on BLI/tumor volume—were removed and the mice were randomly distributed into groups of 7 mice each. On experimental day 8, the treatment was started. The animals in the antibody treatment group were dosed weekly for 3 consecutive weeks (days 0, 7, 14 and 21) with 30 mg/kg of antibody. At day 0 of the treatment the animals receive twice the loading dose, i.e. 60 mg/kg of antibody. The final imaging was carried out at day 31.

All six bispecifics were shown to significantly decrease BxPC-3 tumour outgrowth in the model (p<0.001) (FIG. 8). However, there was no significant difference between the therapeutic effect of the comparator antibody MEHD7945A and two of these six bispecifics, PB4522 and PB4510 (data not shown). Therefore, a dose-escalation study was performed with one of the bispecific antibodies, PB4522, and the comparator antibody MEHD7945A. Using the exact same in vivo model and dosing schedule, different groups of mice were treated with a decreasing antibody dose, lowered from 30 mg/kg to 3 and finally 0.3 mg/kg. FIG. 9 shows the data for the groups treated with 0.3 mg/kg. There was no significant difference in therapeutic effect between all groups treated with either MEHD7945A or PB4522 at 30 and 3 mg/kg (data not shown). However, there was a significant difference in therapeutic effect between treatment with MEHD7945A and PB4522 at the 0.3 mg/kg dose, the latter being more potent in tumour growth reduction. After mice were taken out of the study, the weight of all their tumours was determined ex vivo. FIG. 10 shows that the average weight of tumours taken from mice treated with PB4522 (at 0.3 mg/kg) was significantly lower (P=0.007, unpaired T-Test) than that of mice treated with MEHD7945A (at 0.3 mg/kg).

Comparison of the Potency of Different Antibody Formats in BxPC-3 Cell Proliferation Inhibition To compare the potency of different antibody formats in cell proliferation inhibition, purified bispecific anti-EGFR× HER3 antibodies were tested for their ability to inhibit BxPC-3 cell proliferation in comparison with an equimolar mix of the parental antibodies. In every assay plate, MEHD7945A was used as positive control to be able to compare the IC50 of the antibody being tested directly with the 'two-in-one' MEHD7945A. Titrations were performed starting from 10 µg/ml and in 6 ten-fold dilutions. These serial dilutions of antibodies were tested in duplicate over the whole concentration range. From the obtained sigmoidal curves, IC50 values were calculated using the GraphPad Prism software. Table 6 summarises the data.

As can be seen in Table 6, in all cases the bispecific format was more potent then the mix of the two parental antibodies in inhibiting the proliferation of BxPC-3 tumour cells and this format was therefore the preferred format for co-targeting of EGFR and HER3. When the IC50 value for proliferation inhibition of same bispecific was measured several times, slightly different values were obtained in the different assays. However, these differences were considered to be unavoidable small experimental variations.

Keratinocyte Assay

EGFR blockade has been demonstrated to affect chemokine expression in keratinocytes (Pastore, Mascia et al. 2005). Recent analyses of EGFR-Inhibitor (EGFRI) skin toxicities show that the early inflammatory infiltrate of the rash is dominated by dendritic cells, macrophages, granulocytes, mast cells and T-cells. EGFR inhibition induces the expression of chemokines (CCL2, CCL5, CCL27, CXCL14) in epidermal keratinocytes, while the production of antimicrobial peptides and skin barrier proteins such as Rnase 7 is impaired. The skin toxicity observed in vivo could be translated in vitro using a primary keratinocyte system in combination with Q-PCR analysis. (Lichtenberger, Gerber et al., Science Translational Medicine, 2013). The effect of PB4522 in comparison to MEHD7945A and cetuximab was tested at 10 and 100 nM concentrations on human primary epidermal keratinocytes. Human primary epidermal keratinocytes were isolated and seeded at a density of 100.000 cells per well in 6 well plates in SFM cell growth medium (Invitrogen) at 37° C., 5% CO2. Cells were treated in the absence or presence of 10 ng/ml TNF-α (AbD Serotec, Kidlington, UK) and 5 ng/ml IL-1β (R&D Systems, Inc., Minneapolis, Minn.) for 24H. Duplicates of each condition were prepared. Twenty-four hours later cells were harvested and RNA was extracted from cells by using the TRIzol® Reagent. cDNA was synthesized from different messenger RNA (mRNA) templates using reverse transcriptase enzyme Superscript II (Invitrogen, Carlsbad, Calif.). Gene specific oligonucleotides for qPCR were obtained as a TaqMan® Gene Expression Assays by Applied Biosystems. The expression of CXCL14 and Rnase 7 as well as 18S and GAPDH housekeeping genes were determined. PB4522 induces less CXCL14 compared to Cetuximab and MEHD7945A. In contrast Rnase 7 expression was less severe hampered by PB4522 compared to Cetuximab and MEHD7945A.

PB4522 Shows Superior ADCC Activity Compared to MEHD7945A

ADCC activity is an important anti-tumour mechanism of action for therapeutic antibodies in cancer. Human monoclonal antibodies directed to the HER family of receptors like cetuximab and trastuzumab induce ADCC. Multiple strategies have been used to achieve ADCC enhancement including glycoengineering and mutagenesis. All of these seek to improve Fc binding to low-affinity activating FcγRIIIa and/or reducing binding to the low-affinity inhibitory FcγRIIb. One of the methods used in glycoengineering to achieve ADCC enhancement is the removal of fucose. Removal of fucose has resulted in increased anti-tumour activity in several in vivo models [Junttila, 2010]. To maximize PB4522 activity, this afucosylation technology was applied (Liu and Lee. 2009 [13-17]) to remove fucose from the N-linked carbohydrate structure in the Fc region.

To determine ADCC activity of PB4522 in comparison to MEDH7945a and cetuximab the ADCC Reporter Bioassay (Promega) was used. Three different cell lines where tested; the EGFR amplified and high EGFR expressing head and neck cell line A431, the intermediate EGFR expressing lung cancer cell line A549 and the intermediate EGFR expressing pancreatic cancer cell line BxPC3.

The bioassay uses engineered Jurkat cells stably expressing either the FcγRIIIa receptor V158 (high affinity) or F158 (low affinity) variant, and an NFAT response element driving expression of firefly luciferase which is a measure for FcγR activation. The assay has been validated by comparing data obtained with this ADCC Reporter Bioassay to the classical 51Cr release assay and both assays yield similar results. The ADCC assays were performed using the Promega ADCC Bioassay kit using 384 white well plates. In this experimental setup A431 cells, BxPC3 cells and A549 cells were plated at a density of 1000 cells/well in 30 µl assay medium (RPMI with 4% low IgG serum) 20-24H before the bioassay. The next day, the culture medium was removed. Next, a serial dilution of antibodies, PB4522 and its comparator antibodies cetuximab, MEHD7945A and a Ctrl antibody were prepared in duplicates. 10 µl of these antibody dilutions were added to the wells. The starting concentrations of the antibodies were 10 µg/ml and a 10 points 5-fold serial dilutions were generated to provide full dose-response curves. Finally, 5 µl of ADCC Bioassay effector cells (15000 cells/well, V158) were added.

The cells were incubated for 6H at 37° C. Next, 15 µl BIO-Glo luciferase substrate was added and 5 minutes later luminescence was detected in a plate reader. The obtained data are shown in FIG. 13. Both PB4522 and cetuximab showed ADCC activity towards the medium EGFR expressing cells BxPC3 and A549 whereby the EC50 of cetuximab was lower compared to PB4522. The total ADCC activity—Area Under the Curve (AUC)—and the maximal ADCC activity however of PB4522 were higher compared to cetuximab. All three antibodies showed ADCC activity towards the EGFR amplified cell line A431, whereby cetuximab showed the highest ADCC activity followed by PB4522 and Cetuximab. Of note is that the intermediate EGFR expressing cell lines are representative for the number of EGFR expressed on patient derived tumor cell samples. In all three cell lines the maximal ADCC and the AUC of PB4522 are higher compared to MEHD7945A. In all three cell lines the EC50 of PB4522 is lower compared to MEHD7945A.

HER3

Binding analysis of PG3178 IgG at 0.25 µg/ml to HER3 ECD mutants in FACS resulted in the identification of two so-called 'critical' residues (F409, R426) for which mutation to alanine caused substantial loss of binding compared to WT HER3, while binding of the control mAb was retained (Table 7 and FIG. 17). Both residues are located in Domain III of HER3 and spatially distant. Moreover, F409 is buried in the HER3 hydrophobic core, which makes it unlikely to be part of the PG3178 epitope.

Confirmation Experiments HER3 Epitope

CHO-K1 cells were transfected with HER3 ECD mutation constructs (listed in Table 7), WT HER3 ECD and two control constructs (H407A and Y424A). PG3178 binding to the HER3 ECD variants was tested in a FACS titration experiment. Two control antibodies, binding Domain I (MM-121) and Domain III (MEHD7945A) of HER3 were included to verify HER3 ECD expression on the cell surface. Mean MFI values were plotted and for each curve the AUC was calculated using GraphPad Prism 5 software. WT HER3 binding was used to normalize the data. The R426A mutation was shown to be critical for PG3178 binding whereas the binding to F409A could not be confirmed due to loss of cell surface expression (FIG. 18).

REFERENCES CITED IN THE EXAMPLES

1. Schmitz, K. R. and K. M. Ferguson, *Interaction of antibodies with ErbB receptor extracellular regions.* Exp Cell Res, 2009. 315(4): p. 659-70.
2. de Haard, H. J., et al., *A large non-immunized human Fab fragment phage library that permits rapid isolation and kinetic analysis of high affinity antibodies.* J Biol Chem, 1999. 274(26): p. 18218-30.
3. Marks, J. D., et al., *By-passing immunization. Human antibodies from V-gene libraries displayed on phage.* J Mol Biol, 1991. 222(3): p. 581-97.
4. Meulemans, E. V., et al., *Selection of phage-displayed antibodies specific for a cytoskeletal antigen by competitive elution with a monoclonal antibody.* J Mol Biol, 1994. 244(4): p. 353-60.
5. Giard, D. J., et al., *In vitro cultivation of human tumors: establishment of cell lines derived from a series of solid tumors.* J Natl Cancer Inst, 1973. 51(5): p. 1417-23.
6. Merlino, G. T., et al., *Amplification and enhanced expression of the epidermal growth factor receptor gene in A431 human carcinoma cells.* Science, 1984. 224(4647): p. 417-9.
7. Cochran, J. R., et al., *Domain-level antibody epitope mapping through yeast surface display of epidermal growth factor receptor fragments.* J Immunol Methods, 2004. 287(1-2): p. 147-58.
8. Ledon, N., et al., *Comparative analysis of binding affinities to epidermal growth factor receptor of monoclonal antibodies nimotuzumab and cetuximab using different experimental animal models.* Placenta, 2011. 32(7): p. 531-4.
9. Gulli, L. F., et al., *Epidermal growth factor-induced apoptosis in A431 cells can be reversed by reducing the tyrosine kinase activity.* Cell Growth Differ, 1996. 7(2): p. 173-8.
10. Pastore S, Mascia F, Mariotti F, Dattilo C, Mariani V, Girolomoni G. ERK1/2 regulates epidermal chemokine expression and skin inflammation. *J Immunol.* 2005; 174(8):5047-5056.
11. Lichtenberger B M, Gerber P a., Holcmann M, et al. Epidermal EGFR Controls Cutaneous Host Defense and Prevents Inflammation. *Sci Transl Med.* 2013; 5:199ra111-199ra111. doi:10.1126/scitranslmed.3005886.
12. PCT/NL2013/050294
13. ADCC Enhancement Technologies for Next Generation Therapeutic Antibody. Cheng Liu and Andreia Lee. Antibody therapeutics—Trends in Bio/Pharmaceutical Industry 2009 [13-17]

TABLE 1

Overview of the phage antibody libraries generated from EGFR-immunised mice.

| Library no. | Mouse | Library size | Insert frequency | Unique clones |
|---|---|---|---|---|
| ML1155 | E094#12 and E094#18 | 8.30E+06 | 96% | 97% |
| ML1156 | E094#14 and E094#16 | 8.60E+06 | 100% | 97% |

TABLE 2

Overview of known anti-EGFR antibodies used to epitope map the selected phage antibodies.

| Antibody name | PG nr/supplier: | Cat. Nr. | Domain specificity |
|---|---|---|---|
| ICR10 | Abcam | ab231 | I |
| EGFR.1 | Thermo scientific | MS-311-P | II |
| MatuzuMab | PG2982p02 | n/a | III |
| Cetuximab | Merck (clinical batch) | n/a | III |

N/A: not applicable.

TABLE 3

Overview of the domain specificity (as assessed by FACS using the 'swap domain' mutants and functionality of anti-EGFR antibodies. Functionality was compared to the clinically used antibody cetuximab. Activity of anti-EGFR cLC IgG (PG codes) in inhibiting EGF-induced cell death in A431 cells, compared to the activity of cetuximab in that assay. ND not determined. Variant III: EGFR variant III specific. PG codes represent full length IgG1 monoclonal antibodies.

| Cluster nr. | Representative antibody tested: | Origen of antibody | EGFR domain specificity | Mouse cross-reactivity | Cynomolgus cross-reactivity | EGFR blocking activity compared to cetuximab |
|---|---|---|---|---|---|---|
| 1 | PG3998 | MeMo | III | No | Yes | >100% |
|  | PG4010 | MeMo |  |  |  |  |

TABLE 3-continued

Overview of the domain specificity (as assessed by FACS using the 'swap domain' mutants and functionality of anti-EGFR antibodies. Functionality was compared to the clinically used antibody cetuximab. Activity of anti-EGFR cLC IgG (PG codes) in inhibiting EGF-induced cell death in A431 cells, compared to the activity of cetuximab in that assay. ND not determined. Variant III: EGFR variant III specific. PG codes represent full length IgG1 monoclonal antibodies.

| Cluster nr. | Representative antibody tested: | Origen of antibody | EGFR domain specificity | Mouse cross-reactivity | Cynomolgus cross-reactivity | EGFR blocking activity compared to cetuximab |
|---|---|---|---|---|---|---|
| 2 | PG4289 | MeMo | I | No | Yes | 80% |
|   | PG4003 | MeMo |   |   |   |   |
| 3 | PG4000 | MeMo | IV | No | Yes | <5% |
| 4 | PG4016 | MeMo | I | No | Yes | <5% |
| 5 | PG4033 | MeMo | II | No | Yes | 0% |
| 6 | PG4034 | MeMo | II | No | Yes | 0% |
| 7 | PG4035 | MeMo | IV | No | Yes | 0% |
| 8 | PG4032 | MeMo | III | No | Yes | <5% |
| 9 | PG4284 | MeMo | III | No | Yes | 30% |
| 10 | PG4358 | MeMo | III | No | Yes | ND |
| 11 | PG4280 | MeMo | III | No | Yes | 100% |
| 12 | PG4283 | MeMo | Variant III | No | Yes | 0% |
| 13 | PG4281 | MeMo | III | No | Yes | 70% |
| 14 | PG4286 | MeMo | III/IV | No | Yes | <10% |
| 15 | PG4285 | MeMo | Variant III | No | Yes | 0% |
| 16 | PG4287 | MeMo | III | No | Yes | <10% |
| 17 | PG4359 | MeMo | ND | No | Yes | ND |
| 18 | PG3370 | Synthetic library | III | Yes | Yes | 80% |

TABLE 4

List of antagonistic anti-EGFR × anti-HER3 bispecific antibodies (PB codes) tested for BxPC3-Luc2 cell proliferation inhibition. These anti-EGFR and anti-HER3 arms were all shown to be active as mono-specific monoclonal antibody in inhibiting ligand (EGF- or NRG-) driven growth of tumour cells. The table shows the number of the bispecific protein (PB) that is composed of the respective EGFR- and HER3 binding arms (e.g. PB4510 is composed of MG3998 and MG3178). The VH chain sequence of various MG chains are indicated with MF followed by the number in FIG. 11. PB codes represent full length IgG1 bispecific antibodies

| EGFR | HER3 | | | | | |
|---|---|---|---|---|---|---|
|  | MG3178 | MG3176 | MG3163 | MG3157 | MG3156 | MG3125 |
| MG3998 | PB4510 | PB4556 | PB4533 | PB4579 | PB4631 | PB4654 |
| MG3999 | PB4511 | PB4557 | PB4534 | PB4580 | PB4616 | PB4639 |
| MG4010 | PB4512 | PB4558 | PB4535 | PB4581 | PB4617 | PB4640 |
| MG4013 | PB4514 | PB4560 | PB4537 | PB4583 | PB4618 | PB4641 |
| MG3751 | PB4518 | PB4564 | PB4541 | PB4587 | PB4620 | PB4643 |
| MG3752 | PB4519 | PB4565 | PB4542 | PB4588 | PB4621 | PB4644 |
| MG4025 | PB4521 | PB4567 | PB4544 | PB4590 | PB4622 | PB4645 |
| MG4280 | PB4522 | PB4568 | PB4545 | PB4591 | PB4623 | PB4646 |
| MG4290 | PB4523 | PB4569 | PB4546 | PB4592 | PB4624 | PB4647 |
| MG4281 | PB4524 | PB4570 | PB4547 | PB4593 | PB4625 | PB4648 |
| MG4284 | PB4525 | PB4571 | PB4548 | PB4594 | PB4626 | PB4649 |
| MG3370 | PB4526 | PB4572 | PB4549 | PB4595 | PB4627 | PB4650 |
| MG4002 | PB4527 | PB4573 | PB4550 | PB4596 | PB4628 | PB4651 |
| MG4003 | PB4528 | PB4574 | PB4551 | PB4597 | PB4629 | PB4652 |
| MG4289 | PB4529 | PB4575 | PB4552 | PB4598 | PB4630 | PB4653 |
| MG4011 | PB4513 | PB4559 | PB4536 | PB4582 | PB4632 | PB4655 |
| MG4014 | PB4515 | PB4561 | PB4538 | PB4584 | PB4633 | PB4656 |
| MG3756 | PB4517 | PB4563 | PB4540 | PB4586 | PB4634 | PB4657 |
| MG4023 | PB4520 | PB4566 | PB4543 | PB4589 | PB4635 | PB4658 |

TABLE 5

List of six anti-EGFR × anti-HER3 bispecific antibodies that were selected for in vivo testing in the BxPC3-Luc2 orthotopic model and their IC50 value for ligand-driven BxPC-3 cell proliferation inhibition.

| PB nr. | HER3 arm | EGFR arm | Domain specificity EGFR arm | IC50 for BxPC-3 ligand-driven cell proliferation inhibition (pM) |
|---|---|---|---|---|
| PB4510 | MG3178 | MG3998 | Domain III | 7 |
| PB4522 | MG3178 | MG4280 | Domain III | 13 |
| PB4528 | MG3178 | MG4003 | Domain I | 29 |
| PB4535 | MG3163 | MG4010 | Domain III | 65 |
| PB4549 | MG3163 | MG3370 | Domain III | 250 |
| PB4552 | MG3163 | MG4289 | Domain I | 62 |
| MEHD7945A | N/A | N/A | Domain III | 260 |

TABLE 6

IC50 values for inhibition of BxPC-3 cell proliferation determined for the different antibody formats tested: the bispecific (PB) anti-EGFR × HER3 leads, or a mix of the mono-specific, bivalent parental (PG) antibodies.

| Antibody tested | HER3 arm | EGFR arm | IC50 for BxPC-3 ligand-driven cell proliferation inhibition (pM) |
|---|---|---|---|
| PB4510 | MG3178 | MG3998 | 13 |
| PG3178 + PG3998 | | | 260 |
| PB4522 | MG3178 | MG4280 | 27 |
| PG3178 + PG4280 | | | 390 |
| PB4528 | MG3178 | MG4003 | 29 |
| PG3178 + PG4003 | | | 80 |
| PB4535 | MG3163 | MG4010 | 65 |
| PG3163 + PG4010 | | | 670 |
| PB4549 | MG3163 | MG3370 | 253 |
| PG3163 + PG3370 | | | 753 |
| PB4552 | MG3163 | MG4289 | 62 |
| PG3163 + PG4289 | | | 767 |
| MEHD7945A | N/A | N/A | 287 |

TABLE 7

The mean binding protein reactivities (and ranges) are listed for both critical residues. Critical residues involved in PG3178 binding were identified as those mutated in clones that were negative for PG3178 mAb binding (<20% WT) but positive for the control mAb 66223 binding (>70% WT). Residue numbering is that of PDB ID #4P59.

| HER3 Residue | Mutation | PG3178 binding % of wt binding (range) | Control mAb binding % of wt binding (range) | Designation |
|---|---|---|---|---|
| 409 | F409A | 16.74 (8) | 79.63 (0) | Possibly critical |
| 426 | R426A | 3.17 (5) | 93.08 (36) | Critical |

TABLE 8

List of exposed residues within 11.2 Å radius of Arg 426 in HER3:

| Leu 423 | L423 |
| Tyr 424 | Y424 |
| Asn 425 | N425 |
| Gly 427 | G427 |
| Gly 452 | G452 |
| Arg 453 | R453 |
| Tyr 455 | Y455 |
| Glu 480 | E480 |
| Arg 481 | R481 |
| Leu 482 | L482 |
| Asp 483 | D483 |
| Lys 485 | K485 |

REFERENCES CITED IN THE SPECIFICATION

1. Garrett T P, McKern N M, Lou M, Elleman T C, Adams T E, Lovrecz G O, Zhu H J, Walker F, Frenkel M J, Hoyne P A, Jorissen R N, Nice E C, et al. Crystal structure of a truncated epidermal growth factor receptor extracellular domain bound to transforming growth factor alpha. Cell 2002; 110:763-73.
2. Ogiso H, Ishitani R, Nureki O, Fukai S, Yamanaka M, Kim J H, Saito K, Sakamoto A, Inoue M, Shirouzu M, Yokoyama S. Crystal structure of the complex of human epidermal growth factor and receptor extracellular domains. Cell 2002; 110: 775-87.
3. Ferguson K M. Structure-based view of epidermal growth factor receptor regulation. Annu Rev Biophys 2008; 37: 353-73.
4. Yarden Y. The EGFR family and its ligands in human cancer. Signalling mechanisms and therapeutic opportunities. Eur J Cancer 2001; 37 (Suppl 4):53-58.
5. Jorissen R N, Walker F, Pouliot N, Garrett T P, Ward C W, Burgess A W. Epidermal growth factor receptor: mechanisms of activation and signalling Exp Cell Res 2003; 284:31-53.
6. Buday L, Downward J. Epidermal growth factor regulates p21ras through the formation of a complex of receptor, Grb2 adapter protein, and Sos nucleotide exchange factor. Cell 1993; 73: 611-20.
7. Gale N W, Kaplan S, Lowenstein E J, Schlessinger J, Bar-Sagi D. Grb2 mediates the EGF-dependent activation of guanine nucleotide exchange on Ras. Nature 1993; 363:88-92.
8. Soltoff S P, Carraway K L, III, Prigent S A, Gullick W G, Cantley L C. ErbB3 is involved in activation of phosphatidylinositol 3-kinase by epidermal growth factor. Mol Cell Biol 1994; 14:3550-8.
9. Prigent S A, Gullick W J. Identification of cErbB-3 binding sites for phosphatidylinositol 30-kinase and SHC using an EGF receptor/c-ErbB-3 chimera. EMBO J 1994; 13:2831-41.
10. Uberall I, Kolar Z, Trojanec R, Berkovcova J, Hajduch M. The status and role of ErbB receptors in human cancer. Exp Mol Pathol 2008; 84:79-89.
11. Robertson S C, Tynan J, Donoghue D J. RTK mutations and human syndromes: when good receptors turn bad. Trends Genet 2000; 16:368.
12. Patel DK. Clinical use of anti-epidermal growth factor receptor monoclonal antibodies in metastatic colorectal cancer. Pharmacotherapy 2008; 28:31S-41S
13. Merchant et al. Nature Biotechnology, Vol. 16 July 1998 pp 677-681
14. Nissim A, Hoogenboom H R, Tomlinson I M, Flynn G, Midgley C, Lane D, Winter G. 1994. Antibody fragments from a 'single pot' phage display library as immunochemical reagents. EMBO J. 1994 Feb. 1; 13(3):692-8.
15. WO2004/009618
16. WO2009/157771
17. WO 2008/027236
18. WO 2010/108127
19. Schaefer et al. Cancer Cell 20, 472-486, October 2011
20. Olayioye M A et al.; EMBO J (2000) Vol 19: pp 3159-3167)
21. Kubota T, Niwa R, Satoh M, Akinaga S, shitara K, Hanai N. Engineered therapeutic antibodies with improved effector functions. Cancer Sci. 2009 September; 100(9): 1566-72.
22. US Patent Application 20030078385
23. Gunasekaran (JBC 2010, vol 285, pp 19637-19646)
24. WO 2013/157954 A1

The invention claimed is:

1. A bispecific antibody comprising a first variable domain comprising a first antigen-binding site that binds domain III of EGFR, wherein said first variable domain comprises a heavy chain variable region comprising a CDR1 comprising SEQ ID NO: 9, a CDR2 comprising SEQ ID NO: 11, and a CDR3 comprising SEQ ID NO: 13; and a second variable domain comprising a second antigen-binding site that binds domain III of Erb-B3, wherein said second variable domain comprises a heavy chain variable region comprising a CDR1 comprising SEQ ID NO: 90, a CDR2 comprising SEQ ID NO: 156, and a CDR3 comprising SEQ ID NO: 92, wherein said first and said second variable domains each comprise a common light chain comprising SEQ ID NO: 153, and wherein the heavy chain variable regions of the bispecific antibody are different from each other.

2. The bispecific antibody of claim 1, wherein the antibody has a half maximal growth inhibitory concentration (IC50) for inhibiting EGFR and Erb-B3 ligand induced growth of BxPC3 cells (ATCC CRL 1687) or BxPC3-luc2 cells (Perkin Elmer 125058) of less than 100 pM.

3. The bispecific antibody of claim 1, that can reduce a ligand-induced receptor function of Erb-B3 on an EGFR and Erb-B3 positive cell.

4. The bispecific antibody of claim 2, wherein said ligand induced BxPC3 cells are EGFR and Erb-B3 ligand induced BxPC3 cells.

5. The bispecific antibody of claim 4, wherein said BxPC3 cells are induced with a ligand comprising EGF, neuregulin1, or a combination thereof.

6. The bispecific antibody of claim 1, wherein the antibody can reduce ligand-induced growth of an EGFR and Erb-B3 positive cell.

7. The bispecific antibody of claim 1, wherein the affinity (KD) of said second antigen-binding site for an Erb-B3 positive cell is lower than or equal to 2.0 nM.

8. The bispecific antibody of claim 1, comprising an antigen-binding site that binds at least one amino acid of domain III of Erb-B3 selected from the group consisting of R426 and surface-exposed amino acid residues that are located within 11.2 Å from R426 in the native Erb-B3 protein.

9. The bispecific antibody of claim 1, wherein said first variable domain comprises a heavy chain variable region at least 90% identical to SEQ ID NO: 7.

10. The bispecific antibody of claim 1, wherein said second variable domain comprises a heavy chain variable region at least 90% identical to SEQ ID NO: 120.

11. The bispecific antibody of claim 1, which is afucosylated in order to enhance ADCC.

12. The bispecific antibody of claim 1, comprising two different immunoglobulin heavy chains with compatible heterodimerization domains.

13. The bispecific antibody of claim 12, wherein said compatible hetero-dimerization domains are compatible immunoglobulin heavy chain CH3 hetero-dimerization domains.

14. A pharmaceutical composition comprising the bispecific antibody of claim 10.

15. The bispecific antibody of claim 1, wherein the common light chain comprises a light chain variable region IGKV1-39.

16. The bispecific antibody of claim 15, wherein the common light chain comprises a germ-line light chain variable region IGKV1-39.

17. The bispecific antibody of claim 1, wherein said first variable domain comprises a heavy chain variable region comprising SEQ ID NO: 7.

18. The bispecific antibody of claim 17, wherein said second variable domain comprises a heavy chain variable region comprising SEQ ID NO: 120.

* * * * *